(12) United States Patent
Caplan et al.

(10) Patent No.: US 8,246,945 B2
(45) Date of Patent: *Aug. 21, 2012

(54) METHODS AND REAGENTS FOR DECREASING CLINICAL REACTION TO ALLERGY

(75) Inventors: Michael J. Caplan, Woodbridge, CT (US); H. Kim Bottomly, Wellesley, MA (US); Howard B. Sosin, Fairfield, CT (US); A. Wesley Burks, Chapel Hill, NC (US); Hugh A. Sampson, Larchmont, NY (US)

(73) Assignees: University of Arkansas, Little Rock, AR (US); Mount Sinai School of Medicine of New York University, New York, NY (US); Allertein Therapeutics, LLC, Fairfield, CT (US)

(*) Notice: Subject to any disclaimer, the term of this patent is extended or adjusted under 35 U.S.C. 154(b) by 0 days.

This patent is subject to a terminal disclaimer.

(21) Appl. No.: 12/572,599

(22) Filed: Oct. 2, 2009

(65) Prior Publication Data
US 2010/0166802 A1    Jul. 1, 2010

Related U.S. Application Data

(63) Continuation of application No. 10/899,551, filed on Jul. 26, 2004, now abandoned, which is a continuation-in-part of application No. 09/731,375, filed on Dec. 6, 2000, now Pat. No. 8,153,414, application No. 12/572,599, which is a continuation-in-part of application No. 10/100,303, filed on Mar. 18, 2002, now abandoned.

(60) Provisional application No. 60/195,035, filed on Apr. 6, 2000.

(51) Int. Cl.
- C12N 1/21 (2006.01)
- C12N 15/70 (2006.01)
- A61K 39/35 (2006.01)
- A61K 39/36 (2006.01)
- A61K 39/40 (2006.01)

(52) U.S. Cl. .............. 424/93.2; 424/93.4; 424/241.1; 424/275.1; 435/252.33; 536/23.6

(58) Field of Classification Search ................ None
See application file for complete search history.

(56) References Cited

U.S. PATENT DOCUMENTS

| | | |
|---|---|---|
| 3,097,141 A | 7/1963 | Wilcox et al. |
| 3,645,852 A | 2/1972 | Axen et al. |
| 3,720,760 A | 3/1973 | Bennich et al. |
| 4,171,299 A | 10/1979 | Hamburger |
| 4,338,297 A | 7/1982 | Michael et al. |
| 4,469,677 A | 9/1984 | Michael et al. |
| 4,535,010 A | 8/1985 | Axen et al. |
| 4,579,840 A | 4/1986 | Hahn |
| 4,658,022 A | 4/1987 | Knowles et al. |
| 4,659,678 A | 4/1987 | Forrest et al. |
| 4,696,915 A | 9/1987 | Horecker |
| 4,816,449 A | 3/1989 | Hahn |
| 4,849,337 A | 7/1989 | Calenoff et al. |
| 4,849,404 A | 7/1989 | Iwai et al. |
| 4,900,556 A | 2/1990 | Wheatley et al. |
| 4,959,314 A | 9/1990 | Mark et al. |
| 5,026,545 A | 6/1991 | Saint-Remy et al. |
| 5,049,390 A | 9/1991 | Wojdani |
| 5,061,790 A | 10/1991 | Elting et al. |
| 5,091,318 A | 2/1992 | Anawis et al. |
| 5,169,933 A | 12/1992 | Anderson et al. |
| 5,314,991 A | 5/1994 | Oka et al. |
| 5,328,991 A | 7/1994 | Kuo |
| 5,389,368 A | 2/1995 | Gurtiss, III |
| 5,449,669 A | 9/1995 | Metcalfe et al. |
| 5,480,972 A | 1/1996 | Avjioglu et al. |
| 5,486,452 A | 1/1996 | Gordon et al. |
| 5,496,554 A | 3/1996 | Oka et al. |
| 5,543,144 A | 8/1996 | Chang |
| 5,547,669 A | 8/1996 | Rogers et al. |
| 5,558,869 A | 9/1996 | Burks, Jr. et al. |
| 5,583,046 A | 12/1996 | Valenta et al. |
| 5,591,433 A | 1/1997 | Michael et al. |
| 5,597,895 A | 1/1997 | Gaynor et al. |

(Continued)

FOREIGN PATENT DOCUMENTS

CA     2157596     9/1994

(Continued)

OTHER PUBLICATIONS

U.S. Appl. No. 07/998,377, filed Dec. 3, 1992.
U.S. Appl. No. 08/158,704, filed Nov. 29, 1993.
U.S. Appl. No. 08/610,424, filed Mar. 4, 1996.
U.S. Appl. No. 09/015,657, filed Jan. 28, 1999.
U.S. Appl. No. 09/336,463, filed Jun. 18, 1999.
U.S. Appl. No. 60/009,455, filed Dec. 29, 1995.
U.S. Appl. No. 08/717,933, filed Sep. 23, 1996.
U.S. Appl. No. 09/106,872, filed Jun. 29, 1998.
U.S. Appl. No. 60/077,763, filed Mar. 13, 1998.
U.S. Appl. No. 09/267,719, filed Mar. 11, 1999.
U.S. Appl. No. 60/073,283, filed Jan. 31, 1998.
U.S. Appl. No. 60/074,690, filed Feb. 13, 1998.
U.S. Appl. No. 60/074,624, filed Feb. 13, 1998.

(Continued)

*Primary Examiner* — Phuong Huynh
(74) *Attorney, Agent, or Firm* — Choata, Hall & Stewart LLP; Brenda Herschbach Jarrell; Brian E. Reese

(57) ABSTRACT

The present invention provides methods and compositions for treating or preventing allergic reactions, particularly anaphylactic reactions. Methods of the present invention involve administering microorganisms to allergic subjects, where the microorganisms contain a recombinant version of the protein allergen. The recombinant version can be wild-type or may include mutations within IgE epitopes of the protein allergen. Preferably the compositions are administered rectally. Particularly preferred microorganisms are bacteria such as *E. coli*. Any allergen may be used in the inventive methods. Particularly preferred allergens are anaphylactic allergens including protein allergens found in foods, venoms, drugs and latex. The inventive compositions and methods are demonstrated in the treatment of peanut-induced anaphylaxis.

24 Claims, 38 Drawing Sheets

U.S. PATENT DOCUMENTS

| | | | |
|---|---|---|---|
| 5,616,559 A | 4/1997 | Androphy et al. | |
| 5,625,039 A | 4/1997 | Washida et al. | |
| 5,637,454 A | 6/1997 | Harley | |
| 5,648,242 A | 7/1997 | Valenta et al. | |
| 5,652,122 A | 7/1997 | Frankel et al. | |
| 5,667,965 A | 9/1997 | Androphy et al. | |
| 5,670,617 A | 9/1997 | Frankel et al. | |
| 5,674,980 A | 10/1997 | Frankel et al. | |
| 5,693,495 A | 12/1997 | Breiteneder et al. | |
| 5,710,126 A | 1/1998 | Griffith et al. | |
| 5,731,157 A | 3/1998 | Miller et al. | |
| 5,736,149 A | 4/1998 | Avjioglu et al. | |
| 5,747,641 A | 5/1998 | Frankel et al. | |
| 5,759,572 A | 6/1998 | Sugimoto et al. | |
| 5,773,003 A | 6/1998 | Swain et al. | |
| 5,786,466 A | 7/1998 | Breitenbach et al. | |
| 5,804,604 A | 9/1998 | Frankel et al. | |
| 5,807,746 A | 9/1998 | Lin et al. | |
| 5,811,128 A | 9/1998 | Tice et al. | |
| 5,820,862 A | 10/1998 | Garman et al. | |
| 5,820,880 A | 10/1998 | Alving et al. | |
| 5,830,463 A | 11/1998 | Duke et al. | |
| 5,834,246 A | 11/1998 | Holmgren et al. | |
| 5,837,550 A | 11/1998 | Breitenbach et al. | |
| 5,843,672 A | 12/1998 | Morgenstern et al. | |
| 5,843,710 A | 12/1998 | Cobon et al. | |
| 5,869,040 A | 2/1999 | Oin | |
| 5,888,762 A | 3/1999 | Joliot et al. | |
| 5,888,799 A | 3/1999 | Curtiss, III | |
| 5,891,432 A | 4/1999 | Hoo | |
| 5,891,716 A | 4/1999 | Morgenstern et al. | |
| 5,939,283 A | 8/1999 | Morgenstern et al. | |
| 5,973,121 A | 10/1999 | Burks, Jr. et al. | |
| 5,989,814 A | 11/1999 | Frankel et al. | |
| 5,998,583 A | 12/1999 | Korsmeyer | |
| 6,004,815 A | 12/1999 | Portnoy et al. | |
| 6,008,340 A | 12/1999 | Ball et al. | |
| 6,025,162 A | 2/2000 | Rogers et al. | |
| 6,060,082 A | 5/2000 | Chen et al. | |
| 6,086,898 A | 7/2000 | DeKruyff et al. | |
| 6,187,311 B1 | 2/2001 | Nishiyama et al. | |
| 6,218,371 B1 | 4/2001 | Krieg et al. | |
| 6,221,648 B1 | 4/2001 | Le Page et al. | |
| 6,239,116 B1 | 5/2001 | Krieg et al. | |
| 6,270,723 B1 | 8/2001 | Laugharn, Jr. et al. | |
| 6,486,311 B1 | 11/2002 | Burks, Jr. et al. | |
| 6,506,388 B1 | 1/2003 | Shionoya et al. | |
| 2002/0187158 A1 | 12/2002 | Mahler et al. | |
| 2003/0035810 A1* | 2/2003 | Caplan | 424/199.1 |
| 2003/0082190 A1 | 5/2003 | Saxon et al. | |
| 2003/0202980 A1* | 10/2003 | Caplan et al. | 424/185.1 |
| 2004/0208894 A1* | 10/2004 | Caplan | 424/199.1 |
| 2004/0234548 A1* | 11/2004 | Caplan | 424/199.1 |
| 2005/0063994 A1* | 3/2005 | Caplan et al. | 424/200.1 |

FOREIGN PATENT DOCUMENTS

| | | |
|---|---|---|
| CA | 2158047 | 9/1994 |
| EP | 0080806 | 6/1983 |
| EP | 0080806 A1 | 6/1983 |
| EP | 0684812 | 12/1995 |
| EP | 0819763 | 1/1998 |
| EP | 0877033 | 11/1998 |
| JP | 06253851 | 9/1994 |
| JP | 07095887 | 4/1995 |
| JP | 072 85875 | 10/1995 |
| WO | WO8809669 | 12/1988 |
| WO | WO-8809669 | 12/1988 |
| WO | WO90/04025 | 4/1990 |
| WO | WO91/06571 | 5/1991 |
| WO | WO91/11718 | 8/1991 |
| WO | WO92/02621 | 2/1992 |
| WO | WO92/03551 | 3/1992 |
| WO | WO92/11859 | 7/1992 |
| WO | WO9214487 | 9/1992 |
| WO | WO-9214487 | 9/1992 |
| WO | WO93/21223 | 10/1993 |
| WO | WO94/05303 | 3/1994 |
| WO | WO-9724139 | 3/1994 |
| WO | WO94/10194 | 5/1994 |
| WO | WO9420614 | 9/1994 |
| WO | WO94/23035 | 10/1994 |
| WO | WO94/24281 | 10/1994 |
| WO | WO95/07933 | 3/1995 |
| WO | WO95/34578 | 12/1995 |
| WO | WO96/14876 | 5/1996 |
| WO | WO-9614876 | 5/1996 |
| WO | WO9614876 | 5/1996 |
| WO | WO96/36880 | 11/1996 |
| WO | WO97/05265 | 2/1997 |
| WO | WO97/24139 | 7/1997 |
| WO | WO9724139 | 7/1997 |
| WO | WO98/23763 | 6/1998 |
| WO | WO9823763 | 6/1998 |
| WO | WO-9823763 | 6/1998 |
| WO | WO98/32866 | 7/1998 |
| WO | WO98/39029 | 9/1998 |
| WO | WO98/43657 | 10/1998 |
| WO | WO98/44096 | 10/1998 |
| WO | WO9844096 | 10/1998 |
| WO | WO-9844096 | 10/1998 |
| WO | WO99/16467 | 4/1999 |
| WO | WO-9925387 | 5/1999 |
| WO | WO9925387 | 5/1999 |
| WO | WO99/34826 | 7/1999 |
| WO | WO99/38978 | 8/1999 |
| WO | WO-9938978 | 8/1999 |
| WO | WO9938978 | 8/1999 |
| WO | WO99/49879 | 10/1999 |
| WO | WO0054803 | 9/2000 |
| WO | WO01/36621 | 5/2001 |

OTHER PUBLICATIONS

U.S. Appl. No. 60/074,633, filed Feb. 13, 1998.
U.S. Appl. No. 09/241,101, filed Jan. 29, 1999.
U.S. Appl. No. 09/248,673, filed Feb. 11, 1999.
U.S. Appl. No. 09/248,674, filed Feb. 11, 1999.
U.S. Appl. No. 60/073,171, filed Jan. 30, 1998.
U.S. Appl. No. 09/238,448, filed Jan. 28, 1999.
U.S. Appl. No. 09/090,375, filed Jun. 4, 1998.
U.S. Appl. No. 09/141,220, filed Aug. 27, 1998.
U.S. Appl. No. 09/478,668, filed Jan. 6, 2000.
U.S. Appl. No. 09/240,557, filed Jan. 29, 1999.
U.S. Appl. No. 60/122,450, filed Mar. 2, 1999.
U.S. Appl. No. 60/112,452, filed Mar. 2, 1999.
U.S. Appl. No. 60/122,560, filed Mar. 2, 1999.
U.S. Appl. No. 60/122,565, filed Mar. 2, 1999.
U.S. Appl. No. 60/122,566, filed Mar. 2, 1999.
U.S. Appl. No. 09/494,096, filed Jan. 28, 2000.
U.S. Appl. No. 60/090,390, filed Jun. 23, 1998.
U.S. Appl. No. 09/339,068, filed Jun . 23, 1999.
U.S. Appl. No. 09/216,117, filed Dec. 18, 1998.
U.S. Appl. No. 09/247,406, filed Feb. 10, 1999.
U.S. Appl. No. 09/218,345, filed Dec. 22, 1998.
U.S. Appl. No. 09/470,293, filed Dec. 22, 1999.
U.S. Appl. No. 60/124,595, filed Mar. 16, 1999.
U.S. Appl. No. 60/125,071, filed Mar. 17, 1999.
U.S. Appl. No. 60/169,330, filed Dec. 6, 1999.
U.S. Appl. No. 09/455,294, filed Dec. 6, 1999.
U.S. Appl. No. 60/105,806, filed Oct. 27, 1999.
U.S. Appl. No. 60/122,960, filed Mar. 3, 1999.
Aalberse et al, 2000, J Allerg Clin Immunol, 106:228-38.
Andrews et al, 1996, Gene, 182:101-9.
Blumental et al, 2004, Allergens and Allergen Immunotherapy, 3rd Ed, 37-50.
Burks et al, 1995, J. Clin. Invest., 96:1715-21.
Burks et al, 1997, Eur J Biochem, 245:334-39.
Burks et al, 1999, Int Arch Allerg Immunol, 118:313-14.
Chatel et al, 2003, Allergy, 58:641-47.
Chong et al, 1997, Transgenic Res, 289-296.
Colman et al, 1994, Res Immunol, 145:33-36.
Dizier et al, 1999, Gen Epidemiol, 16:305-15.
Eidelman et al, 1988, Am Rev Respir Dis, 137:1033-37.

Eko et al, 1999, Vaccine, 17:1643-49.
Evans et al, 1998, FEMS Microbiol Immunol, 47:117-25.
Fasler et al, 1998, J Aller Clin Immunol, 101:521-30.
Fenton et al, 1995, J Natl Canc Inst, 87:1853-61.
Ferreira et al, 1996, J. Exp. Med., 183:599-609.
Ferreira et al, 1998, FASEB J, 12:231-42.
Gentschev et al, 1996, Gene, 179:133-40.
Gottlieb et al, 1999, BMJ, 318:894.
Greenspan et al, 1999, Nat Biotechnol, 17:936-37.
Hansen et al, 2000, J. Immunol., 164:223-30.
Harvey et al, 1990, Remington's Pharmaceutical Sciences, 18th Ed., Chapter 35, p. 711.
Hess et al, 1996, Proc Natl Acad Sci, USA, 93:1458-63.
Higgins et al, 1999, Mol Microbiol, 31:1631-41.
Hoffman et al, 1975, Immunochemistry, 12:535-38.
Ingram et al, 1980, J Bact, 144:481-88.
James et al, 1997, J Allerg Clin Immunol, 99(1):239-44 part 2.
Kleber-Janke et al, 2000, Prot Exp Purificat, 19:419-24.
Komanapalli et al, 1998, Appl Microbiol Biotechnol, 49:766-69.
Kraft et al, 1999, Intl Arch Allerg Immunol, 118:171-76.
Leclerc et al, 1990, J Immunol, 144:3174-82.
Li et al, 2003, J. Allergy Clin. Immunol., 112(1):160-167.
Li, 1999, J. Immunol., 162:3045-52.
Mekalanos, 1992, Gen Eng Vaccines, 327:43.
Rabjohn et al, 1999, J Clin Invest, 103:535-42.
Reese et al, 2005, J Immunol, 175:8354-64.
Skolnick et al, 2000, Trend Biotech, 18:34-39.
Stanley et al, 1997, Arch Biochem Biophys, 342:244-53.
Till, 2004, Allergens and Allergen Immunotherapy, 3rd Ed, 85-104.
Vrtala et al, 1995, Int Arch Allerg Immunol, 107:290-94.
Vrtala et al, 1997, J Clin Invest, 99(7):1673-81.
Walker et al, 1994, Vaccine, 12:387-400.
Yeung et al, 1998, J Immunol, 161:4146-52.
Chatel, et al., "Various Factors (Allergen Nature, Mouse Strain, CpG/Recombinant Protein Expressed) Influence the Immune Response Elicited by Genetic Immunization", Allergy, 58: 641-647, 2003.
Evans, et al., "Non-Replicating Oral Whole Cell Vaccine Protective Against Enterotoxigenic *Escherichia coli* (ETEC) Diarrhea: Stimuation of Anti-CFA (CFA/I) and Anti-Enterotoxin (Anti-LT) Intestinal IgA and Protection Against Challenge with ETEC Belonging to Heterologous Serotypes", FEMS Microbiology Immunology, 47: 117-126, 1988.
Gotlieb, "Scientists Develop Vaccine Strategy for Peanut Allergy", BMJ, 318: 894, 1999.
Vrtala, et al., "Conversion of the Major Birch Pollen Allergen, Bet v 1, into Two Nonanaphylactic T Cell Epitope-Containing Fragments", J. Clin. Invest. 99(7): 1673-1681, 1997.
Banks, et al., "Chemistry and Pharmacology of Honey-Bee Venom", Venoms of the Hymenoptera, 329-416, 1986.
Eko, et al., "New Strategies for Combination Vaccines Based on the Extended Recombinant Bacterial Ghost System", Vaccine, 17: 1643-1649, 1999.
Gentschev, et al., "Development of Antigen-Delivery Systems, Based on the *Escherichia coli* Hemolysin Secretion Pathway", Gene, 179: 133-140, 1996.
Hess, et al., "Superior Efficacy of Secreted Over Somatic Antigen Display in Recombinant *Salmonella* Vaccine Induced Protection Against Listeriosis", Proc. Natl. Acad. Sci. USA, 93: 1458-1463, 1996.
Koppelman, et al., "Peanut Allergen Ara h 3: Isolation from peanuts and biochemical characterization", Allergy, 58: 1144-1151, 2003.
Triozzi, et al., "Effects of a b-Human Chorionic Gonadotropin Sub-unit Immunogen Administered in Aqueous Solution with a Novel Nonionic Block Copolymer Adjuvant in Patients with Advanced Cancer", Clinical Cancer Research, 3: 2355-2362, 1997.
Hansen, "Vaccination with Heat-Killed *Listeria* as Adjuvant Reverses Established Allergen-Induced Airway Hyperreactivity and Inflammation: Role of CD8+ T Cells and IL-18", The Journal of Immunology, 164: 223-230, 2000.
Mekalanos, "Bacterial Mucosal Vaccines" in Genetically Engineered Vaccines, Edited by Ciardi et al., Plenum Press, pp. 43-50, 1992.

Amorim, et al., "Suppression of Airway Eosinophilia by Killed *Mycobacterium vaccae*-Induced Allergen-Specific Regulatory T-Cells", Nature Medicine, 8(6): 625-629, 2002.
Asturias, et al., "Is Tropomyosin an Allergen in *Anisakis*?", Aller., 55: 898-890, 2000.
Asturias, et al., "Cloning, Isolation, and IgE-Binding Properties of *Helix aspersa* (Brown Garden Snail) Tropomyosin", Int. Arch Allergy Immunol. 128: 90-96, 2002.
Asturias, et al., "Molecular Characterization of American Cockroach Tropomyosin (*Periplaneta americana* Allergen 7), a Cross-Reactive Allergen", The Journal of Immunology, 162: 4342-4348, 1999.
Bannon, et al., "Engineering, Characterization and in Vitro Efficacy of the Major Peanut Allergens for Use in Immunotherapy", Int. Arch. Allergy Immunol, 124: 70-72, 2001.
Barderas, et al., "Identification and Characterization of Che a 1 Allergen from *Chenopodium album* Pollen", Int. Arch. Allergy Immunol. 127: 47-54, 2002.
Barnes, P.J., "IL-10: A Key Regulator of Allergic Disease", Clinical and Experimental Allergy, 31: 667-669, 2001.
Bashir, et al., "An Enteric Helminth Infection Protects Against an Allergic Response to Dietary Antigen", The Journal of Immunology, 169: 3284-3292, 2002.
Batanero, et al., "Purification, Amino Acid Sequence and Immunological Characterization of Ole e 6, a Cysteine-Enriched Allergen from Olive Tree Pollen", FEBS Letters, 410: 293-296, 1997.
Beck, et al., "The Polyclonal and Antigen-Specific IgE and IgG Subclass Response of Mice Injected with Ovalbumin in Alum or Complete Freund's Adjuvant", Cellular Immunology, 123: 1-8, 1989.
Bissonnette, et al., "Inhibition of Mast Cell-Mediated Cytotoxicity by IFN-oc/r3 and -y1", The Journal of Immunology, 145: 3385-3390, 1990.
Bock, et al., "The Natural History of Food Sensitivity", J. Allergy Clin. Immunol. 69: 173-177, 1982.
Bock, et al., "Fatalities Due to Anaphylactic Reactions to Foods", J. Allergy Clin. Immunol. 107: 191-193, 2001.
Brandtzaeg, et al., "Current Understanding of Gastrointestinal Immunoregulation and Its Relation to Food Allergy", Ann. NY. Acad. Sci., 964: 13-45, 2002.
Burks, et al., "Modification of a Major Peanut Allergen Leads to Loss of IgE Binding", Int. Arch. Allergy Immunol. 118: 313-314, 1999.
Bush, et al., "Molecular Cloning of a Major Alternaria Alternata Allergen, rAlt a 2", J. Allergy Clin. Immunol. 104: 665-671, 1999.
Chang, et al., "Characterization of Enolase Allergen from *Rhodotorula mucilaginosa*", J. Biomed. Sci. 9: 645-655, 2002.
Dandeu, et al., "Hydrophobic Interaction Chromatography for Isolation and Purification of Equ.cl, the Horse Major Allergen", Journal of Chromatography, 621: 23-31, 1993.
De Jong, et al., "Identification and Partial Characterization of Multiple Major Allergens in Peanut Proteins", Clinical and Experimental Allergy, 28: 743-751, 1998.
Diaz-Perales, et al., "Lipid-Transfer Proteins as Potential Plant Panallergens: Cross-Reactivity Among Proteins of *Artemisia* Pollen, *Castanea* Nut and Rosaceae Fruits, with Different IgE Binding Capacities", Clinical and Experimental Allergy, 30: 1403-1410, 2000.
Diaz-Perales, et al., "Characterization of Asparagus Allergens: A Relevant Role of Lipid Transfer Proteins", J. Allergy Clin. Immunol. 110: 790-796, 2002.
Dorion, et al., "The Production of Interferon-y in Response to a Major Peanut Allergy, Ara h ll, Correlates with Serum Levels of IgE Anti-Ara h ll", J. Allergy Clin. Immunol. 93: 93-99, 1994.
Durham, et al., "Immunologic Changes Associated with Allergen Immunotherapy", The Journal of Allergy and Clinical Immunology, 102(2): 157-164, 1998.
Erb, et al., "Atopic Disorders: A Default Pathway in the Absence of Infection?", Immunol. Today, 20: 317-322, 1999.
Eriksson, et al., "Cloning and Characterisation of a Group II Allergen from the Dust Mite *Tyrophagus putrescentiae*", Eur. J. Biochem. 251: 443-447, 1998.
Eriksson, et al., "Cloning of Three New Allergens from the Dust Mite Lepidoglyphus Destructor Using Phage Surface Display Technology", Eur. J. Biochem. 268: 287-294, 2001.

Fahlbusch, et al., "Purification and Partial Characterization of the Major Allergen, Cav p 1, from Guinea Pig *Cavia porcellus*", Allergy, 57: 417-422, 2002.

Fiorentino, et al., "Two Types of Mouse T Helper Cell", J. Exp. Med. 170: 2081-2095, 1989.

Francis, et al., "Induction of IL-10+CD4+CD25+ T Cells by Grass Pollen Immunotherapy", J. Allergy Clin. Immunol. 111: 1255-1261, 2003.

Gafvelin, et al., "Cross-Reactivity Studies of a New Group 2 Allergen from the Dust Mite *Glycyphagus domesticus*, Gly d 2, and Group 2 Allergens from *Dermatophagoides pteronyssinus*, Lepidoglyphus Destructor, and *Tyrophagus putrescentiae* with Recombinant Allergens", J. Allergy Clin. Immunol. 107: 511-518, 2001.

Giuliani, et al., "Isolation and Purification of a Major Allergen from *Parietaria officinalis* Pollen", Allergy, 42: 434-440, 1987.

Hansen, et al., "Vaccination with Heat-Killed *Listeria* as Adjuvant Reverses Established Allergen-Induced Airway Hyperreactivity and Inflammation: Role of CD8+ T Cells and IL-18", The Journal of Immunology, 164: 223-230, 2000.

Helm, et al., "Isolation and Characterization of a Clone Encoding a Major Allergen (Bla g Bd9OK) Involved in IgE-Mediated Cockroach Hypersensitivity", J. Allergy Clin. Immunol. 98:172-180, 1996.

Hilger, et al., "Sequence of the Gene Encoding cat (*Felis domesticus*) Serum Albumin", Gene, 169: 295-296, 1996.

Himly, et al., "Art v 1, the Major Allergen of Mugwort Pollen, is a Modular Glycoprotein with a Defensin-Like and a Hydroxyproline-Rich Domain", FASEB J., 17: 106-108, 2003.

Hoffman, et al., "Occupational Allergy to Bumblebees: Allergens of *Bombus terrestris*", J. Allergy Clin. Immunol. 108: 855-860, 2001.

Hoffman, et al., "Allergens in Hymenoptera Venom XXVII: Bumblebee Venom Allergy and Allergens", J. Allergy Clin. Immunol. 97: 812-821, 1996.

Hoffman, et al., "Allergens in Bee Venom, III. Identification of Allergen B of Bee Venom as an Acid Phosphatase", J. Allergy Clin. Immunol. 59(5): 364-366, 1977.

Horiuti, et al., "Variable Expression of Pathogenesis-Related Protein Allergen in Mountain Cedar (*Juniperus ashei*) Pollen", The Journal of Immunology, 164: 2188-2192, 2000.

Homer, et al., "Identfiication of the Allergen Psi c 2 from the Basidiomycete *Psilocybe cubensis* as a Fungal Cyclophilin". Int. Arch Allergy Immunol. 107: 298-300, 1995.

Howard, et al., "Regulation of B-Cell Growth and Differentiation by Soluble Factors", Ann. Rev. Immunol. 1: 307-333, 1983.

Hsu, et al., "Differential Effects of IL-4 and IL-4 and IL-10 on IL-2-Induced IFN-y Synthesis and Lymphokine-Activated Killer Activity", International Immunology, 4(5): 563-569, 1992.

Ichikawa, et al., "Molecular Cloning, Expression and Modelling of Cat Allergen, Cystatin (Fel d 3), A Cysteine Protease Inhibitor", Clinical and Experimental Allergy, 31: 1279-1286, 2001.

Jankulovic, et al.. "Isolation and Biochemical Characterization of a Thaumatin-Like Kiwi Allergen", J. Allergy Clin. Immunol. 110: 805-810, 2002.

Kalliomaki, et al., "Transforming Growth Factor-13 in Breast Milk: A Potential Regular of Atopic Disease at an Early Age", J. Allergy Clin. Immunol. 104(6): 1251-1257, 1999.

Kleine-Tebbe, et al., "Severe Oral Allergy Syndrome and Anaphylactic Reactions Caused by a Bet v 1-Related PR-10 Protein in Soybean, SAM22", J. Allergy Clin. Immunol. 110: 797-804, 2002.

Kowalski, et al., "Mechanisms of Specific Immunotherapy of Allergic Diseases", Allergy, 53: 485-492, 1998.

Ledesman, et al., "Cloning, Expression and Characterization of a Novel Four EF-Hand Ca2+—Binding Protein from Olive Pollen with Allergenic Activity", FEBS Letter, 466: 192-196, 2000.

Lee, et al., "Oral Administration of 11-12 Suppresses Anaphylactic Reactions in a Murine Model of Peanut Hypersensitivity", Clinical Immunology, 101(2): 220-228, 2001.

Leung, et al., "Effect of Anti-IgE Therapy in Patients with Peanut Allergy", N. Engl. J. Med. 348: 986-993, 2003.

Li, et al., "A Murine Model of Peanut Anaphylaxis: T- and B-Cell Responses to a Major Peanut Allergen Mimic Human Responses", J. Allergy Clin. Immunol. 106: 150-158, 2000.

Li, et al., "Novel Approaches for the Treatment of Food Allergy", Current Opinion in Allergy and Clinical Immunology, 2: 273-278, 2002.

Li, et al., "Engineered Recombinant Peanut Protein and Heat-Killed *Listeria monocytogenes* Coadministration Protects Against Peanut-Induced Anaphylaxis in a Murine Model", The Journal of Immunology, 170: 3289-3295, 2003.

Et al., "Strain-Dependent Induction of Allergic Sensitization Caused by Peanut Allergen DNA Immunization in Mice", The Journal of Immunology, 162: 3045-3052, 1999.

Lombardero, et al., "cDNA Sequence Analysis of the Main Olive Allergen, Ole e l", Clinical and Experimental Allergy, 24: 765-770, 1994.

Lopata, et al., "Characteristics of Hypersensitivity Reactions and Identification of a Unique 49 kd IgE-Binding Protein (Hal-m-1) in Abalone (*Haliotis midae*)", J. Allergy Clin. Immunol. 100: 642-648, 1997.

Lorentz, et al., "Human Intestinal Mast Cells Produce IL-5 in Vitro Upon IgE Receptor Cross Linking and In Vivo in the Course of Intestinal Inflammatory Disease" Eur. J. Immunol. 29: 1496-1503, 1999.

Melen, et al., "Molecular Cloning of Per a 1 and Definition of the Cross-Reactive Group 1 Cockroach Allergens", J. Allergy Clin. Immunol. 103: 859-864, 1999.

Moneo, et al., "Isolation and Characterization of Tha p 1, A Major Allergen from the Pine Processionary Caterpillar *Thaumetopoea pityocampa*", Aller , 58: 34-37, 2003.

Moneo, et al., "Isolation and Characterization of a Major Allergen from the Fish Parasite *Anisakis simplex*", J. Allergy Clin. Immunol. 106: 177-182, 2000.

Monsalve, et al.. "Detection, Isolation and Complete Amino Acid Sequence of an Aeroallergenic Protein from Rapeseed Flour", Clinical and Experimental Aller , 27: 833-841, 1997.

Morafo, et al., "Genetic Susceptibility to Food Allergy is Linked to Differential TH2-TH1 Responses in C3H/HeJ and BALB/c Mice", J. Allergy Clin. Immunol. 111: 1122-1128, 2003.

Mosmann, et al., "Thi and Th2 Cells: Different Patterns of Lymphokine Secretion Lead to Different Functional Properties", Ann. Rev. Immunol. 7: 145-173, 1989.

Mutius, et al., "The Environmental Predictors of Allergic Disease", J. Allergy Clin. Immunol. 105: 9-19, 2000.

Onishi, et al., "Two-Dimensional Electrophoresis of *Malassezia* Allergens for Atopic Dermatitis and Isolation of Mal f 4 Homologs with Mitochondrial Malate Dehydrogenase", Eur. J. Biochem. 261: 148-154, 1999.

Onizuka, et al., "Purification of the Major Allergen of Red Soft Coral (*Dendronephthya nipponica*)", Int. Arch. Allergy Immunol, 125: 135-143, 2001.

Oppenheimer, et al., "Treatment of Peanut Allergy with Rush Immunotherapy", J. Allergy Clin. Immunol. 90: 256-262, 1992.

Paddock, et al., "Identification, Cloning, and Recombinant Expression of Procalin, a Major *Triatomine* Allergen", The Journal of Immunology, 167: 2694-2699, 2001.

Palosuo, et al., "Wheat co-5 Gliadin is a Major Allergen in Children with Immediate Allergy to Ingested Wheat", 1 Allergy Clin. Immunol. 108: 634-638, 2001.

Pastorello, et al., "The Major Allergen of Sesame Seeds (*Sesamum indicum*) is a 2S Albumin", Journal of Chromatography B, 756: 85-93, 2001.

Pastorello, et al., "Allergenic Cross-Reactivity Among Peach, Apricot, Plum, and Cherry in Patients with Oral Allergy Syndrome: An In Vivo and in Vitro Study", J. Allergy Clin. Immunol. 94: 699-707, 1994.

Pierkes, et al., "Decreased Release of Histamine and Sulfidoleukotrienes by Human Peripheral Blood Leukocytes After Wasp Venom Immunotherapy is Partially Due to Induction of IL-10 and LEN-y Production of T Cells", J. Allergy Clin. Immunol. 103: 326-332, 1999.

Pomes, et al., "Novel Allergen Structures with Tandem Amino Acid Repeats Derived from German and American Cockroach", The Journal of Biological Chemistry, 273(46): 30801-30807, 1998.

Ramos, et al., "cDNA Cloning and Expression of Blo t 11, the Blomia Tropicalis Allergen Homologous to Paramyosin", Int. Arch. Allergy Immunol. 126: 286-293, 2001.

Rasool, et al., "Cloning, Characterization and Expression of Complete Coding Sequences of Three IgE Binding *Malassezia furfur* Allergens, Mal f 7, Mal f 8 and Mal f 9", Eur. 1 Biochem. 267: 4355-4361, 2000.

Romagnani, et al., "The Role of Lymphocytes in Allergic Disease", J. Allergy Clin. Immunol. 105: 399-408, 2000.

Rook, et al., "Give us this Day our Daily Germs", Immunology Today, 19: 113-116, 1998.

Saarinen, et al., "Transforming Growth Factor-131 in Mothers' Colostrum and Immune Responses to Cows' Milk Proteins in Infants with Cows' Milk Allergy", J. Allergy Clin. Immunol. 104: 1093-1098, 1999.

Saarne, et al., "Cloning and Characterisation of Two IgE-Binding Proteins, Homologous to Tropomyosin and a-Tubulin, from the Mite Lepidoglyphus Destructor", Int. Arch Allergy Immunol. 130: 258-265, 2003.

Sampson, et al., "Fatal and Near-Fatal Anaphylactic Reactions to Food in Children and Adolescents", N. Engl. J. Med. 327: 380-384, 1992.

Sampson, Hugh., "Food Allergy. Part 1: Immunopathogenesis and Clinical Disorders", The Journal of Allergy and Clinical Immunology, 103(5): 717-728, 1999.

Sanchez-Monge, et al., "Isolation and Characterization of Relevant Allergens from Boiled Lentils", J. Allergy Clin. Immunol. 106: 955-961, 2000.

Santos, et al., "Cockroach Allergens and Asthma in Brazil: Identification of Tropomyosin as a Major Allergen with Potential Cross-Reactivity with Mite and Shrimp Allergens", J. Allergy Clin. Immunol. 104: 329-337, 1999.

Saxena, et al., "cDNA Cloning, Expression and Characterization of an Allergenic L3 Ribosomal Protein of *Aspergillus fumigatus*" Clin. Exp. Immunol, 134: 86-91, 2003.

Schade, et al., "Differences in Antigen-Specific T-Cell Responses Between Infants with Atopic Dermatitis with and without Cow's Milk Allergy: Relevance of TH2 Cytokines", J. Allergy Clin. Immunol. 106: 1155-1162, 2000.

Shen, et al., "Characterization of Allergens from *Penicillium oxalicum* and *P. notatum* by Immunoblotting and N-Terminal Amino Acid Sequence Analysis", Clinical and Experimental Aller , 29: 642-651, 1999.

Shen, et al., "Molecular Cloning and Immunological Characterization of the House Dues Mite Allergen Der f 7", Clinical and Experimental Allergy, 25: 1000-1006, 1995.

Sicherer, et al., "Prevalence of Peanut and Tree Nut Allergy in the US Determined by a Random Digit Dial Telephone Survey", J. Allergy Clin. Immunol. 103: 559-562, 1999.

Smith, et al., "Sequence Polymorphisms and Antibody Binding to the Group 2 Dust Mite Allergens", Int. Arch. Allergy Immunol. 124: 61-63, 2001.

Smith, et al., "The Molecular Basis of Antigenic Cross-Reactivity Between the Group 2 Mite Allergens", J. Allergy Clin Immunol. 107: 977-984, 2001.

Snapper, et al., "Interferon-y and B Cell Stimulatory Factor-1 Reciprocally Regulate Ig Isotype Production", Science, 236: 944-947, 1987.

Sommergruber, et al., "Molecular Characterization of Dau c 1, the Bet v 1 Homologous Protein from Carrot and its Cross-Reactivity with Bet v 1 and Api g 1", Clinical and Experimental Allergy, 29: 840-847, 1999.

Stanley, et al., "Identification and Mutational Analysis of the Immunodominant IgE Binding Epitopes of the Major Peanut Allergen Ara h 2", Archives of Biochemistry and Biophysics, 342(2): 244-253, 1997.

Strobel, et al., "Immune Responses to Dietary Antigens: Oral Tolerance", Immunology Today, 19: 173-181, 1998.

Strobel, et al., "Oral Tolerance, Systemic Immunoregulation, and Autoimmunity" Ann. N.Y. Acad. Sci. 958: 47-58, 2002.

Tejera, et al., "Identification, Isolation, and Characterization of Ole e 7, a New Allergen of Olive Tree Pollen", J. Allergy Clin Immunol, 104: 797-802, 1999.

Tinghino, et al., "Molecular Characterization of a Cross-Reactive *Juniperus oxycedrus* Pollen Allergen, Jun o 2: A Novel Calcium-Binding Allergen", J. Allergy Clin Immunol, 101: 772-777, 1998.

Tsai, et al., "Sequence Analysis and Expression of a cDNA Clone Encoding a 98-kDa Allergen in *Dermatophagoides farinae*", Clinical and Experimental Allergy, 29: 1606-1613, 1999.

Turcanu, et al., "Characterization of Lymphocyte Responses to Peanuts in Normal Children, Peanut-Allergic Children, and Allergic Children who Acquired Tolerance to Peanuts", The Journal of Clinical Investigation, 111(7): 1065-1072, 2003.

Weiner, et al., "Oral Tolerance: Immune Mechanisms and Treatment of Autoimmune Diseases", Immunology Today, 18: 335-343, 1997.

Wopfner, et al., "Molecular and Immunological Characterization of Profilin from Mugwort Pollen", Biol. Chem. 383: 1779-1789, 2002.

Wu, et al., "Sequencing Analysis of cDNA Clones Encoding the American Cockroach Cr-Pl Allergens", The Journal of Biological Chemistry, 271(30): 17937-17943, 1996.

Wu, et al., "Cloning of the American Cockroach Cr-PlI Allergens: Evidence for the Existence of Cross-Reactive Allergens Between Species", J. Allergy Clin. Immunol, 101: 832-840, 1998.

Wu, et al., "Sequencing and Immunochemical Characterization of the American Cockroach Per a 3 (Cr-Pl) Isoallergenic Variants", Molecular Immunology, 34(1): 1-8, 1997.

Xu, et al., "Cloning, Expression and Immunological Characterization of Ory s 1, the Major Allergen of Rice Pollen", Gene, 164: 255-259, 1995.

Yasueda, et al., "Identification and Cloning of Two Novel Allergens from the Lipophilic Yeast, *Malassezia furfur*", Biochemical and Biophysical Research Communications, 248: 240-244, 1998.

Del Val, et al., "Thioredoxin Treatment Increases Digestibility and Lowers Allergenicity of Milk", J. Allergy Clin. Immunol. 103(4): 690-697, 1999.

Hoyne, et al., "Peptide-Mediated Regulation of the Allergic Immune Response", Immunol. Cell Biol. 74(2): 180-186, 1996.

Vailes, et al., "Fine Specificity of B-Cell Epitopes on *Felis domesticus* Allergen I (Fel d 1): Effect of Reduction and Alkylation or Deglycosylation of Fel d 1 Structure and Antibody Binding", J. Allergy Clin. Immunol. 93(1): 22-33, 1994.

Burns, et al., "Selective Reduction of Disulfides by Tris (2-Carboxyethyl) Phosphine", J. Org. Chem. 56(8): 2648-2650, 1991.

Gray, et al., "Echistatin Disulfide Bridges: Selective Reduction and Linkage Assignment", The Protein Society, 1749-1755, 1993.

Gray, et al., "Disulfide Structures of Highly Bridged Peptides: A New Strategy for Analysis", The Protein Society,1732-1748, 1993.

Herbert, et al., "Reduction and Alkylation of Proteins in Preparation of Two-Dimensional Map Analysis: Why, When, and How?" Electrophoresis, 22: 2046-2057, 2001.

Nakamura, et al., "Mass Spectrometric-Based Revision of the Structure of a Cysteine-Rich Peptide Toxin with Gamma-Carboxyglutamic Acid, TxVIIA, from the Sea Snail, *Conus textile*", Protein Science, 5(3): 524-530, 1996.

Olsson, et al., "Contribution of Disulphide Bonds to Antigenicity of Lep d 2, the Major Allergen of the Dust Mite Lepidoglyphus Destructor", Molecular Immunology, 35: 1017-1023, 1998.

Smith, et al., "Localization of Antigenic Sites on Der p2 Using Oligonucleotide-Directed Mutagenesis Targeted to Predicted Surface Residues", Clinical and Experimental Aller , 27: 593-599, 1997.

Smith, et al., "Recombinant Allergens for Immunotherapy: A Der p2 Variant with Reduced IgE Reactivity Retains T-Cell Epitopes",1 Allergy Clin. Immunol. 101(3): 423-425, 1998.

Smith, et al., "Reduction in IgE Binding to Allergen Variants Generated by Site-Directed Mutagenesis: Contribution of Disulfide Bonds to the Antigenic Structure of the Major House Dust Mite Allergen Der p 2", Molecular Immunology, 33(4/5): 399-405, 1996.

Wu, et al., "A Novel Methodology for Assignment of Disulfide Bond Pairing in Proteins", Protein Science, 6(2): 391-398, 1997.

Zhou, et al., "Assignment of Disulfide Bonds in Proteins by Partial Acid Hydrolysis and Mass Spectrometry", Journal of Protein Chemistry, 9(5): 523-532, 1990.

Aas, et al., "Physico-Chemical Properties and Specific Activity of a Purified Allergen (Codfish)", Dev. Biol. Stand. 29: 90-98, 1975.

Aki, et al., "Immunochemical Characterization of Recombinant and Native Tropomyosins as a New Allergen from the House Dust Mite, *Dermatophagoides farinae*", J. Allergy Clin. Immunol., 96:74-83, 1995.

Alenius, et al., "Prohevein from the Rubber Tree (*Hevea brasiliensis*) is a Major Latex Allergen," Clin. Exp. Allergy, 25(7): 659-665, 1995.

Alenius, et al., "The Main IgE-Binding Epitope of a Major Latex Allergen, Prohevein, is Present in its N-Terminal 43-Amino Acid Fragment, Hevein" J. Immunol. 156(4): 1618-1625, 1996.

Alenius, et al., "IgE Reactivity to 14-kD and 27-kD Natural Rubber Proteins in Latex-Allergic Children with Spina Bifida and Other Congenital Anomalies", Int. Arch. Allergy Immunol., 102:61-66, 1993.

Ansari, et al., "An Investigation of Human Response to Perenninal Ryegrass", J. Allergy Clin. Immunol. 80: 229-235, 1987.

Ansari, et al., "Complete Amino Acid Sequence of a *Lolium perenne* (Perennial Rye Grass) Pollen Allergen, Lol p ll" J. Biol. Chem., 264:11181-11185, 1989.

Ansair, et al., "Complete Primary Structure of a *Lolium perenne* (Perrennial Rye Grass) Pollen Allergen, Lol P lll: Comparison with Known Lol p l and ll Sequences", Biochemistry, 28:8665-8670, 1989.

Apold, et al., "The Allergenic Structure of Allergen M from Cod. III. Studies on the Antigenic of Long-Sequence Peptides", Int Arch Allergy Appl Immunol. 58(3): 337-43, 1979.

Arruda, et al., "Molecular Cloning of a Major Cockroach (*Blattella germanica*) Allergen, Bla g 2", J. Biol. Chem., 270:19563-19568, 1995.

Arruda, et al., "Cloning of Cockroach Allergen, Bla g 4, Identifies Ligand Binding Proteins (or Calycins) as a Cause of IgE Antibody Responses" J. Biol. Chem. 270: 31196-31201, 1995.

Arruda, et al., "Molecular Cloning of German Cockroach (*Blattella germanica*) Allergens", Int. Arch Allergy Immunol., 107:295-297, 1995.

Asturias, et al., "Cloning and High Level Expression of *Cynodon dactylon* (Bermuda Grass) Pollen Profilin (Cyn d 12) in *Escherichia coli*: Purification and Characterization of the Allergen" Clin. Exp. Allergy, 27:1307-1313, 1997.

Asturias, et al., "Cloning and Expression of the Panallergen Profilin and the Major Allergen (Ole e 1) from Olive Tree Pollen", J. Allergy Clin Immunol 100:365-372, 1997.

Attanayaka, et al., "Molecular Cloning and Nucleotide Sequencing of the Rubber Elongation Factor Gene from *Hevea brasilienis*", Plant Mol. Biol., 16:1079-1081, 1991.

Aukrust, L., "Purification of Allergens in *Cladosporium herbarum*", Allergy, 35: 206-207, 1980.

Aukrust, et al., "Partial Purification and Characterization of Two *Cladosporium herbarum* Allergens", Int Arch Allergy Appl Immunol., 60:68-79, 1979.

BSAC Working Party, "Position Paper on Allergen Immunotherapy," Clin. Exp. Allergy, 23: 1-44 (1993).

Ball, et al., "A Major Continuous Allergenic Epitope of Bovine Beta-Lactoglobulin Recognized by Human IgE Binding", Clin. Exp. Allergy, 24: 758-764, 1994.

Bannon, et al., "Tertiary Structure and Biophysical Properties of a Major Peanut Allergen, Implications for the Production of a Hypoallergenic Protein", Int. Arch Allergy Immunol. 118(2-4), 315-6, Feb.-Apr. 1999.

Barnett, et al., "Multiplicity of Allergens in Peanuts," J. Allergy Clin. Immunol., 72: 61-8, 1983.

Barnett, et al., "Partial Characterization of an Allergenic Glycoproteins from Peanut", Biochimica et Biophysica Acta 882: 97-105, 1986.

Batanero, et al., "Ole e 3, an Olive-Tree Allergen, Belongs to a Widespread Family of Pollen Proteins" Eur. J. Biochem., 241:772-778, 1996.

Bauer, et al., "Modulation of the Allergic Immune Response in BALB/c Mice by Subcutaneo Injection of High Doses of the Dominant T Cell Epitope from the Major Birch Pollen Allergen Bet v 1", Clin Exp Immunol, 107(3): 536-41, Mar. 1997.

Bayard, et al., "Mapping of IgE Binding Regions in the Major Rat Urinary Protein, Alpha 2u-Globulin, Using Overlapping Peptides", Immunol. Invest, 28(5-6): 323-38, Sep.-Dec. 1999.

Bernhisel-Broadbent, et al., "Cross-Allergenicity in the Legume Botanical Family in Children with Food Hypersensitivity. II. Laboratory correlates" J Allergy Clin. Immunol., 84: 701-709 (1989).

Bevier, "Flea Allergy Dermatitis Testing Breakthrough", Canine Practice, 22(2-3): 49-50, 1997.

Bock, "Natural History of Severe Reactions to Foods in Young Children," J. Pediatr. 107: 676-680, 1985.

Bock, "The Natural History of Peanut Allergy", J. Allergy Clin. Immunol., 83: 900-904 (1989).

Botros, H., "Cross-Antigenicity of Horse Serum Albumin with Dog and Cat Albumins: Study of Three Short Peptides with Siginificant Inhibitory Activity Towards Specific Human IgE and IgG Antibodies", Immunology, 88: 340-47, 1996.

Boulet, et al., "Inhibitory Effects of an Anti-IgE Antibody E25 on Allergen-Induced Early Asthmatic Response," Am J. Respir Crit Care Med., 155: 1835-1840, 1997.

Brand, et al., "Allergen-Specific Immune Deviation from a TH2 to TH1 Response Induced by Dendritic Cells and Collagen Type 1", J. Allergy Clin. Immunol. 104(5): 1052-58, Nov. 1999.

Breiteneder, et al., "Diversity of Human T Cell Receptor Sequences of T Cell Clones with Specificit Bet v 1 Peptide/MHC II Complexes", Adv Exp Med Biol. 409:365-74, 1996.

Breiteneder, et al., "Four Recombinant Isoforms of Cor a 1, the Major Allergen of Hazel Pollen, Show Different IgE-Bjnding Properties", Europ. J. Biochem. 212:355-362, 1993.

Breiteneder, et al., "Complementary DNA Cloning and Expression in *Escheria coli* of Aln g l, the Major Allergen in Pollen odf alder (*Alnus glutinosa*)," J. Allergy Clin. Immunol., 90: 909-917 (1992).

Briner, et al., "Peripheral T-Cell Tolerance Induced in Naive and Primed Mice by Subcutaneo Injection of Peptides From the Major Cat Allergen Fel D l", Proc. Natl Acad Sci USA , 90(16): 7608-12, Aug. 15, 1993.

Bulone, A., "Separation of Horse Dander Allergen Proteins by Two-Dimensional Electrophoresis Molecular Characterisation and Identification of Equ c 2.0101 and Equ c 2.0102 as Lipocalin Proteins", Eur J. Biochem., 253:202-211, 1998.

Burks, et al., "Allergeicity of Peanut and Soybean Extracts Altered by Chemical or Thermal Denaturation in Patients with Atopic Dermatitis and Positive Food Challenges", J. Allergy Clin Immunol, 90(6 pt 1): 889-97, 1992.

Burks, et al., "Anaphylactic Reactions Following Gammaglibulin Administration in Patients with Hypgammaglobulinema: Detection of IgE antibodies to IgA," N. Eng. J. Med. 314: 560-4, 1986.

Burks, et al., "Antibody Response to Milk Proteins in Patients with Milk-Protein Intolerance Documented by Challenge," J. Allergy Clin. Immunol. 85: 921-7, 1990.

Burks, et al., Épitope Specificity and Immunoaffinity Purification of the Major Peanut Allergen, Ara h l, , J. Allergy Clin Immunol. 93(4): 743-50 (1994).

Burks, et al., "Identification and Characterization of a Second Major Peanut Allergen, Ara h ll, with Use of the Sera of Patients with Atopic Dermatitis and Positive Peanut Challenge," J Allergy Clin Immunol.. 90(6 pt 1):962-9 (1992).

Burks, et al., "Identification of a Second Major Peanut Allergen in Patients with Atopic Dermatitis and Peanut Hypersensivity," J. Allergy Clin. Immunol. 87:211, 1991.

Burks, et al., "Identification of Peanut Agglutinin and Soybean Trypsin Inhibitor as Minor Legume Allergens," Int Arch Allergy Immunol. 105(2): 143-9, 1994.

Burks, et al., "Identification of a Major Peanut Allergen Ara h 1, in Patients with Atopic Dermatitis and Positive Peanut Challenge," J. Allergy Clin. Immunol. 88, 172-179, 1991.

Burks, et al., "Isolation, Identification, and Characterization of Clones Encoding Antigens Responsible for Peanut Hypersensitivity", Int. Arch. Allergy Immunol. 107(1-3): 248-50, May-Jun. 1995.

Burks, et al., "Mapping and Mutational Analysis of the IgE-Binding Epitopes on Ara h 1, a Legume Vicilin Protein and a Major Allergen in Peanut Hypersensitvity", Eur J. Biochem. 245(2): 334-9, Apr. 1997.

Burks, et al., "Modification of a Major Peanut Allergen Leads to Loss of IgE Binding", Int. Arch Allergy Immunol. 118(2-4), 313-4, Feb.-Apr. 1999.

Burks, et al., "Peanut Allergens", Allergy, 53(8): 725-30, Aug. 1998.

Burks, et al., Production of Murine Monoclonal (mAb) Antibodies to Ara H1, A 63.5 kD Allergen in Peanuts, J. Allergy Clin. Immunol. 87: 210, 1991.

Burks, et al., "Recombinant Peanut Allergen Ara h 1 Expression and IgE Binding in Patients with Peanut Hypersensitivity", J. Clin. Invest. 96(4): 1715-21, Oct. 1996.

Butch, et al., "Properties of Human Follicular Dendritic Cells Purified with HJ2, a New Monoclonal Antibody", Cellular Immunology, 155, 27-41 (1994).

Cardaba, et al., "Antibody Response to Olive Pollen Antigens: Association Between HLA Class II Genes and IgE Response to Ole e l" J. Allergy Clin. Immunol. 91:338, 1993.

Chaloin, et al., "Conformations of Primary Amphipathic Carrier Peptides in Membrane Mimicking Environments", Biochemistry, 36: 11179-11187, 1997.

Chapman, et al., "Purification of Allergens," Curr. Opin. Immunol., 1: 647-53, 1989.

Chen, et al., "Allergenic and Antigenic Determinants of Latex Allergen Hev B 1: Peptide Mapping of Epitopes Recognized by Human, Murine and Rabbit Antibodies", Clin Exp Allergy, 26(4): 406-15, Apr. 1996.

Chen, et al., "Isolation and Identification of Hevein as a Major IgE-Binding Polypeptide in Hevea Latex," J. Allergy Clin. Immunol. 99(3): 402-409, 1997.

Cheng, et al., "House Dust Mite-Induced Sensitivity in Mice", Journal of Allergy and Clinical Immunology, 101(1): 51-59, 1998.

Cheng, et al., "House-Dust Mite (HDM) Induced Hypersensitivity in Mice", Faseb Journal, 5(4): 801, 1995.

Cheng, et al., "House-Dust Mite (HDM) Induced Hypersensitivity in Mice", Journal of Allergy and Clinical Immunology, 95(1): 380, 1995.

Christie, et al., "N-Terminal Amino Acid Sequence Identity Between a Major Allergen of *Asacris lumbricoides* and *Ascaris suum*, and MHC-Restricted IgE Responses to it", Immunology, 69:596-602, 1990.

Chua, et al., "Sequence Analysis of cDNA Coding for a Major House Dust Mite Allergen" J. Exp. Med. 167:175-182, 1988.

Chua, et al., "Isolation of cDNA Coding for the Major Mite Allergen Der p ll by IgE Plaque Immunoassay", Int. Arch. Allergy Appl. Immunol. 91:118-123, 1990.

Clarke, et al., "Structure of Mouse Major Urinary Protein Genes: Different Splicing Configurations in the 3'—Non-Coding Region", EMBO J., 3:1045-1052, 1984.

Cockrell, et al., "Monoclonal Antibody Enzyme-Linked Immunosorbent Assay (ELISA) for Ara H 1. A Major Peanut Allergen," J Aller. Clin. Immunol., 89:Abstract 613, 1992.

Colman, "Production of Proteins in the Milk of Transgenic Livestock: Problems, Solutions, and successes," Am J. Clin. Nutr. 63(4): 639S-6455S, 1996.

Colman, A. "Production of Therapeutic Proteins in the Milk of Transgenic Livestock" Biochem. Soc. Symp. 63: 141-147, 1998.

Cooke & Sampson, "Allergenic Properties of Ovomucoid in Man," J. Immunol. 159(4): 2026-32, 1997.

Corbi, et al., "Identification of IgE Binding Polypeptides Cross-Reactive with the *Parietaria judaica* Main Allergenic Polypeptide", Mol Immunol. 23(12): 1357-63, Dec. 1986.

Counsell, et al., "Definition of the Human T-Cell Epitopes of Fel D 1, the Major Allergen of the Domestic Cat", J Allergy Clin Immunol. 98(5 Pt 1): 884-94, Nov. 1996.

Czisch, et al., "Conformations of Peptide Fragments Comprising the Complete Sequence of Component III of Chi t 1 and Their Relationship to T-Cell Stimulation", Biochemistry 33(32): 9420-7, Aug. 1994.

Czuppon, et al., "Allergens, IgE, Mediators, Inflammatory Mechanisms", The Rubber Elongation Factor of Rubber Trees (*Hevea brasiliensis*) is the Major Allergen in Latex, J. Allergy Clin Immunol., 92:690-697, 1993.

Daul, et al., "Identification of the Major Brown Shrimp (*Penaeus aztecus*) Allergen as the Muscle Protein Tropomyosin", Int Arch Allergy Immunol. 105: 49-55, 1994.

Day, "Genetic Modification of Proteins in Food," Critical Reviews in Food Science and Nutrition, 36(S): S49-S67, 1996.

De Palma, et al., "Use of Antagonist Peptides to Inhibit in Vitro T Cell Responses to Par j1, The M Allergen of *Parietaria judaica* Pollen", J. Immunol. 162(4): 1982-7, Feb. 15, 1999.

De Jong, et al., "Food Allergen (Peanut)-Specific TH2 Clones Generated from the Peripheral Blood of a Patient with Peanut Allergy," J Allergy Clin Immunol. 98(1): 73-81, 1996.

Demerec, et al., "A Proposal for a Uniform Nomenclature in Bacterial Genetics", Genetics, 54: 61-75, 1966.

de Groot, "Affinity Purification of a Major and a Minor Allergen from Dog Extract: Serologic Activity of Affinity-Purified Can f 1 and of Can f 1-Depleted Extract" J Allergy Clin. Immunol., 87:1056-1065, 1991.

Demoly, et al., "Anti-IgE Therapy for Asthma," American J. Resp. Crit Care Med. 155: 1825-1827, 1997.

Derossi, et al., "Cell Internalization of the Third Helix of the Antennapedia Homeodomain is Receptor-Independent", The Journal of Biological Chemistry, 271(30): 18188-18193, 1996.

Deuell, et al., "Trichophyton Tonsurans Allergen I, Characterization of a Protein That Causes Immediate But Not Delayed Hypersensitivity" J. Immunol., 147:96-101, 1991.

Dilworth, et al.,"Sequence Analysis of cDNA Coding for a Major House Dust Mite Allergen, Der f 1" Clin. Exp. Allergy, 21:25-32, 1991.

Directions for Use, Pharmacia Diagnostics AB, Uppsala, Sweden 1985 (Revised 1988).

Dolecek, et al., "Molecular Characterization of Phl p. ll, a Major Timothy Grass (*Phleum pratense*) Pollen Allergen", FEBS Letter., 335:299-304, 1993.

Ebner, et al., "Multiple T Cell Specificities for Bet v 1, the Major Birch Pollen Allergen, with Single Individuals. Studies using Specific T Cell Clones and Overlapping Pepti", Eur J Immunol. 23(7): 1523-7, Jul. 1993.

Eichler & Houghten, "Generation and Utilization of Synthetic Combinatorial Libraries," Mol. Med. Today, 1(4): 174-80, 1995.

Eigenmann, et al., "Identification of Unique Peanut and Soy Allergens in Sera Adsorbed with Cross-Reacting Antibodies", J. Allergy Clin Immunol, 98(5 pt 1):969-78, Nov. 1996.

Ekramoddoullah, "Allergenic Cross Reactivity of Cytochrome c From Kentucky Bluegrass and Perennial Ryegrass Pollens".,Moll Immunol. 19: 1527-1534, 1982.

Elfman, et al., "IgE Binding Capacity of Synthetic and Recombinant Peptides of the Major Stor Mite (*Lepidoglyphus destructor*) Allergen, Lep d 2", Int Arch Allergy Immunol. 117(3): 167-73, Nov. 1998.

Elsayed, et al., "A Synthetic Hexadecapeptide Derived from Allergen M Imposing Allergenic Antigenic Reactivity", 12(2): 171-5, 1980.

Elsayed, et al., "Allergenic Synthetic Peptide Corresponding to the Second Calcium-Binding of Cod Allergen M", Scand J Immunol. 14(2): 207-11, Aug. 1981.

Elsayed, et al., "Antigenic and Allergenic Determinants of Ovalbumin. I. Peptide Mapping, Cleavage at the Methionyl Peptide Bonds and Enzymic Hydrolysis of Native A Carboxymethyl OA", Int Arch Allergy Appl Immunol. 79(1): 101-7, 1986.

Elsayed, et al., "Synthetic Allergenic Epitopes from the Amino-Terminal Regions of the Major Allergens of Hazel and Birch Pollen", Int Arch Allergy Appl Immunol. 89: 410-415, 1989.

Elsayed, et al., "Tryptic Cleavage of a Homogenous Cod Fish Allergen and Isolation of Two Ac Polypeptide Fragments" Immunochemistry, 9(6): 647-61, Jun. 1972.

Elsayed, et al., "The Primary Structure of Fragment TM2 of Allergen M from Cod", Scand J. Immunol., 3: 683-686, 1974.

Elsayed, et al., "Cod Fish Allergen Structure", Immunochemistry, 9:647-661, 1972.

Enomoto, et al., "Antibodies Raised Against Peptide Fragments of Bovine Alpha s1-Casein Cross-with the Intact Protein Only When the Peptides Contain Both B and T Cell Determinants", Mol Immunol. 27(6): 581-6, Jun. 1990.

Epton, et al., "High-Molecular-Weight Allergens of the House Dust Mite: An Apolipophorin-Li cDNA has Sequence Identity with the Major M-177 Allergen and the IgE-Bin Peptide Fragments Mag1 and Mag3", Int Arch Allergy Immunol. 120(3): 185-91, Nov. 1999.

Espanion, "Methods of Production and Perspectives for Use of Transgenic Domestic Animals," DTW Dtsch Tierarzti Wochenschr. 103(8-9): 320-8, 1996.

Ezhevsky, et al., "Hypo-Phosphorylation of the Retinoblastoma Protein (pRb) by Cyclin: D:Cdk4/6 Complexes Results in Active pRb", Proc. Natl. Acad. Sci. USA, 94:10699-10704, 1997.
Fahhoum, et al., "Immunologic Variables in a Murine Model of House Dust Mite Sensitivity", Journal of Allergy and Clinical Immunology, 99(1): 676, 1997.
Fahhoum, et al., "Tolerization of House Dust Mite Sensitive Mice Using a Major HDM Peptide", Journal of Allergy and Clinical Immunology, 101(1): 252, 1998.
Fahy, et al., "The Effect of an Anti-IgE Monoclonal Antibody on the Early-and Late-Phase Responses to Allergen Inhalation in Asthmatic Subjects," American J Respir Crit Care Med, 155: 1828-1834, 1997.
Fang, et al., "cDNA Cloning and Primary Structure of a White-Face Hornet Venom Allergen, Antigen 5", Natl. Acad. Sci., USA, 85:895-899, 1988.
Fasler, et al., "Antagonistic Peptides Specifically Inhibit Proliferation, Cytokine Production, CD40L Expression, and Help for IgE Synthesis by Der p 1-Specific Human T-Cell Clones", J Allergy Clin Immunol. 101(4 Pt 1): 521-30, Apr. 1998.
Fasler, et al., "Peptide-Induced Anergy in Allergen-Specific Human Th2 Cells Results in Lack Cytokine Production and B Cell Help for IgE Synthesis. Reversal IL-2, not IL-4 or IL-13", J Immunol. 155(9): 4199-206, Nov. 1, 1995.
Ferreira, et al., "Modulation of IgE reactivity of allergens by Site-Directed Mutagenesis: Potential Use of Hypoallergenic Variants for Immunotherapy", FASEB J, 12: 231-242 (1998).
Fields, et al., "Solid Phase Peptide Synthesis Utilizing 9-Fluorenylmethoxycarbonyl Amino Acids," Int J Pept Protein Res. 35(3): 161-214, 1990.
Fischer, et al., "Characterization of Phl p 4, a Major Timothy Grass (*Phleum pratense*) Pollen Allergen" J. Allergy Clin Immunol. 98: 189-198, 1996.
Fitzsimmons, et al., "Immunotherapy-Definition and Mechanism," Allergy Proc., 11: 156 (1990).
Fuchs, et al., "Ingredients for Fat Replacement," Food Tech. 51: 82-87, 1997.
Fung-Leung, et al., Transgenic Mice Expressing the Human High-Affinity Immonoglobulin (Ig) E Receptor Alpha Chain Respond to Human IgE in Mast Cell Degranualtion and in Allergic Reactions, J. Exp. Med. 183: 49-56 (1996).
Garcia, et al., "Nonspecific Changes in Immunotherapy with House dut extract", J. Invest Alergol. Clin Immunol. 5 18-24 (1995).
Geluk, et al., "HLA-DR3 Molecules can Bind Peptides Carrying Two Alternative Specific Submotifs", J Immunol. 152(12): 5742-8, Jun. 15, 1994.
Ghosh, et al., "Cloning and Expression of Immunologically Active Recombinant Amb a V Allergen of Short Ragweed Pollen", J. Immunol., 150: 5391-5399, 1993.
Gjesing, et al., "Immunochemistry of Food Antigens", Ann. Allergy, 53:602-608, 1984.
Gibbs, et al., "Evolution of Legume See Storage Proteins—a Domain Common to Legumins and Vicilins is Duplicated in Vicilins," Mol. Biol. Evol., 6: 614-623 (1989).
Gieni, et al., Allergen-Specific Modulation of Cytokins Synthesis Patterns and IgE Responses in Vivo with Chemically Modified Allergen, The Journal of Immunol., 150: 302-310 (1993).
Gius, et al., "Transduced p16INK4a Peptides Inhibit Hypophosphorylation of the Retinoblastoma Protein and Cell Cycle Progression Prior to Activation of Cdk2 Complexes in Late G11" Cancer Research, 59:2577-2580, 1999.
Gmachl, et al., "Bee Venom Hyaluronidase is Homologous to a Membrane Protein of Mammalian Sperm", Proc. Natl. Acad. Sci. USA., 90:3569-3573, 1993.
Gonzalez, et al., "Soybean Hydrophobic Protein and Soybean Hull Allergy" Lancet, 346:48-49, 1995.
Goodfriend, et al., "Ra5G, A Homologue of Ras5 in Giant Ragweed Pollen: Isolation, HLA-DR-Associated Activity and Amino Acid Sequence", Mol. Immunol. 22: 899-906, 1985.
Gordon, Future Immunotherapy: What Lies Ahead?, Otolaryngol Head Neck Surg., 113: 603-605 (1995).
Greene, "Characterization of Allergens of the Cat Flea, *Ctenocephalides felis*: Detection and Frequency of IgE Antibodies in Canine Sera," Parasit Immunology, 15: 69-74, 1993.

Greene, et al., IgE and IgG Binding of Peptides Expressed from Fragments of cDNA Encoding the Major House Dust Mite Allergen Der p 1 J Immunol. 147(11): 3768-73, Dec. 1, 1997.
Griffith, et al., "cDNA Cloning of Cry j r, The Major Allergen of *Cryptomeria japonica* (Japanese Cedar)" J. Allergy. Clin. Immunol. 91:339, 1993.
Griffith, et al., Sequence Poymorphisms of Amb a l and Amb a ll, The Major Allergens in *Ambrosia artemisiifolia* (Short Ragweed). Int. Arch. Allergy Appl. Immunol. 96: 296-304, 1991.
Griffith, et al., "Expression and Genomic Structure of the Genes Encoding Fdl, the Major Allergen from the Domestic Cat", Gene, 113: 263-268, 1992.
Griffith, et al., "Cloning and Sequencing of Lol pl, the Major Allergenic Protein of Rye-Grass Pollen", FEBS Letters, 279:210-215, 1991.
Gross, et al., "Isolation and Partial Characterization of the Allergen in Mountain Cedar Pollen", Scand J. Immunol., 8:437-441, 1978.
Guerin-Marchand, et al., "Cloning, Sequencing and Immunological Characterization of Dac g 3, A Major Allergen From *Dactylis glomerata* Pollen", Mol. Immunol. 33:797-806, 1996.
Habermann, E., "Bee and Wasp Venoms", Science, 177:314-322, 1972.
Halliwell, "Aspects of the Immunopathogenisis of Flea Allergy Dermatitis in Dogs," Veterinary Immunology and Immunopathology, 17: 483-494, 1987.
Halliwell, IgE and IgG Antibodies to Flea Antigen in Differing Dog Populations, Veterinary Immunology and Immunopathology, 8: 215-223, 1985.
Halmepuro, et al., "Crawfish and Lobster Allergens: Identification and Structural Similarities with Other Crustacea", Int. Arch Allergy Appl. Immun. 84: 165-72, 1987.
Haselden, et al., "Immunoglobulin E-independent Major Histocompatibility Complex-restricted T Cell Peptide Epitope-induced Late Asthmatic Reactions" J Exp Med. 189(12): 1885-94, Jun. 21, 1999.
Hawrylowicz, et al., "T-Cell Receptor Peptides that Inhibit the T-Cell Response to Allergen Induce Transforming Growth Factor-Beta 1 Production", J Allergy Clin Immunol. 97(2): 707-9, Feb. 1996.
Hefle, et al., "Isolation of Peanut Allergens Using Monoclonal Antibodies," J. Allergy and Clinical Immunology, 87: Abstract, 209, 1991.
Heiner, et al., "RAST Analyses of Peanut Allergens," J. Allergy Clin. Immunol., 55: 82, 1975.
Helm, et al., "A Major Allergen Involved in IgE Mediated Cockroach Hypersensitivity is a 90 kD Protein with Multiple IgE Binding Domains", Adv Exp Med Biol. 409: 267-8, 1996.
Helm, et al., "Cellular and Molecular Characterization of a Major Soybeam Allergen", Int. Arch Allergy Immunol. 117(1), 29-37, Sep. 1998.
Helm, et al., "Isolation and Characterization of Clones Encoding Cockroach Allergens", Int. Arch Allergy Immunol. 107(1-3): 462-3, May-Jun. 1995.
Helm, et al., "Isolation and Characterization of a Clone Encoding a Major Allergen (Bla g Bd90K) Involved in IgE-Mediated Cockroach Hypersensitivity", J Allergy Clin Immunol. 98(1): 172-80, Jul. 1996.
Helm, et al., "Mutational Analysis of the IgE-binding Epitopes of P34/Gly m Bd 30K", J Allergy Clin. Immunol. 105(2): 378-84, Jan. 2000.
Higgins, et al., "Overlapping T-Cell Epitopes in the Group I Allergen of *Dermatophagoides* sp Restricted by HLA-DP and HLA-DR Class II Molecules", J Allergy Clin Immunol. 93(5): 891-9, May, 1994.
Herian, et al., "Identification of Soybean Allergens by Immunoblotting with Sera from Soy-Allergic Adults," Int. Arch. Allergy Appl. Immunol. 92: 193-198, 1990.
Hetzel, et al., "Peptide-Mediated Immunoregulation", Int Arch Allergy Immunol. 107:(1-3): 275-7, May-Jun. 1995.
Higgins, et al., "Peptide-Induced Nonresponsiveness of HLA-DP Restricted Human T Cells rea with *Dermatophagoides* spp", J Allergy Clin Immunol. 90(5): 749-56, Nov. 1992.
Hirahara, et al., "Oral Administration of A Dominant T-Cell Determinant Peptide Inhibits Allergen-Specific TH1 and TH2 Cell Responses in Cry J 2-Primed Mice", J Allergy Clin Immunol. 102(6 Pt 1): 961-7, Dec. 1998.

Ho, et al., "Comparison of the Immunogenicity of Wasp Venom Peptides With or Without Carbohydrate Moieties", Toxicon. 36(1): 217-21, Jan. 1998.

Hoffman, et al., "Allergens in Hymenoptera Venom XXV: The Amino Acid Sequences of Antigen 5 Molecules and the Structural Basis of Antigenic Cross-Reactivity", J. Allergy Clin. Immunol., 92:707-716, 1993.

Hoffman, et al., "Allergens in Hymenoptera Venom XXIV: The Amino Acid Sequences of Imported Fire Ant Venom Allergens Sol i II, Sol i III, and Sol i IV" J. Allergy Clin. Immunol., 91:71-78, 1993.

Hoffman, D.R., "Immunochemical Identification of the Allergens in Egg White", J. Allergy Clin. Immunol. 71:481-486, 1983.

Hong, et al., "Pepsin-Digested Peanut Contains T-Cell Epitopes But no IgE Epitopes", J. Allergy Clin. Immunol. 104: 473-7, 1999.

Homer, et al., "Identification of the Allergen Psi c 2 from the Basidiomycete *Psilocybe cubensis* as a Fungal Cyclophilin", Int. Arch. Allergy Immunol., 107:298-300, 1995.

Hoyne, et al., "Inhibition of T-Cell Responses by Feeding Peptides Containing Major and Cryp Epitopes: Studies with the Der p l Allergen", Immunology 83(2): 190-5, Oct. 1994.

Hoyne, et al., "Peptide Modulation of Allergen-Specific Immune Responses", Curr Opin Immunol. 7(6): 757-61, Dec. 1995.

Hsu, et al., "Inhibitition of Specific IgE Response in Vivo by Allergen-Gene Transfer," Int. Immunol. 8:1405-1411, 1996.

Jacobson, et al., "Characterization of Bumblebee Venom Allergens" J. Allergy Clin. Immunol. 91:187, 1993.

Jacobson, et al., "The Cross-Reactivity Between Bee and Vespid Hyaluronidases has a Structural Basis" J. Allergy Clin. Immunol., 89:292, 1992.

James, et al., "Wheat ?-Amylase Inhibitor: A Second Route of Allergic Sensitization", J Allergy Clin Immunol. 99(2): Feb. 1997.

Jeannin, et al., "Immunogenicity and Antigenicity of Synthetic Peptides Derived from the Mite Allergen Der p l", Mol Immunol. 30(16): 1511-8, Nov. 1993.

Jameson, et al., "The Antigenic Index: A Novel Algorithm for Predicting Antigenic Determinants," Comput. Appl. Bioscil, 4: 181-186 (1988).

Jansen, et al., "Prevalance of Food Allergy and Intolerance in the Adult Dutch Population," J. Allergy Clin. Immunol., 93: 446-456 (1994).

Jensen-Jarolim, et al., "Nonapeptides Selected by Phage Display Mimic the Binding Sites of Monoclonal Antibodies BIP1 and BIP4 on Bet v 1, The Major Birch Pollen Allergen", Int Arch Allergy Immunol. 118(2-4): 224-5, Feb.-Apr. 1999.

Jarman, et al., "Inhibition of Human T-Cell Responses to House Dust Mite Allergens by a T-Cell Receptor Peptide", J Allergy Clin Immunol. 94(5): 844-52, Nov. 1994.

Jeannin, et al., "Specific Histamine Release Capacity of Peptides Selected from the Modelized Der p l Protein, a Major Allergen of *Dermatophagoides pteronyssinus*", Mol Immunol. 29(6): 739-49, Jun. 1992.

Jensen-Jarolim, et al., "Allergen Mimotopes in Food Enhance Type I Allergic Reactions in Mice", The FASEB Journal, 13: 1586-92, Sep. 1999.

Jensen-Jarolim, et al., "Peptide Mimitopes Displayed by Phage Inhibit Antibody Binding to Bet v 1, the Major Birch Pollen Allergen, and Induce Specific IgG Response in Mice", FASEB J. 12(15): 1635-42, Dec. 1998.

Jimenez, et al., Sensitization to Sunflower Pollen: Only an Occupational Allergy? Int. Arch Allergy Immunol. 105:297-307, 1994.

Jusko, "Cortiocosteroid Pharmacodynamics: Models for Broad Array of Receptor-mediate Pharmacologic Effects," Clin. Pharmacol, 30: 303-10, 1990.

Kaminogawa, "Food Allergy, Oral Tolerance and Immunomodulation—Their Molecular and Cellular Mechanisms," Biosci. Biotech, Biochem. 60: 1749-1756, 1996.

Kammerer, et al/. "Modulation of T-Cell Response to Phospholipase A2 and Phospholipase A2-Derived Peptides by Conventional Bee Venom Immunotherapy", J Allergy Clin Immunol. 100(1): 96-103, Jul. 1997.

Kapitany, et al., "A High Resolution PAS Stain for Polyacrylamide Gel Electrophoresis," Anal. Biochem., 56: 361-9, 1973.

Keating, et al. "Immunoassay of Peanut Allergens in Food-Processing Materials and Finished Foods," J. Allergy Clin. Immunol. 86: 41-44, 1990.

Kettner, et al., "IgE and T-Cell Responses to High-Molecular Weight Allergens from Bee Venom", Clin. Exp. Allergy, 29(3): 394-401, Mar. 1999.

KielisZewski, et al. "Potato Lectin: A Modular Protein Sharing Sequence Similarities with the Extensin Family, the Hevein Lectin Family, and Snake Venom Disintegrins (Platelet Aggregation Inhbitiors)," Plant J. 5(6): 849-861, 1994.

Kim, et al., "Suppressive Vaccination at Allergen-Induced Immunoglobulin E Production by the Naked DNA Vaccine", Journal of Investigative Medicine, 46(3): A243, 1998.

Kim, et al., "Suppressive Vaccination of Allergen-Induced Immunoglobulin E Production by the Naked DNA Vaccine" Faseb Journal, 12(5): 6148, 1998.

King, et al., "Isolation and Characterization of Allergen from Ragweed Pollen" Biochemistry, 3: 458-468, 1964.

Kohler, et al., "Continuous Cultures of Fused Cells Secreting Antibody of Predefined Specificity," Nature, 256: 495-497, 1975.

King, et al., "The Isolation and Characterization of a Novel Collagenolytic Serine Protease Allergen (Der p 9) from the Dust Mite *Dermatophagoides pteronyssinus*", J. Allergy Clin Immunol., 98:739-747, 1996.

King, et al., "Structural Studies of a Hornet Venom Allergen Antigen 5, Dol m V and its Sequence Similarity with Other Proteins" Prot. Seq. Data Anal., 3:263-266, 1990.

King, et al., "Yellow Jacket Venom Allergens, Hyaluronidase and Phospholipase: Sequence Similarity and Antigenic Cross-Reactivity with Their Hornet and Wasp Homologs and Possible Implications for Clinical Allergy" Allergy Clin. Immunol., 98:588-600, 1996.

Klapper, et al., "Amino Acid Sequence of Ragweed Allergen Ra3", Biochemistry, 19: 5729-5734, 1980.

Klysner, et al., "Group V Allergens in Grass Pollens: IV. Similarities in Amino Acid Compositions and NH2- Terminal Sequences of the Group V Allergens from *Lolium perenne, Poa pratensis* and *Dactylis glomerata*", Clin. Exp. Allergy, 22:491-497, 1992.

Kwon, et al., "The Effect of the Intradermal Vaccination with DNA Encoding the T-Cell Receptor on the Induction of Experimental Autoimmune Encephalomyelitis in Mice", Journal of Allergy and Clinical Immunology, 103: 76, 1999.

Kricek, et al., "IgE-Related Peptide Mimotopes, Basic Structures for Anti-Allergy Vaccine Development", Int Arch Allergy Immunol. 118 (2-4): 222-3, Feb.-Apr. 1999.

Krieg, et al., "CpG Motifs in Bacterial DNA Trigger Direct B-Cell Activation," Nature, 374(6522): 546-9, 1995.

Kuchler, et al., "Analysis of the cDNA for Phospholipase A2 from Honeybee Venom Glands; The Deduced Amino Acid Sequence Reveals Homology to the Corresponding Vertebrate Enzymes", Eur. J. Biochem., 184:249-254, 1989.

Kumar, et al., "Isolation and Characterization of a Recombinant Heat Shock Protein of *Aspergillus fumigatus*", J. Allergy Clin. Immunol., 91:1024-1030, 1993.

Kurup, et al., "Immunodominant Peptide Epitopes of Allergen, Asp F 1 from the Fungus *Aspergillus fumigatus*", Peptides, 19(9): 1469-77, 1998.

Kwon, et al., "Immunoprotective Effect of Vaccination with DNA Encoding T Cell Epitopes on the Der p Induced IgE Production" Journal of Allergy and Clinical Immunology, 103: 418, 1999.

Lacroix, et al., "Attenuation of Allergen-Evoked Nasal Responses by Local Pretreatment with Exogenous Neuropeptide Y in Atopic Patients", J Allergy Clin Immunol. 98(3):611-6, Sep. 1996.

Lake, et al., "House Dust Mite-Derived Amylase: Allergenicity and Physicochemical Characterization", J. Allergy Clin. Immunol. 87:1035-1042, 1991.

Langeland, T., "A Clinical and Immunological Study of Allergy to Hen's Egg White", Allergy, 38:493-500, 1983.

Laperche, et al., "Tissue-Specific Control of a2u Globulin Gene Expression: Constitutive Synthesis in the Submaxillary Gland" Cell, 32:453-460, 1983.

Larsen, et al., "PCR Based Cloning and Sequencing of Isogenes Encoding the Tree Pollen Major Allergen Car b 1 from *Carpinus betulus*, Hornbeam", Mol. Immunol. 29: 703-711, 1992.

Lehrer, et al., "Reactivity of IgE Antibodies with Crustacea and Oyster Allergens: Evidence for Common Antigenic Structures", J Allergy Clin. Immunol. 80(2): 133-39, Aug. 1987.

Lemanske & Taylor, "Standardized Extracts, Foods," Clin. Rev. Allergy, 5: 23-26, 1987.

Leung, et al., "Identification and Molecular Characterization of *Charybdis feriatus* Tropomyosin, The Major Crab Allergen", J. Allergy Clin Immunol. 847-852, Nov. 1998.

Leung, et al., "IgE Reactivity Against a Cross-Reactive Allergen in Crustacea and Mollusca: Evidence for Tropomyosin as the Common Allergen", J. Allergy Clin Immunol. 98(5), 954-961, Nov. 1996.

Liebers, et al., "Epitope Mapping with Peptides of Chi t 1 Component III and Immunomodula of the Chi t Immune Response", J Allergy Clin Immunol. 92(2): 334-9, Aug. 1993.

Lind, et al., "The Binding of Mouse Hybridoma and Human IgE Antibodies to the Major Fecal Allergen, Der p 1, of *Dermatophagoides pteronyssinus*, Relative Binding Site Location and Species Specificity Studied by Solid-Phase Inhibition Assays with Radiolabeled Antigen", J. Immunol., 140:4256-4262, 1988.

Marsh, et al., "Allergen Nomenclature", Bull WHO 64: 767-770, 1986.

Litwin, et al., "Regulation of the Human Immune Response to Ragweed Pollen by Immunotherapy. A Controlled Trial Comparing the Effect of Immunosuppressive Peptic Fragments of Short Ragweed with Standard Treatment", Clin Exp. Allergy. 21(4): 457-65, Jul. 1991.

Litwin, et al., "Regulation of the Immune Response to Allergens by Immunosuppressive Allergenic Fragments, Peptic Framents of Honey Bee Venom Phospholipase", Int Arch Allergy Appl Immunol. 87(4): 361-6, 1988.

Lopata, et al., "Characteristics of Hypersensitivity Reactions and Identification of a Unique 49 kd IgE-Binding Protein (Hal-m-1) in Abalone (*Haliotis midae*)" J. Allergy Clin. Immunol. , 1997.

Lowenstein, H., "Timothy Pollen Allergens" Allergy: 35: 188-191, 1980.

Lu, et al., "Sequence Analysis and Antigenic Cross-Reactivity of a Venom Allergen, Antigen 5, From Hornets, Wasps, and Yellow Jackets" The Journal of Immunology, 150:2823-2830, 1993.

Maguire, et al., "The Safety and Efficacy of Allervax Cat in Cat Allergic Patients" Clin Immunol. 93(3): 222-31, Dec. 1999.

Metcalfe, "Food Allergens," Clin Rev Allergy, 3:331-49, 1985.

Marcotte, et al., "Effects of Peptide Therapy on Ex Vivo T-Cell Responses", J Allergy Clin Immunol. 101(4 Pt 1): 506-13, Apr. 1998.

Mathison, et al., "A Peptide from the Submandibular Glands Modulates Inflammatory Responses", Int Arch Allergy Immunol. 113 (1-3): 337-8, May-Jul. 1997.

Miyazawa, et al., "Identification of the First Major Allergen of a Squid (*Todarodes pacificus*)", J. Allergy Clin. Immunol., 98:948-953, 1996.

Matsuoka, et al., "Altered TCR Ligands Affect Antigen-Presenting Cell Responses: Up-Regulation IL-12 by an Analogue Peptide", J Immunol. 157(11): 4837-43, Dec. 1996.

McKeon, "IgG and IgE Antibodies Against Antigens of the Cat Flea, *Ctenocephalides felis Felis* in Sera of Allergic and Non-Allergic Dogs," Int. J. Parasitology, 24(2): 259-263, 1994.

Mecheri, et al., "Purification and Characterization of a Major Allergen from *Dactylis glomerata* Pollen: The Ag Dg1", Int. Arch. Allergy Appl. Immunol., 78:283-289.

Mena, et al., "A Major Barley Allergen Associated with Baker's Asthma Disease is a Glycosylated Monomeric Inhibitor o f Insect a-Amylase: cDNA Cloning and Chromosomal Location of the Gene", Plant Molec. Biol. 20:451-458, 1992.

Menedez-Arias, et al., "Primary Structure of the Major Allergen of Yellow Mustard (*Sinapis alba* L.) Seed, Sin ? I" Eur. J. Biochem., 177:159-166, 1988.

Metzler, et al., "Determination of the Three-Dimensional Solution Structure of Ragweed Allergen Amb t V by Nuclear Magnetic Resonance Spectroscopy". Biochemistry, 31: 5117-5127, 1992.

Metzler, et al., "Proton Resonance Assignments and Three-Dimensional Solution Structure of the Ragweed Allergen Amb a V by Nuclear Magnetic Resonance Spectroscopy" Biochemistry, 31: 8697-8705, 1992.

Miller, et al., "Allergy to Bovine Beta-Lactoglobulin: Specificity of Immunoglobulin E Gener in the Brown Norway Rat to Tryptic and Synthetic Peptides", Clin. Exp. Allergy, 29(12): 1696-704, Dec. 1999.

Mohapatra, SS, "Modulation of Allergen-Specific Antibody Responses by T-Cell-Based Peptide Vaccine(s). Principles and Potential", Clin Rev Allergy. 12(1): 3-22, Spring, 1994.

Moneret-Vautrin, "Modifications of Allergenicity Linked to Food Technologies," Allerg Immunol, 30(1): 9-13, 1998.

Monsalve, et al., "Characterization of a New Oriental-Mustard (*Brassica juncea*) Allergen, Bra j IE: Detection of an Allergenic Epitope" Biochem. J., 293:625-632, 1993.

Morgenstern, et al., "Amino Acid Sequence of Fel d 1, the Major Allergen of the Domestic Cat: Protein Sequence Analysis and cDNA Cloning" Proc. Natl. Acad. Sci. USA, 88: 9690-9694, 1991.

Muckerheide, et al., "Immunosuppressive Properties of a Peptic Fragment of BSA", The Journal of Immunology, 119(4): 1340-45, Oct. 1977.

Muckerheide, et al., "Kinetics of Immunosuppression Induced by Peptic Fragments of Bovine Serum Albumin", Cellular Immunology, 50, 340-47, 1980.

Muller, et al., "Successful Immunotherapy with T-Cell Epitope Peptides of Bee Venom Phospholipase A2 Induces Specific T-Cell Anergy in Patients Allergic to Bee Venom" J Allergy Clin Immunol. 101(6 Pt 1): 747-54, Jun. 1998.

Nagahara, et al., "Transduction of Full-Length TAT Fusion Proteins into Mammalian Cells: TAT-p27Kip1 Induces Cell Migration", Nature Medicine, 4(12): 1449-1452, 1998.

Nair, Smita et al., Soluble Proteins Delivered to Dendritic Cells Via pH-sensitive Liposomes Induce Primary Cytotoxic T Lymphocyte Responses In Vitro, J. Exp. Med., 175 Feb. 1992 609-612.

Nelson, et al., "Treatment of Anaphylactic Sensitivity to Peanuts by Immunotherapy with Injections of Aqueous Peanut Extract," J. Allergy Clin. Immunol. 99: 744-751, 1997.

Nicodemus, et al., "Integrated Clinical Experience with Tolerogenic Peptides", Int Arch Allergy Immunol. 113:(1-3): 326-8, May-Jul. 1997.

Nishiyama, et al., "Determination of Three Disulfide Bonds in a Major House Dust Mite Allergen, Der f ll", Int. Arch. Allergy Immunol., 101:159-166, 1993.

Noon, "Prophylactic Inoculatio Against Hay Fever," Lancet, 1: 1572-73, 1911.

Nordlee, et al., "Allergenicity of Various Peanut Products as Determined by RAST Inhibition," J. Allergy Clin. Immunol. 68: 376-82, 1981.

Norman, et al., "Clinical and Immunologic Effects of Component Peptides in Allervax Cat", Int Arch Allergy Immunol. 113(1-3): 224-6, May-Jul. 1997.

Norman, et al., "Multicenter Study of Several Doses of ALLERVAX® Cat Peptides in the Treatment of Cat Allergy," Journal of Allergy and Clinical Immunology, 99: S127, 1997.

Norman, et al., "Treatment of Cat Allergy with T-Cell Reactive Peptides" Am J Respir Crit Care Med. 154(6 Pt 1): 1623-8, Dec. 1996.

Obispo, et al., "The Main Allergen of *Olea europaea* (Ole e 1) is Also Present in other Species of the Oleaceae Family", Clin. Exp. Allergy, 23:311-316, 1993.

O'Brien, et al., "An Immunogenetic Analysis of T-Cell Reactive Regions on the Major Allergen from the House Dust Mite, Der p 1, with Recombinant Truncated Fragments", J Allergy Clin Immunol. 93(3): 628-34, Mar. 1994.

O'Farrell, "High Resolution Two-Dimensional Electrophoresis of Proteins," J. Biol. Chem. 250: 4007-21, 1975.

O'Hehir, et al., "House Dust Mite Allergy: From T-Cell Epitopes to Immunotherapy", Eur J Clin Invest. 23(12): 763-72, Dec. 1993.

O'Hehir, et al., An In Vitro Model of Peptide-Mediated Immunomodulation of the Human T c Response to *Dermatophagoides* spp (House Dust Mite) J Allergy Clin Immunol. 87(6): 1120-7, Jun. 1991.

Phadebas Rast Radioimmunoassay Reagents for 100 or 300 Tubes, Pharmacia Diagnostics AB, Uppsala Sweden 1985, Revised Jan. 1988.

O'Neil, et al., "Cloning and Characterization of a Major Allergen of the House Dust Mite, *Dermatophagoides pteronyssinus*, Homologous with Glutathione S-Transferase", Biochimica et Biophysica Acta, 1219:521-528, 1994.

Oppenheimer, et al., "Treatment of Peanut Allergy with Rush Immunotherapy", J Allergy Clin Immunol. 90: 256-62, 1992.

Park, et al., "Pediatric IgE Anibody binding to the Most Common Seafood Proteins in Korea", Journal of Allergy and Clinical Immunology, 101(1): 377, 1998.

Pecquet, et al., "Immunoglobulin E Suppression and Cytokine Modulation in Mice Orally Tolerized to ?-Lactoglobulin", Immunology, 96, 278-85, 1999.

Pene, et al., "Immunotherapy with Fel D 1 Peptides Decreases IL-4 Release by Peripheral Blood T Cells of Patients Allergic to Cats", 102: (4 Pt 1): 571-8, Oct. 1998.

Perez, et al., "cDNA Cloning and Immunological Characterization of the Rye Grass Allergen Lol p l" J. Biol. Chem. 265:16210-16215, 1990.

Pesce, et al., "Modulation of the Immune Response to Allergens: Phospholipase A Degradation Products Suppress IgG and IgE Response in Mice", Int Arch Allergy Appl Immunol, 92, 88-93, 1990.

Roberts, et al., "Nucleotide Sequence of cDNA Encoding the Group II Allergen of Cocksfoot/Orchard Grass (*Dactylis glomerata*), Dac g ll", Allergy, 48:615-623, 1993.

Pisetsky, "Immune Activation by Bacterial DNA: A New Genetic Code," Immunity, 5(4): 303-10, 1996.

Pollart, et al., "Identification, Quantitation, and Purification of Cockroach Allergens using Monoclonal Antibodies," J. Allergy Clin. Immunol., 87: 511-521, 1991.

Posch, et al., "Characterization and Identification of Latex Allergens by Two-Dimensional Electrophoresis and Protein Microsequencing," J. Allergy Clin. Immunol, 99(3): 385-395, 1997.

Pucheu-Haston, "Allergenic Cross-Reactivities in Flea-Reactive Canine Serum Samples," AJVR 57(7): 1000-1005, 1996.

Rolfsen, "Detection of Specific IgE Antibodies Towards Cat Flea (*Ctenocephalides felis Felis*) in Patients with Suspected Cat Allergy," Allergy, 42: 177-181 (1987).

Rabjohn, et al., "Molecular Cloning and Epitope Analysis of the Peanut Allergen Ara h 3", J. Clin. Invest. 103(4), 535-42, Feb. 1999.

Rooney, et al., "Antiparallel, Intramolecular Triplex DNA Stimulates Homologous Recombination in Human Cells," Proc. Natl. Acad. Sci. USA, 92: 2141-2144, 1995.

Rafner, et al., "Cloning of Amb a l (Antigen E), the Major Allergens Family of Short Ragweed Pollen", J. Biol. Chem. 266: 1229-1236, 1991.

Raz, et al., "Intradermal Gene Immunization: The Possible role of DNA Uptake in the Induction of Cellular Immunity to Viruses," Proc Nat Acad Sci USA, 91:9519-9523, 1994.

Reese, et al., "Characterization of Recombinant Shrimp Allergen Pen a 1 (Tropomyosin)", Int Arch Allergy Immunol, 113: 240-242, 1997.

Remy, et al., "Topical Peptides: Percutaneous Absorption of a Vasopressin Derivate, Grass Pollen, and Other Allergens by Iontophoresis in Men", J Invest Dermatol. 91(6): 606, Dec. 1988.

Roebber, et al., "Immunochemical and Genetic Studies of Amb t V (Ra5G), an Ra5 Homologue from Giant Ragweed Pollen", J. Immunol. 134: 3062-3069, 1985.

Roebber, et al., "Isolation and Characterization of Allergen Amb a Vll from Short Ragweed Pollen", J. Allergy Clin. Immunol. 87: 324, 1991.

Rogers, et al., "Potential Therapeutic Recombinant Proteins Comprised of Peptides Containing Recombined T Cell Epitopes", Mol Immunol. 31(13): 955-66, Sep. 1994.

Rogers, et al., "Complete Sequence of the Allergen Amb a ll: Recombinant Expression and Reactivity with T Cells from Ragweed Allergic Patients", J. Immunol. 147: 2547-2552, 1991.

Rolland, et al., "Immunotherapy of Allergy: Anergy, Deletion, and Immune-Deviation", Current Opinion in Immunology, 10: 640-45, 1998.

Sachs, et al., "Isolation and Partial Characterization of a Major Peanut Allergen," J. Allergy Clin. Immunol. 67: 27-34, 1981.

Sakaguchi, et al., "Identification of the Second Major Allergen of Japanese Cedar Pollen", Allergy, 45:309-312, 1990.

Sampson, "Peanut Anaphylaxis," J Allergy Clin Immunol., 86: 1-3, 1990.

Sampson, "Role of Immediate Food Hypersensitivity in the Pathogenesis of Atopic Dematitis," J. Allergy Clin. Immunol. 71: 473-80, 1993.

Sampson, et al., "Fatal and Near-Fatal Anaphylactic Reactions to Food in Children and Adolescents", The New England Journal of Medicine, 327(6): 380-84, Aug. 1992.

Sampson, et al., "Food Allergy and the Role of Immunotherapy," J Allergy Clin. Immun, 90:151-52, 1992.

Sampson, et al., "Mechanisms of Food Allergy," Annu. Rev. Nutr, 16: 161-77, 1996.

Reisman, "Fifteen yeas of hymenoptera Venom Immunotherapy," J. Allergy Clin Immunol., 90: 256-62 (1992).

Scheiner, "Recombinant Allergens: Biological, Immunological and Practical Aspects," Int. Arch. Allergy Immunol., 98: 93-96 (1992).

Schemmer, "Efficacy of Alum-Precipitated Flea Antigen for Hyposensitization of Flea-Allergic Dogs," Seminars in Veterinary Medicine and Surgery (Small Animal), 2(3): 195-198, 1987.

Schmidt, et al., "cDNA Analysis of the Mite Allergen Lep d 1 Identifies Two Different Isoallergens and Variants", FEBS Letter, 370:11-14, 1995.

Schmidt, et al., "The Complete cDNA Sequence and Expression of the First Major Allergenic Protein of *Malassezia furfur*, Mal f 1", Eur J. Biochem., 246:181-185, 1997.

Schmidt, et al., "Nucleotide Sequence of cDNA Encoding the Fire Ant Venom Protein Sol i ll", FEBS Letter, 319:138-140, 1993.

Sidoli, et al., "Cloning, Expression, and Immunological Characterization of Recombinant *Lolium-perenne* Allergen Lol p ll", J. Biol Chem., 268:21819-21825, 1993.

Secrist, et al., "Allergen Immunotherapy Decreases Interleuken 4 Production in CD4+ T Cells From Allergic Individuals," J. Exp. Med. 178 2123-2130 (1993).

Sehra, et al., "Role of Liposomes in Selective Proliferation of Splenic Lymphocytes" Molecular and Cellular Biochemistry, 183: 133-139, 1998.

Smith, et al., "Cloning and Expression in Yeast *Pichia pastoris* of a Biologically Active Form of Cyn d 1, the Major Allergen of Bermuda Grass Pollen", J. Allergy Clin. Immunol. 98:331-343, 1996.

Sevier, et al., "Monoclonal Antibodies in Clinical Immunology," Clin. Chem. 27(11): 1797-1806, 1981.

Shanti, et al., "Identification of Tropomyosin as the Major Shrimp Allergen and Characterization of its IgE-Binding Epitopes: ," J. Immunol, 151: 5354-5363, 1993.

Sharif, et al., "Biodegradable microparticles as a delivery system for the allergens of *Dermatophagoides pteronyssinus* (house dust mite): I. Preparation and characterization of microparticles", International Journal of Pharmaceutics, 119 1995) 239-246.

Shen, et al., "Molecular Cloning of a House Dust Mite Allergen with Common Antibody Binding Specificities with Multiple Components in Mite Extracts'", Clin. Exp. Allergy, 23: 934-940, 1993.

Shen, et al., "Studies on Allergens of *Aspergillus flavus*", J. Allergy Clin. Immunol., 103:S157, 1999.

Shen, et al., "Allergenic Components in Three Different Species of *Penicillium*: Crossreactivity Among Major Allergens" Clin. Exp. Allergy, 26:444-451, 1996.

Shen, et al., "Molecular Cloning of cDNA Coding for the 68 kDa Allergen of *Penicillium notatum* Using MoAbs", Clin Exp. Allergy, 25:350-356, 1995.

Shen, et al., "The 40-Kilodalton Allergen of *Candida albicans* is an Alcohol Dehydrogenase: Molecular Cloning and Immunological Analysis Using Monoclonal Antibodies", Clin Exp. Allergy, 21:675-681, 1991.

Shin, et al., "Biochemical and Structural Analysis of the IgE Binding Sites on Ara h 1, An Abundant and Highly Allergenic Peanut Protein", J. Biol. Chem. 273(22): 13753-9, May, 1998.

Stanworth, et al., "Nomenclature for Synthetic Peptides Respresentative of Immunoglobulin Chain Sequences", Bulletin WHO, 68: 109-111, 1990.

Steinberger, et al., "Construction of a Combinatorial IgE Library from an Allergic Patient. Isolation and Characterization of Human IgE Fabs with Specificity for the Major Timothy Grass Pollen Allergen, Phl p 5", J. Biol. Chem. 271: 10967-10982, 1996.

Sunderasan, et al., "Latex B-Serum -1,3-Glucanase (Hev b II) and a Component of the Microhelix (Hev b IV) are Major Latex Allergens" J. Nat Rubb Res.,10:82-99, 1995.

Simons, et al., "Fel D 1 Peptides: Effect on Skin Tests and Cytokine Synthesis in Cat-Allergic Human Subjects", Int Immunol. 8(12): 1937-45, Dec. 1996.

Singh, et al., "Isolation of cDNA Encoding a Newly Identified—Major Allergenic P, rotein of Rye-Grass Pollen: Intracellular Targeting to the Amyloplast", Proc. Natl. Acad. Sci., 88:1384-1388, 1991.

Smith, et al., "Comparative Analysis of the Genes Encoding Group 3 Allergens from *Dermatophagoides pteronyssinus* and *Dermatophagoides farinae*", Int Arch Allergy Immunol., 109:133-140, 1996.

Soldatova, et al., "Sequence Similarity of a Hornet (*D. maculata*) Venom Allergen Phospholipase A1 with Mammalian Lipases", FEBS Letters, 320:145-149, 1993.

Sone, et al., "T Cell Epitopes in a Japanese Cedar (*Cryptomeria japonica*) Pollen Allergens: Choice of Major T Cell Epitopes in Cry j 1 and Cry j 2 Toward Design of the Peptide-Immunotherapeutics for the Management of Japanese Cedar Pollinosis", J. Immunol. 161(1): 448-57, Jul. 1, 1998.

Sparholt, et al., The Allergen Specific B-Cell Response During Immunotherapy. Clinical and Experimental Allergy, 22: 648-653 (1992).

Stadler, et al., "Mimotope and Anti-Idiotypic Vaccines to Induce an Anti-IgE Response", Int Arch Allergy Immunol. 118(2-4): 119-21, Feb.-Apr. 1999.

Stanley, et al., "Biochemistry of Food Allergens", Clin Rev. Allergy Immunol. 17(3): 279-91, 1999.

Stanley, et al., "Identification and Mutational Analysis of the Immunodominant IgE Binding Epitopes of the Major Peanut Allergen Ara h 2", Arch Biochem Biophys. 342(2): 244-53, Jun. 1997.

Stanley, et al., "Peanut Hypersensitivity. IgE Binding Characterictics of a Recombinant Ara h 1 Protein", Adv. Exp Med. Biol. 409: 213-6, 1996.

Teshima, et al., "Isolation and Characterization of a Major Allergenic Component (gp55) of *Aspergillus fumigatus*", J. Allergy Clin. Immunol. 92:698-706, 1993.

Texier, et al., "HLA-DR Restricted Peptide Candidates for Bee Venom Immunotherapy", J. Immunol,. 164(6): 3177-84, Mar. 15, 2000.

Thomas, et al., "Purification of Membrane Proteins," Meth. Enzymol., 182:499-520, 1990.

Stanworth, et al., "Allergy Treatment with a Peptide Vaccine", Lancet. 336(8726): 1279-81, Nov. 24, 1990.

Sunderasan, et al., "Latex B-Serum b-1,3-Glucanase (Hey b II) and a Component of the Microhelix (Hev b IV) are Major Latex Allergens" J. Nat Rubb Res.,10:82-99, 1995.

Suphioglu, et al., "Peptide Mapping Analysis of Group I Allergens of Grass Pollens", Int Arch Allergy Immunol. 102(2): 144-51, 1993.

Suphioglu, et al., "Molecular Cloning and Immunological Characterisation of Cyn D 7, A Novel Calcium-Binding Allergen from Bermuda Grass Pollen", FEBS Letter. 402:167-172, 1997.

Suphioglu, et al., "Cloning, Sequencing and Expression in *Escherichia coli* of Pha a 1 and Four Isoforms of Pha a 5, The Major Allergens of Canary Grass Pollen", Clin. Exp. Allergy, 25:853-865, 1995.

Sutton, et al., "Detection of IgE and IgG Binding Proteins After Electrophoresis Transfer From Polyacrylamide Gels", Journal of Immunological Methods, 52:183-86, 1982.

Svirshchevskaya, et al., "Intravenous Injection of Major and Cryptic Peptide Epitopes of Ribotoxin, Asp F1 Inhibits T Cell Response Induced by Crude *Aspergillus fumigatus* Antigens in Mice", 21(1): 1-8, Jan. 1, 2000.

Sward-Nordmo, et al., The Glycoprotein Allergen Ag-54 (Cla h ll) From *Cladosporium herbarum*", Structural Studies of the Carbohydrate Moiety", Int. Arch. Allergy Appl. Immunol., 85:288-294, 1988.

Szostak, "In Vitro Genetics", TIBS, 19:89, 1992.

Takai, et al., "Engineering of the Major House Dust Mite Allergen Der f 2 for Allergen-specific Immunotherapy," Nature Biotechnology, 15:754-58 (1997).

Takashi, et al., "Engineering of Hypoallergenic Mutants of the *Brassica* Pollen Allergen, Bra r 1, for Immunotherapy," FEBS Letters, 434: 255-260 (1998).

Taniai, et al., N-Terminal Amino Acid Sequence of a Major Allergen of Japanese Cedar Pollen (Cry j 1) FEBS Letter, 239:329-332, 1988.

Taylor, et al., "Peanut Oil is Not Allergenic to Peanut Sensitive Individuals", J. Allergy Clin. Immunol., 68: 372-375 (1981).

Taylor, et al., "Evidence for the Ecistence of Multiple Allergens in Peanuts," J. Allergy Clin. Immunol. 69:128, 1982.

Tovey, et al., "Cloning and Sequencing of a cDNA Expressing a Recombinant House Dust Mite Protein that Binds Human IgE and Corresponds to an Important Low Molecular Weight Allergen", J. Exp. Med. 170:1457-1462, 1989.

Towbin, et al., "Electrophoretic Transfer of Proteins from Polyacrylamide Gels to Nitrocellulose Sheets: Procedure and Some Applications," Proc. Natl. Acad. Sci. USA, 176: 4350-54, 1979.

Trudinger, et al., "cDNA Encoding the Major Mite Allergen Der f ll" Clin. Exp. Allergy, 21:33-38, 1991.

Twardosz, "Molecular Characterization, Expression i *Escherichia coli*, and Epitope Analysis of a Two EF-Hand Calcium-Binding Birch Pollen Allergen, Bet v 4," Biochem. Biophys. Res. Commun, 239:197-204, 1997.

Van Der Stoep, et al., "In vivo and in Vitro IgE Isotype Switching in Human B Lymphocytes: Evidence for a Predominantly direct IgM to IgE class Switch Program", European J. Immunol, 24 1307-1311 (1994).

Van Hage-Hamsten, "Skin Test Evaluation of Genetically Engineered Hypoallergenic Derivatives of the Major Birch Pollen Allergen, Bet v 1: Results Obtained with a Mix of Two Recombinant Bet v 1 Fragments and Recombinant Bet v 1 Trimer in a Swedish Population Before the Birch Pollen Season", J Allergy Clin Immunol. 104(5): 969-77, Nov. 1999.

Van Hage-Hamsten, et al., "N-Terminal Aminoacid Sequence of Major Allergen of the Mite Lepidoglyphus Destructor," J. Allergy Clin. Immunol. 91:353, 1993.

Van Hoeyveld, et al., "Allergenic and Antigenic Activity of Peptide Fragments in a Whey Hydrolysate Formula", 28(9): 1131-7, Sep. 1998.

Van Kampen, et al., "Analysis of B-cell Epitopes in the N-Terminal Region of Chi t 1 component III using Monoclonal Antibodies," MolecularImmunol. 31: 1133-1140 (1994).

Van Millgen, et al., Differences Between Specificities of IgE and IgG4 Antibodies: Studies Using Recombinant Chain 1 and Chain 2 of the Major Cat Allergen *Felis domesticus* (d) I. Clin Exp Allergy 25(3): 247-51, Mar. 1995.

Van Milligen, et al., "IgE and IgG4 Binding to Synthetic Peptides of the Cat (*Felis domesticus*) Maj Allergen Fel dl" Int Arch Allergy Immunol. 103(3): 274-9, 1994.

Van Milligen, et al., "IgE Epitopes on the Cat (*Felis domesticus*) Major Allergen Fel D 1: A Study Wit Overlapping Synthetic Peptides", J Allergy Clin Immunol. 93(1 Pt 1): 34-43, Jan. 1994.

Van Ree, et al., "Rabbit IgG Directed to a Synthetic C-Terminal Peptide of the Major Grass Pollen Allergen Lol p 1 Inhibits Human Basophil Histamine Release Induced by Natural p 1". Int Arch Allergy Immunol. 106(3): 250-7, Mar. 1995.

Van Ree R, et al., "Lol p XI, a New Major Grass Pollen Allergen, is a Member of a Family of Soybean Trypsin Inhibitor-Related Protein", J. Allergy Clin Immunol. 95:970-978, 1995.

Van't Hof, et al., "Epitope Mapping of the Cat (*Felis domesticus*) Major Allergen Fel D 1 by Overlapping Synthetic Peptides and Monoclonal Antibodies Against Native and Denatured Fel D 1", Allergy, 48(4) 255-63, May 1993.

Van't Hof, et al., Epitope Mapping of the *Dermatophagoides pteronyssinus* House Dust Mite Major Allergen Der p ll Using Overlapping Synthetic Peptides, 28(11): 1225-32, Nov. 1991.

Varela, et al., "Primary Structure of Lep d 1, the Main Lepidoglyphus Destructor Allergen", Eur J. Biochem., 225:93-98, 1994.

Villalba, et al., "The Amino Acid Sequence of Ole e 1, the Major Allergen From Olive Tree (*Olea europaea*) Pollen", Europ. J. Biochem., 216:863-869, 1993.

Williams, et al., "Indentification of Epitopes Within Beta Lactoglobulin Recognised by Polyclonal Antibodies Using Phage Display and PEPSCAN", J Immunol Methods. 213(1): 1-17, Apr. 1998.

Woodfolk, et al., "Trichophyton Antigens Associated with IgE Antibodies and Delayed Type Hypersensitivity", J. Biol. Chem. 273:29489-29496, 1998.

Wu, et al., "Isolation and Preliminary Characterization of cDNA Encoding American Cockroach Allergens", J. Allergy Clin. Immunol., 96:352-359, 1995.

Yamamoto, et al., "DNA From Bacteria, But Not From Vertebrates, Induces Interferons, Activates Natural Killer Cells and Inhibits Tumor Growth," Microbiol. Immunol. 36(9): 983-97, 1992.

Yang, et al., "Immunologic Characterization of a Recombinant Kentucky Bluegrass (*Poapratensis*) Allergenic Peptide", J Allergy Clin Immunol. 87(6): 1096-104, Jun. 1991.

Yeang, et al., "The 14.6 kd Rubber Elongation Factor (Hev b 1) and 24 kd (Hev b 3) Rubber Particle Proteins are Recognized by IgE from Patients with Spina Bifida and Latex Allergy" J. Allergy Clin Immunol, 98(3): 628-639, 1996.

Yssel, et al., "Peptide Induced Anergy of Human Allergen-Specific T Cells" Adv Exp. Med Biol. 409: 405-10, 1996.

Yunginger, et al., "Fatal Food-Induced Anaphylaxis," JAMA, 260: 1450-2, 1988.

Zimmerman, et al., "CpG Oligodexoynucleotides Trigger Protective and Curative Th1 Responses in Lethal Murine Leishmaniasis," J. Immunol. 160(8): 3627-30, 1998.

Vives, et al., "A Truncated HIV-1 Tat Protein Basic Domain Rapaidly Translocates Through the Plasma Membrane and Accumulates in the Cell Nucleus", The Journal of Biological Chemistry, 272(25): 16010-16017, 1997.

Voller, et al., "Enzyme-Linked Immunosorbent Assay," Manual of Clinical Laboratory Immunology, Rose, ed., Chapter 17, Third Edition, 99-109, 1986.

Vrtala, "High Level Expression in *Escherichia coli* and Purification of Recombinant Plant Profilins: Comparison of IgE Binding Capacity and Allergenic Activity," Biochem. Biophys. Res. Comm, 226: 42-50, 1996.

Vrtala, et al., "Conversion of the Major Birch Pollen Allergen, Bet v 1, Into Two Nonanaphylactic T Cell Epitope-Containing Fragments: Candidates for a Novel Form of Specific Immunotherapy", J. Clin. Invest. 99(7): 1673-81, Apr. 1997.

Vrtala, et al., "Division of the Major Birch Pollen Allergen, Bet v 1, Into Two Non-Anaphylactic Fragments", Int Arch Allergy Immunol., 113: 246-48, 1997.

Wallner, et al., "Immunotherapy with T-Cell Reactive Peptides Derived from Allergens" Allergy 49(5): 302-8, May 1994.

Watanabe, et al., "Primary Structure of an Allergenic Peptide Occurring in the Chymotryptic Hydrolysate of Gluten", Biosci Biotechnol Biochem. 59(8): 1596-7, Aug. 1995.

Weber, et al., "Characteristics of the Aspargine-Linked Oligosaccharide from Honey-Bee Venom Phospholipase A2". Comp. Biochem. Physiol. 83B: 321-324, 1986.

Weber, et al., "Specific Interaction of IgE Antibodies with a Carbohydrate Epitope of Honey Bee Venom Phospholipase A2", Allergy, 42: 464-470, 1987.

Wiedermann, et al., "Suppression of Antigen-Specific T- and B-Cell Responses by Intranasal or Oral Administration of Recombinant Bet v 1, The Major Birch Pollen Allergen, in a Murine Model of Type I Allergy", J. Allergy Clin Immunol., 103(6): 1202-10, Jun. 1999.

Avjioglu, et al.,"Sequence Analysis of Sor H l, The Group I Allergen of Johnson Grass Pollen and Its Comparison to Rye-Grass Lol p l" J. Allergy Clin. Immunol. 91:340 (1993).

Bannon, et al., "Ara h 3, A Peanut Allergen Identified by Using Peanut Sensitive Patient Sera Adsorbed with Soy Proteins" J. Allergy Clin. Immunol. 99:A568, (1997) Abstract.

Burks, et al,, "The Identification of a Family of Vicilin-Like Genes Encoding Allergens Responsible for Peanut Hyper-Sensitivity" J. Allergy Clin. Immunol. 95:A765, (1995) Abstract.

Burks, et al., "Cloning, Epitope Mapping and Mutational Analysis of Ara H 2, A Major Peanut Allergen" J. Allergy Clin. Immunol. 99:A569, (1997), Abstract.

Burks, et al., "Cloning of the Ara H ll Peanut Allergen by Polymerase Chain Reaction (PCR) Amplification" J. Allergy Clin. Immunol. 91:341, A802 (1993), Abstract.

Crameri, "Epidemiology and Molecular Basis of the Involvement of *Aspergillus fumigatus* in Allergic Diseases", Contrib Microbiol. Basel. Karger, 2: 44-56, (1999).

Goodfriend, et al., "Cytochromes C: New Ragweed Pollen Allergens", Fed. Proc. 38: 1415, (1979).

Helm, et al., "Cloning of a Portion of Ara H 3: A Peanut Allergen", Presented at American Chemical Society Meeting, (1997), Abstract.

Helm, et al., "IgE-Binding of Homologous Legume Vicilins and Glycinins of Soybean and Peanut Allergens" J. Allergy Clin. Immunol. 101:A997 (1998), Abstract.

James, et al., "Serum IgE Antibodies From Wheat-Allergenic Patients Bind a 50 kD Wheat Protein" J. Allergy Clin. Immunol. 95:332, A767 (1995), Abstract.

Janssen, et al., "Modulation of Th2 Responses by Peptide Analogues in a Murine Model of Alle Asthma: Amelioration or Deterioration of the Disease Process Depends on the Th1 or Th2 Skewing Characteristics of the Therapeutic Peptide", J Immunol.164:580-588 (2000).

King, et al., "Modulation of the Allergenicity of a Major Peanut Allergen, Ara h 2 by Mutagenesis of Its Immunodominant IgE Binding Epitopes" J. Allergy Clin. Immunol. 103:258, S67 (1999), Abstract.

Kopper, et al., "Rapid Isolation of Peanut Allergens and Their Physical Chemical and Biological Characterization" J. Allergy Clin. Immunol. 101:A994 (1998), Abstract.

Ling, et al., "Construction and Characterization of Human IgE Fab Fragments Specific to Peanut Allergens"J. Allergy Clin. Immunol. 107:952, S290 (2001), Abstract.

Maleki, et al., "T-Cell Responses in Food Allergy: Identification of T-Cell Epitopes on a Major Peanut Allergen" J. Allergy Clin. Immunol. 101:A609 (1998), Abstract.

Matthiesen, et al., "Group V Allergens in Grass Pollens. I. Purification and Characterization of the Group V Allergen from *Phleum pratense* Pollen, Phl p V" Clin. Exp. Allergy, 21:297-307 (1991).

Rabjohn, et al., "Glycinin, A Third Major Peanut Allergen Identified by Soy-Adsorbed Serum IgE from Peanut Sensitive Individuals"J. Allergy Clin. Immunol. 101:A996 (1998), Abstract.

Rabjohn, et al., "Mutational Analysis of the IgE-Binding Epitopes of the Peanut Allergen, Ara h 3: A Member of the Glycinin Family of Seed-Storage Proteins" J. Allergy Clin. Immunol. 103:387, S101 (1999), Abstract.

Sen, et al., "Allergen Structure May Dictate Why Some IgE Binding Epitopes Become Immunodominant Within a Food Allergic Population" J. Allergy Clin. Immunol. 107:614, S184 (2001), Abstract.

Shin, et al., "Tertiary Structure of the Major Peanut Allergen Ara h 1: Implications for the Bioengineering of a Hypoallergenic Protein" J. Allergy Clin. Immunol. 101:A379 (1998), Abstract.

Shin, et al., Characterization of a Major Peanut Allergen: Mutational Analysis of the Ara h 1 IgE Binding Epitopes and Strategies for the Creation of a Hypoallergenic Peanut Clone J. allergy Clin. Immunol. 99:A570 (1997), Abstract.

Shin, Modulation of the Reactivity of the Major Peanut Allergen Ara h 1 Through Epitope Characterization, Structural Analysis, and Mutation J. Allergy Clin. Immunol. 103:376, S99 (1999), Abstract.

Stanley, et al., "Isolation and Quantitation of mRNA Differentially Expressed in Stimulated T Lymphocytes from Peanut Hypersensitive Individuals" J. Allergy Clin. Immunol. 101:A607 (1998), Abstract.

Stanley, et al., "Mapping of the B-Cell Epitopes on Ara h 1 and Ara h ll, Legume Storage Proteins and Major Allergens Involved in Peanut Hypersensitivity"Presented at ASMB/ASIP/AAI Joint Meeting, New Orleans (Jun. 1996), Abstract.

Watson, et al., "Trapping and Identification of Folding Intermediates of Disulfide Bond-Forming Proteins Based on Cyanylation, Cleavage, and Analysis by Mass Spectrometry", http:/www.abrf.org/JBT/Articles/JBT0014/JBT0014.html. pp. 1-12, (1998).

Bolhaar et al., Clin Exp Allergy, 35(12): 1638-44, 2005.

Burks, et al., "Atopic Dermatitis: Clinical Relevance of Food Hypersensitivity Reactions", J. Pediatr.113: 447-451, 1988.

Burks, et al., "Epitope Specificity of the Major Peanut Allergen, Ara h ll", J. Allergy Clin. Immunol. 95: 607-611, 1995.

EMBL Accession No. L77197 (Mar. 1996).

Foster, "Allergy Testing for Skin Disease in the Cat In Vivo vs. In Vitro tests," Veterinary Immunology 4(3):111-115 (1993).

Gadermaier et al., Int Arch Allergy Immunol., 139(1): 53-62, 2006.

Gayler, et al., "Biosynthesis, cDNA and Amino Acid Sequences of a Precursor of Conglutin ?, A Sulphur-Rich Protein from *Lupinus angustifolius*", Plant Molecular Biology, 15: 879-893, 1990.

Holm, et al., J. of Immunology, 173: 5258-5267, 2004.

Ichikawa, et al., "Solution Structure of Der f 2, the Major Mite Allergen for Atopic Disease", J. Mol. Chem., 273: 356-360, 1998.

International Search Report issued for corresponding PCT application PCT/US02/09108.

Li, et al., "Strain-Dependent Induction of Allergic Sensitization Caused by Peanut Allergen DNA Immunization in Mice", The Journal of Immunology, 162: 3045-3052, 1999.

Medaglini, et al., "Mucosal and Systemic Immune Responses to a Recombinant Protein Expressed on the Surface of the Oral Commensal Bacterium *Streptococcus gordonii* After Oral Colonization", Proceedings of the National Academy of Sciences of the United States of America, 92(15): 6868-6872, 1995.

Nishiyama, et al., "Analysis of the IgE-epitope of Der f 2, a Major Mite Allergen, by in vitro Mutagenesis", Mol. Immunol., 32: 1021-1029, 1995.

Nishiyama, et al., "Effects of Amino Acid Variations in Recombinant Der f ll on its Human IgE and Mouse IgG Recognition", Int. Arch. Allergy Immunol., 105: 62-69, 1994.

Okano, et al., "Population Analysis of Cellular Respones to Synthetic Peptides of Der p ll, a Major Allergen Molecule of *Dermatophagoides pteronyssinus*, in Allergic and Nonallergic Subjects", Allergy. 49(6): 436-41, Jul. 1994.

Sampson & McCaskill, "Food Hypersensitivity in Atopic Determatitis: Evaluation of 113 Patients," J. Pediatr. 107: 669-75, 1995.

Schramm et al., The J. of Immunology, 162: 2406-2414, 1999.

Takai, et al., "Determination of the N- and C-terminal Sequences to Bind Human IgE of the Major House Dust Mite Allergen Der f 2 and Epitope Mapping for Monoclonal Antibodies", Mol. Immunol., 34: 255-261, 1997.

Takai, et al., "Effect of Proline Mutations in the Major House Dust Mite Allergen Der f 2 on IgE-binding and Histamine-releasing Activity", Eur. J. Biochem., 267: 6650-6656, 2000.

Takai, et al., "Non-anaphylactic Combination of Partially Deleted Fragments of the Major House Dust Mite Allergen Der f 2 for Allergen-specific Immunotherapy", Mol. Immunol., 36: 1055-1065, 1999.

Vrtala, et al., "Humoral Immune Responses to Recombinant Tree Pollen Allergens (Bet v 1 and Bet v ll) in Mice: Construction of a Live Oral Allergy Vaccine", International Archives of Allergy and Immunology, 107: (1-3): 290-294, 1995.

Yeung, et al., "Heat-Killed *Listeria monocytogenes* as an Adjuvant Converts Established Murine Th2-Dominated Immune Responses into Th1-Dominated Responses", The Journal of Immunology, 161: 4146-4152, 1998.

Yocum, et al., "Epidemiology of Anaphylaxis in Olmsted County: A Population-Based Study", J. Allergy Clin. Immunol. 104: 452-456, 1999.

Yokoyama, et al., "Purification, Identification, and cDNA Cloning of Jun a 2, the Second Major Allergen of Mountain Cedar Pollen", Biochemical and Biophysical Research Communications, 275: 195-202, 2000.

Yu, et al., "Proteomics and Immunological Analysis of a Novel Shrimp Allergen, Pen M 2", The Journal of Immunology, 170: 445-453, 2003.

* cited by examiner

Ara h 1 - cDNA clone sequence

```
SEQ ID NO:1

AATAATCATATATATTCATCAATCATCTATATAAGTAGTAGCAGGAGCAATGAGAGGGAGGGTTTCTCCA    70
CTGATGCTGTTGCTAGGGATCCTTGTCCTGGCTTCAGTTTCTGCAACGCATGCCAAGTCATCACCTTACC   140
AGAAGAAAACAGAGAACCCCTGCGCCCAGAGGTGCCTCCAGAGTTGTCAACAGGAACCGGATGACTTGAA   210
GCAAAAGGCATGCGAGTCTCGCTGCACCAAGCTCGAGTATGATCCTCGTTGTGTCTATGATCCTCGAGGA   280
CACACTGGCACCACCAACCAACGTTCCCCTCCAGGGGAGCGGACACGTGGCCGCCAACCCGGAGACTACG   350
ATGATGACCGCCGTCAACCCCGAAGAGAGGAAGGAGGCCGATGGGGACCAGCTGGACCGAGGGAGCGTGA   420
AGAGAAGAAGACTGGAGACAACCAAGAGAAGATTGGAGGCGACCAAGTCATCAGCAGCCACGGAAAATA   490
AGGCCCGAAGGAAGAGAAGGAGAACAAGAGTGGGGAACACCAGGTAGCCATGTGAGGGAAGAAACATCTC   560
GGAACAACCCTTTCTACTTCCCGTCAAGGCGGTTTAGCACCCGCTACGGGAACCAAAACGGTAGGATCCG   630
GGTCCTGCAGAGGTTTGACCAAAGGTCAAGGCAGTTTCAGAATCTCCAGAATCACCGTATTGTGCAGATC   700
GAGGCCAAACCTAACACTCTTGTTCTTCCCAAGCACGCTGATGCTGATAACATCCTTGTTATCCAGCAAG   770
GGCAAGCCACCGTGACCGTAGCAAATGGCAATAACAGAAAGAGCTTTAATCTTGACGAGGGCCATGCACT   840
CAGAATCCCATCCGGTTTCATTTCCTACATCTTGAACCGCCATGACAACCAGAACCTCAGAGTAGCTAAA   910
ATCTCCATGCCCGTTAACACACCCGGCCAGTTTGAGGATTTCTTCCCGGCGAGCAGCCGAGACCAATCAT   980
CCTACTTGCAGGGCTTCAGCAGGAATACGTTGGAGGCCGCCTTCAATGCGGAATTCAATGAGATACGGAG  1050
GGTGCTGTTAGAAGAGAATGCAGGAGGTGAGCAAGAGGAGAGAGGGCAGAGGCGATGGAGTACTCGGAGT  1120
AGTGAGAACAATGAAGGAGTGATAGTCAAAGTGTCAAAGGAGCACGTTGAAGAACTTACTAAGCACGCTA  1190
AATCCGTCTCAAAGAAAGGCTCCGAAGAAGAGGGAGATATCACCAACCCAATCAACTTGAGAGAAGGCGA  1260
GCCCGATCTTTCTAACAACTTTGGGAAGTTATTTGAGGTGAAGCCAGACAAGAAGAACCCCCAGCTTCAG  1330
GACCTGGACATGATGCTCACCTGTGTAGAGATCAAAGAAGGAGCTTTGATGCTCCCACACTTCAACTCAA  1400
AGGCCATGGTTATCGTCGTCGTCAACAAAGGAACTGGAAACCTTGAACTCGTGGCTGTAAGAAAAGAGCA  1470
ACAACAGAGGGGACGGCGGGAAGAAGAGGAGGACGAAGACGAAGAAGAGGAGGGAAGTAACAGAGAGGTG  1540
CGTACGTACACAGCGAGGTTGAAGGAAGCGATGTGTTCATCATGCCAGCAGCTCATCCAGTAGCCATCA   1610
ACGCTTCCTCCGAACTCCATCTGCTTGGCTTCGGTATCAACGCTGAAAACAACCACAGAATCTTCCTTGC  1680
AGGTGATAAGGACAATGTGATAGACCAGATAGAGAAGCAAGCGAAGGATTTAGCATTCCCTGGGTCGGGT  1750
GAACAAGTTGAGAAGCTCATCAAAAACCAGAAGGAATCTCACTTTGTGAGTGCTCGTCCTCAATCTCAAT  1820
CTCAATCTCCGTCGTCTCCTGAGAAAGAGTCTCCTGAGAAAGAGGATCAAGAGGAGGAAAACCAAGGAGG  1890
GAAGGGTCCACTCCTTTCAATTTTGAAGGCTTTTAACTGAGAATGGAGGCAACTTGTTATGTATCGATAA  1960
TAAGATCACGCTTTTGTACTCTACTATCCAAAAACTTATCAATAAATAAAAACGTTTGTGCGTTGTTTCT  2030
CC
```

FIGURE 1

Ara h 1 – Full length native amino acid sequence

```
SEQ ID NO:2

MRGRVSPLMLLLGILVLASVSATHAKSSPYQKKTENPCAQRCLQSCQQEPDDLKQKACESRCTKLEYDPR    70
CVYDPRGHTGTTNQRSPPGERTRGRQPGDYDDDRRQPRREEGGRWGPAGPREREREEDWRQPREDWRRPS   140
HQQPRKIRPEGREGEQEWGTPGSHVREETSRNNPFYFPSRRFSTRYGNQNGRIRVLQRFDQRSRQFQNLQ   210
NIIRIVQIEAKPNTLVLPKHADADNILVIQQGQATVTVANGNNRKSFNLDEGHALRIPSGFISYILNRHDN   280
QNLRVAKISMPVNTPGQFEDFFPASSRDQSSYLQGFSRNTLEAAFNAEFNEIRRVLLEENAGGEQEERGQ   350
RRWSTRSSENNEGVIVKVSKEHVEELTKHAKSVSKKGSEEEGDITNPINLREGEPDLSNNFGKLFEVKPD   420
KKNPQLQDLDMMLTCVEIKEGALMLPHFNSKAMVIVVVNKGTGNLELVAVRKEQQQRGRREEEEDEDEEE   490
EGSNREVRRYTARLKEGDVFIMPAAHPVAINASSELHLLGFGINAENNHRIFLAGDKDNVIDQIEKQAKD   560
LAFPGSGEQVEKLIKNQKESHFVSARPQSQSQSPSSPEKESPEKEDQEEENQGGKGPLLSILKAFN

MRGRVSPLMLLLGILVLASVSA = signal peptide (SEQ ID NO:59)
```

FIGURE 2

Ara h 2 – cDNA clone sequence

SEQ ID NO:3

```
GCTCACCATACTAGTAGCCCTCGCCCTTTTCCTCCTCGCTGCCCACGCATCTGCGAGGCAGCAGTGGGAA    70
CTCCAAGGAGACAGAAGATGCCAGAGCCAGCTCGAGAGGGCGAACCTGAGGCCCTGCGAGCAACATCTCA   140
TGCAGAAGATCCAACGTGACGAGGATTCATATGAACGGGACCCGTACAGCCCTAGTCAGGATCCGTACAG   210
CCCTAGTCCATATGATCGGAGAGGCGCTGGATCCTCTCAGCACCAAGAGAGGTGTTGCAATGAGCTGAAC   280
GAGTTTGAGAACAACCAAAGGTGCATGTGCGAGGCATTGCAACAGATCATGGAGAACCAGAGCGATAGGT   350
TGCAGGGGAGGCAACAGGAGCAACAGTTCAAGAGGGAGCTCAGGAACTTGCCTCAACAGTGCGGCCTTAG   420
GGCACCACAGCGTTGCGACTTGGACGTCGAAAGTGGCGGCAGAGACAGATACTAAACACCTATCTCAAAA   490
AAAGAAAAGAAAAGAAAAGAAAATAGCTTATATATAAGCTATTATCTATGGTTATGTTTAGTTTTGGTAA   560
TAATAAAGATCATCACTATATGAATGTGTTGATCGTGTTAACTAAGGCAAGCTTAGGTTATATGAGCACC   630
TTTAGAGTGCTTTTATGGCGTTGTCTATGTTTTGTTGCTGCAGAGTTGTAACCATCTTGAAATAATATAA   700
AAAGATCATGTTTGTT
```

FIGURE 3

Ara h 2 - Full length native amino acid sequence

SEQ ID NO:4

MAKLTILVALALFLLAAHASARQQWELQGDRRCQSQLERANLRPCEQHLMQKIQRDEDSYERDPYSPSQD 70
PYSPSPYDRRGAGSSQHQERCCNELNEFENNQRCMCEALQQIMENQSDRLQGRQQEQQFKRELRNLPQQC 140
GLRAPQRCDLDVESGGRDRD

MAKLTILVALALFLLAAHAS = signal peptide (SEQ ID NO:60)

FIGURE 4

Ara h 3 – cDNA clone sequence

SEQ ID NO:5

```
CGGCAGCAACCGGAGGAGAACGCGTGCCAGTTCCAGCGCCTCAATGCGCAGAGACCTGACAATCGCATTG    70
AATCAGAGGGCGGTTACATTGAGACTTGGAACCCCAACAACCAGGAGTTCGAATGCGCCGGCGTCGCCCT   140
CTCTCGCTTAGTCCTCCGCCGCAACGCCCTTCGTAGGCCTTTCTACTCCAATGCTCCCCAGGAGATCTTC   210
ATCCAGCAAGGAAGGGGATACTTTGGGTTGATATTCCCTGGTTGTCCTAGACACTATGAAGAGCCTCACA   280
CACAAGGTCGTCGATCTCAGTCCCAAAGACCACCAAGACGTCTCCAAGGAGAAGACCAAAGCCAACAGCA   350
ACGAGATAGTCACCAGAAGGTGCACCGTTTCGATGAGGGTGATCTCATTGCAGTTCCCACCGGTGTTGCT   420
TTCTGGCTCTACAACGACCACGACACTGATGTTGTTGCTGTTTCTCTTACTGACACCAACAACAACGACA   490
ACCAGCTTGATCAGTTCCCCAGGAGATTCAATTTGGCTGGGAACACGGAGCAAGAGTTCTTAAGGTACCA   560
GCAACAAAGCAGACAAAGCAGACGAAGAAGCTTACCATATAGCCCATACAGCCCGCAAAGTCAGCCTAGA   630
CAAGAAGAGCGTGAATTTAGCCCTCGAGGACAGCACAGCCGCAGAGAACGAGCAGGACAAGAAGAAGAAA   700
ACGAAGGTGGAAACATCTTCAGCGGCTTCACGCCGGAGTTCCTGGAACAAGCCTTCCAGGTTGACGACAG   770
ACAGATAGTGCAAAACCTAAGAGGCGAGACCGAGAGTGAAGAAGAGGGAGCCATTGTGACAGTGAGGGGA   840
GGCCTCAGAATCTTGAGCCCAGATAGAAAGAGACGTGCCGACGAAGAAGAGGAATACGATGAACATGAAT   910
ATGAATACGATGAAGAGGATAGAAGGCGTGGCAGGGGAAGCAGAGGCAGGGGGAATGGTATTGAAGAGAC   980
GATCTGCACCGCAAGTGCTAAAAAGAACATTGGTAGAAACAGATCCCCTGACATCTACAACCCTCAAGCT  1050
GGTTCACTCAAAACTGCCAACGATCTCAACCTTCTAATACTTAGGTGGCTTGGACCTAGTGCTGAATATG  1120
GAAATCTCTACAGGAATGCATTGTTTGTCGCTCACTACAACACCAACGCACACAGCATCATATATCGATT  1190
GAGGGGACGGCTCACGTGCAAGTCGTGGACAGCAACGGCAACAGAGTGTACGACGAGGAGCTTCAAGAG  1260
GGTCACGTGCTTGTGGTGCCACAGAACTTCGCCGTCGCTGGAAAGTCCCAGAGCGAGAACTTCGAATACG  1330
TGGCATTCAAGACAGACTCAAGGCCCAGCATAGCCAACCTCGCCGGTGAAAACTCCGTCATAGATAACCT  1400
GCCGGAGGAGGTGGTTGCAAATTCATATGGCCTCCAAAGGGAGCAGGCAAGGCAGCTTAAGAACAACAAC  1470
CCCTTCAAGTTCTTCGTTCCACCGTCTCAGCAGTCTCCGAGGGCTGTGGCTTAA
```

FIGURE 5

Ara h 3 – Full length native amino acid sequence

SEQ ID NO:6

```
MAKLLELSFCFCFLVLGASSISFRQQPEENACQFQRLNAQRPDNRIESEGGYIETWNPNNQEFECAGVAL    70
SRLVLRRNALRRPFYSNAPQEIFIQQGRGYFGLIFPGCPSTYEEPAQQGRRSQSQRPPIRLQGEDQSQQQ   140
RDSHQKVHRFDEGDLIAVPTGVAFWLYNDHDTDVVAVSLTDTNNNDNQLDQFPRRFNLAGNHEQEFLRYQ   210
QQSRQSRRRSLPYSPYSPQSQPRQEEREFSPRGQHSRRERAGQEEENEGGNIFSGFTPEFLEQAFQVDDR   280
QIVQNLRGENESEEEGAIVTVRGGLRILSPDRKRRADEEEEYDEDEYEYDEEDRRRGRGSRGRGNGIEET   350
ICTASAKKNIGRNRSPDIYNPQAGSLKTANDLNLLILRWLGPSAEYGNLYRNALFVAHYNTNAHSIIYRL   420
RGRAHVQVVDSNGNRVYDEELQEGHVLVVPQNFAVAGKSQSENFEYVAFKTDSRPSIANLAGENSVIDNL   490
PEEVVANSYGLQREQARQLKNNNPFKFFVPPSQQSPRAVA
```

MAKLLELSFCFCFLVLGASS = signal peptide (SEQ ID NO:61)

FIGURE 6

Ara h 1 – A wild-type recombinant amino acid sequence

SEQ ID NO:53

```
    MASMTGGQQMGRDPNSSSTHAKSSPYQKKTENPCAQRCLQSCQQEPDDLKQKACESRCTKLEYDPR   70
CVYDPRGHTGTTNQRSPPGERTRGRQPGDYDDDRRQPRREEGGRWGPAGPREREREEDWRQPREDWRRPS  140
HQQPRKIRPEGREGEQEWGTPGSHVREETSRNNPFYFPSRRFSTRYGNQNGRIRVLQRFDQRSRQFQNLQ  210
NHRIVQIEAKPNTLVLPKHADADNILVIQQGQATVTVANGNNRKSFNLDEGHALRIPSGFISYILNRHDN  280
QNLRVAKISMPVNTPGQFEDFFPASSRDQSSYLQGFSRNTLEAAFNAEFNEIRRVLLEENAGGEQEERGQ  350
RRWSTRSSENNEGVIVKVSKEHVEELTKHAKSVSKKGSEEEGDITNPINLREGEPDLSNNFGKLFEVKPD  420
KKNPQLQDLDMMLTCVEIKEGALMLPHFNSKAMVIVVVNKGTGNLELVAVRKEQQQRGRREEEEDEDEEE  490
EGSNREVRRYTARLKEGDVFIMPAAHPVAINASSELHLLGFGINAENNHRIFLAGDKDNVIDQIEKQAKD  560
LAFPGSGEQVEKLIKNQKESHFVSARPQSQSQSPSSPEKESPEKEDQEEENQGGKGPLLSILKAFNKLAA  610
ALEHHHHHH
```

MASMTGGQQMG = T7-tag (SEQ ID NO:49)

RDPNSSS = N-terminal vector derived amino acids (SEQ ID NO:51)

KLAAALE = C-terminal vector derived amino acids (SEQ ID NO:52)

HHHHHH = His-tag (SEQ ID NO:50)

FIGURE 7

Ara h 2 – A wild-type recombinant amino acid sequence

SEQ ID NO:56

MASMTGGQQMGRGSEFARQQWELQGDRRCQSQLERANLRPCEQHLMQKIQRDEDSYERDPYSPSQD    70
PYSPSPYDRRGAGSSQHQERCCNELNEFENNQRCMCEALQQIMENQSDRLQGRQQEQQFKRELRNLPQQC 140
GLRAPQRCDLDVESGGRDRDAAALEHHHHHH

MASMTGGQQMG = T7-tag (SEQ ID NO:49)

RGSEF = N-terminal vector derived amino acids (SEQ ID NO:54)

AAALE = C-terminal vector derived amino acids (SEQ ID NO:55)

HHHHHH = His-tag (SEQ ID NO:50)

FIGURE 8

Ara h 3 – A wild-type recombinant amino acid sequence

SEQ ID NO:58

```
        MASMTGGQQMGISFRQQPEENACQFQRLNAQRPDNRIESEGGYIETWNPNNQEFECAGVAL   70
SRLVLRRNALRRPFYSNAPQEIFIQQGRGYFGLIFPGCPSTYEEPAQQGRRSQSQRPPIRLQGEDQSQQQ  140
RDSHQKVHRFDEGDLIAVPTGVAFWLYNDHDTDVVAVSLTDTNNNDNQLDQFPRRFNLAGNHEQEFLRYQ  210
QQSRQSRRRSLPYSPYSPQSQPRQEEREFSPRGQHSRRERAGQEEENEGGNIFSGFTPEFLEQAFQVDDR  280
QIVQNLRGENESEEEGAIVTVRGGLRILSPDRKRRADEEEEYDEDEYEYDEEDRRRGRGSRGRGNVDKLA  350
AALEHHHHHH
```

MASMTGGQQMG = T7-tag (SEQ ID NO:49)

VDKLAAALE = C-terminal vector derived amino acids (SEQ ID NO:59)

HHHHHH = His-tag (SEQ ID NO:50)

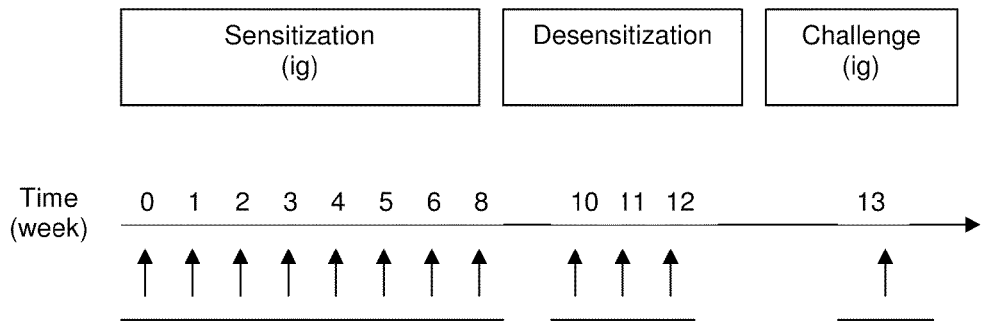

| | Sensitization (ig) | Desensitization | Challenge (ig) |

Time (week): 0 1 2 3 4 5 6 8    10 11 12    13

Subcutaneous (sc) desensitization:
G2          CPE + CT          HKE-MP123, 90 μg          CPE
G3          CPE + CT          HKE-MP123, 45 μg          CPE
G4          CPE + CT          HKE-MP123, 15 μg          CPE
G9          CPE + CT          HKL                       CPE
G10         CPE + CT          HKL-MP123, 90 μg          CPE Intragastric (ig) desensitization:
G5          CPE + CT          HKE-MP123, 150 μg         CPE Rectal (pr) desensitization:
G6          CPE + CT          HKE-MP123, 90 μg          CPE
G7          CPE + CT          MP123, 90 μg              CPE Control:
G1 (sham)   CPE + CT          None                      CPE
G8 (naïve)  None              None                      CPE

FIGURE 12

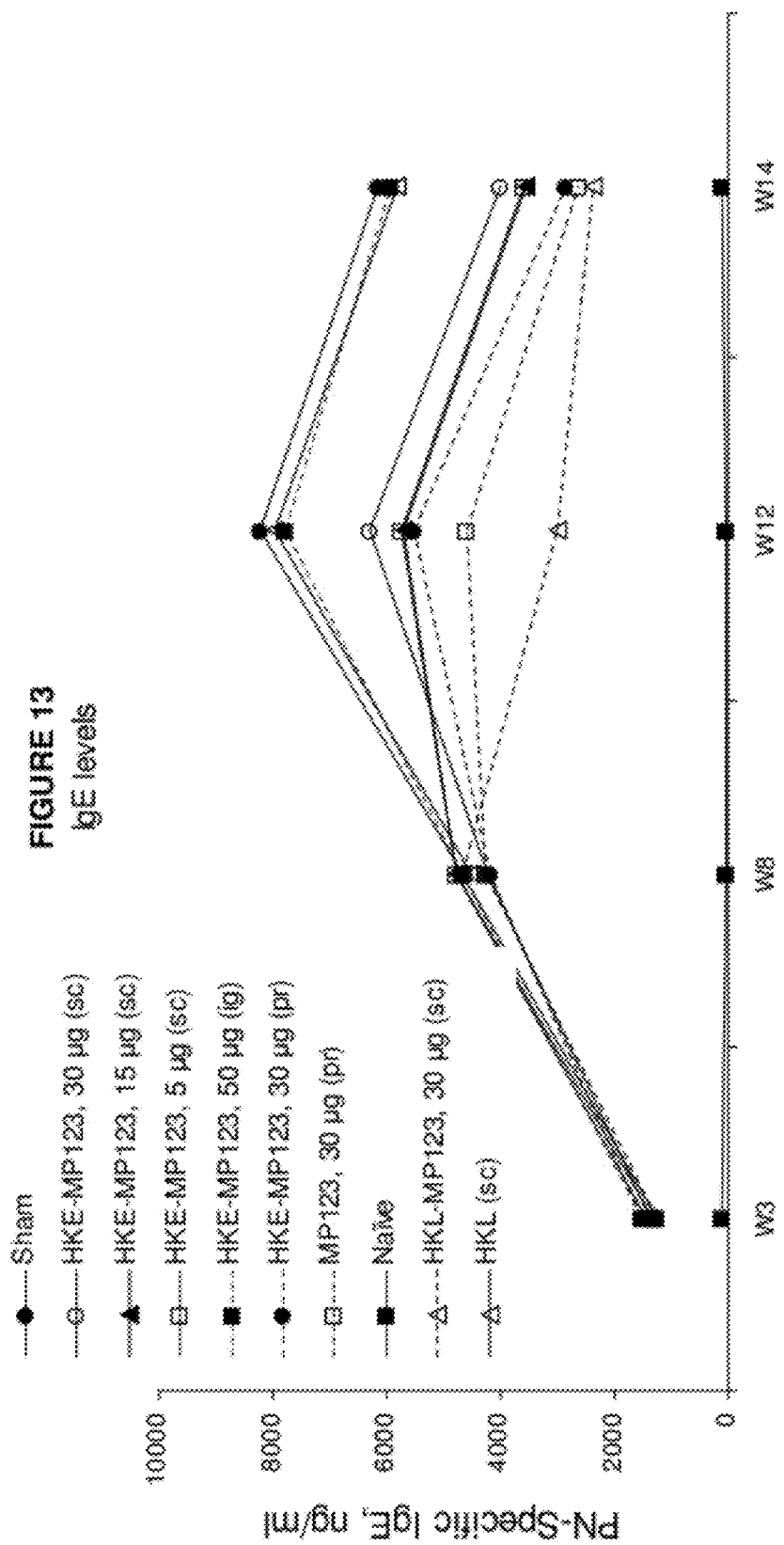

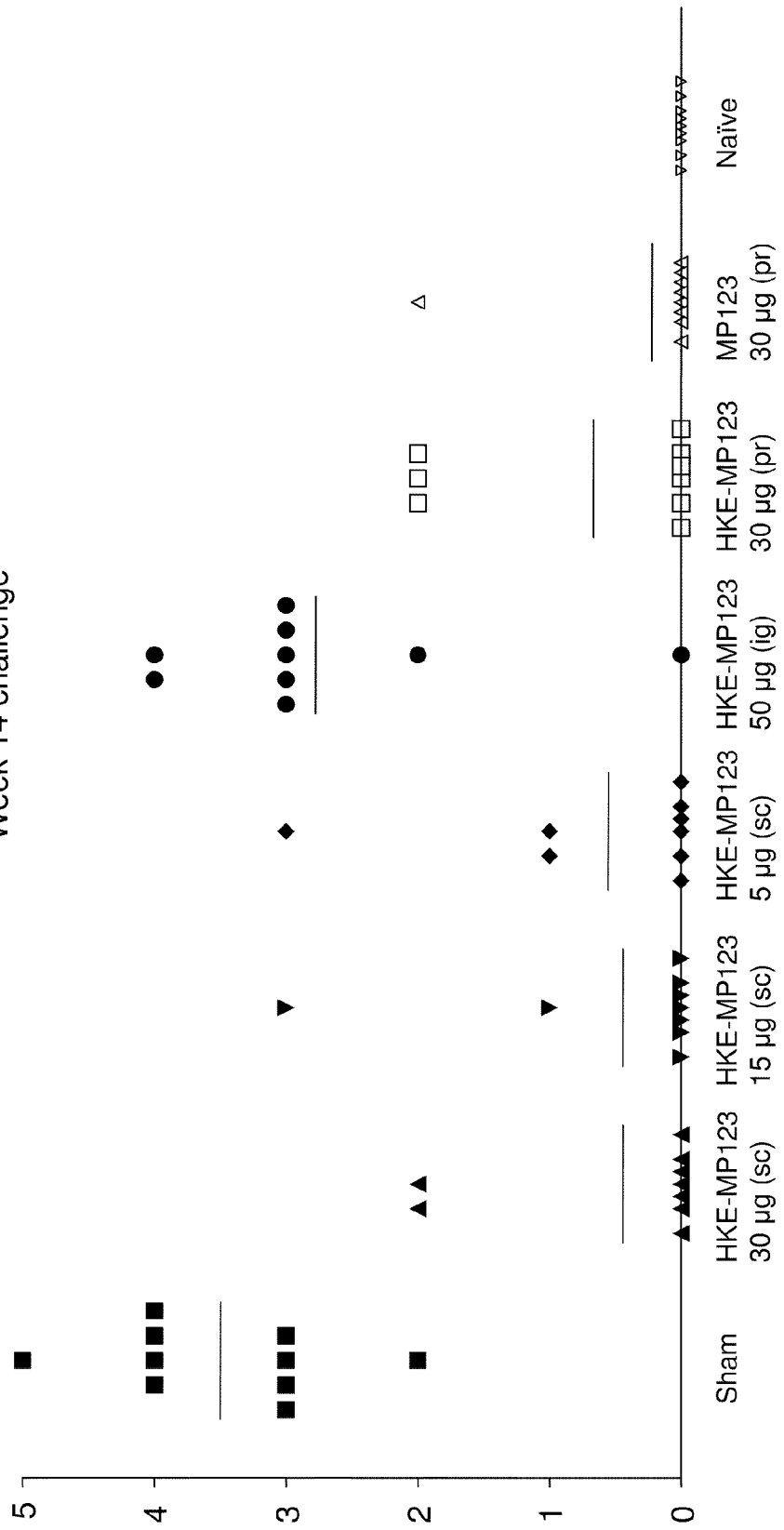

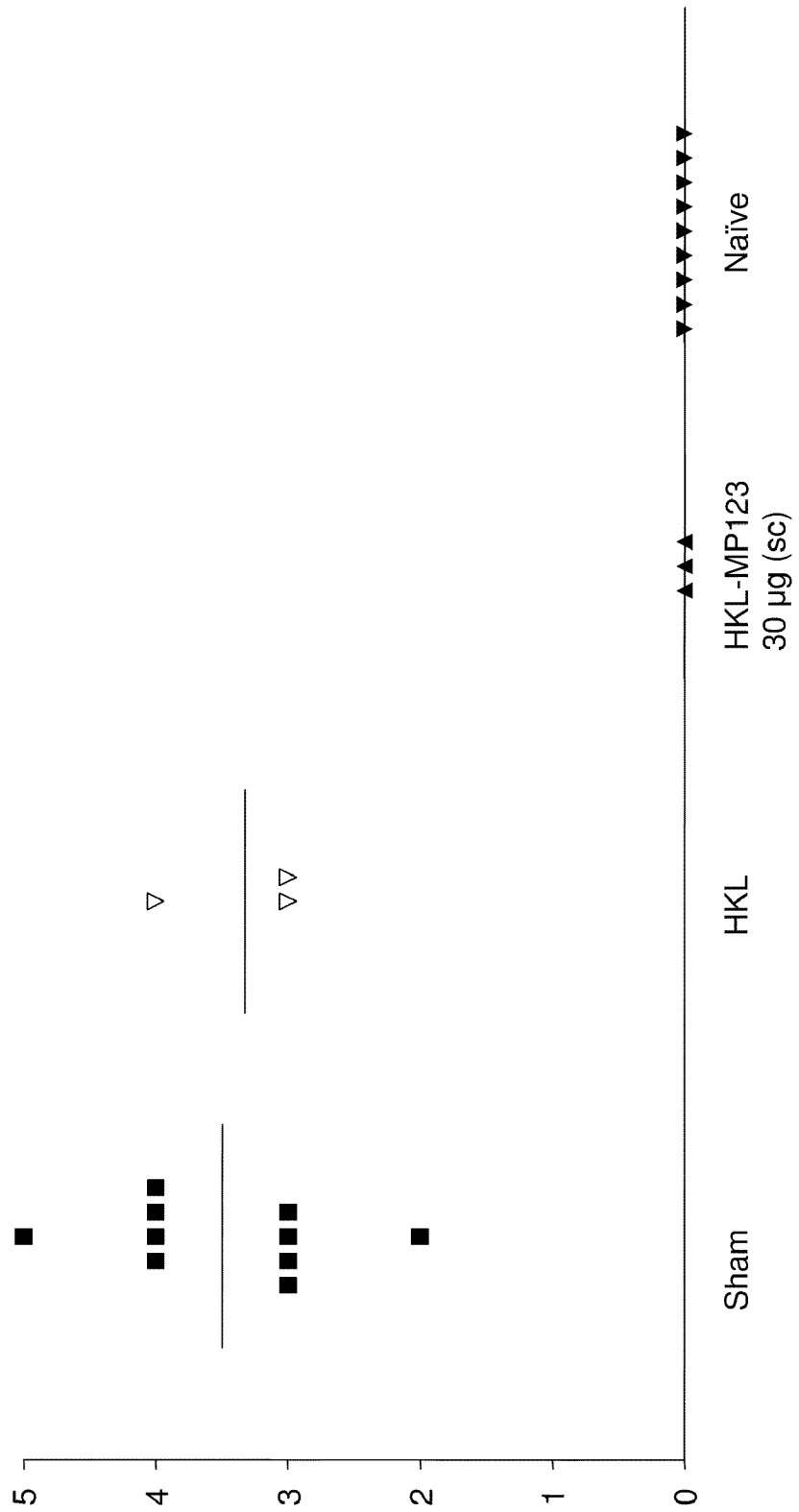

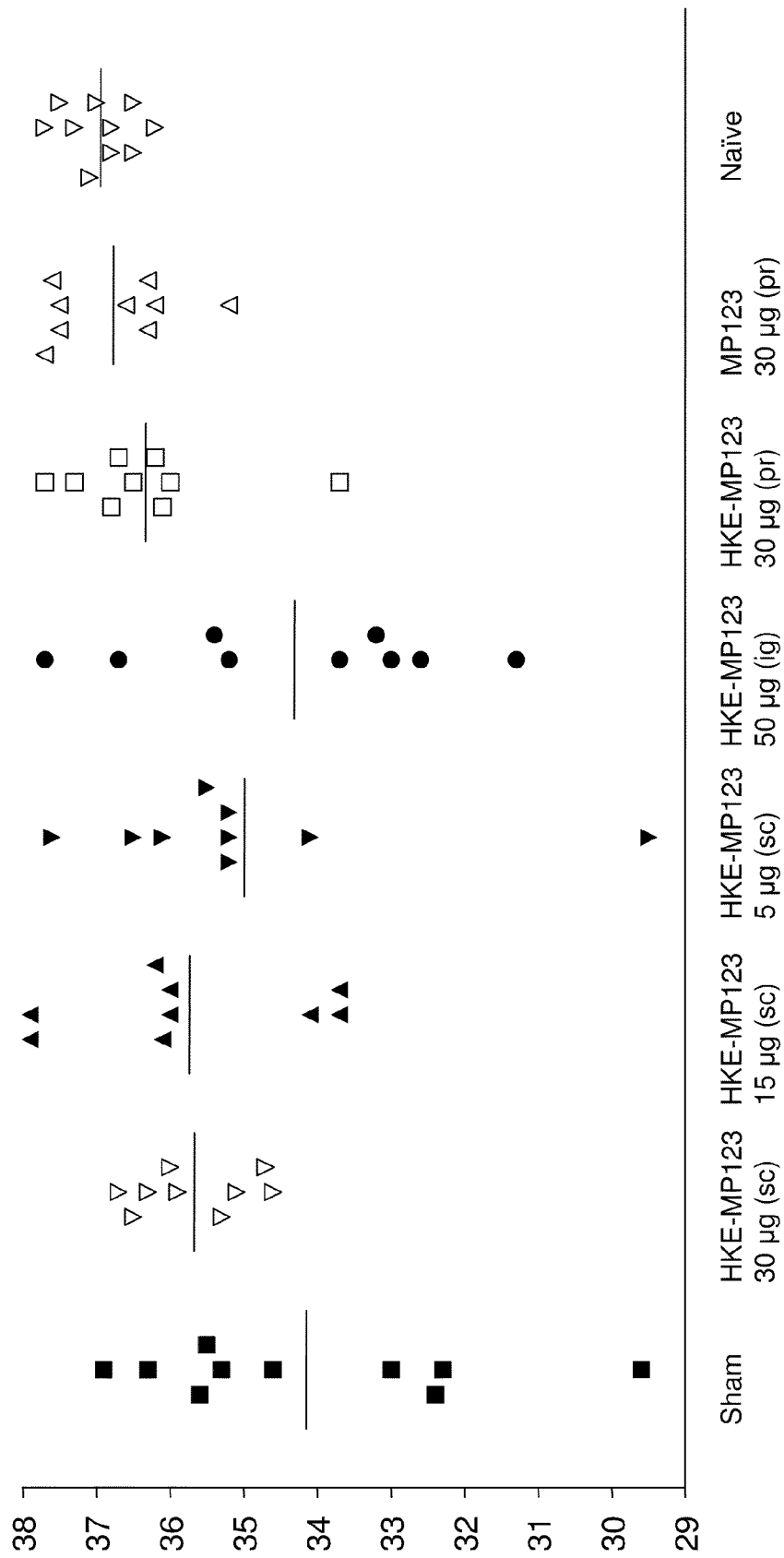

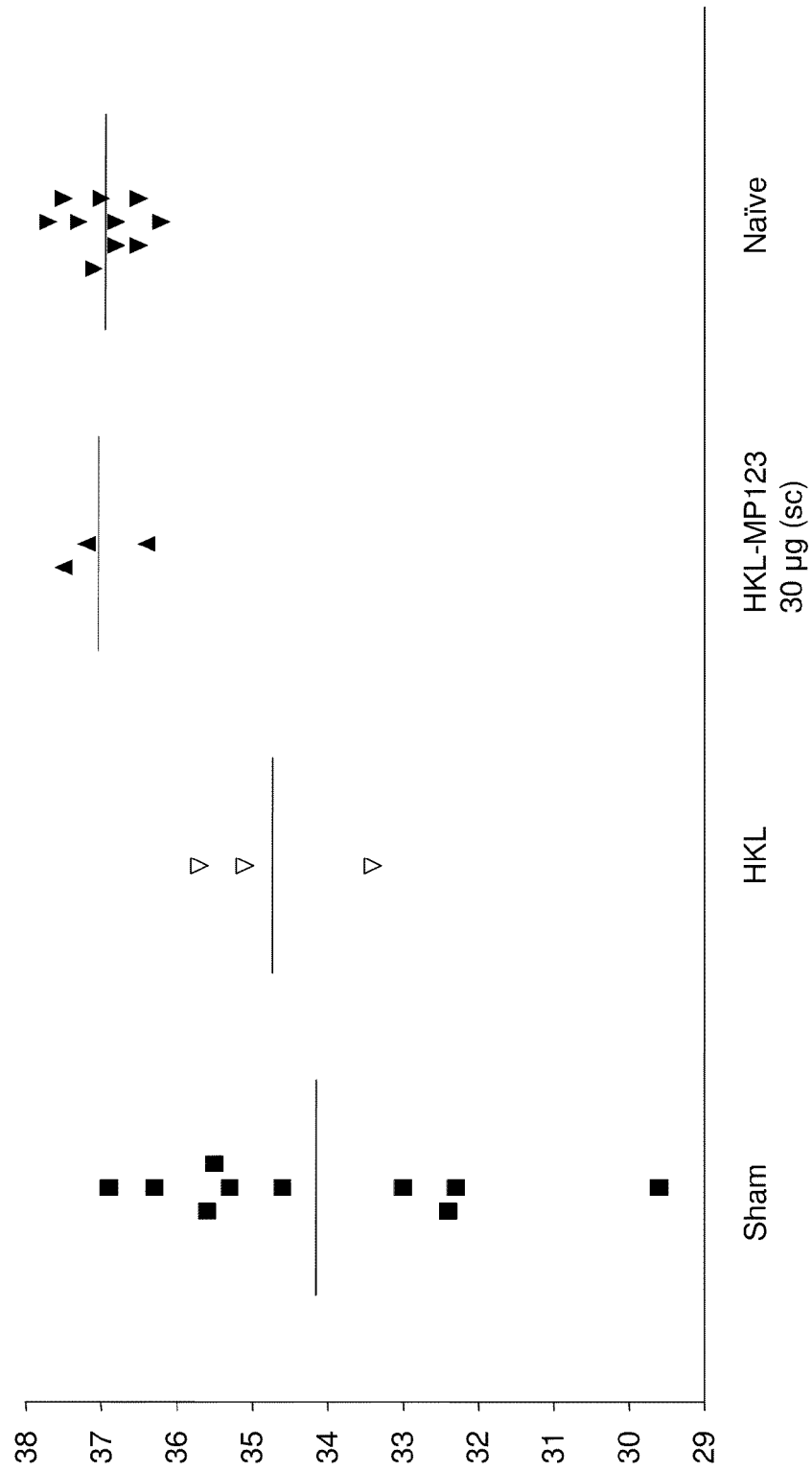

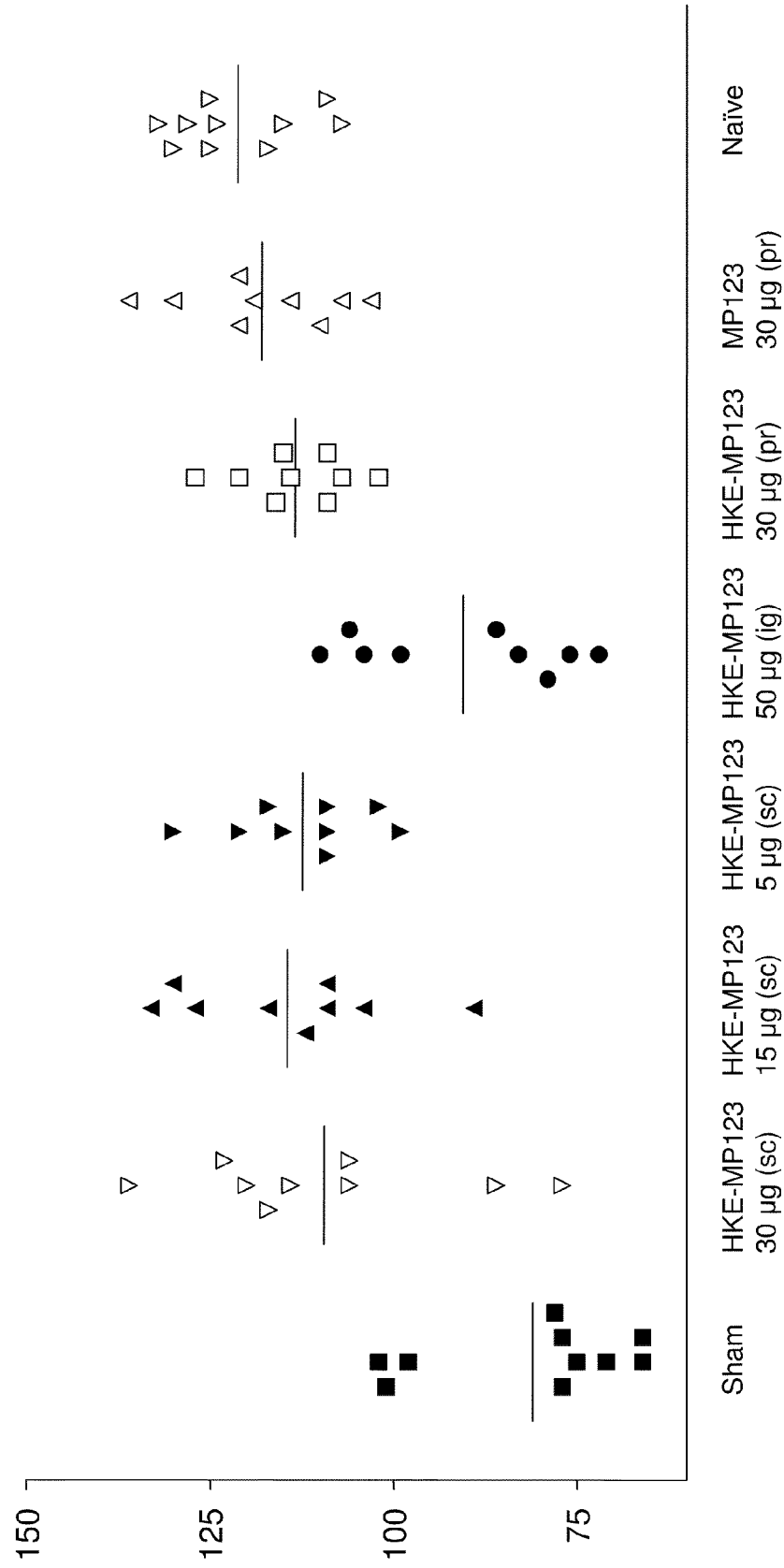

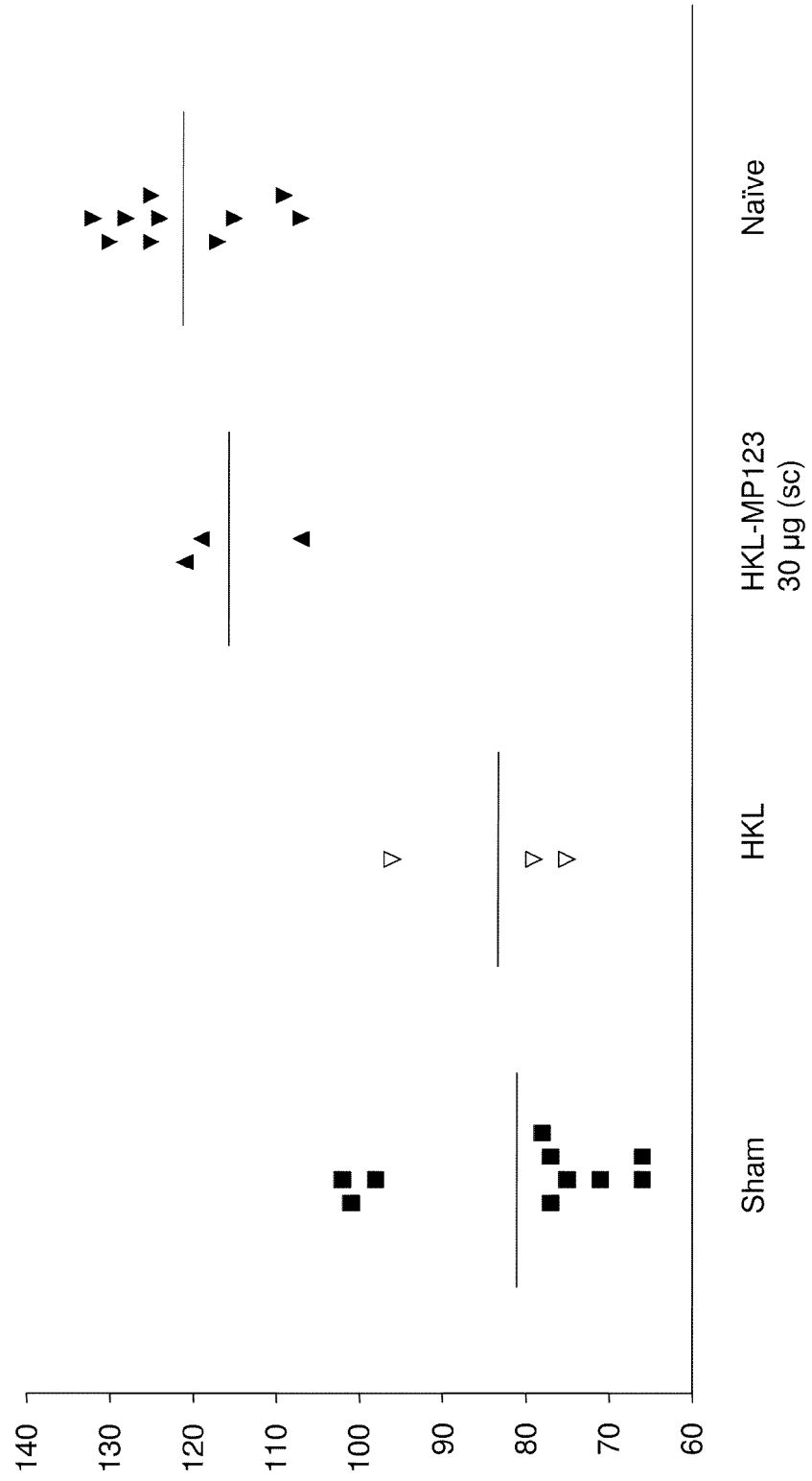

Plasma Histamine Levels

IL-4 Levels

IL-5 Levels

Clinical Study – Part II

SEQUENCE LISTING

<160> NUMBER OF SEQ ID NOS: 61

<210> SEQ ID NO 1
<211> LENGTH: 2032
<212> TYPE: DNA
<213> ORGANISM: Artificial Sequence
<220> FEATURE:
<223> OTHER INFORMATION: Arachis hypogea

<400> SEQUENCE: 1

```
aataatcata tatattcatc aatcatctat ataagtagta gcaggagcaa tgagagggag      60
ggtttctcca ctgatgctgt tgctagggat ccttgtcctg gcttcagttt ctgcaacgca     120
tgccaagtca tcaccttacc agaagaaaac agagaacccc tgcgcccaga ggtgcctcca     180
gagttgtcaa caggaaccgg atgacttgaa gcaaaaggca tgcgagtctc gctgcaccaa     240
gctcgagtat gatcctcgtt gtgtctatga tcctcgagga cacactggca ccaccaacca     300
acgttcccct ccaggggagc ggacacgtgg ccgccaaccc ggagactacg atgatgaccg     360
ccgtcaaccc cgaagagagg aaggaggccg atggggacca gctggaccga gggagcgtga     420
aagagaagaa gactggagac aaccaagaga agattggagg cgaccaagtc atcagcagcc     480
acggaaaata aggcccgaag gaagagaagg agaacaagag tggggaacac caggtagcca     540
tgtgagggaa gaaacatctc ggaacaaccc tttctacttc ccgtcaaggc ggtttagcac     600
ccgctacggg aaccaaaacg gtaggatccg ggtcctgcag aggtttgacc aaaggtcaag     660
gcagtttcag aatctccaga atcaccgtat tgtgcagatc gaggccaaac ctaacactct     720
tgttcttccc aagcacgctg atgctgataa catccttgtt atccagcaag ggcaagccac     780
cgtgaccgta gcaaatggca ataacagaaa gagctttaat cttgacgagg gccatgcact     840
cagaatccca tccggtttca tttcctacat cttgaaccgc catgacaacc agaacctcag     900
agtagctaaa atctccatgc ccgttaacac acccggccag tttgaggatt tcttcccggc     960
gagcagccga gaccaatcat cctacttgca gggcttcagc aggaatacgt tggaggccgc    1020
cttcaatgcg gaattcaatg agatacggag ggtgctgtta gaagagaatg caggaggtga    1080
gcaagaggag agagggcaga ggcgatggag tactcggagt agtgagaaca atgaaggagt    1140
gatagtcaaa gtgtcaaagg agcacgttga agaacttact aagcacgcta aatccgtctc    1200
```

-continued

```
aaagaaaggc tccgaagaag agggagatat caccaaccca atcaacttga gagaaggcga    1260
gcccgatctt tctaacaact ttgggaagtt atttgaggtg aagccagaca agaagaaccc    1320
ccagcttcag gacctggaca tgatgctcac ctgtgtagag atcaaagaag gagctttgat    1380
gctcccacac ttcaactcaa aggccatggt tatcgtcgtc gtcaacaaag gaactggaaa    1440
ccttgaactc gtggctgtaa gaaaagagca acaacagagg ggacggcggg aagaagagga    1500
ggacgaagac gaagaagagg agggaagtaa cagagaggtg cgtaggtaca cagcgaggtt    1560
gaaggaaggc gatgtgttca tcatgccagc agctcatcca gtagccatca acgcttcctc    1620
cgaactccat ctgcttggct tcggtatcaa cgctgaaaac aaccacagaa tcttccttgc    1680
aggtgataag gacaatgtga tagaccagat agagaagcaa gcgaaggatt tagcattccc    1740
tgggtcgggt gaacaagttg agaagctcat caaaaaccag aaggaatctc actttgtgag    1800
tgctcgtcct caatctcaat ctcaatctcc gtcgtctcct gagaaagagt ctcctgagaa    1860
agaggatcaa gaggaggaaa accaaggagg gaagggtcca ctcctttcaa ttttgaaggc    1920
ttttaactga gaatggaggc aacttgttat gtatcgataa taagatcacg cttttgtact    1980
ctactatcca aaaacttatc aataaataaa aacgtttgtg cgttgtttct cc            2032
```

<210> SEQ ID NO 2
<211> LENGTH: 626
<212> TYPE: PRT
<213> ORGANISM: Artificial Sequence
<220> FEATURE:
<223> OTHER INFORMATION: Arachis hypogea

<400> SEQUENCE: 2

```
Met Arg Gly Arg Val Ser Pro Leu Met Leu Leu Leu Gly Ile Leu Val
1               5                   10                  15

Leu Ala Ser Val Ser Ala Thr His Ala Lys Ser Ser Pro Tyr Gln Lys
            20                  25                  30

Lys Thr Glu Asn Pro Cys Ala Gln Arg Cys Leu Gln Ser Cys Gln Gln
        35                  40                  45

Glu Pro Asp Asp Leu Lys Gln Lys Ala Cys Glu Ser Arg Cys Thr Lys
    50                  55                  60

Leu Glu Tyr Asp Pro Arg Cys Val Tyr Asp Pro Arg Gly His Thr Gly
65                  70                  75                  80

Thr Thr Asn Gln Arg Ser Pro Pro Gly Glu Arg Thr Arg Gly Arg Gln
                85                  90                  95

Pro Gly Asp Tyr Asp Asp Asp Arg Arg Gln Pro Arg Arg Glu Glu Gly
            100                 105                 110

Gly Arg Trp Gly Pro Ala Gly Pro Arg Glu Arg Glu Arg Glu Glu Asp
        115                 120                 125

Trp Arg Gln Pro Arg Glu Asp Trp Arg Arg Pro Ser His Gln Gln Pro
    130                 135                 140

Arg Lys Ile Arg Pro Glu Gly Arg Glu Gly Gln Glu Trp Gly Thr
145                 150                 155                 160

Pro Gly Ser His Val Arg Glu Glu Thr Ser Arg Asn Asn Pro Phe Tyr
                165                 170                 175

Phe Pro Ser Arg Arg Phe Ser Thr Arg Tyr Gly Asn Gln Asn Gly Arg
            180                 185                 190

Ile Arg Val Leu Gln Arg Phe Asp Gln Arg Ser Arg Gln Phe Gln Asn
        195                 200                 205

Leu Gln Asn His Arg Ile Val Gln Ile Glu Ala Lys Pro Asn Thr Leu
    210                 215                 220
```

```
Val Leu Pro Lys His Ala Asp Ala Asp Asn Ile Leu Val Ile Gln Gln
225                 230                 235                 240

Gly Gln Ala Thr Val Thr Val Ala Asn Gly Asn Asn Arg Lys Ser Phe
                245                 250                 255

Asn Leu Asp Glu Gly His Ala Leu Arg Ile Pro Ser Gly Phe Ile Ser
            260                 265                 270

Tyr Ile Leu Asn Arg His Asp Asn Gln Asn Leu Arg Val Ala Lys Ile
        275                 280                 285

Ser Met Pro Val Asn Thr Pro Gly Gln Phe Glu Asp Phe Phe Pro Ala
    290                 295                 300

Ser Ser Arg Asp Gln Ser Ser Tyr Leu Gln Gly Phe Ser Arg Asn Thr
305                 310                 315                 320

Leu Glu Ala Ala Phe Asn Ala Glu Phe Asn Glu Ile Arg Arg Val Leu
                325                 330                 335

Leu Glu Glu Asn Ala Gly Gly Glu Gln Glu Glu Arg Gly Gln Arg Arg
            340                 345                 350

Trp Ser Thr Arg Ser Ser Glu Asn Glu Gly Val Ile Val Lys Val
        355                 360                 365

Ser Lys Glu His Val Glu Glu Leu Thr Lys His Ala Lys Ser Val Ser
    370                 375                 380

Lys Lys Gly Ser Glu Glu Gly Asp Ile Thr Asn Pro Ile Asn Leu
385                 390                 395                 400

Arg Glu Gly Glu Pro Asp Leu Ser Asn Asn Phe Gly Lys Leu Phe Glu
                405                 410                 415

Val Lys Pro Asp Lys Lys Asn Pro Gln Leu Gln Asp Leu Asp Met Met
            420                 425                 430

Leu Thr Cys Val Glu Ile Lys Glu Gly Ala Leu Met Leu Pro His Phe
        435                 440                 445

Asn Ser Lys Ala Met Val Ile Val Val Asn Lys Gly Thr Gly Asn
    450                 455                 460

Leu Glu Leu Val Ala Val Arg Lys Glu Gln Gln Gln Arg Gly Arg Arg
465                 470                 475                 480

Glu Glu Glu Glu Asp Glu Asp Glu Glu Glu Gly Ser Asn Arg Glu
                485                 490                 495

Val Arg Arg Tyr Thr Ala Arg Leu Lys Glu Gly Asp Val Phe Ile Met
            500                 505                 510

Pro Ala Ala His Pro Val Ala Ile Asn Ala Ser Ser Glu Leu His Leu
        515                 520                 525

Leu Gly Phe Gly Ile Asn Ala Glu Asn Asn His Arg Ile Phe Leu Ala
    530                 535                 540

Gly Asp Lys Asp Asn Val Ile Asp Gln Ile Glu Lys Gln Ala Lys Asp
545                 550                 555                 560

Leu Ala Phe Pro Gly Ser Gly Glu Gln Val Glu Lys Leu Ile Lys Asn
                565                 570                 575

Gln Lys Glu Ser His Phe Val Ser Ala Arg Pro Gln Ser Gln Ser Gln
            580                 585                 590

Ser Pro Ser Ser Pro Glu Lys Glu Ser Pro Glu Lys Glu Asp Gln Glu
        595                 600                 605

Glu Glu Asn Gln Gly Gly Lys Gly Pro Leu Leu Ser Ile Leu Lys Ala
    610                 615                 620

Phe Asn
625

<210> SEQ ID NO 3
```

```
<211> LENGTH: 717
<212> TYPE: DNA
<213> ORGANISM: Artificial Sequence
<220> FEATURE:
<223> OTHER INFORMATION: Arachis hypogea

<400> SEQUENCE: 3
gctcaccata ctagtagccc tcgcccttt  cctcctcgct gcccacgcat ctgcgaggca     60
gcagtgggaa ctccaaggag acagaagatg ccagagccag ctcgagaggg cgaacctgag    120
gccctgcgag caacatctca tgcagaagat ccaacgtgac gaggattcat atgaacggga    180
cccgtacagc cctagtcagg atccgtacag ccctagtcca tatgatcgga gaggcgctgg    240
atcctctcag caccaagaga ggtgttgcaa tgagctgaac gagtttgaga caaccaaag     300
gtgcatgtgc gaggcattgc aacagatcat ggagaaccag agcgataggt tgcaggggag    360
gcaacaggag caacagttca gagggagct  caggaacttg cctcaacagt gcggccttag    420
ggcaccacag cgttgcgact tggacgtcga agtggcggc  agagacagat actaaacacc    480
tatctcaaaa aagaaaaga  aaagaaaaga aaatagctta tatataagct attatctatg    540
gttatgttta gttttggtaa taataaagat catcactata tgaatgtgtt gatcgtgtta    600
actaaggcaa gcttaggtta tatgagcacc tttagagtgc ttttatggcg ttgtctatgt    660
tttgttgctg cagagttgta accatcttga aataatataa aagatcatg  ttttgtt      717

<210> SEQ ID NO 4
<211> LENGTH: 160
<212> TYPE: PRT
<213> ORGANISM: Artificial Sequence
<220> FEATURE:
<223> OTHER INFORMATION: Arachis hypogea

<400> SEQUENCE: 4

Met Ala Lys Leu Thr Ile Leu Val Ala Leu Ala Leu Phe Leu Leu Ala
1               5                   10                  15

Ala His Ala Ser Ala Arg Gln Gln Trp Glu Leu Gln Gly Asp Arg Arg
                20                  25                  30

Cys Gln Ser Gln Leu Glu Arg Ala Asn Leu Arg Pro Cys Glu Gln His
            35                  40                  45

Leu Met Gln Lys Ile Gln Arg Asp Glu Asp Ser Tyr Glu Arg Asp Pro
    50                  55                  60

Tyr Ser Pro Ser Gln Asp Pro Tyr Ser Pro Ser Pro Tyr Asp Arg Arg
65                  70                  75                  80

Gly Ala Gly Ser Ser Gln His Gln Glu Arg Cys Cys Asn Glu Leu Asn
                85                  90                  95

Glu Phe Glu Asn Asn Gln Arg Cys Met Cys Glu Ala Leu Gln Gln Ile
            100                 105                 110

Met Glu Asn Gln Ser Asp Arg Leu Gln Gly Arg Gln Gln Glu Gln Gln
        115                 120                 125

Phe Lys Arg Glu Leu Arg Asn Leu Pro Gln Gln Cys Gly Leu Arg Ala
    130                 135                 140

Pro Gln Arg Cys Asp Leu Asp Val Glu Ser Gly Gly Arg Asp Arg Asp
145                 150                 155                 160

<210> SEQ ID NO 5
<211> LENGTH: 1524
<212> TYPE: DNA
<213> ORGANISM: Artificial Sequence
<220> FEATURE:
<223> OTHER INFORMATION: Arachis hypogea
```

-continued

```
<400> SEQUENCE: 5
cggcagcaac cggaggagaa cgcgtgccag ttccagcgcc tcaatgcgca gagacctgac      60
aatcgcattg aatcagaggg cggttacatt gagacttgga accccaacaa ccaggagttc     120
gaatgcgccg gcgtcgccct ctctcgctta gtcctccgcc gcaacgccct tcgtaggcct     180
ttctactcca atgctcccca ggagatcttc atccagcaag aaggggata ctttgggttg      240 atattccctg gttgtcctag acactatgaa gagcctcaca caaggtcg tcgatctcag       300 tcccaaagac caccaagacg tctccaagga gaagaccaaa gccaacagca acgagatagt     360
caccagaagg tgcaccgttt cgatgagggt gatctcattg cagttcccac cggtgttgct     420
ttctggctct acaacgacca cgacactgat gttgttgctg tttctcttac tgacaccaac     480
aacaacgaca accagcttga tcagttcccc aggagattca atttggctgg aacacggag      540 caagagttct taaggtacca gcaacaaagc agacaaagca gacgaagaag cttaccatat     600
agcccataca gcccgcaaag tcagcctaga caagaagagc gtgaatttag ccctcgagga     660
cagcacagcc gcagagaacg agcaggacaa gaagaagaaa acgaaggtgg aaacatcttc     720
agcggcttca cgccggagtt cctgaacaa gccttccagg ttgacgacag acagatagtg      780
caaaacctaa gaggcgagac cgagagtgaa gagagggag ccattgtgac agtgagggga     840
ggcctcagaa tcttgagccc agatagaaag agacgtgccg acgaagaaga ggaatacgat     900
gaagatgaat atgaatacga tgaagaggat agaaggcgtg gcagggaag cagaggcagg      960 gggaatggta ttgaagagac gatctgcacc gcaagtgcta aaagaacat tggtagaaac     1020 agatcccctg acatctacaa ccctcaagct ggttcactca aaactgccaa cgatctcaac    1080
cttctaatac ttaggtggct tggacctagt gctgaatatg gaaatctcta caggaatgca    1140
ttgtttgtcg ctcactacaa caccaacgca cacagcatca tatatcgatt gaggggacgg    1200
gctcacgtgc aagtcgtgga cagcaacggc aacagagtgt acgacgagga gcttcaagag    1260
ggtcacgtgc ttgtggtgcc acagaacttc gccgtcgctg gaaagtccca gagcgagaac    1320
ttcgaatacg tggcattcaa gacagactca aggcccagca tagccaacct cgccggtgaa    1380
aactccgtca tagataaccct gccggaggag gtggttgcaa attcatatgg cctccaaagg    1440
gagcaggcaa ggcagcttaa gaacaacaac cccttcaagt tcttcgttcc accgtctcag    1500
cagtctccga gggctgtggc ttaa                                            1524
```

<210> SEQ ID NO 6
<211> LENGTH: 530
<212> TYPE: PRT
<213> ORGANISM: Artificial Sequence
<220> FEATURE:
<223> OTHER INFORMATION: Arachis hypogea

<400> SEQUENCE: 6

Met Ala Lys Leu Leu Glu Leu Ser Phe Cys Phe Cys Phe Leu Val Leu
1               5                   10                  15

Gly Ala Ser Ser Ile Ser Phe Arg Gln Gln Pro Glu Glu Asn Ala Cys
            20                  25                  30

Gln Phe Gln Arg Leu Asn Ala Gln Arg Pro Asp Asn Arg Ile Glu Ser
        35                  40                  45

Glu Gly Gly Tyr Ile Glu Thr Trp Asn Pro Asn Gln Glu Phe Glu
    50                  55                  60

Cys Ala Gly Val Ala Leu Ser Arg Leu Val Leu Arg Arg Asn Ala Leu
65                  70                  75                  80

Arg Arg Pro Phe Tyr Ser Asn Ala Pro Gln Glu Ile Phe Ile Gln Gln

```
                    85                  90                  95
Gly Arg Gly Tyr Phe Gly Leu Ile Phe Pro Gly Cys Pro Ser Thr Tyr
                100                 105                 110
Glu Glu Pro Ala Gln Gln Gly Arg Arg Ser Gln Ser Gln Arg Pro Pro
            115                 120                 125
Ile Arg Leu Gln Gly Glu Asp Gln Ser Gln Gln Gln Arg Asp Ser His
        130                 135                 140
Gln Lys Val His Arg Phe Asp Glu Gly Asp Leu Ile Ala Val Pro Thr
145                 150                 155                 160
Gly Val Ala Phe Trp Leu Tyr Asn Asp His Asp Thr Asp Val Val Ala
                165                 170                 175
Val Ser Leu Thr Asp Thr Asn Asn Asp Asn Gln Leu Asp Gln Phe
                180                 185                 190
Pro Arg Arg Phe Asn Leu Ala Gly Asn His Glu Gln Glu Phe Leu Arg
            195                 200                 205
Tyr Gln Gln Ser Arg Gln Ser Arg Arg Ser Leu Pro Tyr Ser
        210                 215                 220
Pro Tyr Ser Pro Gln Ser Gln Pro Arg Gln Glu Glu Arg Glu Phe Ser
225                 230                 235                 240
Pro Arg Gly Gln His Ser Arg Arg Glu Arg Ala Gly Gln Glu Glu Glu
                245                 250                 255
Asn Glu Gly Gly Asn Ile Phe Ser Gly Phe Thr Pro Glu Phe Leu Glu
                260                 265                 270
Gln Ala Phe Gln Val Asp Asp Arg Gln Ile Val Gln Asn Leu Arg Gly
            275                 280                 285
Glu Asn Glu Ser Glu Glu Glu Gly Ala Ile Val Thr Val Arg Gly Gly
        290                 295                 300
Leu Arg Ile Leu Ser Pro Asp Arg Lys Arg Arg Ala Asp Glu Glu Glu
305                 310                 315                 320
Glu Tyr Asp Glu Asp Glu Tyr Glu Tyr Asp Glu Glu Asp Arg Arg Arg
                325                 330                 335
Gly Arg Gly Ser Arg Gly Arg Gly Asn Gly Ile Glu Glu Thr Ile Cys
                340                 345                 350
Thr Ala Ser Ala Lys Lys Asn Ile Gly Arg Asn Arg Ser Pro Asp Ile
            355                 360                 365
Tyr Asn Pro Gln Ala Gly Ser Leu Lys Thr Ala Asn Asp Leu Asn Leu
        370                 375                 380
Leu Ile Leu Arg Trp Leu Gly Pro Ser Ala Glu Tyr Gly Asn Leu Tyr
385                 390                 395                 400
Arg Asn Ala Leu Phe Val Ala His Tyr Asn Thr Asn Ala His Ser Ile
                405                 410                 415
Ile Tyr Arg Leu Arg Gly Arg Ala His Val Gln Val Val Asp Ser Asn
                420                 425                 430
Gly Asn Arg Val Tyr Asp Glu Glu Leu Gln Glu Gly His Val Leu Val
            435                 440                 445
Val Pro Gln Asn Phe Ala Val Ala Gly Lys Ser Gln Ser Glu Asn Phe
        450                 455                 460
Glu Tyr Val Ala Phe Lys Thr Asp Ser Arg Pro Ser Ile Ala Asn Leu
465                 470                 475                 480
Ala Gly Glu Asn Ser Val Ile Asp Asn Leu Pro Glu Glu Val Val Ala
                485                 490                 495
Asn Ser Tyr Gly Leu Gln Arg Glu Gln Ala Arg Gln Leu Lys Asn Asn
                500                 505                 510
```

```
Asn Pro Phe Lys Phe Phe Val Pro Pro Ser Gln Gln Ser Pro Arg Ala
        515                 520                 525
Val Ala
    530

<210> SEQ ID NO 7
<211> LENGTH: 10
<212> TYPE: PRT
<213> ORGANISM: Artificial Sequence
<220> FEATURE:
<223> OTHER INFORMATION: Arachis hypogea

<400> SEQUENCE: 7

Ala Lys Ser Ser Pro Tyr Gln Lys Lys Thr
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Arachis hypogea

<400> SEQUENCE: 8

Gln Glu Pro Asp Asp Leu Lys Gln Lys Ala
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Arachis hypogea

<400> SEQUENCE: 9

Leu Glu Tyr Asp Pro Arg Leu Val Tyr Asp
1               5                   10

<210> SEQ ID NO 10
<211> LENGTH: 10
<212> TYPE: PRT
<213> ORGANISM: Artificial Sequence
<220> FEATURE:
<223> OTHER INFORMATION: Arachis hypogea

<400> SEQUENCE: 10

Gly Glu Arg Thr Arg Gly Arg Gln Pro Gly
1               5                   10

<210> SEQ ID NO 11
<211> LENGTH: 10
<212> TYPE: PRT
<213> ORGANISM: Artificial Sequence
<220> FEATURE:
<223> OTHER INFORMATION: Arachis hypogea

<400> SEQUENCE: 11

Pro Gly Asp Tyr Asp Asp Asp Arg Arg Gln
1               5                   10

<210> SEQ ID NO 12
<211> LENGTH: 10
<212> TYPE: PRT
<213> ORGANISM: Artificial Sequence
<220> FEATURE:
<223> OTHER INFORMATION: Arachis hypogea

<400> SEQUENCE: 12
```

```
Pro Arg Arg Glu Glu Gly Gly Arg Trp Gly
1               5                   10

<210> SEQ ID NO 13
<211> LENGTH: 10
<212> TYPE: PRT
<213> ORGANISM: Artificial Sequence
<220> FEATURE:
<223> OTHER INFORMATION: Arachis hypogea

<400> SEQUENCE: 13

Arg Glu Arg Glu Glu Asp Trp Arg Gln Pro
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Arachis hypogea

<400> SEQUENCE: 14

Glu Asp Trp Arg Arg Pro Ser His Gln Gln
1               5                   10

<210> SEQ ID NO 15
<211> LENGTH: 10
<212> TYPE: PRT
<213> ORGANISM: Artificial Sequence
<220> FEATURE:
<223> OTHER INFORMATION: Arachis hypogea

<400> SEQUENCE: 15

Gln Pro Arg Lys Ile Arg Pro Glu Gly Arg
1               5                   10

<210> SEQ ID NO 16
<211> LENGTH: 10
<212> TYPE: PRT
<213> ORGANISM: Artificial Sequence
<220> FEATURE:
<223> OTHER INFORMATION: Arachis hypogea

<400> SEQUENCE: 16

Thr Pro Gly Gln Phe Glu Asp Phe Phe Pro
1               5                   10

<210> SEQ ID NO 17
<211> LENGTH: 10
<212> TYPE: PRT
<213> ORGANISM: Artificial Sequence
<220> FEATURE:
<223> OTHER INFORMATION: Arachis hypogea

<400> SEQUENCE: 17

Ser Tyr Leu Gln Glu Phe Ser Arg Asn Thr
1               5                   10

<210> SEQ ID NO 18
<211> LENGTH: 10
<212> TYPE: PRT
<213> ORGANISM: Artificial Sequence
<220> FEATURE:
<223> OTHER INFORMATION: Arachis hypogea

<400> SEQUENCE: 18

Phe Asn Ala Glu Phe Asn Glu Ile Arg Arg
```

<210> SEQ ID NO 19
<211> LENGTH: 9
<212> TYPE: PRT
<213> ORGANISM: Artificial Sequence
<220> FEATURE:
<223> OTHER INFORMATION: Arachis hypogea

<400> SEQUENCE: 19

Glu Gln Glu Glu Arg Gly Arg Arg Trp
1               5

<210> SEQ ID NO 20
<211> LENGTH: 10
<212> TYPE: PRT
<213> ORGANISM: Artificial Sequence
<220> FEATURE:
<223> OTHER INFORMATION: Arachis hypogea

<400> SEQUENCE: 20

Asp Ile Thr Asn Pro Ile Asn Leu Arg Glu
1               5                   10

<210> SEQ ID NO 21
<211> LENGTH: 10
<212> TYPE: PRT
<213> ORGANISM: Artificial Sequence
<220> FEATURE:
<223> OTHER INFORMATION: Arachis hypogea

<400> SEQUENCE: 21

Asn Asn Phe Gly Lys Leu Phe Glu Val Lys
1               5                   10

<210> SEQ ID NO 22
<211> LENGTH: 10
<212> TYPE: PRT
<213> ORGANISM: Artificial Sequence
<220> FEATURE:
<223> OTHER INFORMATION: Arachis hypogea

<400> SEQUENCE: 22

Gly Thr Gly Asn Leu Glu Leu Val Ala Val
1               5                   10

<210> SEQ ID NO 23
<211> LENGTH: 10
<212> TYPE: PRT
<213> ORGANISM: Artificial Sequence
<220> FEATURE:
<223> OTHER INFORMATION: Arachis hypogea

<400> SEQUENCE: 23

Arg Arg Tyr Thr Ala Arg Leu Lys Glu Gly
1               5                   10

<210> SEQ ID NO 24
<211> LENGTH: 10
<212> TYPE: PRT
<213> ORGANISM: Artificial Sequence
<220> FEATURE:
<223> OTHER INFORMATION: Arachis hypogea

<400> SEQUENCE: 24

Glu Leu His Leu Leu Gly Phe Gly Ile Asn
1               5                   10

```
<210> SEQ ID NO 25
<211> LENGTH: 10
<212> TYPE: PRT
<213> ORGANISM: Artificial Sequence
<220> FEATURE:
<223> OTHER INFORMATION: Arachis hypogea

<400> SEQUENCE: 25

His Arg Ile Phe Leu Ala Gly Asp Lys Asp
1               5                   10

<210> SEQ ID NO 26
<211> LENGTH: 10
<212> TYPE: PRT
<213> ORGANISM: Artificial Sequence
<220> FEATURE:
<223> OTHER INFORMATION: Arachis hypogea

<400> SEQUENCE: 26

Ile Asp Gln Ile Glu Lys Gln Ala Lys Asp
1               5                   10

<210> SEQ ID NO 27
<211> LENGTH: 10
<212> TYPE: PRT
<213> ORGANISM: Artificial Sequence
<220> FEATURE:
<223> OTHER INFORMATION: Arachis hypogea

<400> SEQUENCE: 27

Lys Asp Leu Ala Phe Pro Gly Ser Gly Glu
1               5                   10

<210> SEQ ID NO 28
<211> LENGTH: 10
<212> TYPE: PRT
<213> ORGANISM: Artificial Sequence
<220> FEATURE:
<223> OTHER INFORMATION: Arachis hypogea

<400> SEQUENCE: 28

Lys Glu Ser His Phe Val Ser Ala Arg Pro
1               5                   10

<210> SEQ ID NO 29
<211> LENGTH: 10
<212> TYPE: PRT
<213> ORGANISM: Artificial Sequence
<220> FEATURE:
<223> OTHER INFORMATION: Arachis hypogea

<400> SEQUENCE: 29

Pro Glu Lys Glu Ser Pro Glu Lys Glu Asp
1               5                   10

<210> SEQ ID NO 30
<211> LENGTH: 6
<212> TYPE: PRT
<213> ORGANISM: Artificial Sequence
<220> FEATURE:
<223> OTHER INFORMATION: Arachis hypogea

<400> SEQUENCE: 30

Asp Pro Tyr Ser Pro Ser
1               5

<210> SEQ ID NO 31
```

```
<211> LENGTH: 10
<212> TYPE: PRT
<213> ORGANISM: Artificial Sequence
<220> FEATURE:
<223> OTHER INFORMATION: Arachis hypogea

<400> SEQUENCE: 31

His Ala Ser Ala Arg Gln Gln Trp Glu Leu
1               5                   10

<210> SEQ ID NO 32
<211> LENGTH: 10
<212> TYPE: PRT
<213> ORGANISM: Artificial Sequence
<220> FEATURE:
<223> OTHER INFORMATION: Arachis hypogea

<400> SEQUENCE: 32

Gln Trp Glu Leu Gln Gly Asp Arg Arg Cys
1               5                   10

<210> SEQ ID NO 33
<211> LENGTH: 10
<212> TYPE: PRT
<213> ORGANISM: Artificial Sequence
<220> FEATURE:
<223> OTHER INFORMATION: Arachis hypogea

<400> SEQUENCE: 33

Asp Arg Arg Cys Gln Ser Gln Leu Glu Arg
1               5                   10

<210> SEQ ID NO 34
<211> LENGTH: 10
<212> TYPE: PRT
<213> ORGANISM: Artificial Sequence
<220> FEATURE:
<223> OTHER INFORMATION: Arachis hypogea

<400> SEQUENCE: 34

Leu Arg Pro Cys Glu Gln His Leu Met Gln
1               5                   10

<210> SEQ ID NO 35
<211> LENGTH: 10
<212> TYPE: PRT
<213> ORGANISM: Artificial Sequence
<220> FEATURE:
<223> OTHER INFORMATION: Arachis hypogea

<400> SEQUENCE: 35

Lys Ile Gln Arg Asp Glu Asp Ser Tyr Glu
1               5                   10

<210> SEQ ID NO 36
<211> LENGTH: 10
<212> TYPE: PRT
<213> ORGANISM: Artificial Sequence
<220> FEATURE:
<223> OTHER INFORMATION: Arachis hypogea

<400> SEQUENCE: 36

Tyr Glu Arg Asp Pro Tyr Ser Pro Ser Gln
1               5                   10

<210> SEQ ID NO 37
<211> LENGTH: 10
<212> TYPE: PRT
```

```
<213> ORGANISM: Artificial Sequence
<220> FEATURE:
<223> OTHER INFORMATION: Arachis hypogea

<400> SEQUENCE: 37

Ser Gln Asp Pro Tyr Ser Pro Ser Pro Tyr
1               5                   10

<210> SEQ ID NO 38
<211> LENGTH: 10
<212> TYPE: PRT
<213> ORGANISM: Artificial Sequence
<220> FEATURE:
<223> OTHER INFORMATION: Arachis hypogea

<400> SEQUENCE: 38

Asp Arg Leu Gln Gly Arg Gln Gln Glu Gln
1               5                   10

<210> SEQ ID NO 39
<211> LENGTH: 10
<212> TYPE: PRT
<213> ORGANISM: Artificial Sequence
<220> FEATURE:
<223> OTHER INFORMATION: Arachis hypogea

<400> SEQUENCE: 39

Lys Arg Glu Leu Arg Asn Leu Pro Gln Gln
1               5                   10

<210> SEQ ID NO 40
<211> LENGTH: 10
<212> TYPE: PRT
<213> ORGANISM: Artificial Sequence
<220> FEATURE:
<223> OTHER INFORMATION: Arachis hypogea

<400> SEQUENCE: 40

Gln Arg Cys Asp Leu Asp Val Glu Ser Gly
1               5                   10

<210> SEQ ID NO 41
<211> LENGTH: 15
<212> TYPE: PRT
<213> ORGANISM: Artificial Sequence
<220> FEATURE:
<223> OTHER INFORMATION: Arachis hypogea

<400> SEQUENCE: 41

Ile Glu Thr Trp Asn Pro Asn Asn Gln Glu Phe Glu Cys Ala Gly
1               5                   10                  15

<210> SEQ ID NO 42
<211> LENGTH: 15
<212> TYPE: PRT
<213> ORGANISM: Artificial Sequence
<220> FEATURE:
<223> OTHER INFORMATION: Arachis hypogea

<400> SEQUENCE: 42

Gly Asn Ile Phe Ser Gly Phe Thr Pro Glu Phe Leu Glu Gln Ala
1               5                   10                  15

<210> SEQ ID NO 43
<211> LENGTH: 15
<212> TYPE: PRT
<213> ORGANISM: Artificial Sequence
<220> FEATURE:
```

<223> OTHER INFORMATION: Arachis hypogea

<400> SEQUENCE: 43

Val Thr Val Arg Gly Gly Leu Arg Ile Leu Ser Pro Asp Arg Lys
1               5                   10                  15

<210> SEQ ID NO 44
<211> LENGTH: 15
<212> TYPE: PRT
<213> ORGANISM: Artificial Sequence
<220> FEATURE:
<223> OTHER INFORMATION: Arachis hypogea

<400> SEQUENCE: 44

Asp Glu Asp Glu Tyr Glu Tyr Asp Glu Glu Asp Arg Arg Arg Gly
1               5                   10                  15

<210> SEQ ID NO 45
<211> LENGTH: 10
<212> TYPE: PRT
<213> ORGANISM: Artificial Sequence
<220> FEATURE:
<223> OTHER INFORMATION: Arachis hypogea

<400> SEQUENCE: 45

Glu Gln Glu Phe Leu Arg Tyr Gln Gln Gln
1               5                   10

<210> SEQ ID NO 46
<211> LENGTH: 10
<212> TYPE: PRT
<213> ORGANISM: Artificial Sequence
<220> FEATURE:
<223> OTHER INFORMATION: Arachis hypogea

<400> SEQUENCE: 46

Phe Thr Pro Glu Phe Leu Glu Gln Ala Phe
1               5                   10

<210> SEQ ID NO 47
<211> LENGTH: 10
<212> TYPE: PRT
<213> ORGANISM: Artificial Sequence
<220> FEATURE:
<223> OTHER INFORMATION: Arachis hypogea

<400> SEQUENCE: 47

Glu Tyr Glu Tyr Asp Glu Glu Asp Arg Arg
1               5                   10

<210> SEQ ID NO 48
<211> LENGTH: 10
<212> TYPE: PRT
<213> ORGANISM: Artificial Sequence
<220> FEATURE:
<223> OTHER INFORMATION: Arachis hypogea

<400> SEQUENCE: 48

Leu Tyr Arg Asn Ala Leu Phe Val Ala His
1               5                   10

<210> SEQ ID NO 49
<211> LENGTH: 11
<212> TYPE: PRT
<213> ORGANISM: Artificial Sequence
<220> FEATURE:
<223> OTHER INFORMATION: Arachis hypogea

```
<400> SEQUENCE: 49

Met Ala Ser Met Thr Gly Gly Gln Gln Met Gly
1               5                   10

<210> SEQ ID NO 50
<211> LENGTH: 6
<212> TYPE: PRT
<213> ORGANISM: Artificial Sequence
<220> FEATURE:
<223> OTHER INFORMATION: Arachis hypogea

<400> SEQUENCE: 50

His His His His His His
1               5

<210> SEQ ID NO 51
<211> LENGTH: 7
<212> TYPE: PRT
<213> ORGANISM: Artificial Sequence
<220> FEATURE:
<223> OTHER INFORMATION: Arachis hypogea

<400> SEQUENCE: 51

Arg Asp Pro Asn Ser Ser Ser
1               5

<210> SEQ ID NO 52
<211> LENGTH: 7
<212> TYPE: PRT
<213> ORGANISM: Artificial Sequence
<220> FEATURE:
<223> OTHER INFORMATION: Arachis hypogea

<400> SEQUENCE: 52

Lys Leu Ala Ala Ala Leu Glu
1               5

<210> SEQ ID NO 53
<211> LENGTH: 635
<212> TYPE: PRT
<213> ORGANISM: Artificial Sequence
<220> FEATURE:
<223> OTHER INFORMATION: Arachis hypogea

<400> SEQUENCE: 53

Met Ala Ser Met Thr Gly Gly Gln Gln Met Gly Arg Asp Pro Asn Ser
1               5                   10                  15

Ser Ser Thr His Ala Lys Ser Ser Pro Tyr Gln Lys Lys Thr Glu Asn
            20                  25                  30

Pro Cys Ala Gln Arg Cys Leu Gln Ser Cys Gln Glu Pro Asp Asp
        35                  40                  45

Leu Lys Gln Lys Ala Cys Glu Ser Arg Cys Thr Lys Leu Glu Tyr Asp
    50                  55                  60

Pro Arg Cys Val Tyr Asp Pro Arg Gly His Thr Gly Thr Thr Asn Gln
65                  70                  75                  80

Arg Ser Pro Pro Gly Glu Arg Thr Arg Gly Arg Gln Pro Gly Asp Tyr
                85                  90                  95

Asp Asp Asp Arg Arg Gln Pro Arg Arg Glu Glu Gly Gly Arg Trp Gly
            100                 105                 110

Pro Ala Gly Pro Arg Glu Arg Glu Arg Glu Glu Asp Trp Arg Gln Pro
        115                 120                 125

Arg Glu Asp Trp Arg Arg Pro Ser His Gln Gln Pro Arg Lys Ile Arg
    130                 135                 140
```

```
Pro Glu Gly Arg Glu Gly Glu Gln Glu Trp Gly Thr Pro Ser His
145                 150                 155                 160

Val Arg Glu Glu Thr Ser Arg Asn Asn Pro Phe Tyr Phe Pro Ser Arg
            165                 170                 175

Arg Phe Ser Thr Arg Tyr Gly Asn Gln Asn Gly Arg Ile Arg Val Leu
            180                 185                 190

Gln Arg Phe Asp Gln Arg Ser Arg Gln Phe Gln Asn Leu Gln Asn His
            195                 200                 205

Arg Ile Val Gln Ile Glu Ala Lys Pro Asn Thr Leu Val Leu Pro Lys
210                 215                 220

His Ala Asp Ala Asp Asn Ile Leu Val Ile Gln Gln Gly Gln Ala Thr
225                 230                 235                 240

Val Thr Val Ala Asn Gly Asn Asn Arg Lys Ser Phe Asn Leu Asp Glu
            245                 250                 255

Gly His Ala Leu Arg Ile Pro Ser Gly Phe Ile Ser Tyr Ile Leu Asn
            260                 265                 270

Arg His Asp Asn Gln Asn Leu Arg Val Ala Lys Ile Ser Met Pro Val
            275                 280                 285

Asn Thr Pro Gly Gln Phe Glu Asp Phe Pro Ala Ser Ser Arg Asp
290                 295                 300

Gln Ser Ser Tyr Leu Gln Gly Phe Ser Arg Asn Thr Leu Glu Ala Ala
305                 310                 315                 320

Phe Asn Ala Glu Phe Asn Glu Ile Arg Arg Val Leu Leu Glu Glu Asn
            325                 330                 335

Ala Gly Gly Glu Gln Glu Glu Arg Gly Gln Arg Arg Trp Ser Thr Arg
            340                 345                 350

Ser Ser Glu Asn Asn Glu Gly Val Ile Val Lys Val Ser Lys Glu His
            355                 360                 365

Val Glu Glu Leu Thr Lys His Ala Lys Ser Val Ser Lys Lys Gly Ser
            370                 375                 380

Glu Glu Glu Gly Asp Ile Thr Asn Pro Ile Asn Leu Arg Glu Gly Glu
385                 390                 395                 400

Pro Asp Leu Ser Asn Asn Phe Gly Lys Leu Phe Glu Val Lys Pro Asp
            405                 410                 415

Lys Lys Asn Pro Gln Leu Gln Asp Leu Asp Met Met Leu Thr Cys Val
            420                 425                 430

Glu Ile Lys Glu Gly Ala Leu Met Leu Pro His Phe Asn Ser Lys Ala
            435                 440                 445

Met Val Ile Val Val Asn Lys Gly Thr Gly Asn Leu Glu Leu Val
450                 455                 460

Ala Val Arg Lys Glu Gln Gln Arg Gly Arg Glu Glu Glu
465                 470                 475                 480

Asp Glu Asp Glu Glu Glu Gly Ser Asn Arg Glu Val Arg Arg Tyr
            485                 490                 495

Thr Ala Arg Leu Lys Glu Gly Asp Val Phe Ile Met Pro Ala Ala His
            500                 505                 510

Pro Val Ala Ile Asn Ala Ser Ser Glu Leu His Leu Gly Phe Gly
            515                 520                 525

Ile Asn Ala Glu Asn Asn His Arg Ile Phe Leu Ala Gly Asp Lys Asp
            530                 535                 540

Asn Val Ile Asp Gln Ile Glu Lys Gln Ala Lys Asp Leu Ala Phe Pro
545                 550                 555                 560

Gly Ser Gly Glu Gln Val Glu Lys Leu Ile Lys Asn Gln Lys Glu Ser
```

```
                    565                 570                 575
His Phe Val Ser Ala Arg Pro Gln Ser Gln Ser Gln Ser Pro Ser Ser
                580                 585                 590

Pro Glu Lys Glu Ser Pro Glu Lys Glu Asp Gln Glu Glu Glu Asn Gln
            595                 600                 605

Gly Gly Lys Gly Pro Leu Leu Ser Ile Leu Lys Ala Phe Asn Lys Leu
        610                 615                 620

Ala Ala Ala Leu Glu His His His His His His
625                 630                 635

<210> SEQ ID NO 54
<211> LENGTH: 5
<212> TYPE: PRT
<213> ORGANISM: Artificial Sequence
<220> FEATURE:
<223> OTHER INFORMATION: Arachis hypogea

<400> SEQUENCE: 54

Arg Gly Ser Glu Phe
1               5

<210> SEQ ID NO 55
<211> LENGTH: 5
<212> TYPE: PRT
<213> ORGANISM: Artificial Sequence
<220> FEATURE:
<223> OTHER INFORMATION: Arachis hypogea

<400> SEQUENCE: 55

Ala Ala Ala Leu Glu
1               5

<210> SEQ ID NO 56
<211> LENGTH: 167
<212> TYPE: PRT
<213> ORGANISM: Artificial Sequence
<220> FEATURE:
<223> OTHER INFORMATION: Arachis hypogea

<400> SEQUENCE: 56

Met Ala Ser Met Thr Gly Gly Gln Gln Met Gly Arg Gly Ser Glu Phe
1               5                   10                  15

Ala Arg Gln Gln Trp Glu Leu Gln Gly Asp Arg Arg Cys Gln Ser Gln
            20                  25                  30

Leu Glu Arg Ala Asn Leu Arg Pro Cys Glu Gln His Leu Met Gln Lys
        35                  40                  45

Ile Gln Arg Asp Glu Asp Ser Tyr Glu Arg Asp Pro Tyr Ser Pro Ser
    50                  55                  60

Gln Asp Pro Tyr Ser Pro Ser Pro Tyr Asp Arg Arg Gly Ala Gly Ser
65                  70                  75                  80

Ser Gln His Gln Glu Arg Cys Cys Asn Glu Leu Asn Glu Phe Glu Asn
                85                  90                  95

Asn Gln Arg Cys Met Cys Glu Ala Leu Gln Gln Ile Met Glu Asn Gln
            100                 105                 110

Ser Asp Arg Leu Gln Gly Arg Gln Gln Glu Gln Gln Phe Lys Arg Glu
        115                 120                 125

Leu Arg Asn Leu Pro Gln Gln Cys Gly Leu Arg Ala Pro Gln Arg Cys
    130                 135                 140

Asp Leu Asp Val Glu Ser Gly Gly Arg Asp Arg Asp Ala Ala Ala Leu
145                 150                 155                 160
```

```
Glu His His His His His His
                165

<210> SEQ ID NO 57
<211> LENGTH: 9
<212> TYPE: PRT
<213> ORGANISM: Artificial Sequence
<220> FEATURE:
<223> OTHER INFORMATION: Arachis hypogea

<400> SEQUENCE: 57

Val Asp Lys Leu Ala Ala Ala Leu Glu
1               5

<210> SEQ ID NO 58
<211> LENGTH: 351
<212> TYPE: PRT
<213> ORGANISM: Artificial Sequence
<220> FEATURE:
<223> OTHER INFORMATION: Arachis hypogea

<400> SEQUENCE: 58

Met Ala Ser Met Thr Gly Gly Gln Gln Met Gly Ile Ser Phe Arg Gln
1               5                   10                  15

Gln Pro Glu Glu Asn Ala Cys Gln Phe Gln Arg Leu Asn Ala Gln Arg
                20                  25                  30

Pro Asp Asn Arg Ile Glu Ser Glu Gly Gly Tyr Ile Glu Thr Trp Asn
            35                  40                  45

Pro Asn Asn Gln Glu Phe Glu Cys Ala Gly Val Ala Leu Ser Arg Leu
        50                  55                  60

Val Leu Arg Arg Asn Ala Leu Arg Arg Pro Phe Tyr Ser Asn Ala Pro
65                  70                  75                  80

Gln Glu Ile Phe Ile Gln Gln Gly Arg Gly Tyr Phe Gly Leu Ile Phe
                85                  90                  95

Pro Gly Cys Pro Ser Thr Tyr Glu Glu Pro Ala Gln Gln Gly Arg Arg
                100                 105                 110

Ser Gln Ser Gln Arg Pro Pro Ile Arg Leu Gln Gly Glu Asp Gln Ser
            115                 120                 125

Gln Gln Gln Arg Asp Ser His Gln Lys Val His Arg Phe Asp Glu Gly
        130                 135                 140

Asp Leu Ile Ala Val Pro Thr Gly Val Ala Phe Trp Leu Tyr Asn Asp
145                 150                 155                 160

His Asp Thr Asp Val Val Ala Val Ser Leu Thr Asp Thr Asn Asn Asn
                165                 170                 175

Asp Asn Gln Leu Asp Gln Phe Pro Arg Arg Phe Asn Leu Ala Gly Asn
                180                 185                 190

His Glu Gln Glu Phe Leu Arg Tyr Gln Gln Gln Ser Arg Gln Ser Arg
            195                 200                 205

Arg Arg Ser Leu Pro Tyr Ser Pro Tyr Ser Pro Gln Ser Gln Pro Arg
        210                 215                 220

Gln Glu Glu Arg Glu Phe Ser Pro Arg Gly Gln His Ser Arg Arg Glu
225                 230                 235                 240

Arg Ala Gly Gln Glu Glu Glu Asn Glu Gly Gly Asn Ile Phe Ser Gly
                245                 250                 255

Phe Thr Pro Glu Phe Leu Glu Gln Ala Phe Gln Val Asp Asp Arg Gln
                260                 265                 270

Ile Val Gln Asn Leu Arg Gly Glu Asn Glu Ser Glu Glu Glu Gly Ala
            275                 280                 285
```

```
Ile Val Thr Val Arg Gly Gly Leu Arg Ile Leu Ser Pro Asp Arg Lys
            290                 295                 300

Arg Arg Ala Asp Glu Glu Glu Tyr Asp Glu Asp Glu Tyr Glu Tyr
305                 310                 315                 320

Asp Glu Glu Asp Arg Arg Gly Arg Gly Ser Arg Gly Arg Gly Asn
                325                 330                 335

Val Asp Lys Leu Ala Ala Ala Leu Glu His His His His His His
            340                 345                 350

<210> SEQ ID NO 59
<211> LENGTH: 22
<212> TYPE: PRT
<213> ORGANISM: Artificial Sequence
<220> FEATURE:
<223> OTHER INFORMATION: Arachis hypogea

<400> SEQUENCE: 59

Met Arg Gly Arg Val Ser Pro Leu Met Leu Leu Gly Ile Leu Val
1               5                   10                  15

Leu Ala Ser Val Ser Ala
            20

<210> SEQ ID NO 60
<211> LENGTH: 20
<212> TYPE: PRT
<213> ORGANISM: Artificial Sequence
<220> FEATURE:
<223> OTHER INFORMATION: Arachis hypogea

<400> SEQUENCE: 60

Met Ala Lys Leu Thr Ile Leu Val Ala Leu Ala Leu Phe Leu Leu Ala
1               5                   10                  15

Ala His Ala Ser
            20

<210> SEQ ID NO 61
<211> LENGTH: 20
<212> TYPE: PRT
<213> ORGANISM: Artificial Sequence
<220> FEATURE:
<223> OTHER INFORMATION: Arachis hypogea

<400> SEQUENCE: 61

Met Ala Lys Leu Leu Glu Leu Ser Phe Cys Phe Cys Phe Leu Val Leu
1               5                   10                  15

Gly Ala Ser Ser
            20
```

METHODS AND REAGENTS FOR DECREASING CLINICAL REACTION TO ALLERGY

PRIORITY INFORMATION

The present application is a continuation of U.S. Ser. No. 10/899,551 filed Jul. 26, 2004, now abandoned which is a continuation-in-part of U.S. Ser. No. 09/731,375 filed Dec. 6, 2000 now U.S. Pat. No. 8,153,414 which claims the benefit of U.S. Ser. No. 60/195,035 filed Apr. 6, 2000. The present application is also a continuation-in-part of U.S. Ser. No. 10/100,303 filed Mar. 18, 2002 now abandoned. These and every other U.S. Patent Application cited herein are incorporated in their entirety by reference.

GOVERNMENT FUNDING

The United States government may have rights in this invention by virtue of grants AI-43668 and AI-01666 from the National Institute of Health.

In accordance with 37 C.F.R. §1.52(e)(5), a Sequence Listing in the form of a text file (entitled "Sequence_Listing.txt," created on Dec. 2, 2009, and 36 kilobytes) is incorporated herein by reference in its entirety.

BACKGROUND OF THE INVENTION

Allergic disease is a common health problem affecting humans and companion animals (mainly dogs and cats) alike. Allergies exist to pollens, mites, animal danders or excretions, fungi, insects, foods, latex, drugs and other substances present in the environment. It is estimated that up to 8% of young children and 2% of adults have allergic reactions just to foods alone. Some allergic reactions (especially those to insects, foods, latex and drugs) can be so severe as to be life threatening.

Allergic reactions result when an individual's immune system overreacts, or reacts inappropriately, to an encountered allergen. Typically, there is no allergic reaction the first time an individual is exposed to a particular allergen. However, it is the initial response to an allergen that primes the system for subsequent allergic reactions. In particular, the allergen is taken up by antigen presenting cells (APCs; e.g., macrophages and dendritic cells) that degrade the allergen and then display allergen fragments to T-cells. T-cells, in particular CD4+ "helper" T-cells, respond by secreting a collection of cytokines that have effects on other immune system cells. The profile of cytokines secreted by responding CD4+ T-cells determines whether subsequent exposures to the allergen will induce allergic reactions. Two classes of CD4+ T-cells (Th1 and Th2; T-lymphocyte helper type 1 and 2) influence the type of immune response that is mounted against an allergen.

The Th1-type immune response involves the stimulation of cellular immunity to allergens and is characterized by the secretion of IL-2, IL-6, IL-12, IFN-γ and TNF-β by CD4+ T helper cells and the production of IgG antibodies. Exposure of CD4+ T-cells to allergens can also activate the cells to develop into Th2 cells, which secrete IL-4, IL-5, IL-10 and IL-13. One effect of IL-4 production is to stimulate the maturation of B-cells that produce IgE antibodies specific for the allergen. These allergen-specific IgE antibodies attach to receptors on the surface of mast cells and basophils, where they act as a trigger to initiate a rapid immune response to the next exposure to allergen. When the individual encounters the allergen a second time, the allergen is quickly bound by these surface-associated IgE molecules. Each allergen typically has more than one IgE binding site, so that the surface-bound IgE molecules quickly become crosslinked to one another through their simultaneous (direct or indirect) associations with allergen. Such cross-linking induces mast cell and basophil degranulation, resulting in the release of histamines and other substances that trigger allergic reactions. Individuals with high levels of IgE antibodies are known to be particularly prone to adverse allergic reactions.

The Th1- and Th2-type responses are antagonistic. In other words, one response inhibits secretions characterized by the other immune response. Thus, therapies to control the Th1- and Th2-mediated immune responses are highly desirable to control immune responses to allergens.

Other than avoidance and drugs (e.g., antihistamines, decongestants and steroids) that 1) only treat symptoms, 2) can have unfortunate side effects and 3) often only provide temporary relief, the only currently medically accepted treatment for allergies is immunotherapy. Immunotherapy involves the repeated injection of allergen extracts, over a period of years, to desensitize a patient to the allergen. Unfortunately, traditional immunotherapy is time consuming, usually involving years of treatment and often fails to achieve its goal of desensitizing the patient to the allergen. Furthermore, it is not the recommended treatment for anaphylactic allergens including food allergens (such as peanut allergens) due to the risk of anaphylaxis.

Noon first introduced allergen injection immunotherapy in 1911, a practice based primarily on empiricism with non-standardized extracts of variable quality (Noon, *Lancet* 1:1572, 1911). More recently the introduction of standardized extracts has made it possible to increase the efficacy of immunotherapy and double-blind placebo-controlled trials have demonstrated the efficacy of this form of therapy in allergic rhinitis, asthma and bee-sting hypersensitivity (BSAC Working Party, *Clin. Exp. Allergy* 23:1, 1993). However, an increased risk of anaphylaxis has accompanied this increased efficacy. For example, initial trials of immunotherapy to food allergens has demonstrated an unacceptable safety to efficacy ratio (Oppenheimer et al., *J. Allergy Clin. Immun.* 90:256, 1992; Sampson, *J. Allergy Clin. Immun.* 90:151, 1992; and Nelson et al., *J. Allergy Clin. Immun.* 99:744, 1996). Results like these have prompted investigators to seek alternative forms of immunotherapy as well as to seek other forms of treatment.

Initial trials with allergen-non-specific anti-IgE antibodies to deplete the patient of allergen-specific IgE antibodies have shown early promise (Boulet et al., *American J. Respir. Crit. Care Med.* 155:1835, 1997; Fahy et al., *American J. Respir. Crit. Care Med.* 155:1828, 1997; and Demoly and Bousquet *American J. Resp. Crit. Care Med.* 155:1825, 1997). On the other hand, trials utilizing immunogenic peptides that represent T-cell epitopes have been disappointing (Norman et al., *J. Aller. Clin. Immunol.* 99:S127, 1997). Another form of allergen-specific immunotherapy which utilizes injection of plasmid DNA remains unproven (Raz et al., *Proc. Nat. Acad. Sci. USA* 91:9519, 1994 and Hsu et al., *Int. Immunol.* 8:1405, 1996).

There remains a need for a safe and efficacious therapy for allergies, especially anaphylactic allergies such as food allergies where traditional immunotherapy is ill advised due to risk to the patient or lack of efficacy.

SUMMARY OF THE INVENTION

The present invention provides methods and compositions for treating or preventing allergic reactions, particularly anaphylactic reactions. Methods of the present invention involve administering microorganisms to allergic subjects, where the microorganisms contain a recombinant version of the protein allergen. The recombinant version can be wild-type or may include mutations within IgE epitopes of the protein allergen. Preferably the compositions are administered rectally. Particularly preferred microorganisms are bacteria such as *E. coli*. Any allergen may be used in the inventive methods. Particularly preferred allergens are anaphylactic allergens including protein allergens found in foods, venoms, drugs and latex. The inventive compositions and methods are demonstrated in the treatment of peanut-induced anaphylaxis.

ABBREVIATIONS

The following abbreviations are used throughout the application:
APC=antigen-presenting cell.
CPE=crude peanut extract.
CT=cholera toxin.
ig=intragastric gavage.
pr=per rectal.
sc=subcutaneous.
HKE=heat-killed *E. coli*.
HKL=heat-killed *L. monocytogenes*.
P123=a mixture of equal proportions of wild-type recombinant proteins Ara h 1, Ara h 2 and Ara h 3.
MP123=a mixture of equal proportions of mutant recombinant proteins Ara h 1, Ara h 2 and Ara h 3.
NP 12=a mixture of equal proportions of native proteins Ara h 1 and Ara h 2 that have been purified from crude peanut extract.
HKE-P123=a mixture of equal proportions of heat-killed *E. coli* cells expressing wild-type Ara h 1, Ara h 2 and Ara h 3.
HKE-MP123=a mixture of equal proportions of heat-killed *E. coli* cells expressing mutant Ara h 1, Ara h 2 and Ara h 3.
SPC=splenocyte.

BRIEF DESCRIPTION OF THE DRAWING

FIG. 1 shows the nucleotide sequence of a cDNA clone of peanut allergen Ara h 1 (SEQ ID NO:1). This cDNA sequence has been deposited in GenBank under Accession No. L34402 (see also Burks et al., *J. Clin. Invest.* 96:1715, 1995).

FIG. 2 shows a full length native Ara h 1 amino acid sequence (SEQ ID NO:2). This amino acid sequence was predicted from the cDNA clone of SEQ ID NO:1.

FIG. 3 shows the nucleotide sequence of a cDNA clone of peanut allergen Ara h 2 (SEQ ID NO:3). This cDNA sequence has been deposited in GenBank under Accession No. L77197 (deposited by Stanley et al., 1996).

FIG. 4 shows a full length native Ara h 2 amino acid sequence (SEQ ID NO:4). Amino acids 1-3 of SEQ ID NO:4 are not encoded by the cDNA clone of SEQ ID NO:3. These amino acids were added based on a second cDNA clone of Ara h 2 that has been deposited in GenBank (Accession No. AY007229, see Viquez et al., *J. Allergy Clin. Immunol.* 107: 713, 2001). Also, the C-terminal amino acid predicted from SEQ ID NO:3 is a tyrosine. However, sequencing of the native protein indicates that the C-terminal amino acid is an aspartic acid as shown in SEQ ID NO:4.

FIG. 5 shows the nucleotide sequence of a cDNA clone of peanut allergen Ara h 3 (SEQ ID NO:5). This cDNA sequence has been deposited in GenBank under Accession No. AF093541 (see also Rabjohn et al., *J. Clin. Invest.* 103:535, 1999).

FIG. 6 shows a full length native Ara h 3 amino acid sequence (SEQ ID NO:6). Amino acids 110, 111, 116, 117, 129, 202 and 290 of SEQ ID NO:6 are not encoded by SEQ ID NO:5. These amino acids have been amended after some sequencing errors were noted in the original published cDNA clone sequence. The signal peptide and amino acids 21-23 of SEQ ID NO:6 are not encoded by SEQ ID NO:5. These amino acids have been added based on a second cDNA clone of Ara h 3 that has been deposited in TrEMBL (Accession No. Q9SQH7, see Kleber-Janke et al., *Int. Arch. Allergy Immunol.* 119:265, 1999). A slightly different signal peptide is also present within a third cDNA clone of Ara h 3 that has also been deposited in TrEMBL (Accession No. Q8LKN1, deposited by Viquez et al., 2002).

FIG. 7 shows the amino acid sequence of an inventive wild-type recombinant Ara h 1 allergen (SEQ ID NO:53). The numbering is based on that of the full length native Ara h 1 amino acid sequence (see FIG. 2 and SEQ ID NO:2).

FIG. 8 shows the amino acid sequence of an inventive wild-type recombinant Ara h 2 allergen (SEQ ID NO:56). The numbering is based on that of the full length native Ara h 2 amino acid sequence (see FIG. 4 and SEQ ID NO:4).

FIG. 9 shows the amino acid sequence of an inventive wild-type recombinant Ara h 3 allergen (SEQ ID NO:58). The numbering is based on that of the full length native Ara h 3 amino acid sequence (see FIG. 6 and SEQ ID NO:6). Amino acids 346-530 of SEQ ID NO:6 (the C-terminal region) were not included in this wild-type recombinant Ara h 3 since this regions lacks linear IgE epitopes.

FIG. 12 is an outline of the sensitization, desensitization and challenge protocols that were used for the ten groups of mice (G1-G10) in the experiments of Example 11. Mice were first sensitized intragastrically with peanut over an 8 week period. Mice were then treated with different compositions and via different routes 10-12 weeks after the initial sensitization. All mice were then challenged intragastrically with peanut 13 weeks after the initial sensitization.

FIG. 13 compares the average peanut-specific IgE levels at weeks 3, 8, 12, and 14 for the ten groups of mice (G1-G10) described in FIG. 12.

FIG. 14 compares the individual (symbols) and average (solid line) anaphylactic symptom scores that were determined after challenge for eight (G1-G8) of the ten groups of mice described in FIG. 12.

FIG. 15 compares the individual (symbols) and average (solid line) anaphylactic symptom scores that were determined after challenge for four (G1, and G8-G10) of the ten groups of mice described in FIG. 12.

FIG. 16 compares the individual (symbols) and average (solid line) body temperatures (° C.) that were determined after challenge for eight (G1-G8) of the ten groups of mice described in FIG. 12.

FIG. 17 compares the individual (symbols) and average (solid line) body temperatures (° C.) that were determined after challenge for four (G1, and G8-G10) of the ten groups of mice described in FIG. 12.

FIG. 18 compares the individual (symbols) and average (solid line) airway responses (peak expiratory flow in ml/min) that were determined after challenge for eight (G1-G8) of the ten groups of mice described in FIG. 12.

FIG. 19 compares the individual (symbols) and average (solid line) airway responses (peak expiratory flow in ml/min) that were determined after challenge for four (G1, and G8-G10) of the ten groups of mice described in FIG. 12.

DEFINITIONS

Figure 10A:
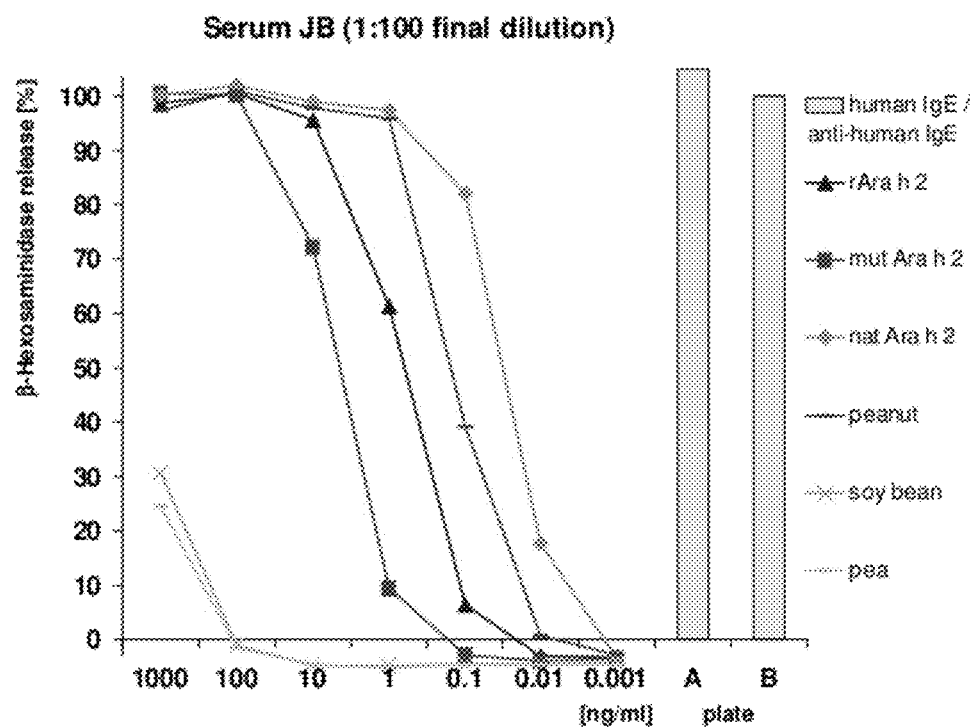
FIGS. 10A-C are graphs of allergen-specific release levels obtained with the cell-based mediator release assay of Example 7 as a function of cross-linking agent concentration (range: 0.001-1000 ng/ml).

"Animal": The term "animal", as used herein, refers to humans as well as non-human animals, including, for example, mammals, birds, reptiles, amphibians and fish. Preferably, a non-human animal is a mammal (e.g., a rodent, a mouse, a rat, a rabbit, a monkey, a dog, a cat, a primate, or a pig). An animal may be a transgenic animal.

"Antigen": The term "antigen", as used herein, refers to a molecule that elicits production of an antibody (i.e., a humoral response) and/or an antigen-specific reaction with T-cells (i.e., a cellular response) in an animal.

"Allergen": The term "allergen", as used herein, refers to a subset of antigens which elicit the production of IgE antibodies. The allergens of the present invention are protein allergens. The Appendices describe a variety of known protein allergens that are encompassed by the present invention.

"Allergic reaction": An "allergic reaction", as defined herein, is an immune response that is IgE mediated with clinical symptoms primarily involving the cutaneous (e.g., uticana, angiodema, pruritus), respiratory (e.g., wheezing, coughing, laryngeal edema, rhinorrhea, watery/itching eyes), gastrointestinal (e.g., vomiting, abdominal pain, diarrhea) and cardiovascular (i.e., if a systemic reaction occurs) systems. For the purposes of the present invention, an asthmatic reaction is considered to be a form of allergic reaction.

"Anaphylactic allergen": An "anaphylactic allergen", as defined herein, belongs to a subset of allergens that are recognized to present a risk of anaphylactic reaction in allergic individuals when encountered in its natural state (e.g., within a food extract). For example, for the purposes of the present invention, pollen allergens, mite allergens, allergens in animal danders or excretions (e.g., saliva, urine) and fungi allergens are not generally considered to be anaphylactic allergens. On the other hand, food allergens, insect allergens and rubber allergens (e.g., from latex) are generally considered to be anaphylactic allergens. Food allergens are particularly preferred anaphylactic allergens for use in the practice of the present invention. In particular, nut and legume allergens (e.g., from peanut, walnut, almond, pecan, cashew, hazelnut, pistachio, pine nut, brazil nut), dairy allergens (e.g., from egg, milk), seed allergens (e.g., from sesame, poppy, mustard), soybean, wheat and seafood allergens (e.g., from shrimp, crab, lobster, clams, mussels, oysters, scallops, crayfish) are anaphylactic food allergens according to the present invention. Particularly interesting anaphylactic allergens are those to which reactions are commonly so severe as to create a risk of death.

"Anaphylaxis" or "anaphylactic reaction": "Anaphylaxis" or an "anaphylactic reaction", as defined herein, belong to a subset of allergic reactions characterized by mast cell degranulation secondary to cross-linking of the high-affinity IgE receptor on mast cells and basophils induced by an anaphylactic allergen with subsequent mediator release and the production of severe systemic pathological responses in target organs, e.g., airway, skin digestive tract and cardiovascular system. As is known in the art, the severity of an anaphylactic reaction may be monitored, for example, by assaying cutaneous reactions, puffiness around the eyes and mouth, vomiting and/or diarrhea, followed by respiratory reactions such as wheezing and labored respiration. The most severe anaphylactic reactions can result in loss of consciousness and/or death.

"Antigen presenting cell": An "antigen presenting cell" or "APC", as defined herein, is a cell which processes and presents antigens to T-cells to elicit an antigen-specific response, e.g., macrophages and dendritic cells.

"Associated with": When two entities are "associated with" one another as described herein, they are linked by a direct or indirect covalent or non-covalent interaction. Indirect interactions might involve a third entity that is itself associated with both the first and second entities. Desirable non-covalent interactions include, for example, hydrogen bonding, van der Walls interactions, hydrophobic interactions, magnetic interactions, etc. In certain embodiments, the non-covalent interactions are ligand/receptor type interactions. Any ligand/receptor pair with a sufficient stability and specificity to operate in the context of the invention may be employed to associate two entities. To give but an example, a first entity may be covalently linked with biotin and a second entity with avidin. The strong non-covalent binding of biotin to avidin would then allow for association of the first entity with the second entity. In general, possible ligand/receptor pairs include antibody/antigen, protein/co-factor and enzyme/substrate pairs. Besides the commonly used biotin/avidin pair, these include without limitation, biotin/streptavidin, digoxigenin/anti-digoxigenin, FK506/FK506-binding protein (FKBP), rapamycin/FKBP, cyclophilin/cyclosporin and glutathione/glutathione transferase pairs. Other suitable ligand/receptor pairs would be recognized by those skilled in the art, e.g., monoclonal antibodies paired with a epitope tag such as, without limitation, glutathione-S-transferase (GST), c-myc, FLAG® and maltose binding protein (MBP) and further those described by Kessler pp. 105-152 of *Advances in Mutagenesis*" Ed. by Kessler, Springer-Verlag, 1990 and further those described in "*Affinity Chromatography: Methods and Protocols (Methods in Molecular Biology)*" Ed. by Pascal Baillon, Humana Press, 2000 and "*Immobilized Affinity Techniques*" by Hermanson et al, Academic Press, 1992.

"Epitope": The term "epitope", as used herein, refers to a binding site including an amino acid motif of between approximately six and fifteen amino acids which can be bound by an immunoglobulin (e.g., IgE, IgG, etc.) or recognized by a T-cell receptor when presented by an APC in conjunction with the major histocompatibility complex (MHC). A linear epitope is one where the amino acids are recognized in the context of a simple linear sequence. These linear epitopes are also commonly referred to as sequential epitopes in the art. A conformational epitope is one where the amino acids are recognized in the context of a particular three dimensional structure.

"Immunodominant epitope": A particular epitope is considered to be "immunodominant" if it is (i) responsible for a significant fraction of the binding for a particular immunoglobulin type (e.g., IgE) observed with the native allergen and/or (ii) recognized by the particular immunoglobulin type in a significant fraction of sensitive individuals. An immunodominant epitope is often defined in reference to the other observed epitopes. For example, all IgE epitopes in a given allergen can be assayed simultaneously (e.g., by immunoblot) and the immunodominant epitopes can be identified by their strength as compared with the other epitopes. Usually, but not always, an immunodominant epitope will contribute at least 10% of the binding reactivity observed in such a study. Alternatively or additionally, an epitope can be classified as immunodominant if it is recognized by sera of a significant fraction, preferably at least a majority, more preferably at least about 60%, 70%, 80%, 90%, 95%, 99%, or 100%, of sensitive individuals.

"Population": The term "population", as used herein, refers to human as well as non-human populations, including, for example, populations of mammals, birds, reptiles, amphibians and fish. Preferably, the non-humans are mammals (e.g., rodents, mice, rats, rabbits, monkeys, dogs, cats, primates, or pigs). As used herein the terms "individual" or "subject" encompass any member of these populations.

"Wild-type recombinant allergen": A "wild-type recombinant allergen", as defined herein, is a protein that (a) includes substantially, and in certain embodiments exactly, the same amino acid sequence as a naturally occurring protein allergen and (b) was produced in a non-natural host of the protein allergen. In certain embodiments, a recombinant allergen is produced in culture, preferably in a unicellular host and more preferably in a bacterial host. In certain embodiments all immunodominant linear IgE epitopes within the protein allergen are preserved within a "wild-type" recombinant allergen. In certain embodiments, all non-immunodominant linear IgE epitopes are also preserved. In certain embodiments, a "wild-type" recombinant allergen may include the exact same amino acid sequence as a naturally occuring protein allergen. In other embodiments, a recombinant allergen may include substantially the same amino acid sequence. It is preferred that the "wild-type" recombinant allergen include an amino acid sequence that is at least 90%, 95%, or 99% identical to the sequence of the protein allergen. In particular, a "wild-type" recombinant allergen may include a small number of amino acid mutations outside of the linear IgE epitopes. Preferably these mutations are conservative substitutions. In certain embodiments, a recombinant allergen may include one or more terminal amino acids that are absent from the naturally occuring protein allergen. In particular, terminal amino acids may be added to increase expression of the recombinant allergen, as a consequence of the vector used for expression, etc. In addition, amino acid segments that are absent from the protein allergen may be added to the amino and/or carboxyl terminus of a recombinant allergen, e.g., tags for purification, labels for detection, tags that increase the solubility of the recombinant allergen, tags that increase the stability and/or bioavailability of the recombinant allergen, etc. A proteolytic cleavage site may be introduced at the junction of the added amino acid segment and the recombinant allergen terminus to enable removal of the added segment after the recombinant allergen has been purified, absorbed, etc. Common terminal modifications used in recombinant technology are described in *Current Protocols in Molecular Biology* Ed. by Ausubel et al., John Wiley & Sons, New York, N.Y., 1989 and *Molecular Cloning: A Laboratory Manual* Ed. by Sambrook et al., Cold Spring Harbor Press, Plainview, N.Y., 1989.

Further, it will be appreciated that the amino acid sequence of a protein allergen encountered by an APC in vivo (i.e., within an exposed animal) may, in certain cases, differ from the full length amino acid sequence that is encoded by a cDNA clone of the naturally occuring protein allergen. It is to be understood that the methods of the present invention encompass the preparation and testing of recombinant versions of these naturally occuring "non-full length" protein allergens. For example, in certain embodiments, a protein allergen may include a terminal signal peptide that is cleaved in the natural host after translation of the full length protein. In addition, in other embodiments APCs may encounter digestion fragments of the full length protein allergen. This is particularly the case for food allergens that must negotiate the acidic environment of the stomach and a variety of proteolytic enzymes on their journey from ingestion to absorption.

"Mutant recombinant allergen": A "mutant recombinant allergen", as defined herein, has the same properties as a "wild-type recombinant allergen" (defined above) expect that it further includes one or more mutations within one or more IgE epitopes. In certain preferred embodiments, the one or more mutations are located within one or more linear IgE epitopes of the naturally occuring allergen. Preferably the mutations reduce IgE binding to the one or more IgE epitopes.

"Reduced allergic (or anaphylactic) reaction": A "reduced allergic (or anaphylactic) reaction", as defined herein, involves a decrease in the clinical symptoms that are associated with exposure to an allergen (or anaphylactic allergen), when exposure occurs via the route through which an individual would naturally encounter the allergen (or anaphylactic allergen), e.g., via cutaneous, respiratory, gastrointestinal, ocular, nasal, aural, etc. exposure or via a subcutaneous injection (e.g., in the form of a bee sting) depending on the nature of the allergen (or anaphylactic allergen).

"Th1 response" and "Th2 response": Certain preferred compositions of the present invention are characterized by their ability to suppress a Th2 response and/or to stimulate a Th1 response preferentially as compared with their ability to stimulate a Th2 response. Th1 and Th2 responses are well-established alternative immune system responses that are characterized by the production of different collections of cytokines and/or cofactors. For example, Th1 responses are generally associated with production of cytokines such as IL-1$\beta$, IL-2, IL-12, IL-18, IFN-$\alpha$, IFN-$\gamma$, TNF-$\beta$, etc; Th2 responses are generally associated with the production of cytokines such as IL-4, IL-5, IL-10, etc. The extent of T-cell subset suppression or stimulation may be determined by any available means including, for example, intra-cytoplasmic cytokine determination. In preferred embodiments of the invention, Th2 suppression is assayed, for example, by quantitation of IL-4, IL-5, and/or IL-13 in stimulated T-cell culture supernatant or by assessment of T-cell intra-cytoplasmic (e.g., by protein staining or analysis of mRNA) IL-4, IL-5, and/or IL-13. Similarly, in preferred embodiments of the invention, Th1 stimulation is assayed, for example, by quantitation of IFN-$\alpha$, IFN-$\gamma$, IL-2, IL-12, and/or IL-18 in activated T-cell culture supernatant or by assessment of intra-cytoplasmic levels of these cytokines.

DETAILED DESCRIPTION OF CERTAIN EMBODIMENTS OF THE INVENTION

The present application references various patents, patent applications and published references. The contents of each such reference are hereby incorporated by reference.

The present invention provides methods and compositions for treating or preventing allergic reactions. It is an aspect of the present invention that undesirable allergic reactions are treated or prevented by administering microorganisms that express recombinant allergens of interest. In certain preferred embodiments, the invention provides methods for treating anaphylaxis including anaphylactic reactions to food allergens. In some embodiments, IgE epitopes within the recombinant allergens are mutated to reduce binding to IgE antibodies. In certain embodiments the microorganisms are bacteria, preferably *E. coli*. The present invention encompasses the finding that subcutaneous and preferably rectal administration of the inventive compositions has a potent and persistent, therapeutic effect on allergy. Examples 1-14 describe the preparation and use of inventive compositions in the treatment of peanut-induced anaphylaxis in a mouse model. As described in detail below, peanut-induced anaphylaxis is the gold-standard of allergies—it is rarely outgrown and until the present invention there was no known treatment.

A. Host Microorganisms

Any microorganism capable of expressing recombinant allergens may be used as a delivery vehicle in accordance with the present invention. Such microorganisms include but are not limited to bacteria, viruses, fungi (including yeast), algae and protozoa. Bacteria are preferred, particularly bacteria such as *E. coli* that naturally colonize within humans, e.g., in the gastrointestinal tract.

Generally, microorganisms are single cell, single spore or single virion organisms. Microorganisms that can be genetically manipulated to produce a desired recombinant allergen are preferred (e.g., see Ausubel et al., *Current Protocols in Molecular Biology*. Wiley and Sons, Inc. 1999, incorporated herein by reference). Genetic manipulation includes mutation of the host genome, insertion of genetic material into the host genome, deletion of genetic material from the host genome, transformation of the host with extrachromosomal genetic material, transformation with linear plasmids, transformation with circular plasmids, insertion of genetic material into the host (e.g., injection of mRNA), insertion of transposons, and/ or chemical modification of genetic material. Methods for constructing nucleic acids (including an expressible gene), and introducing such nucleic acids into an expression system to express the encoded protein are well established in the art (see, for example, Sambrook et al., *Molecular Cloning: A Laboratory Manual,* 2nd Ed., Cold Spring Harbor Laboratory Press, Cold Spring Harbor, N.Y., 1989, incorporated herein by reference).

Some of the motivations for utilizing a microorganism for delivering recombinant allergens include (i) integrity of the delivery system prior to endocytosis and avoidance of accidental exposure to IgE antibodies, (ii) known mechanisms of endocytosis (often including targeting to particular cell types), (iii) ease of production of the delivered recombinant allergens, (iv) experimental accessibility of the organisms, including ease of genetic manipulation, (v) ability to guarantee release (e.g., by secretion) of the recombinant allergen after endocytosis, and (vi) the possibility that the encapsulating organism will also act as an adjuvant (e.g., *L. monocytogenes, E. coli*, etc.).

As demonstrated in the Examples, use of microorganisms such as bacteria as therapeutic delivery vehicles in accordance with the present invention offers many advantages over delivery of allergens that are not encapsulated inside microorganisms. First, encapsulation reduces exposure of the recombinant allergen to IgE antibodies and thereby provides protection from IgE-mediated allergic responses. Second, a range of microorganisms are known to act as adjuvants that downregulate Th2-type responses and/or upregulate Th1-type responses (for a review, see for example, Freytag et al. *Curr Top Microbiol Immunol* 236:215-36, 1999).

As noted, bacteria are preferred microorganisms of the present invention. Generally, bacteria are classified as gram-negative or gram-positive depending on the structure of the cell walls. Those skilled in the art are capable of identifying gram-negative and gram-positive bacteria which may be used to express recombinant allergens in accordance with the present invention. Non-limiting examples of genera and species of gram-negative bacteria include *Escherichia coli, Vibro cholera, Salmonella, Listeria, Legionella, Shigella, Yersenia, Citrobacter, Enterobacter, Klebsiella, Morganella, Proteus, Providencia, Serratia, Plesiomonas*, and *Aeromonas*. Non-limiting examples of genera and species of gram-positive bacteria which may be used in the present invention include *Bacillus subtilis, Sporolactobacillus, Clostridium, Arthrobacter, Micrococcus, Mycobacterium, Peptococcus, Peptostreptococcus*, and *Lactococcus*.

Gram-negative bacterial systems for use as delivery vehicles are known and may be used in the present invention. For example, *E. coli* is a well-studied bacteria, and methods of protein expression in *E. coli* are well-established. Most strains of *E. coli* have the advantage of being non-pathogenic since *E. coli* is found naturally in the gut. Therefore, *E. coli* is preferred as a delivery vehicle in the present invention and was employed in the Examples. In addition, Calderwood et al. (U.S. Pat. No. 5,747,028) utilize *Vibrio cholerae* as a delivery vehicle for production of antigens for use as a live vaccine against infectious organisms. Miller and Mekalanos (U.S. Pat. No. 5,731,196) utilize *Salmonella* as delivery vehicle for production of antigens for use as a live vaccine against infectious organisms. Hess et al. (*Proc. Natl. Acad. Sci. USA* 93:1458-1463, 1996) utilize recombinant attenuated *Salmonella* which secretes antigenic determinants of *Listeria* as a live vaccine to protect against listeriosis. Donner et al. (WO 98/50067) utilize attenuated *Salmonella typhimurium* as a gram-negative host for secretion of polypeptides for controlling fertility and also teach that other attenuated gram-negative strains including *Yersinia* may be used to express and secrete such polypeptides. Gram-positive bacteria have also been studied as delivery vehicles for proteins (e.g., see WO 97/14806 that describes the use of *Lactococcus*).

In another preferred embodiment, yeast are used as protein delivery microorganisms. It is well known that yeast are amenable to genetic manipulation to express a protein or proteins of choice (Ausubel et al., supra). Furthermore, in general most yeast are non-pathogenic. Without limitation to these species, two well-characterized species of yeast are the budding yeast *Saccharomyces cerevisiae*, and the fission yeast, *Schizosaccharomyces pombe*. Moreover, the administration of yeast that express protein antigens to alter an immune response has been studied (e.g., see U.S. Pat. No. 5,830,463).

Microorganisms of the present invention may be administered to a subject as live or dead microorganisms. Preferably if the microorganisms are administered as live microorganisms, they are non-pathogenic or attenuated pathogenic microorganisms. Use of non-pathogenic, attenuated and/or killed microorganisms reduces or eliminates toxicity which may be associated with the bacteria. For applications of the invention where live microorganisms are administered to individuals, preferably the microorganisms are attenuated and/or are administered in suitable encapsulation materials to decrease immune responses to the microorganism. Generally, attenuation involves genetically modifying the infectious pathogenic microorganism to reduce or eliminate the infectious ability of the microorganism. Preferably, the microorganism is attenuated such that an individual inoculated with the microorganism does not suffer any cytotoxic effects from the presence of the microorganism. Particularly preferred attenuated microorganisms are infectious intracellular pathogens which are phagocytosed by APCs in individuals who are exposed to the microorganism. Examples of microorganisms which are intracellular pathogens include *Salmonella, Mycobacterium, Leishmania, Legionella, Listeria*, and *Shigella.*

In certain preferred embodiments, the microorganisms of the present invention are administered to subjects after killing the microorganisms. Any method of killing the microorganisms may be utilized that does not greatly alter the expressed polypeptides. Methods of killing microorganism include but are not limited to using heat, antibiotics, chemicals such as iodine, bleach, ozone, and alcohols, radioactivity (i.e., irradiation), UV light, electricity, and pressure. Preferred methods of killing microorganisms are reproducible and kill at least 99% of the microorganisms. Particularly preferred is the use of heat above 50° C. for a period of time that kills greater than 99% of the cells and preferably 100% of the cells.

B. Protein Allergens

In general, recombinant versions of any naturally occuring protein allergen may be expressed in a microorganism of the present invention. The recombinant versions can be "wild-type" or "mutant" versions of the natural allergen. Without limitation, preferred natural protein allergens are anaphylactic allergens, including those found in certain foods, venoms, drugs or rubber. Food allergens are particularly preferred. In particular, nut and legume allergens (e.g., from peanut, walnut, almond, pecan, cashew, hazelnut, pistachio, pine nut, brazil nut), dairy allergens (e.g., from egg, milk), seed allergens (e.g., from sesame, poppy, mustard), soybean, wheat and seafood allergens (e.g., from shrimp, crab, lobster, clams, mussels, oysters, scallops, crayfish) are preferred food allergens of the present invention.

The Appendices that are attached hereto present a representative and non-limiting list of certain known protein allergens that may be used in the present invention including numerous anaphylactic and food allergens. This list was adapted from the Danish Biotechnological Database ("Bio-Base") which is maintained by the University of Aarhus, Denmark. As indicated, amino acid sequences are known for many of these proteins, either through knowledge of sequences of their cognate genes or through direct knowledge of protein sequences, or both. In addition, to date, over two thousand protein allergen sequences have been deposited in the protein and gene databases that are maintained by the National Center for Biotechnology Information (NCBI, Bethesda, Md.). Thus, it will be appreciated that a large number of naturally occuring allergens are known and that recombinant allergens corresponding to these are readily identifiable. It will also be appreciated that these recombinant allergens are readily expressed within inventive microorganisms. Methods for preparing recombinant proteins in microorganisms are well known in the art and are described in great detail in the Examples and further in *Current Protocols in Molecular Biology* Ed. by Ausubel et al., John Wiley & Sons, New York, N.Y., 1989 and *Molecular Cloning: A Laboratory Manual* Ed. by Sambrook et al., Cold Spring Harbor Press, Plainview, N.Y., 1989.

A variety of methods are also known for isolating, cloning and sequencing unknown protein allergens including, but not limited to, those methods described in the references cited in the Appendices; those described in reviews, e.g., Crameri, *Allergy* 56:S30, 2001; Appenzeller et al., *Arch. Immunol. Ther. Exp.* 49:19, 2001; Deviller, *Allerg. Immunol. (Paris)* 27:316, 1995; and Scheiner, *Int. Arch. Allergy Immunol.* 98:93, 1992; and those described in reference collections, e.g., *Current Protocols in Molecular Biology* Ed. by Ausubel et al., John Wiley & Sons, New York, N.Y., 1989 and *Molecular Cloning: A Laboratory Manual* Ed. by Sambrook et al., Cold Spring Harbor Press, Plainview, N.Y., 1989.

The amino acid sequence of a protein allergen encountered in vivo (i.e., within an exposed animal) may, in certain cases, differ from the full length amino acid sequence that is encoded by a cDNA clone of the natural allergen. The methods of the present invention encompass the use of microorganisms that express recombinant versions of these non-full length protein allergens. For example, in certain embodiments a protein allergen may include a signal peptide that is cleaved in the natural host after translation of the full length protein. In certain preferred embodiments of the present invention amino acid sequences predicted from cDNA clones may be compared with N-terminal and/or C-terminal sequences determined by amino acid sequencing of the isolated allergen. As is well known in the art, such comparisons allow post-translational modifications (e.g., signal peptide cleavages) to be identified and hence mature allergens to be fully characterized.

In addition, in other embodiments digestion fragments of the full length protein allergen may be encountered in vivo. This is particularly common for food allergens that must negotiate the acidic environment of the stomach and a variety of proteolytic enzymes on their journey from ingestion to absorption. Accordingly, in certain embodiments, it may prove advantageous to identify and characterize the amino acid sequence of an allergen or its fragments subsequent to processing within an animal. In certain embodiments, allergen fragments may be isolated from in vivo samples using standard purification techniques (e.g., samples taken from the blood, the gastrointestinal tract, etc. of an animal that has been exposed to the protein allergen). Alternatively, the fragments can be generated in vitro, e.g., by proteolytic digestion of a protein allergen by one or more gastric, pancreatic and intestinal proteases such as pepsin, parapepsin I and II, trypsin, chymotrypsin, elastase, carboxypeptidases, enterokinase, aminopeptidases and/or dipeptidases.

As noted above, in certain embodiments the recombinant allergens are "wild-type" versions of the natural allergen. In other embodiments the recombinant allergens are "mutant" versions of the natural allergen. Preferably the mutant recombinant allergens bind less IgE than the naturally occuring allergen. This is generally achieved by mutation of one or more IgE epitopes of the natural allergen as described in Examples 1-3 and in WO 97/24139, WO 99/38978, and WO 01/40264 each of which is incorporated herein by reference.

Briefly, the majority of natural occuring protein allergens include conformational and/or linear epitopes for immunoglobulins such as IgE. These have been identified for a large number of known allergens. For example, without limitation, IgE epitopes have been identified for allergens from the following foods: cow milk (Ball et al., *Clin. Exp. Allergy* 24:758, 1994), egg (Cooke and Sampson, *J. Immunol.* 159:2026, 1997), codfish (Aas and Elsayed, *Dev. Biol. Stand.* 29:90, 1975), hazel nut (Elsayed et al., *Int. Arch. Allergy Appl. Immunol.* 89:410, 1989), peanut (Burks et al., *Eur. J. Biochemistry* 245:334, 1997 and Stanley et al., *Arch. Biochem. Biophys.* 342:244, 1997), soybean (Herein et al., *Int. Arch. Allergy Appl. Immunol.* 92:193, 1990), and shrimp (Shanty et al., *J. Immunol.* 151:5354, 1993).

A variety of methods are also known in the art that can be used to identify the amino acids involved in conformational and/or linear epitopes (e.g., see Benjamin et al., *Ann. Rev. Immunol.* 2:67, 1984; Atassi, *Eur. J. Biochem.* 145:1, 1984; Getzoff et al., *Adv. Immunol.* 43:1, 1988; Jemmerson and Paterson, *Biotechniques* 4:18, 1986; Geysen et al., *J. Immunol. Methods* 102:259, 1987; see also, *Current Protocols in Immunology* Ed. by Coligan et al., John Wiley & Sons, New York, N.Y., 1991).

For example, conformational epitopes can be determined using phage display libraries (see, for example, Eichler and Houghten, *Molecular Medicine Today* 1:174, 1995 and Jensen-Jarolim et al., *J. Appl. Clin. Immunol.* 101:5153a, 1997) and by cross-linking antibodies to whole protein or protein fragments, typically antibodies obtained from a pooled patient population known to be allergic to the natural allergen. Once some or all of the conformational IgE epitopes are known, it is possible to modify one or more of the amino acids that comprise the epitope(s), using site directed mutagenesis by any of a number of techniques.

Similarly, linear epitopes can be determined using a technique commonly referred to as "scanning" (see Geysen et al., 1987, supra). As described in greater detail in Examples 1-3, the approach uses collections of overlapping peptides that span the entire length of the allergen. The peptides may be chosen such that they span the length of the amino acid sequence predicted from a cDNA clone; the length of the mature protein (i.e., including any post-translational modifications); or the length of an allergen fragment (e.g., a digestion resistant fragment). The approximate location of linear epitopes within a given amino acid sequence can, for example, be determined using peptides that are 6-15 amino acids in length and offset by 1-5 residues. It is to be understood that peptides having any length and offset may be used according to the present invention; however, the use of longer peptides decreases the resolution of individual epitopes and the use of shorter peptides increases the risk of missing an epitope. For long amino acid sequences, where cost of peptide synthesis is a major consideration, longer peptides and offsets are preferred. For example, peptides that include a linear IgE epitope are identified using a standard immunoassay with serum IgE taken from an individual or a pool of individuals that are known to be allergic to the allergen. It will be recognized that different individuals may generate IgE that recognize different epitopes on the same allergen. Thus, it is typically desirable to expose the peptides to a representative pool of serum samples, e.g., taken from at least 5-10, preferably at least 15, individuals with demonstrated allergy to the allergen. Comparing binding between individual sera is also advantageous since it allows immunodominant epitopes to be identified. Once peptides that include a linear IgE epitope have been identified, the specific amino acids that are involved in each of the linear IgE epitopes can be determined by repeating the process using different sets of shorter overlapping peptides that span the length of these peptides.

In preferred embodiments, once the specific amino acids that are involved in each of the linear IgE epitopes have been identified, sets of peptides that cover each linear IgE epitope are prepared that each include a single mutation (e.g., substitution, deletion or addition). As described in detail in Examples 1-3, these mutated peptides can be used to identify those amino acids that are most important for IgE binding and hence cause the largest reduction in IgE binding when mutated. Identification of these amino acid positions facilitates the preparation of mutated recombinant allergens with reduced IgE binding.

In preferred embodiments, the mutant recombinant allergen includes one or more mutations that disrupt one or more of the IgE epitopes. It is to be understood that the mutations may involve substitutions for any other amino acid and that the methods are in no way limited to substitutions with alanine or methioinine residues as described in the Examples. Additionally or alternatively, the mutations may involve one or more deletions within one or more IgE epitopes. Typically linear IgE epitopes are about 6 to about 10 amino acids in length. As shown in Examples 1-3, single mutations within these linear epitopes can dramatically reduce IgE binding. In certain embodiments 2, 3, 4, 5, 6 or more amino acids can be mutated within a linear IgE epitope of a mutant recombinant allergen.

In some embodiments, the mutant recombinant allergen retains the ability to activate T-cells and/or the capacity to bind IgG. As is well known in the art, the methods described above can also be used to detect IgG epitopes. T-cell epitopes can also be detected in this manner using, for example, a T-cell proliferation assay. In certain embodiments, it will be advantageous to compare the locations of IgE, IgG, and T-cell epitopes within the sequence of a natural allergen of interest. According to such embodiments, mutations within regions of overlap between IgE and IgG and/or T-cell epitopes are preferably avoided.

C. Inducible Systems

In certain embodiments of the invention, expression of recombinant allergens by a microorganism is regulated so that synthesis occurs at a controlled time after a live microorganism has been administered to a subject. Preferably induction of protein synthesis is regulated so that activation occurs after the microorganism is taken up by APCs and phagocytosed into the endosome. A desirable result of this regulation is that production of the allergen of interest occurs inside the APCs and therefore reduces or eliminates the exposure of the allergen to IgE molecules bound to the surface of histamine-releasing mast cells and basophils. This further reduces or eliminates the risk of anaphylaxis during administration of microorganisms that produce anaphylactic allergens.

Any method of controlling protein synthesis in the microorganism may be used in accordance with the present invention. Preferably, the method of controlling protein synthesis utilizes an inducible promoter operatively-linked to the gene of interest (e.g., a gene which encodes a signal peptide and recombinant allergen). Many systems for controlling transcription of a gene using an inducible promoter are known (e.g., see Ausubel et al. *Current Protocols in Molecular Biology*. Wiley and Sons. New York. 1999). Generally, inducible systems either utilize activation of the gene or derepression of the gene. It is preferred that the present invention utilizes activation of a gene to induce transcription. However, inducible systems using derepression of a gene may also be used in the present invention. Systems using activation are preferred because these systems are able to tightly control inactivation (and hence basal level synthesis) since derepression may result in low levels of transcription if the derepression is not tight.

Methods of inducing transcription include but are not limited to induction by the presence or absence of a chemical agent, induction using a nutrient starvation inducible promoter, induction using a phosphate starvation inducible promoter and induction using a temperature sensitive inducible promoter. A particularly preferred system for regulating gene expression utilizes tetracycline controllable expression system. Systems which utilize the tetracycline controllable expression system are commercially available (Clontech, Palo Alto, Calif.).

Another particularly preferred system for regulating gene expression utilizes an ecdysone-inducible expression system which is also commercially available (Invitrogen, Carlsbad, Calif.). The ecdysone-inducible expression system is based on the ability of ecdysone, an insect hormone, to activate gene expression by binding to the ecdysone receptor. The expression system utilizes a modified heterologous protein containing the ecdysone receptor, a viral trans activation domain (from VP16) and the retinoid X receptor derived from mammalian cells to bind to a modified ecdysone response element in the presence of a ligand such as ecdysone or an analog (e.g. muristerone A or ponasterone A).

It is preferred that inducible systems for use in the present invention utilize inducing agents that are non-toxic to mammalians cells including human cells. Furthermore, it is preferred that transcriptional inducing agents permeate cell membranes. More specifically for activation of protein synthesis in microorganisms after phagocytosis by APCs, transcriptional inducing agents must be able to pass through cell membranes of the APCs and cell membranes of the microorganism. Since both tetracycline and ecdysone are able to pass through cell membranes and are non-toxic, tetracycline-inducible systems and ecdysone-inducible systems are ideally suited for use in the present invention. However, the use of inducible systems in the present invention is not limited to those systems.

It is also preferred that microorganisms that have not been phagocytosed are killed before induction of genes expressing recombinant allergens of interest. A preferred method of killing bacteria is to use antibiotics which are not permeable to mammalian cell membranes such that only bacteria that are not phagocytosed are killed. Those having ordinary skill in the art are readily aware of antibiotics which may be used. Such antibiotics include but are not limited to penicillin, ampicillin, cephalosporin, griseofulvin, bacitracin, polymyxin b, amphotericin b, erythromycin, neomycin, streptomycin, tetracycline, vancomycin, gentamicin, and rifamycin. The use of antibiotics in accordance with the present embodiment reduces or eliminates the production of recombinant allergens by microorganisms outside APCs. It is preferable to reduce or eliminate exposure of allergen-producing microorganisms to the immune system, especially microorganisms that secrete recombinant wild-type anaphylactic allergens, which could elicit a potentially lethal anaphylactic reaction in an individual.

D. Secretion Signals

In other embodiments of the present invention, expressed recombinant allergens (and/or immunomodulatory molecules, such as cytokines; see below) are secreted by the microorganisms. Preferably, secretion of the allergens occurs inside a mammalian cell to reduce or eliminate exposure of recombinant allergens to a subject's immune system. Secretion of recombinant allergens includes secretion into the extracellular medium and secretion into the periplasm of microorganisms such as gram-negative bacteria and yeast. Advantages of secreting recombinant allergens into the periplasm include reducing leakage of the allergens prior to phagocytosis of the microorganism. This advantage is most applicable in non-inducible systems. Advantages of secreting allergens into the extracellular medium in inducible systems include maximizing the amount of allergens available for processing by APCs after phagocytosis.

To express secreted recombinant allergens in bacteria, a variety of bacterial secretion signals known in the art may be used. For example, the Sec-dependent process in *E. coli* is one which is well known (for a review see Driessen et al. *Curr. Opin. Microbiology*. 1:216-22, 1998). In addition, the OmpA signal peptide in *E. coli* has been described by Wong and Sutherland (see U.S. Pat. No. 5,223,407). Fusion proteins containing either of these secretion signal peptides are not fully secreted by the bacteria, but rather transported across the inner membrane of the gram-negative bacteria into the periplasm. These secretion signals may be used in the present invention to transport recombinant allergens into the periplasm of bacteria. After administration of the inventive microorganisms to an individual and subsequent phagocytosis by APCs, the recombinant allergens in the periplasm are released after degradation of the outer membrane by enzymes in the endosome of the APCs. Preferably, the bacteria synthesize and secrete the polypeptides into the periplasm and are killed, preferably heat-killed, before administration. However, it is recognized that attenuated bacteria may also be used.

In another preferred embodiment, fusion proteins containing secretion signal sequences and recombinant allergen sequences are fully secreted into the extracellular medium by the microorganism after synthesis. Such secretion signals include those found in hemolysin and listeriolysin. In a particularly preferred embodiment, the hemolysin complex of *E. coli* is used to transport recombinant allergens across the inner and outer membrane of a microorganism (e.g., *E. coli, Salmonella, Shigella, Vibrio, Yersinia, Citrobacter, Serratia, Pseudomonas*) into the extracellular medium (Spreng et al. *Mol. Microbiol.* 31:1589-1601, 1999, and references therein all of which are incorporated herein by reference). Fusion of HlyAs to proteins has been shown to result in secretion of these fusion proteins utilizing the hemolysin secretion system (Blight and Holland, *Trends Biotechnol.* 12(11):450-5, 1994; Gentschev et al., *Behring Inst Mitt.* 95:57-66, 1994).

The hemolysin protein (HlyA) contains a C-terminal transport signal (HlyAs) which is approximately 50-60 amino acids in length (Hess et al., *Mol Gen Genet.* 224(2):201-8, 1990; Jarchau et al., *Mol Gen Genet.* 245(1):53-60, 1994). The HlyA protein is secreted across the inner and outer cellular membranes by the hemolysin secretion system. This complex contains three membrane proteins. Two of these proteins, HlyB and HlyD, are located in the inner membrane, and the third TolC, is located at the outer membrane. Genes encoding these proteins are part of the hemolysin operon which consists of four genes hlyC, hlyA, hlyB, and hlyD (Wagner et al., *J Bacteriol.* 154(1):200-10, 1983; Gentschev, *Gene.* 179(1):133-40, 1996). In a preferred embodiment for use of the Hly secretion system, DNA plasmids (vectors) are used to express fusion proteins containing the HlyAs signal peptide and the recombinant allergen. The genes encoding the transport complex (hlyB, and hlyD) are encoded by the same vector. It is recognized that multiple vectors can be used to encode and express these genes, or that sequences encoding these genes can be inserted into the host genome for expression. Preferably, a single vector contains the complete hemolysin operon including the hly specific promoter and an enhancer-type regulator hlyR; the HlyA gene where only the minimal polypeptide sequence necessary to transport a fusion protein is present; and the recombinant allergen of interest. TolC protein is generally produced by the host *E. coli* system. However, in systems where tolC DNA is not encoded by a host organism, tolC can be encoded by a vector.

In a particularly preferred embodiment, the secretion plasmid pMOhly1 described in WO 98/50067 ("Donner") is used to express fusion proteins containing secretion signal sequences and recombinant allergens of the invention. The secretion vector pMOhly1 contains the complete hemolysin operon including the hly specific promoter and an enhancer-type regulator hlyR. A majority of the hlyA gene has been deleted so that HlyA encodes only the 34 amino terminal and 61 carboxyl terminal amino acids (HlyA$_s$). A unique Nsi restriction enzyme site between the amino terminal and carboxyl terminal residues of HlyA facilitates the insertion of heterologous genes or gene fragments into the reading frame of HlyA$_s$. The genetic information for recombinant allergens of 10-1000 amino acids can be inserted into this secretion vector pMOhly1, which facilitates secretion in attenuated *Salmonella* and other gram-negative attenuated inoculation strains (e.g. *E. coli, Vibrio cholera, Yersina enterocolitica*). The secretion of fusion proteins using a single plasmid is described by Donner. An advantage of the hemolysin secretion system in comparison to conventional transport systems is the larger size of the fusion proteins that can be synthesized and secreted. Conventional secretion systems for the presentation of antigens are only capable of secreting relatively short peptides to the outer part of the bacterial cell (e.g., Cardenas and Clements, *Clin Microbiol Rev.* 5(3):328-42, 1992).

In certain preferred embodiments, microorganisms that secrete recombinant allergens are provided in association with an encapsulation device as described below in the context of the pharmaceutical compositions of the invention. Encapsulating the microorganisms in this manner provides an additional level of control over accidental exposure of recombinant allergens, particularly wild-type anaphylactic allergens, with IgE molecules bound to the surface of histamine-releasing mast cells and basophils. This further reduces or eliminates the risk of anaphylaxis during administration of microorganisms that produce anaphylactic allergens.

E. Pharmaceutical Compositions

As discussed above, the present invention provides microorganisms expressing recombinant versions of protein allergens that are useful for treating allergies and in particular anaphylactic allergies. Accordingly, in another aspect of the present invention, pharmaceutical compositions are provided, wherein these compositions comprise these microorganisms and a pharmaceutically acceptable carrier. Optionally the compositions include adjuvants and/or immunomodulatory molecules as discussed below. It will be appreciated that certain of the microorganisms of present invention may also be provided by combination or association with one or more other agents such as targeting agents or may be encapsulated as discussed in more detail below.

It will often be desirable to include microorganisms expressing recombinant forms of more than one protein allergen in a composition of the present invention. To give but one example, at least three different protein allergens, Ara h 1, Ara h 2 and Ara h 3, are thought to contribute to peanut allergy; >90% of individuals who are allergic to peanuts have IgE reactive with Ara h 1, >90% of allergic individuals have IgE reactive with Ara h 2 and >44% have IgE reactive with Ara h 3. As described in the Examples, inventive compositions may include a mixture of microorganisms that express recombinant forms of more than one of these proteins, or all of them. Also, it may be desirable to include recombinant forms of a variety of different kinds of protein allergens so that multiple allergies are treated simultaneously (e.g., without limitation, milk and peanut allergens, egg and peanut allergens, milk and egg allergens, etc.).

Pharmaceutically Acceptable Carriers

As used herein, the term "pharmaceutically acceptable carrier" includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. *Remington's Pharmaceutical Sciences* Ed. by Gennaro, Mack Publishing, Easton, Pa., 1995, discloses various carriers used in formulating pharmaceutical compositions and known techniques for the preparation thereof. Except insofar as any conventional carrier medium is incompatible with the microorganisms of the invention, such as by producing any undesirable biological effect or otherwise interacting in a deleterious manner with any other component(s) of the pharmaceutical composition, its use is contemplated to be within the scope of this invention. Some examples of materials which can serve as pharmaceutically acceptable carriers include, but are not limited to, sugars such as lactose, glucose and sucrose; starches such as corn starch and potato starch; cellulose and its derivatives such as hydroxypropyl cellulose, sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. Viscosity-enhancing carriers such as hydroxypropyl cellulose are preferred carriers of the invention for rectal administration (see discussion below) since they facilitate retention of the pharmaceutical composition within the rectum. In addition, in embodiments that involve rectal administration the volume of carrier that is added to the pharmaceutical composition is selected in order to maximize retention of the composition. In particular, the volume should not be so large as to jeopardize retention of the administered composition in the rectal vault.

Immunomodulatory Adjuvants or Molecules

In certain preferred embodiments of the invention, the microorganisms are provided in conjunction with one or more immunomodulatory adjuvants or molecules.

Those of ordinary skill in the art will readily appreciate preferred types of adjuvants for use with the inventive compositions. Preferred adjuvants are characterized by an ability to stimulate a Th1-type response preferentially over Th2-type response and/or to down regulate a Th2-type response. In particular, adjuvants that are known to stimulate Th2-type responses are avoided. In general, suitable adjuvants include gel-type adjuvants (e.g., aluminum hydroxide/aluminum phosphate, calcium phosphate), microbial adjuvants (e.g., immunomodulatory DNA sequences that include CpG motifs; endotoxins such as monophosphoryl lipid A; exotoxins such as cholera toxin, *E. coli* heat labile toxin, and pertussis toxin; and muramyl dipeptide); oil-emulsion and emulsifier-based adjuvants (e.g., Freund's Incomplete Adjuvant, MF59, and SAF); particulate adjuvants (e.g., liposomes, biodegradable microspheres, and saponins); and synthetic adjuvants (e.g., nonionic block copolymers, muramyl peptide analogues, polyphosphazene, and synthetic polynucleotides).

Immunomodulatory DNA sequences are adjuvants of particular interest (see, for example, U.S. Pat. No. 5,830,877; and WO96/02555, WO98/18810, WO98/16247 and WO98/40100). These immunomodulatory sequences of bacterial, viral, or invertebrate origin contain unmethylated CpG motifs and when injected into animals in conjunction with an antigen such as an allergen, appear to skew the immune response towards a Th1-type response. See, for example, Yamamoto et al., *Microbiol. Immunol.* 36:983, 1992; Krieg et al., *Nature* 374:546, 1995; Pisetsky, *Immunity* 5:303, 1996; and Zimmerman et al., *J. Immunol.* 160:3627, 1998. See also WO 00/54803, the contents of which are incorporated herein by reference. Other preferred adjuvants reported to induce Th1-type responses and not Th2-type responses include, for example, AVRIDINE™ (N,N-dioctadecyl-N'N'-bis(2-hydroxyethyl)propanediamine) available from M6 Pharmaceuticals of New York, N.Y.; niosomes (non-ionic surfactant vesicles) available from Proteus Molecular Design of Macclesfield, UK; and CRL 1005 (a synthetic ABA non-ionic block copolymer) available from Vaxcel Corporation of Norcross, Ga. Particularly preferred adjuvants are ones that induce IL-12 production, including microbial extracts such as fixed *Staphylococcus aureus, Streptococcal* preparations, *Mycobacterium tuberculosis*, lipopolysaccharide (LPS), monophosphoryl lipid A (MPLA) from gram negative bacterial lipopolysaccharides (Richards et al. *Infect Immun.* 66(6): 2859-65, 1998), *Listeria monocytogenes, Toxoplasma gondii*, and *Leishmania major*. Some polymers are also adjuvants. For example, polyphosphazenes are described in U.S. Pat. No. 5,500,161. These polymers can be used not only to encapsulate the microorganisms as described below but also to enhance the immune response to the recombinant allergen.

In general, immunomodulatory molecules include cytokines which are small proteins or biological factors (in the range of 5-20 kD) that are released by cells and have specific effects on cell-cell interaction, communication and behavior of other cells. Preferably, the cytokine(s) to be administered is/are selected to reduce production of a Th2 response. One preferred method of reducing a Th2 response is through induction of the alternative response. Cytokines that induce a Th1 response in T-cells include IL-1β, IL-2, IL-12, IL-18, IFN-α, IFN-γ and TNF-β.

In certain embodiments the immunomodulatory adjuvants and/or molecules are comprised or synthesized by the microorganisms of the invention. In other embodiments they may be provided as impure preparations (e.g., isolates of cells expressing a cytokine gene, either endogenous or exogenous to the cell) or purified preparations and mixed with the microorganisms. It is recognized that in preferred embodiments the microorganisms that are utilized to synthesize and deliver the recombinant allergens according to the present invention can act as adjuvants themselves.

Targeting Agents

Inventive compositions of the invention may desirably be associated with a targeting agent that will promote delivery to a particular desired location. In preferred embodiments of the invention, the microorganisms are targeted for uptake by APCs. For example, the microorganisms could be targeted to dendritic cells or macrophages via association with a ligand that interacts with an uptake receptor such as the mannose receptor or an Fc receptor. The microorganisms could be targeted to other APCs via association with a ligand that interacts with the complement receptor.

Alternatively or additionally, a microorganism could be targeted to particular vesicles within APCs. Those of ordinary skill in the art will appreciate that any targeting strategy should allow for proper uptake and processing of the microorganisms by the APCs.

A recombinant allergen of the present invention can be targeted by association of the microorganism with an Ig molecule, or portion thereof. Ig molecules are comprised of four polypeptide chains, two identical "heavy" chains and two identical "light" chains. Each chain contains an amino-terminal variable region and a carboxy-terminal constant region. The four variable regions together comprise the "variable domain" of the antibody; the constant regions comprise the "constant domain". The chains associate with one another in a Y-structure in which each short Y arm is formed by interaction of an entire light chain with the variable region and part of the constant region of one heavy chain and the Y stem is formed by interaction of the two heavy chain constant regions with one another. The heavy chain constant regions determine the class of the antibody molecule and mediate the molecule's interactions with class-specific receptors on certain target cells; the variable regions determine the molecule's specificity and affinity for a particular antigen.

Class-specific antibody receptors, with which the heavy chain constant regions interact, are found on a variety of different cell types and are particularly concentrated on professional antigen presenting cells (pAPCs), including dendritic cells. According to the present invention, inventive compositions may be targeted for delivery to pAPCs through association with an Ig constant domain. In one embodiment, an Ig molecule is isolated whose variable domain displays specific affinity for a protein expressed on the surface of the microorganism to be delivered and the microorganism is delivered in association with the Ig molecule. The Ig may be of any class for which there is an Ig receptor, but in certain preferred embodiments, is an IgG. Also, it is not required that the entire Ig be utilized; any piece including a sufficient portion of the Ig heavy chain constant domain is sufficient. Thus, Fc fragments and single-chain antibodies may be employed in the practice of the present invention.

In one embodiment of the invention, a protein expressed on the surface of the microorganism is prepared as a fusion molecule with at least an Ig heavy chain constant region (e.g., with an Fc fragment), so that a single fusion protein, containing both the surface protein and Ig heavy chain constant region components, is exposed on the surface of the microorganism. This embodiment allows increased flexibility because the length and character of the surface protein is not constrained by the binding requirements of the Ig variable domain cleft. Fc fragments may be prepared by any available technique including, for example, recombinant expression (which may include expression of a fusion protein) proteolytic or chemical cleavage of Ig molecules (e.g., with papain), chemical synthesis, etc.

Encapsulation

In one particularly preferred embodiment of the invention, the inventive microorganisms are provided in association with an encapsulation device (see, for example, the encapsulation devices described in U.S. Patent Publication No. 2001-0031262 A1, incorporated herein by reference). Preferred encapsulation devices are biocompatible and stable inside the body so that the microorganisms and recombinant allergens are not released until after the encapsulation device is taken up into an APC. For example, preferred systems of encapsulation are stable at physiological pH and degrade at acidic pH levels comparable to those found in the endosomes of APCs. Preferably, the encapsulation device is taken up into APC via endocytosis in clathrin-coated pits. Particularly preferred encapsulation compositions include but are not limited to ones comprised of liposomes, polylactide-co-glycolide (PLGA), chitosan, synthetic biodegradable polymers, environmentally responsive hydrogels and/or gelatin PLGA nanoparticles. Inventive microorganisms may be encapsulated in combination with one or more immunomodulatory adjuvants or molecules and targeting entities. Alternatively or additionally the encapsulation device itself may be associated with a targeting agent and/or an immunomodulatory adjuvant or molecule.

Assays for Screening Inventive Compositions

In certain embodiments, once an inventive pharmaceutical composition has been prepared it may be assayed for its allergenicity. Both in vitro and in vivo assays for assessing the allergenicity of compositions are known to those skilled in the art. Conventional in vitro assays include RAST (Sampson and Albergo, *J. Allergy Clin. Immunol.* 74:26, 1984), ELISAs (Burks et al., *N. Engl. J. Med.* 314:560, 1986), immunoblotting (Burks et al., *J. Allergy Clin. Immunol.* 81:1135, 1988), basophil histamine release assays (Nielsen, *Dan. Med. Bull.* 42:455, 1995 and du Buske, *Allergy Proc.* 14:243, 1993) and others (Hoffmann et al., *Allergy* 54:446, 1999). Additionally or alternatively, the allergenicity of a composition may be assessed using an in vivo skin test (Sampson and Albergo, *J. Allergy Clin. Immunol.* 74:26, 1984). In certain preferred embodiments, the allergenicity of an inventive composition is assessed in vivo using a suitable animal model, without limitation a sensitized mouse. The preparation and use of animal models of allergies are described in WO 00/51647 and further in the Examples. When using an animal model to assess the allergenicity of an inventive composition, objective in vivo clinical symptoms may be monitored before and after the administration to determine any change in the clinical symptoms, changes in body temperature, changes in peak expiratory flow, etc. This is described in detail in Example 10. Preferably, an inventive composition exhibits minimal or no allergenicity under these tests (e.g., as compared to control and described in Example 10). In certain embodiments, if a composition is found to exhibit unfavorable levels of allergenicity it may prove advantageous to repeat the tests after washing the composition. According to such embodiments, low levels of exposed recombinant allergen may be responsible for the observed allergenicity and a simple washing step may be sufficient to remove these from the composition.

As noted previously, certain preferred compositions of the present invention are characterized by their ability to suppress a Th2-type response and/or to stimulate a Th1-type response preferentially as compared with their ability to stimulate a Th2-type response. Th1- and Th2-type responses are well-established alternative immune system responses that are characterized by the production of different collections of cytokines and/or cofactors that can be assayed for. For example, Th1-type responses are generally associated with production of cytokines such as IL-2, IL-6, IL-12, IL-18, IFN-α, IFN-γ and TNF-β by CD4+ T helper cells and the production of IgG antibodies. Exposure of CD4+ T-cells to allergens can also activate the cells to develop into Th2 cells, which secrete IL-4, IL-5, IL-10 and IL-13. The extent of T-cell subset suppression or stimulation may be determined by any available means including, for example, intra-cytoplasmic cytokine determination. In preferred embodiments of the invention, Th2 suppression is assayed, for example, by quantitation of IL-4, IL-5, IL-10 and/or IL-13 in stimulated T-cell culture supernatant or assessment of T-cell intra-cytoplasmic (e.g., by protein staining or analysis of mRNA) IL-4, IL-5, IL-10 and/or IL-13; Th1 stimulation is assayed, for example, by quantitation of IFN-α, IFN-γ, TNF-β, IL-2, IL-6, IL-12 and/or IL-18 in activated T-cell culture supernatant or assessment of intra-cytoplasmic levels of these cytokines Suitable cytokine assays are described in greater detail in Examples 12-13.

F. Uses of Pharmaceutical Compositions

In yet another aspect, according to the methods of treatment of the present invention, an individual who suffers from or is susceptible to an allergy may be treated with a pharmaceutical composition, as described herein. It will be appreciated that an individual can be considered susceptible to allergy without having suffered an allergic reaction to the particular protein allergen in question. For example, if the individual has suffered an allergic reaction to a related protein allergen (e.g., one from the same source or one for which shared allergies are common), that individual will be considered susceptible to allergic reaction to the relevant allergen. Similarly, if members of an individual's family react to a particular protein allergen, the individual may be considered to be susceptible to allergic reaction to that protein allergen. Individuals that are susceptible to an allergy but lack any relevant medical history can also be identified by a any known methods including: a prick skin test (Sampson and Albergo, *J. Allergy Clin. Immunol.* 74:26, 1984); measurement of serum titer of allergen-specific IgE (e.g., by RAST as described in Sampson and Albergo, *J. Allergy Clin. Immunol.* 74:26, 1984, by ELISA as described in Burks et al., *N. Engl. J. Med.* 314:560, 1986 or by immunoblotting as described in Burks et al., *J. Allergy Clin. Immunol.* 81:1135, 1988); basophil histamine release assays (Nielsen, *Dan. Med. Bull.* 42:455, 1995 and du Buske, *Allergy Proc.* 14:243, 1993) and other techniques (e.g., see Hoffmann et al., *Allergy* 54:446, 1999).

In general, it is believed that the inventive compositions will be clinically useful in treating or preventing allergic reactions associated with any protein allergen, in particular anaphylactic allergens including but not limited to food allergens, insect allergens and rubber allergens.

It will be appreciated that therapy or desensitization with the inventive compositions can be used in combination with any other known therapy for allergy, e.g., without limitation, allergen-non-specific anti-IgE antibodies that deplete the patient of allergen-specific IgE antibodies (see, Boulet et al., *Am. J. Respir. Crit. Care Med.* 155:1835, 1997; Fahy et al., *Am. J. Respir. Crit. Care Med.* 155:1828, 1997; and Demoly and Bousquet, *Am J. Resp. Crit. Care Med.* 155:1825, 1997).

It will further be appreciated that the therapeutic and prophylactic methods encompassed by the present invention are not limited to treating allergic reactions in humans, but may be used to treat allergies in any animal including but not limited to mammals, e.g., bovine, canine, feline, caprine, ovine, porcine, murine and equine species.

Therapeutically Effective Dose

The invention provides methods for the treatment or prevention of allergies comprising administering a therapeutically effective amount of an inventive pharmaceutical composition comprising a microorganism expressing a recombinant allergen to an individual in need thereof, in such amounts and for such time as is necessary to achieve the desired result. It will be appreciated that this encompasses administering an inventive pharmaceutical composition as a therapeutic measure to treat an individual who suffers from an allergy or as a prophylactic measure to desensitize an individual that is susceptible to an allergy. In this context, it has recently been demonstrated that pollen immunotherapy has a prophylactic effect in reducing the development of asthma in children with seasonal rhinoconjunticivitis (see Möller et al., *J. Allergy Clin. Immunol.* 109:251-6, 2002). In certain embodiments of the present invention a "therapeutically effective amount" of the pharmaceutical composition is that amount effective for preventing an allergic reaction in an individual who suffers from an allergy or an individual who is susceptible to an allergy. The pharmaceutical compositions, according to the method of the present invention, may be administered using any amount and any route of administration effective for preventing an allergic reaction. As described below, rectal and subcutaneous administration are preferred, rectal administration being particularly preferred. Thus, the expression "amount effective for preventing an allergic reaction", as used herein, refers to a sufficient amount of pharmaceutical composition to prevent an allergic reaction. The exact dosage is chosen by the individual physician in view of the patient to be treated and the route of administration. Dosage and administration are adjusted to provide sufficient levels of the recombinant allergen or to maintain the desired effect. Additional factors which may be taken into account include the severity of the allergic reaction; age, weight and gender of the individual; diet, time and frequency of administration, therapeutic combinations, reaction sensitivities and tolerance/response to therapy. Treatment will typically be between twice a week and once a month, continuing for up to 3 months to 5 or more years, although this is highly dependent on the individual patient response. In general, therapeutically effective amounts will be in the microgram to milligram range of recombinant allergen.

In certain embodiments the dosage may be increased in steps, e.g., by doubling the dosage in a series of weekly administrations over an initial period (e.g., 4-16 weeks, preferably 6-10 weeks). As discussed in Example 14, an initial once weekly schedule of administration is a well-established immunotherapy paradigm for escalation to "maintenance" doses of immunotherapeutic extracts. In certain embodiments this may be followed with a biweekly or monthly schedule of administration at the final "high" dosage until the subject is desensitized (e.g., for 2-6 months or more, preferably 3-4 months). For example, without limitation, in certain embodiments, the compositions of the invention may be administered in increasing dosage levels until they reach about 0.1 µg to about 1,000 µg, preferably from about 1 µg to about 500 µg, more preferably 10 µg to about 100 µg of the recombinant allergen per kg of subject body weight. These dosage levels are extrapolated from those that have been shown to be safe and efficient in desensitizing peanut-allergic mice (see Examples 11-14). The increased spacing between administrations during the "maintenance" period may provide the immune system a sufficient period of time, with continued but not relentless exposure, to respond to the treatment and become desensitized. In certain embodiments it may prove advantageous to gradually decrease the dosage over time after this "maintenance" period until the patient is fully desensitized (e.g., as determined by a skin prick test, serum IgE levels, a supervised challenge with the natural allergen, etc.).

The recombinant allergens of the invention are preferably formulated in dosage unit form for ease of administration and uniformity of dosage. The expression "dosage unit form" as used herein refers to a physically discrete unit of recombinant allergen appropriate for the patient to be treated. It will be understood, however, that the total daily, weekly or monthly usage of the compositions of the present invention will be decided by the attending physician within the scope of sound medical judgment. For any inventive recombinant allergen, the therapeutically effective dose can be estimated initially either in cell culture assays or in non-human animal models, usually mice, rabbits, dogs, or pigs (e.g., see Examples 10-13). The non-human animal model is also used to achieve a desirable concentration range. Such information can then be used to determine useful doses for administration in humans (e.g., see discussion in Example 14 and above).

Administration of Pharmaceutical Compositions

After formulation with an appropriate pharmaceutically acceptable carrier in a desired dosage, the pharmaceutical compositions of this invention can be administered to humans and other mammals by a variety of routes. In particular the compositions can be administered topically (as by powders, ointments, or drops), orally, rectally, parenterally, intracisternally, intravaginally, intraperitoneally, subcutaneously, intramuscularly, intragastrically, bucally, ocularly, or nasally, depending on the severity and nature of the allergic reaction being treated or prevented. Preferably the compositions are delivered parenterally, to the gastrointestinal tract (e.g., orally or rectally) or to mucosal tissues.

The inventors have established that subcutaneous and rectal delivery are particularly suitable delivery routes for the inventive compositions. As described in the Examples, administration of heat-killed *E. coli* cells expressing mutated Ara h 1, Ara h 2 and Ara h 3 peanut allergens was found to be more effective for the desensitization of peanut-allergic mice when the composition was administered subcutaneously or rectally. In addition, while some local inflammation was observed with subcutaneous delivery none was observed with rectal delivery. Thus rectal delivery is a particularly preferred route for administration.

Compositions for rectal administration are preferably suppositories which can be prepared by mixing the microorganisms of this invention with suitable non-irritating excipients or carriers such as cocoa butter, polyethylene glycol or a suppository wax which are solid at ambient temperature but liquid at body temperature and therefore melt in the rectal vault and release the microorganisms (e.g., see Williams, *Scand. J. Gastroenterol. Suppl.* 172:60-2, 1990 and Torres-Lugo et al., *Biomaterials* 21(12):1191-6, 2000). Retention enemas and rectal catheters can also be used as is known in the art. Viscosity-enhancing carriers such as hydroxypropyl cellulose are also preferred carriers of the invention for rectal administration since they facilitate retention of the pharmaceutical composition within the rectum. Generally, the volume of carrier that is added to the pharmaceutical composition is selected in order to maximize retention of the composition. In particular, the volume should not be so large as to jeopardize retention of the administered composition in the rectal vault.

Injectable preparations (e.g., for subcutaneous administration) such as sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. Delayed absorption of a parenterally administered composition may be accomplished by dissolving or suspending the microorganisms in an oil vehicle. Injectable depot forms are made by forming microencapsule matrices of the microorganisms in biodegradable polymers such as polylactide-polyglycolide. Depending upon the ratio of microorganisms to polymer and the nature of the particular polymer employed, the rate of microorganism release can be controlled. Examples of other biodegradable polymers include poly(orthoesters) and poly(anhydrides). Depot injectable formulations are also prepared by entrapping the microorganisms in liposomes or microemulsions which are compatible with body tissues.

Liquid dosage forms for oral administration include, but are not limited to, pharmaceutically acceptable emulsions, microemulsions, solutions, suspensions, syrups and elixirs. In addition to the microorganisms, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof. Besides inert diluents, the oral compositions can also include adjuvants such as wetting agents, emulsifying and suspending agents, sweetening, flavoring and perfuming agents.

Dosage forms for topical or transdermal administration of an inventive pharmaceutical composition include ointments, pastes, creams, lotions, gels, powders, solutions, sprays, inhalants, or patches. The microorganisms are admixed under sterile conditions with a pharmaceutically acceptable carrier and any needed preservatives or buffers as may be required. The ointments, pastes, creams and gels may contain, in addition to the microorganisms of this invention, excipients such as animal and vegetable fats, oils, waxes, paraffins, starch, tragacanth, cellulose derivatives, polyethylene glycols, silicones, bentonites, silicic acid, talc, zinc oxide, or mixtures thereof.

Solid dosage forms for oral administration include capsules, tablets, pills, powders and granules. In such solid dosage forms, the microorganisms are mixed with at least one inert, pharmaceutically acceptable excipient or carrier such as sodium citrate or dicalcium phosphate and/or a) fillers or extenders such as starches, lactose, sucrose, glucose, mannitol and silicic acid, b) binders such as, for example, carboxymethylcellulose, alginates, gelatin, polyvinylpyrrolidinone, sucrose and acacia, c) humectants such as glycerol, d) disintegrating agents such as agar-agar, calcium carbonate, potato or tapioca starch, alginic acid, certain silicates and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay and i) lubricants such as talc, calcium stearate, magnesium stearate, solid polyethylene glycols, sodium lauryl sulfate and mixtures thereof.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills and granules can be prepared with coatings and shells such as enteric coatings, release controlling coatings and other coatings well known in the pharmaceutical formulating art. In such solid dosage forms the microorganisms may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the microorganisms only, or preferentially, in a certain part of the intestinal tract, optionally, in a delayed manner. Examples of embedding compositions which can be used include polymeric substances and waxes.

EXAMPLES

Allergy to peanuts is one of the most common and serious of the anaphylactic reactions to foods in terms of persistence and severity of reaction. Unlike the clinical symptoms of many other food allergies, the reactions to peanuts are rarely outgrown, therefore, most diagnosed children will have the disease for a lifetime (Sampson and Burks, *Annu. Rev. Nutr.* 16:161, 1996 and Bock, *J. Pediatr.* 107:676, 1985). The majority of cases of fatal food-induced anaphylaxis involve ingestion of peanuts (Sampson et al., *NEJM* 327:380, 1992 and Kaminogawa, *Biosci. Biotech. Biochem.* 60:1749, 1996). The only effective therapeutic option currently available for the prevention of a peanut hypersensitivity reaction is food avoidance. Unfortunately, for a ubiquitous food such as a peanut, the possibility of an inadvertent ingestion is great.

The major peanut allergen proteins Ara h 1, Ara h 2 and Ara h 3 were therefore chosen as gold-standards to illustrate various aspects of the present invention.

Ara h 1 has a molecular weight of about 63.5 kD and belongs to the vicilin family of seed storage proteins. The cloning and sequencing of Ara h 1 (Accession No. L34402 in GenBank) is described in Burks et al., *J. Clin. Invest.* 96:1715, 1995. The nucleotide sequence of a cDNA clone from that reference (cDNA clone P41b) is depicted in FIG. 1 (SEQ ID NO:1). The predicted amino acid sequence of the Ara h 1 protein encoded by cDNA clone P41b is depicted in FIG. 2 (SEQ ID NO:2).

Ara h 2 has a molecular weight of about 17 kD and belongs to the conglutin family of seed storage proteins. The cloning and sequencing of Ara h 2 (Accession No. L77197 in GenBank) is described in Stanley et al., *Arch. Biochem. Biophys.* 342:244, 1997. The nucleotide sequence of a cDNA clone from that reference (cDNA clone p38) is depicted in FIG. 3 (SEQ ID NO:3). The predicted amino acid sequence of the Ara h 2 protein encoded by cDNA clone p38 is depicted in FIG. 4 (SEQ ID NO:4).

Ara h 3 has a molecular weight of about 60 kD and belongs to the glycinin family of seed storage proteins. The cloning and sequencing of Ara h 3 (Accession No. AF093541 in GenBank) is described in Rabjohn et al., *J. Clin. Invest.* 103:535, 1999. The nucleotide sequence of a cDNA clone of Ara h 3 is depicted in FIG. 5 (SEQ ID NO:5). The predicted amino acid sequence of the protein encoded by this cDNA clone is depicted in FIG. 6 (SEQ ID NO:6).

Examples 1, 2 and 3 describe the mapping and mutational analysis of the linear IgE epitopes of Ara h 1, Ara h 2 and Ara h 3, respectively.

Example 4 describes the methods and constructs that were used to prepare and purify recombinant versions of Ara h 1, Ara h 2 and Ara h 3 (wild-type and mutant).

Example 5 describes in vitro experiments that were performed to compare the binding of wild-type Ara h 1 and mutant Ara h 1 with IgE sera from peanut-sensitive individuals.

Example 6 describes in vitro experiments that were performed to compare the binding of wild-type Ara h 2 and mutant Ara h 2 with IgE sera from peanut-sensitive individuals.

Example 7 describes in vitro cell-based mediator release experiments that were performed to compare the allergenicity of wild-type Ara h 2, mutant Ara h 2, native Ara h 2 purified from crude peanut extract, crude peanut extract, crude soybean extract and crude pea extract.

Example 8 describes in vitro experiments that were performed to compare the binding of wild-type Ara h 3 and mutant Ara h 3 with IgE sera from peanut-sensitive individuals.

Example 9 describes early in vitro and in vivo experiments that were performed to test the encapsulation of wild-type Ara h 1-3 expressed in *E. coli*.

Example 10 describes in vivo safety experiments that were performed with sensitized mice to compare their reactions when challenged with CPE, HKE-P123, HKE-MP123, P123, MP123, and NP12.

Example 11 describes in vivo desensitization experiments that were performed with sensitized mice to compare the efficacy of different desensitizing protocols (i.e., different desensitizing compositions and delivery routes). The desensitization protocols that were compared included HKE-MP123 delivered subcutaneously, HKE-MP123 delivered intragastrically, HKE-MP123 delivered rectally, MP123 delivered rectally, HKL delivered subcutaneously, and HKL-MP123 delivered subcutaneously.

Example 12 describes in vivo desensitization experiments that were performed with sensitized mice to compare the efficacy of rectally delivered HKE-MP123 and MP123.

Example 13 describes in vivo desensitization experiments that were performed with sensitized mice to assess the long-term efficacy of rectally delivered HKE-MP123.

Example 14 describes a prophetic clinical study to demonstrate the safety and efficacy of rectally delivered HKE-MP123 in the treatment of human peanut-allergic patients.

Example 1

Mapping and Mutational Analysis of the Linear IgE Epitopes of Ara h 1

1.1 Introduction

Serum IgE from patients with documented peanut hypersensitivity reactions and overlapping peptides were used to identify the IgE binding epitopes on the major peanut allergen, Ara h 1. At least twenty-three different linear IgE binding epitopes, located throughout the length of the Ara h 1 protein, were identified. All of the epitopes were 6-10 amino acids in length, but there was no obvious sequence motif shared by all peptides. Four of the peptides appeared to be immunodominant IgE binding epitopes in that they were recognized by serum from more than 80% of the patients tested and bound more IgE than any of the other Ara h 1 epitopes. Mutational analysis of the epitopes revealed that single amino acid changes had dramatic effects on IgE binding characteristics.

1.2 Materials and Methods

Serum IgE

Serum from 15 patients with documented peanut hypersensitivity reactions (mean age=25 years) was used to identify the Ara h 1 IgE binding epitopes. Each of these individuals had a positive immediate prick skin test to peanut and either a positive double-blind placebo-controlled food challenge or a convincing history of peanut anaphylaxis (laryngeal edema, severe wheezing, and/or hypotension). Representative individuals with elevated serum IgE levels (who did not have peanut-specific IgE or peanut hypersensitivity) were used as controls in these studies. In some instances, a serum pool was made by mixing equal aliquots of serum IgE from each of the 15 patients with peanut hypersensitivity. This pool was then used in immunoblot analysis experiments to determine the IgE binding characteristics of the population. At least 5 ml venous blood was drawn from each patient and allowed to clot, and the serum collected. All studies were approved by the Human Use Advisory Committee at the University of Arkansas for Medical Sciences.

Computer Analysis of Ara h 1 Sequence

Analysis of the Ara h 1 amino acid sequence (clone P41b, SEQ ID NO:2) and peptide sequences was performed on the University of Arkansas for Medical Sciences' Vax computer using the Wisconsin DNA analysis software package. The predicted antigenic regions on the Ara h 1 protein are based on algorithms developed by Jameson and Wolf (*Comput. Appl. Biosci.* 4:181-186, 1988) that relate antigenicity to hydrophilicity, secondary structure, flexibility, and surface probability.

Peptide Synthesis

Individual peptides were synthesized on a derivatised cellulose membrane using Fmoc amino acid active esters according to the manufacturer's instructions (Genosys Biotechnologies, Woodlands, Tex.). Fmoc-amino acid derivatives were dissolved in 1-methyl-2-pyrrolidone and loaded on marked spots on the membrane. Coupling reactions were followed by acetylation with a solution of 4% (v/v) acetic anhydride in N,N-dimethylformamide (DMF). After acetylation, Fmoc groups were removed by incubation of the membrane in 20% (v/v) piperdine in DMF. The membrane was then stained with bromophenol blue to identify the location of the free amino groups. Cycles of coupling, blocking, and deprotection were repeated until the peptides of the desired length were synthesized. After addition of the last amino acid in the peptide, the amino acid side chains were deprotected using a solution of dichloromethane/trifluoroacetic acid/triisobutylsilane (1/1/0.05). Membranes were either probed immediately or stored at −20° C. until needed.

IgE Binding Assay

Cellulose membranes containing synthesized peptides were incubated with the serum pool or individual serum from patients with peanut hypersensitivity diluted (1:5) in a solution containing Tris/NaCl (10 mM Tris/HCl, 500 mM NaCl, pH 7.5) and 1% bovine serum albumin for at least 12 hours at 4° C. or 2 hours at room temperature. The primary antibody was detected with $^{125}$I-labeled anti-IgE antibody (Sanofi Pasteur Diagnostics, Chaska, Minn.).

1.3 Results

Identification of Multiple IgE Binding Epitopes within Ara h 1

The Ara h 1 amino acid sequence (SEQ ID NO:2) was first analyzed for potential antigenic epitopes using computer-based algorithms. There were 11 possible antigenic regions, each containing multiple antigenic sites, predicted by this analysis along the entire length of the molecule.

Preliminary experiments were then performed to map the major IgE binding regions of Ara h 1. Exo III digestion from the 5' or 3' end of a full length Ara h 1 cDNA clone was used to produce shortened clones whose protein products could then be tested for IgE binding by immunoblot analysis. All constructs bound IgE until they were reduced to the extreme carboxyl terminal (5' Exo III) or amino terminal (3' Exo III) end of the molecule. These results indicate that there are multiple IgE epitopes on the Ara h 1 allergen.

Seventy-seven overlapping peptides representing the entire length of the Ara h 1 protein were then synthesized to characterize the IgE binding regions in greater detail. Each peptide was fifteen amino acids long and offset from the previous peptide by eight amino acids. In this manner, the entire length of the Ara h 1 protein could be studied in large overlapping fragments. These peptides were then probed with a pool of serum IgE from 15 patients with documented peanut hypersensitivity or with serum IgE from a representative control patient with no food allergy. Serum IgE from the control patients did not recognize any of the synthesized peptides. In contrast, twelve IgE binding regions (D1-D12) along the entire length of the Ara h 1 protein were recognized by pooled IgE from the population of patients with peanut hypersensitivity. These IgE binding regions represent amino acid residues 35-72, 89-112, 121-176, 289-326, 337-350, 361-374, 393-416, 457-471, 489-513, 521-535, 544-583, and 593-607 of SEQ ID NO:2. In general, the computer predicted antigenic regions contained or were part of those that were determined by actual IgE binding. However, there were two predicted antigenic regions (between amino acids 221-230 and 263-278 of SEQ ID NO:2) that were not recognized by serum IgE from peanut hypersensitive individuals. In addition, there were numerous IgE binding regions found in the Ara h 1 protein between amino acids 450-600 of SEQ ID NO:2.

To determine the amino acid sequence of the IgE binding epitopes, small overlapping peptides spanning each of the larger IgE binding regions identified were synthesized. By synthesizing smaller peptides (ten amino acids long) that were offset from each other by only two amino acids, it was possible to identify individual IgE binding epitopes within the larger IgE binding regions of the Ara h 1 molecule. Table 1 summarizes the twenty-three IgE binding epitopes (SEQ ID NOs:7-29) and their respective positions within the Ara h 1 protein (SEQ ID NO:2).

The most common amino acids found were acidic (D, E) and basic (K, R) residues comprising 40% of all amino acids found in the IgE epitopes. There were no obvious amino acid sequence motifs shared by all the IgE epitopes.

TABLE 1

Ara h 1 IgE binding epitopes

| SEQ ID NO: | Peptide | Amino acid sequence[1] | Ara h 1 positions[2] |
|---|---|---|---|
| 7 | 1 | AKSSPYQKKT | 25-34 |
| 8 | 2 | QEPDDLKQKA | 48-57 |
| 9 | 3 | LEYDPRLVYD | 65-74 |
| 10 | 4 | GERTRGRQPG | 89-98 |
| 11 | 5 | PGDYDDDRRQ | 97-106 |
| 12 | 6 | PRREEGGRWG | 107-116 |
| 13 | 7 | REREEDWRQP | 123-132 |
| 14 | 8 | EDWRRPSHQQ | 134-143 |
| 15 | 9 | QPRKIRPEGR | 143-152 |
| 16 | 10 | TPGQFEDFFP | 294-303 |

TABLE 1-continued

Ara h 1 IgE binding epitopes

| SEQ ID NO: | Peptide | Amino acid sequence[1] | Ara h 1 positions[2] |
|---|---|---|---|
| 17 | 11 | SYLQEFSRNT | 311-320 |
| 18 | 12 | FNAEFNEIRR | 325-334 |
| 19 | 13 | EQEERGQRRW | 344-353 |
| 20 | 14 | DITNPINLRE | 393-402 |
| 21 | 15 | NNFGKLFEVK | 409-418 |
| 22 | 16 | GTGNLELVAV | 461-470 |
| 23 | 17 | RRYTARLKEG | 498-507 |
| 24 | 18 | ELHLLGFGIN | 525-534 |
| 25 | 19 | HRIFLAGDKD | 539-548 |
| 26 | 20 | IDQIEKQAKD | 551-560 |
| 27 | 21 | KDLAFPGSGE | 559-568 |
| 28 | 22 | KESHFVSARP | 578-587 |
| 29 | 23 | PEKESPEKED | 597-606 |

[1]The underlined portions of each peptide represent the linear IgE epitopes.
[2]The Ara h 1 amino acid positions are taken from SEQ ID NO: 2.

Identification of Immunodominant Ara h 1 Epitopes

In an effort to determine which, if any, of the twenty-three epitopes was immunodominant, each set of twenty-three peptides was probed individually with serum IgE from ten different patients. Serum from five individuals randomly selected from the fifteen patient serum pool and an additional five sera from peanut-hypersensitive patients not represented in the serum pool were used to identify the commonly recognized epitopes. Immunoblot strips containing peptides 1-23 (see Table 1) were incubated with each individual patient's serum. The intensity of IgE binding to each spot was determined as a function of that patient's total IgE binding to these twenty-three epitopes. All of the patient sera tested (10/10) recognized multiple peptides. The most commonly recognized peptides were those that contained epitopes 1, 3, 4, 13, 17 and 22. These epitopes were recognized by IgE from at least 80% of the patient sera tested (8/10). In addition, epitopes 1-4, 8, 12, and 17, when recognized, bound more serum IgE from individual patients than any of the other epitopes. These results suggest that peptides 1, 3, 4, and 17 contain the immunodominant epitopes of the Ara h 1 protein.

Mutational Analysis of Ara h 1 Epitopes

The specific amino acids involved in IgE binding were determined by synthesizing duplicate peptides with single amino acid changes at each position. These peptides were then probed with pooled serum IgE from fifteen patients with peanut hypersensitivity to determine if the changes affected peanut-specific IgE binding. In general, each epitope could be mutated to a non-IgE binding peptide by the substitution of an alanine or methionine for a single amino acid residue. There was no obvious position within each peptide that, when mutated, would result in loss of IgE binding. Furthermore, there was no consensus in the type of amino acid that, when changed to alanine or methionine, would lead to loss of IgE binding. Table 2 summarizes these results.

The amino acids within each epitope were classified according to whether they were hydrophobic, polar, or charged residues. There were a total of 196 amino acids present in the twenty-one epitopes of Ara h 1 that were studied (epitopes 16 and 23 were not included in this study because they were recognized by a single patient who was no longer available to the study). Charged residues occurred most frequently (89/196), with hydrophobic residues (71/196) being the next frequent type of amino acid in the epitopes, and polar residues representing the least frequent amino acid group (36/196). 35% of the mutated hydrophobic residues resulted in loss of IgE binding (<1% IgE binding), whereas only 25 and 17% of mutated polar and charged residues, respectively, had a similar effect. These results indicated that the hydrophobic amino acid residues within these IgE binding epitopes were the most sensitive to changes. In addition results from this analysis indicated that the amino acids located near the center of the epitope were more critical for IgE binding.

TABLE 2

Amino acids mutations that reduce IgE binding to Ara h 1

| SEQ ID NO: | Peptide | Amino acid sequence[1] | Ara h 1 positions[2] |
|---|---|---|---|
| 7 | 1 | AKSSPYQKKT | 25-34 |
| 8 | 2 | QEPDDLKQKA | 48-57 |
| 9 | 3 | LEYDPRLVYD | 65-74 |
| 10 | 4 | GERTRGRQPG | 89-98 |
| 11 | 5 | PGDYDDDRRQ | 97-106 |
| 12 | 6 | PRREEGGRWG | 107-116 |
| 13 | 7 | REREEDWRQP | 123-132 |
| 14 | 8 | EDWRRPSHQQ | 134-143 |
| 15 | 9 | QPRKIRPEGR | 143-152 |
| 16 | 10 | TPGQFEDFFP | 294-303 |
| 17 | 11 | SYLQEFSRNT | 311-320 |
| 18 | 12 | FNAEFNEIRR | 325-334 |
| 19 | 13 | EQEERGQRRW | 344-353 |
| 20 | 14 | DITNPINLRE | 393-402 |
| 21 | 15 | NNFGKLFEVK | 409-418 |
| 23 | 17 | RRYTARLKEG | 498-507 |
| 24 | 18 | ELHLLGFGIN | 525-534 |
| 25 | 19 | HRIFLAGDKD | 539-548 |
| 26 | 20 | IDQIEKQAKD | 551-560 |
| 27 | 21 | KDLAFPGSGE | 559-568 |
| 28 | 22 | KESHFVSARP | 578-587 |

[1]The amino acids that, when altered, lead to loss of IgE binding are shown as the bold, underlined residues. Epitopes 16 and 23 were not included in this study because they were recognized by a single patient who was no longer available to the study.
[2]The Ara h 1 amino acid positions are taken from SEQ ID NO: 2.

1.4 Conclusion

Multiple antigenic sites were predicted for the Ara h 1 allergen based on a computational analysis. At least twenty-three different linear IgE epitopes have been identified within the major peanut allergen Ara h 1. These sites are distributed throughout the protein.

Four of the Ara h 1 epitopes appear to be immunodominant IgE binding epitopes in that they are recognized by more than 80% of patient sera tested and, when recognized, bind more serum IgE from individual patients than any of the other epitopes. Epitope 17, which is located in the C-terminal end of the protein (amino acids 498-507 of SEQ ID NO:2), is in a region that shares significant sequence similarity with vicilins from other legumes (Gibbs et al., *Mol. Biol. Evol.* 6:614-623, 1989). The amino acids important for IgE binding also appear to be conserved in this region and may explain the possible cross-reacting antibodies to other legumes that can be found in sera of patients with a positive double-blind placebo-controlled food challenge to peanuts. Epitopes 1, 3, and 4 located in the N-terminal portion of the protein (amino acids 25-34, 65-74, and 89-98 of SEQ ID NO:2), appear to be unique to this peanut vicilin and do not share any significant sequence similarity with vicilins from other legumes (Gibbs et al., 1989, supra). The amino acids important to IgE binding in this region are not conserved. Hydrophobic amino acid residues appear to play the most important role in immunoglobulin binding.

Example 2

Mapping and Mutational Analysis of the Linear IgE Epitopes of Ara h 2

2.1 Introduction

The major linear IgE-binding epitopes of this allergen were mapped using overlapping peptides synthesized on an activated cellulose membrane and pooled serum IgE from fifteen peanut-sensitive patients. Ten IgE-binding epitopes were identified, distributed throughout the length of the Ara h 2 protein. 63% of the amino acids represented in the epitopes were either polar uncharged or apolar residues. In an effort to determine which, if any, of the ten epitopes were recognized by the majority of patients with peanut hypersensitivity, each set of ten peptides was probed individually with serum IgE from ten different patients. All of the patient sera tested recognized multiple epitopes. Three epitopes (epitopes 3, 6 and 7) were recognized by all patients tested. In addition, these three peptides bound more IgE than all the other epitopes combined, indicating that they are the immunodominant epitopes of the Ara h 2 protein. Mutational analysis of the Ara h 2 epitopes indicates that single amino acid changes result in loss of IgE binding. Two epitopes in the region spanning amino acids 57-74 of SEQ ID NO:4 contained the amino acid sequence DPYSPS (SEQ ID NO:30) that appears to be involved in IgE binding.

2.2 Materials and Methods

Serum IgE, Peptide Synthesis and IgE Binding Assay

Serum IgE was selected as described in Example 1, Section 1.2. Peptides were synthesized as described in Example 1, Section 1.2. The IgE binding assay was performed as described in Example 1, Section 1.2.

2.3 Results

Identification of Multiple IgE Binding Epitopes within Ara h 2

Nineteen overlapping peptides representing the derived amino acid sequence of the Ara h 2 protein were synthesized to determine which regions were recognized by serum IgE. Each peptide was fifteen amino acids long and was offset from the previous peptide by eight amino acids. In this manner, the entire length of the Ara h 2 protein could be studied in large overlapping fragments. These peptides were then probed with a pool of serum from fifteen patients with documented peanut hypersensitivity or serum from a representative control patient with no peanut hypersensitivity (see Example 1). Serum IgE from the control patient did not recognize any of the synthesized peptides. In contrast, three IgE binding regions within the Ara h 2 protein were recognized by the population of patients with peanut hypersensitivity. These IgE-binding regions represent amino acid residues 17-39, 41-80, and 114-157 of SEQ ID NO:4.

In order to determine the exact amino acid sequence of the IgE binding regions, smaller peptides (ten amino acids long offset by two amino acids) representing the larger IgE-binding regions were synthesized. In this manner it was possible to identify individual IgE-binding epitopes within the larger IgE-binding regions of the Ara h 2 molecule. The ten IgE-binding epitopes that were identified in this manner are shown in Table 3. The size of the epitopes ranged from 6 to 10 amino acids in length.

TABLE 3

Ara h 2 IgE binding epitopes

| SEQ ID NO: | Peptide | Amino acid sequence[1] | Ara h 2 positions[2] |
|---|---|---|---|
| 31 | 1 | HASARQQWEL | 15-24 |
| 32 | 2 | QWELQGDRRC | 21-30 |
| 33 | 3 | DRRCQSQLER | 27-36 |
| 34 | 4 | LRPCEQHLMQ | 39-48 |
| 35 | 5 | KIQRDEDSYE | 49-58 |
| 36 | 6 | YERDPYSPSQ | 57-66 |
| 37 | 7 | SQDPYSPSPY | 65-74 |
| 38 | 8 | DRLQGRQQEQ | 115-124 |
| 39 | 9 | KRELRNLPQQ | 127-136 |
| 40 | 10 | QRCDLDVESG | 143-152 |

[1]The underlined portions of each peptide represent the linear IgE epitopes.
[2]The Ara h 2 amino acid positions are taken from SEQ ID NO: 4.

Three epitopes (epitopes 1-3), which partially overlapped with each other, were found in the region of amino acid residues 17-39 of SEQ ID NO:4. Four epitopes (epitopes 4-7) were found in the region represented by amino acid residues 41-80 of SEQ ID NO:4. Finally, three epitopes (epitopes 8-10) were found in the region represented by amino acid residues 114-157 of SEQ ID NO:4. 63% of the amino acids represented in the epitopes were either polar uncharged or apolar residues. There was no obvious amino acid sequence motif that was shared by all the epitopes, with the exception of epitopes 6 and 7, which contained the sequence DPYSPS (SEQ ID NO:30).

Identification of Immunodominant Ara h 2 Epitopes

In an effort to determine which, if any, of the ten epitopes was immunodominant, each set of ten peptides was probed individually with serum IgE from ten different patients. Five patients were randomly selected from the pool of fifteen patients used to identify the common epitopes, and five patients were selected from outside this pool. The intensity of IgE binding to each spot was determined as a function of that patient's total IgE binding to the ten epitopes. All of the patient sera tested (10/10) recognized multiple peptides. Peptides 3, 6 and 7 were recognized by serum IgE of all patients tested (10/10). In addition, serum IgE that recognized these peptides represented the majority of Ara h 2 specific IgE found in these patients. These results suggest that peptides 3, 6, and 7 contain immunodominant IgE epitopes of the Ara h 2 protein.

Mutational Analysis of Ara h 2 Epitopes

The specific amino acids involved in IgE binding were determined by synthesizing duplicate peptides with single amino acid changes at each position. These peptides were then probed with pooled serum IgE from fifteen patients with documented peanut hypersensitivity. In general, each peptide could be mutated to a non-IgE-binding peptide by the substitution of an alanine for a single amino acid residue. Table 4 summarizes these results. There was no obvious position within each peptide that, when mutated, would result in loss of IgE binding. Furthermore, there was no consensus in the type of amino acid that, when changed to alanine, would lead to loss of IgE binding.

TABLE 4

Amino acids mutations that reduce IgE binding to Ara h 2

| SEQ ID NO | Peptide | Amino acid sequence[1] | Ara h 2 positions[2] |
|---|---|---|---|
| 31 | 1 | HASARQQWEL | 15-24 |
| 32 | 2 | QWELQGDRRC | 21-30 |
| 33 | 3 | DRRCQSQLER | 27-36 |
| 34 | 4 | LRPCEQHLMQ | 39-48 |
| 35 | 5 | KIQRDEDSYE | 49-58 |
| 36 | 6 | YERDPYSPSQ | 57-66 |
| 37 | 7 | SQDPYSPSPY | 65-74 |
| 38 | 8 | DRLQGRQQEQ | 115-124 |
| 39 | 9 | KRELRNLPQQ | 127-136 |
| 40 | 10 | QRCDLDVESG | 143-152 |

[1]The amino acids that, when altered, lead to loss of IgE binding are shown as the bold, underlined residues.
[2]The Ara h 2 amino acid positions are taken from SEQ ID NO: 4.

2.4 Conclusion

There are at least ten IgE recognition sites distributed throughout the major peanut allergen Ara h 2. Two epitopes in Ara h 2 share a hexameric peptide (DPYSPS, SEQ ID NO:30). Both of these peptides are recognized by serum IgE from all the peanut hypersensitive patients tested in this study. In addition, serum IgE that recognize these peptides represent the majority of Ara h 2-specific IgE found in these patients.

Example 3

Mapping and Mutational Analysis of the Linear IgE Epitopes of Ara h 3

3.1 Introduction

Serum IgE from peanut allergic patients and overlapping, synthetic peptides were used to map the linear, IgE epitopes of Ara h 3. Several epitopes were found within the primary sequence, with no obvious sequence motif shared by the peptides. One epitope was recognized by all peanut-allergic patients. Mutational analysis of the epitopes revealed that single amino acid changes within these peptides could lead to a reduction or loss of IgE binding.

3.2 Materials and Methods

Serum IgE, Peptide Synthesis and IgE Binding Assay

Serum IgE was selected as described in Example 1, Section 1.2. Peptides were synthesized as described in Example 1, Section 1.2. The IgE binding assay was performed as described in Example 1, Section 1.2.

3.3 Results

Identification of Multiple IgE Binding Epitopes within Ara h 3

Sixty three overlapping peptides were synthesized to determine the regions of Ara h 3 that are recognized by serum IgE. Each peptide synthesized was fifteen amino acids long and offset from the previous peptide by eight amino acids. This approach allowed the analysis of the entire Ara h 3 primary sequence in large, overlapping fragments. These peptides were probed with a serum pool of IgE from peanut-hypersensitive patients who had previously been shown to recognize recombinant Ara h 3. Four IgE-binding regions were identified within the Ara h 3 primary amino acid sequence. These IgE-binding regions were represented by amino acid residues 21-55, 134-154, 231-269, and 271-328 of SEQ ID NO:6. To determine the exact amino acid sequence of the IgE-binding regions, synthetic peptides (fifteen amino acids offset by two amino acids) representing the larger IgE-binding regions were generated and probed with a serum pool of IgE from peanut allergic patients. This process made it possible to distinguish individual IgE-binding epitopes within the larger IgE-binding regions of the Ara h 3 protein. Four IgE-binding epitopes were identified in this manner and are shown in Table 5.

TABLE 5

Ara h 3 IgE binding epitopes

| SEQ ID NO. | Peptide | Amino acid sequence | Ara h 3 positions[1] | Recognition[2] |
|---|---|---|---|---|
| 41 | 1 | IETWNPNNQEFECAG | 33-47 | 25% (2/8) |
| 42 | 2 | GNIFSGFTPEFLEQA | 240-254 | 38% (3/8) |
| 43 | 3 | VTVRGGLRILSPDRK | 279-293 | 100% (8/8) |
| 44 | 4 | DEDEYEYDEEDRRRG | 303-317 | 38% (3/8) |

[1]The Ara h 3 amino acid positions are taken from SEQ ID NO: 6.
[2]The percent recognition is the percentage of patients previously shown to recognize recombinant Ara h 3 whose serum IgE recognized that particular synthetic epitope.

Characterization of the IgE binding regions was repeated using synthetic overlapping peptides which were ten amino acids in length and offset by two amino acids. As with the 15/2 peptides, the 10/2 peptides were probed with a serum pool of IgE from patients who recognized recombinant Ara h 3. The four IgE-binding epitopes identified in this manner are shown in Table 6.

TABLE 6

Ara h 3 IgE binding epitopes

| SEQ ID NO. | Peptide | Amino acid sequence | Ara h 3 positions[1] | Recognition[2] |
|---|---|---|---|---|
| 45 | 5 | EQEFLRYQQQ | 183-192 | 5% (1/20) |
| 46 | 6 | FTPEFLEQAF | 246-255 | 25% (5/20) |
| 47 | 7 | EYEYDEEDRR | 306-315 | 35% (7/20) |
| 48 | 8 | LYRNALFVAH | 379-388 | 100% (20/20) |

[1] The Ara h 3 amino acid positions are taken from SEQ ID NO: 6.
[2] The percent recognition is the percentage of patients previously shown to recognize recombinant Ara h 3 whose serum IgE recognized that particular synthetic epitope.

Identification of Immunodominant Ara h 3 Epitopes

To determine whether any of the four epitopes of Table 5 were immunodominant, each set of four peptides was probed individually with serum IgE from the eight patients previously shown to recognize recombinant Ara h 3 (results summarized in Table 5 as percentage recognition). Epitope 1 was recognized by serum IgE form 25% (2/8) of the patients tested, whereas epitopes 2 and 4 were recognized by serum IgE from 38% (3/8) of the eight patients tested. Epitopes 2 and 4 were recognized by the same three patients. Epitope 3 was recognized by serum IgE from 100% (8/8) of the peanut-allergic patients, classifying it as an immunodominant epitope within the peanut-allergic population. 68% of the amino acids constituting the epitopes were either polar uncharged or apolar residues. However, three was no obvious sequence motif with respect to position or polarity shared by the individual epitopes.

To determine whether any of the four epitopes of Table 6 were immunodominant, each set of four peptides was probed individually with serum IgE form a larger group of twenty patients previously shown to recognize recombinant Ara h 3 (results summarized in Table 6 as percentage recognition).

Mutational Analysis of Ara h 3 Epitopes

The specific amino acids involved in IgE binding to the Ara h 3 epitopes of Table 5 were determined by synthesizing multiple peptides with single amino acid changes at each position. These peptides were probed with a pool of serum IgE from patients who had previously recognized the wild-type peptide, to determine whether amino acid changes affected peanut-specific IgE binding. In general, each epitope could be altered to a non-IgE-binding peptide by the replacement of the wild-type amino acid residue with alanine The results are shown in Table 7.

TABLE 7

Amino acids mutations that reduce IgE binding to Ara h 3

| SEQ ID NO | Peptide | Amino acid sequence[1] | Ara h 3 position[2] |
|---|---|---|---|
| 41 | 1 | IETWNPNNQEFECAG | 33-47 |
| 42 | 2 | GNIFSGFTPEFLEQA | 240-254 |
| 43 | 3 | VTVRGGLRILSPDRK | 279-293 |
| 44 | 4 | DEDEYEYDEEDRRRG | 303-317 |

[1] The amino acids that, when altered, lead to loss of IgE binding are shown as the bold, underlined residues.
[2] The Ara h 3 amino acid positions are taken from SEQ ID NO: 6.

It appears that the central amino acids within each epitope are favored for mutation. All mutations that led to a significant decrease in IgE binding were located at residues found within each core epitope. There was no obvious consensus in the type of amino acid that, when mutated to alanine, leads to complete loss or a decrease in IgE binding.

3.4 Conclusion

By generating synthetic, overlapping peptides representing the entire primary sequence of Ara h 3, we were able to determine that there are several IgE-recognition sites distributed throughout the primary sequence of the protein. One of these sites (within peptide 3 of Table 5) was recognized by serum IgE from every peanut-allergic patient in the group, designating it as an immunodominant epitope. Epitopes located within peptides 3 and 4 (Table 5) are located within the hypervariable region of the acidic chain, a stretch of amino acids that is highly variable in length among 11S storage proteins. This region contains a high proportion of glutamate, aspartate, and arginine residues and will tolerate large, naturally occurring insertions or deletions. Computer predictions from other studies suggest that this region is exposed on the surface of the protein (Nielsen et al., pp. 635-640 in "*NATO Advanced Study Institute on Plant Molecular Biology*", Ed. by R. Hermann and B. Larkins, Plenum Press, New York, N.Y., 1990).

Example 4

Bacterial Expression and Purification of Recombinant Ara h 1-3

4.1 Introduction

This Example describes the constructs and methods that were used to express and purify the recombinant Ara h 1, Ara h 2 and Ara h 3 proteins that were used in the Examples that follow (both "wild-type" and "mutant"). Briefly, *E. coli* cells (BL21 or BLR) were transformed with Ara h 1, Ara h 2 or Ara h 3 constructs and exponentially growing cells were induced with IPTG (isopropyl-beta-D-thiogalactopyranoside). Cells were then pelleted and the recombinant proteins purified by affinity chromatography on a $Ni^{2+}$-resin column.

4.2 Expression Vector Constructs for Ara h 1

"Wild-Type" Ara h 1

The portion of Ara h 1 sequence (SEQ ID NO:1) excluding the first 66 nucleotides, which encodes the signal peptide, was amplified by PCR. The PCR product was ligated into the cloning region of pET24b(+) (Novagen, Madison, Wis.) that carries a selectable marker for kanamycin resistance. The pET24b(+) vector also encodes a T7-tag (MASMTG-GQQMG, SEQ ID NO:49) and a His-tag (HHHHHH, SEQ ID NO:50) that are added to the N- and C-termini, respectively, of the resulting recombinant protein. Some vector derived amino acids (RDPNSSS, SEQ ID NO:51) were included in between the T7-tag and the N-terminus of the Ara h 1 sequence. Some vector derived amino acids (KLAAALE, SEQ ID NO:52) were also included in between the His-tag and the C-terminus of the Ara h 1 sequence. The amino acid sequence of the recombinant Ara h 1 allergen is shown in FIG. 7 (SEQ ID NO:53). This "wild-type" recombinant Ara h 1 allergen included all the linear IgE epitopes that were identified in Example 1.

"Mutant" Ara h 1

Mutant recombinant Ara h 1 was prepared as above except that certain amino acids that were shown to be important for IgE binding in Example 1 were mutated by single-stranded mutagenesis and/or by PCR. Mutations were confirmed by sequence analysis of recombinant Ara h 1 cDNA clones. Three different mutants were prepared (MUT1, MUT2 and MUT3). MUT1 included single mutations in the four immunodominant epitopes (epitopes 1, 3, 4 and 17) and three non-immunodominant epitopes (epitopes 2, 5 and 6). Epitopes 1-6 were also chosen for mutation because they lie within the variable N-terminal domain and are not conserved between vicilins and therefore may be responsible for the extreme allergenicity to peanuts. MUT2 and MUT3 included mutations in twenty-one of the twenty-three linear IgE epitopes that were identified in Example 1 and further in a new epitope that was not identified in Example 1. This new epitope (shown with a *) spans amino acids 365-385 of SEQ ID NO:2. Epitopes 16 and 23 from Example 1 were not mutated since these were only recognized by a single allergic patient that was no longer available for study. MUT2 included some double mutations (epitopes 17 and 21), and a few accidental mutations outside the linear IgE epitopes. The mutations and their locations within the Ara h 1 sequence (SEQ ID NO:2) are listed in Table 8. MUTT was used in Example 6. MUT2 was used in all other Examples.

TABLE 8

Substitutions in mutant recombinant Ara h 1

| [1]Epitope | [3]MUT1 | [2,3]MUT2 | [3]MUT3 |
|---|---|---|---|
| 1 | K32A | K32A | K32A |
| 2 | D52A | D52A | D52A |
| 3 | V72A | V72A | V72A |
| 4 | R91A | R91A | R91A |
| 5 | D103A | D103A | D103A |
| 6 | R109A | R109A | R109A |
| 7 | — | W129A | W129A |
| 8 | — | R137A | R137A |
| 9 | — | I147A | I147A |
| — | — | W158C | — |
| — | — | T246I | — |
| — | — | E260D | — |
| 10 | — | F298M | F298M |
| 11 | — | S317A | S317A |
| 12 | — | F329A | F329A |
| 13 | — | E347A | E347A |
| * | — | K370D | — |
| * | — | V373S | V373S |
| 14 | — | I398A | I398A |
| 15 | — | F415A | F415A |
| [3]16 | — | — | — |
| — | — | Q475R | — |
| 17 | R499A | R499A | R499A |
| 17 | — | K505R | — |
| 18 | — | H527A | H527A |
| 19 | — | K547A | K547A |
| 20 | — | D560A | D560A |
| 21 | — | F563A | F563A |
| 21 | — | G567C | — |
| 22 | — | S584A | S584A |
| [3]23 | — | — | — |

* This represents a new epitope that was not identified in Example 1 and that spans amino acids 365-385 of SEQ ID NO: 2.
[1]Epitopes identified in Example 1.
[2]MUT2 included a few accidental mutations outside the linear IgE epitopes of Ara h 1.
[3]Epitopes 16 and 23 were not mutated since they were only recognized by IgE from a single patient that was no longer available for study (see Example 1).
[3]The Ara h 1 amino acid positions are taken from SEQ ID NO: 2.

4.3 Expression Vector Constructs for Ara h 2

"Wild-Type" Ara h 2

The portion of Ara h 2 sequence (SEQ ID NO:3) excluding the first 54 nucleotides, which encodes part of the signal peptide, was amplified by PCR. The PCR product was ligated into the cloning region of pET24a(+) (Novagen, Madison, Wis.) that carries a selectable marker for kanamycin resistance. The pET24a(+) vector also encodes a T7-tag (MASMTGGQQMG, SEQ ID NO:49) and a His-tag (HHH-HHH, SEQ ID NO:50) that are added to the N- and C-termini, respectively, of the resulting recombinant protein. Some vector derived amino acids (RGSEF, SEQ ID NO:54) were included in between the T7-tag and the N-terminus of the Ara h 2 sequence. Some vector derived amino acids (AAALE, SEQ ID NO:55) were also included in between the His-tag and the C-terminus of the Ara h 2 sequence. The amino acid sequence of the recombinant Ara h 2 allergen is shown in FIG. 8 (SEQ ID NO:56). This "wild-type" recombinant Ara h 2 allergen included all the linear IgE epitopes that were identified in Example 2.

"Mutant" Ara h 2

Mutant recombinant Ara h 2 was prepared as above except that certain amino acids that were shown to be important for IgE binding in Example 2 were mutated by single-stranded mutagenesis and/or by PCR. Mutations were confirmed by sequence analysis of recombinant Ara h 2 cDNA clones. Four different mutants MUT1, MUT2, MUT3 and MUT4 were prepared. MUT1 included single mutations in the three immunodominant epitopes (epitopes 3, 6 and 7) and one non-immunodominant epitope (epitope 4). MUT2 included single mutations in the three immunodominant epitopes (epitopes 3, 6 and 7) and two non-immunodominant epitopes (epitope 1 and 2 that overlap at position 23 of SEQ ID NO:4). MUT3 and MUT4 included mutations in all ten linear IgE epitopes that were identified in Example 2. MUT3 included three mutations within epitope 4. The mutations and their locations within the Ara h 2 sequence (SEQ ID NO:4) are listed in Table 9. MUT1, MUT2 and MUT3 were all used in Example 7. MUT3 only was used in all other Examples.

TABLE 9

Substitutions in mutant recombinant Ara h 2

| [1]Epitope | [2]MUT1 | [2]MUT2 | [2]MUT3 | [2]MUT4 |
|---|---|---|---|---|
| 1, 2 | — | Q23A | — | — |
| 1, 2 | — | — | W25A | W25A |
| 3 | — | Q34A | — | — |
| 3 | E38A | — | E38A | E38A |
| 4 | P44A | — | P44A | P44A |
| 4 | — | — | E46A | — |
| 4 | — | — | Q51R | — |
| 5 | — | — | D56A | D56A |
| 6 | D63A | D63A | D63A | D63A |
| 7 | D70A | D70A | D70A | D70A |
| 8 | — | — | R123A | R123A |
| 9 | — | — | L133A | L133A |
| 10 | — | — | L150A | L150A |

[1]Epitopes identified in Example 2.
[2]The Ara h 2 amino acid positions are taken from SEQ ID NO: 4.

4.4 Expression Vector Constructs for Ara h 3

"Wild-Type" Ara h 3

The Ara h 3 sequence (SEQ ID NO:5) was amplified by PCR (the signal peptide is not encoded by this particular cDNA clone). The PCR product was ligated into the cloning region of pET24b(+) (Novagen, Madison, Wis.) that carries a selectable marker for kanamycin resistance. The pET24b(+) vector also encodes a T7-tag (MASMTGGQQMG, SEQ ID NO:49) and a His-tag (HHHHHH, SEQ ID NO:50) that are added to the N- and C-termini, respectively, of the resulting recombinant protein. Some vector derived amino acids (VD-KLAAALE, SEQ ID NO:57) were included in between the His-tag and the C-terminus of the Ara h 3 sequence. The amino acid sequence of this "wild-type" recombinant Ara h 3 allergen is shown in FIG. 9 (SEQ ID NO:58).

"Mutant" Ara h 2

Mutant recombinant Ara h 3 was prepared as above except that certain amino acids that were shown to be important for IgE binding in Example 3 were mutated by single-stranded mutagenesis and/or by PCR. Mutations were confirmed by sequence analysis of recombinant Ara h 3 cDNA clones. Two different mutants MUT1 and MUT2 were prepared. MUT1 and MUT2 included mutations in all four linear IgE epitopes that were identified in Table 5 of Example 3. MUT1 included two mutations within epitope 4. The mutations and their locations within the Ara h 3 sequence (SEQ ID NO:6) are listed in Table 10. MUT1 was used in all of the following Examples.

TABLE 10

Substitutions in mutant recombinant Ara h 3

| [1]Epitope | [2-4]MUT1 | [2]MUT2 |
|---|---|---|
| 1 | P58A | P58A |
| 2 | F270A | F270A |
| 3 | I307A | I307A |
| 4 | E328A | E328A |
| 4 | D333V | — |

[1]Epitopes identified in Example 3.
[2]The Ara h 3 amino acid positions are taken from SEQ ID NO: 6.
[3]MUT1 only included the first three residues from the "MASMTGGQQMG" T7-tag.
[4]MUT1 lacked the first "I" amino acid of the Ara h 3 sequence.

4.5 Expression

Preparation for Induction

Transformed *E. coli* (BL21 or BLR) cells were picked from a glycerol freezer stock using a sterile toothpick and then inoculated in 100 ml LB broth (Luria-Bertani) containing 30 μg/ml of Kanamycin. The cells were then incubated overnight with shaking at 37° C. 20 ml of the incubated culture was then used to inoculate 1000 ml LB broth containing 30 μg/ml of Kanamycin.

Induction

The culture was then incubated with shaking at 37° C. until the O.D. at 600 nm reached 0.6. Typically this took about 2.5 hours. 1 ml of a 1 M stock solution of IPTG (isopropyl-beta-D-thiogalactopyranoside) was then added to the culture to give a final concentration of 1 mM and incubation was continued overnight. The cells were harvested by centrifugation at 5000 g for 15 minutes at 4° C. (5,5000 rpm in a Sorvall GSA™ rotor). The harvested cells were passed onto purification or stored as frozen pellets at −70° C.

4.6 Purification

Cell Lysis

Harvested cells were re-suspended in 600 ml of 0.1% NONIDET® P40 in binding buffer (0.5 M NaCl, 20 mM Tris-HCl, and 6 M urea at pH 7.9) and then sonicated on ice for 20 minutes using a model 500 Sonic Dismembrator at maximum output (~70%) with a half inch diameter probe (both available from Fisher Scientific, Suwanee, Ga.). The sonication disrupted bacterial cells and sheared DNA. In certain cases the lysate was then incubated overnight with stirring at 4° C. to ensure full dissolution of the recombinant protein—this was particularly useful for wild-type Ara h 1 and mutant Ara h 2. The lysate was then centrifuged at 27,000 g for 60 minutes (13,000 rpm in a Sorvall RC-5B™ centrifuge) to remove cellular debris. The supernatant was removed and re-centrifuged at 27,000 g for 30 minutes. Finally, the supernatant was filtered through a 0.45 μm membrane.

Column Preparation

Recombinant proteins were purified by means of column chromatography using a HIS•BIND® resin. As described above, all recombinant proteins had a 6×-His tag which binds to $Ni^{2+}$ cations that are immobilized on the resin. A large column was packed with a settled bed volume of 25 ml of HIS•BIND® resin from Novagen, Madison, Wis. The binding capacity of the resin was estimated at 8 mg protein/ml using known amounts of 6×-His tagged β-galactosidase. The column was then washed with the following sequence of washes to charge and equilibrate the column (one volume is equivalent to the settled bed volume):

(a) 75 ml (3 volumes) sterile deionized water
(b) 125 ml (5 volumes) 1× charge buffer (50 mM $NiSO_4$)
(c) 75 ml (3 volumes) 1× binding buffer.

Purification

An open gravity flow system was used for purification. A flow rate of 250 ml per hour was used with a bed volume of 25 ml (or 10 volumes per hour). Purification included the following steps:

(a) Binding buffer was allowed to drain to the top of column bed.
(b) 600 ml of the prepared extract was loaded onto the column.
(c) The column was washed with 300 ml (12 volumes) of 1× binding buffer.
(d) The column was washed with 200 ml (8 volumes) of 1× binding buffer with 20 mM imidazole.
(e) The column was washed with 150 ml (6 volumes) of 1× binding buffer.

Protein Refolding and Elution

After the column resin had been washed, a slow refolding step was included to allow the recombinant proteins to refold correctly and to increase the solubility of the final eluted purified protein. The recombinant proteins were refolded using a linear gradient of urea from 6 M down to 0 M in 1× refolding buffer (0.5 M NaCl, 20 mM Tris-HCl and 1 mM PMSF (phenylmethylsulfonyl fluoride) at pH 7.9) over a period of between 2 hours and overnight. The column flow system was closed for the refolding step and a model 750 gradient maker from Life Technologies, Bethesda, Md. was used for this purpose.

The refolded proteins were then eluted from the column using 1 M imidazole in an elution buffer (0.5 M NaCl, 20 mM Tris-HCl and 1 mM PMSF at pH 7.5). Typically, most of the protein could be recovered using 3×25 ml washes.

Processing the Purified Sample

The imidazole and other salts were removed by dialysis into 1×PBS using SPECTRA/POR® 7 dialysis membrane from Spectrum Laboratories, Rancho Dominguez, Calif. These membranes have a molecular weight cut-off of 3,500 kD. Typically, a 200 ml eluate was dialyzed in 4000 ml of 1×PBS for at least 2 hours at 4° C. The dialysis was then repeated with fresh 4000 ml of 1×PBS overnight, again at 4° C. The sample was then exchanged twice using an AMI- CON™ stirred-cell into 1×PBS with 1 mM PMSF as the exchange buffer at room temperature.

Example 5

Ara h 1 Mutant Protein with Reduced IgE Binding

5.1 Introduction

In order to modulate IgE reactivity of Ara h 1 a recombinant Ara h 1 protein was constructed with mutations in the immunodominant IgE binding epitopes (see MUT1 in Example 4, Section 4.2 and Table 8). The abilities of the wild-type and mutant recombinant Ara h 2 proteins to react with IgE were then tested in Western blot analysis with sera from peanut-sensitive individuals. As compared to wild-type Ara h 1, the mutant Ara h 1 protein bound less IgE in 50% of patients tested.

5.2 Materials and Methods

Recombinant wild-type and MUT1 versions of Ara h 1 were prepared as described in Example 4, Section 4.2. MUT1 includes a single alanine mutation in epitopes 1-6 and 17 as shown in Table 11.

TABLE 11

Mutations in MUT1 version of Ara h 1

| Epitope | Mutation |
|---|---|
| 1 | K32A |
| 2 | D52A |
| 3 | V72A |
| 4 | R91A |
| 5 | D103A |
| 6 | R109A |
| 17 | R499A |

A western blot control was performed on the wild-type and mutant Ara h 1 recombinant proteins to ensure that an equal amount of each protein was used in these studies. Equal amounts of wild-type and mutant Ara h 1 were detected and both proteins migrated at their expected molecular weights (~65 kD).

5.3 Results

Western blots of wild-type and mutant recombinant proteins probed with individual peanut-sensitive patient sera were performed. The results are summarized in Table 12. Data for each patient is numbered 1-10 in the first column. The second column lists the epitopes that each patient recognized in the wild-type protein that were changed in the mutant protein. The third column lists the epitopes that each patient recognized in the wild-type protein that were not changed in the mutant protein. The fourth column shows the relative IgE binding affinity of the mutant protein vs. the wild-type protein. In 50% of individual cases IgE binding to the mutant protein was significantly reduced.

TABLE 12

Relative affinity of IgE to wild-type and mutant Ara h 1

| Patient | Mutated epitopes | Wild-type epitopes | Relative binding |
|---|---|---|---|
| 1 | 1, 4, 5, 17 | 8, 13 | Decreased |
| 2 | 2, 3, 4, 17 | 14, 18 | Equal |
| 3 | 4, 5, 17 | 11, 14, 18-20, 22 | Increased |
| 4 | 2, 4, 5, 17 | 9, 23 | Decreased |
| 5 | 1, 4, 17 | 9, 10, 12-15, 18, 21, 22 | Equal |
| 6 | 4, 17 | 8, 9, 20, 23 | Decreased |
| 7 | 1, 2, 4, 17 | 13 | Equal |
| 8 | 1, 3, 4, 17 | 13, 22 | Equal |
| 9 | 1, 2, 4, 17 | 10 | Decreased |
| 10 | 3, 17 | 8, 9, 10, 11 | Decreased |

5.4 Conclusion

These results indicate that it is possible to produce a mutated recombinant Ara h 1 protein that binds substantially lower amounts of serum IgE from peanut-sensitive patients.

Example 6

Ara h 2 Mutant Proteins with Reduced IgE Binding

6.1 Introduction

In order to modulate IgE reactivity of Ara h 2 a variety of recombinant Ara h 2 proteins were constructed with mutations in IgE binding epitopes (see MUT1, MUT2 and MUT3 in Example 4, Section 4.3 and Table 9). The abilities of the wild-type and mutant recombinant Ara h 2 proteins to react with IgE were then tested in Western blot analysis with sera from peanut-sensitive individuals. As compared to wild-type Ara h 2, the mutant Ara h 2 proteins bound less IgE, similar amounts of IgG, and exhibited a comparable ability to stimulate T-cell proliferation.

6.2 Materials and Methods

Recombinant wild-type and MUT1, MUT2 and MUT3 versions of Ara h 2 were prepared as described in Example 4, Section 4.3. The mutations of MUT1, MUT2 and MUT3 are shown in Table 13.

TABLE 13

Mutations in MUT1, MUT2 and MUT3 versions of Ara h 2

| Epitope | Mutation | MUT1 | MUT2 | MUT3 |
|---|---|---|---|---|
| 1, 2 | Q23A | | X | |
| 1, 2 | W25A | | | X |
| 3 | Q34A | | X | |
| 3 | E38A | X | | X |
| 4 | P44A | X | | X |
| 5 | D56A | | | X |
| 6 | D63A | X | X | X |
| 7 | D70A | X | X | X |
| 8 | R123A | | | X |
| 9 | L133A | | | X |
| 10 | L150A | | | X |

6.3 Results

IgE Binding to MUT1 and MUT3 vs. Wild-Type Ara h 2 Using Pooled Sera

Equal amounts of purified wild-type and mutant Ara h 2 proteins (MUT1 and MUT3) were separated by gradient (4-20%) PAGE and electrophoretically transferred onto nitrocellulose paper. The blots were incubated with antibody directed against N-terminal T7-tag or pooled serum from peanut-sensitive patients. While binding to the T7 tag remained relatively constant, IgE binding was dramatically decreased in the mutants.

IgE Binding to MUT1 and MUT3 vs. Wild-Type Ara h 2 Using Individual Sera

IgE binding to mutated recombinant Ara h 2 proteins (MUT1 and MUT3) as compared to the wild-type was then examined in Western blot analysis using individual patient sera. Laser densitometry was used to quantitate relative IgE binding. While IgE binding to MUT3 was dramatically reduced for each individual, some differences were observed between the different individuals in the group with MUT1.

Inhibition of IgE Binding to Native Ara h 2

To further characterize binding of IgE to MUT1 and MUT3, an inhibition binding assay was performed. 0.5 μg of the native Ara h 2 protein purified from crude peanut extract was loaded onto each member of a set of nitrocellulose membranes using a slot-blot apparatus. The membranes were then incubated with pooled patient serum (1:20) in the presence or absence of different concentrations of wild-type Ara h 2, MUT1, MUT3, and as controls rice protein or recombinant wild-type Ara h 1. Membranes were probed for bound IgE with $^{125}$I-labeled anti-human IgE antibody. Laser densitometry of the autoradiograms was used to quantitate the relative amounts of IgE binding. While MUT3 had a negligible effect (same as control) on IgE binding to native Ara h 2, MUT1 inhibited binding at similar levels as recombinant wild-type Ara h 2.

T-Cell Proliferation in Presence of MUT3

Peripheral blood mononuclear cells (PBMCs) were isolated from heparinized venous blood of peanut-sensitive patients by density gradient centrifugation on Ficoll. $2\times10^5$ cells per well were incubated in triplicates for 7 days in RPMI media with 5% human AB serum in the presence of 10 μg/ml of the native Ara h 2 protein purified from the crude peanut extract or recombinant Ara h 2 proteins purified from *E. coli*. Cells incubated in media only were used as a control. Proliferation was measured by the incorporation of tritiated thymidine. The stimulation index (SI) was calculated as a ratio of radioactivity for the cells growing in the presence of allergen to that for the cells growing in media alone. Relatively low proliferation was observed in the presence of MUT3 suggesting that T-cell epitopes may be affected by mutagenesis of overlapping IgE epitopes.

MUT2 Binds Less IgE But Similar Amounts of IgG as Wild-Type Ara h 2

MUT2 includes mutations within IgE epitopes 3, 6, and 7 that were determined to be immunodominant in Example 2. MUT2 was produced and immunoblot analysis performed using serum from peanut-sensitive patients as described above. The results showed that MUT2 bound significantly less IgE than recombinant wild-type Ara h 2 but bound similar amounts of IgG.

MUT2 Retains the Ability to Activate T-Cell Proliferation

MUT2 was also used in T-cell proliferation assays to determine if it retained the ability to activate T-cells from peanut-sensitive individuals. Proliferation assays were performed on T-cell lines grown in short-term culture developed from six peanut-sensitive patients. T-cells lines were stimulated with either 50 μg of crude peanut extract, 10 μg of native Ara h 2, 10 μg of recombinant wild-type Ara h 2, or 10 μg of MUT2 and the amount of incorporated $^3$H-thymidine was determined for each cell line. Results were expressed as the average stimulation index (SI) which reflects the fold increase in $^3$H-thymidine incorporation exhibited by cells challenged with allergen when compared with media treated controls. MUT2 exhibited a comparable ability to stimulate T-cell proliferation as wild-type Ara h 2.

MUT2 Elicits a Smaller Wheal and Flare in Skin Prick Tests than Wild-Type Ara h 2

MUT2 and wild-type recombinant Ara h 2 were used in a skin prick test of a peanut-sensitive individual. 10 μg of these proteins were applied separately to the forearm of a peanut-sensitive individual, the skin pricked with a sterile needle, and 10 minutes later any wheal and flare that developed was measured. The wheal and flare produced by wild-type Ara h 2 (8 mm×7 mm) was approximately twice as large as that produced by MUT2 (4 mm×3 mm). A control subject (no peanut hypersensitivity) tested with the same proteins had no visible wheal and flare but, as expected, gave positive results when challenged with histamine. In addition, the test subject gave no positive results when tested with PBS alone. These results indicate that an allergen with only 50% of its IgE epitopes modified (i.e., 5/10) can give measurable reduction in reactivity in an in vivo test of a peanut-sensitive patient.

Example 7

In Vitro Safety Assay Using a Model Cell System for Mediator Release 7.1 Materials Rat basophil leukemia cells (RBL-2H3) were "humanized" by transfection with the α chain of the human Fc$_ε$RI receptor and thus enabled to bind human IgE. Crude peanut extract was prepared from Southeastern runners as described in Burks et al., *J Allergy Clin. Immunol.*, 88:172, 1991. Crude soybean and crude pea extract were prepared using similar methods. Purified native Ara h 2 (nat Ara h 2) was prepared from crude peanut extract as described in Sen et al., *J. Immunol.* 169:882, 2002. "Wild-type" recombinant Ara h 2 (rAra h 2) was prepared as described in Example 4 above. "Mutant" recombinant Ara h 2 (mut Ara h 2) was prepared with the mutations of MUT3 that are shown in Table 9 of Example 4.

7.2 Methods

Transfectants were cultured in Eagle's MEM with 10% FCS, 0.1% geneticin sulfate, harvested in the stationary phase and transferred to 96-well microtiter plates ($1.5\times10^5$ cells/well) for the mediator release assay as described elsewhere in Hoffmann et al., *J. Allergy Clin. Immunol.* 99:227, 1997. Deviating from this protocol, transfectants were passively sensitized by incubation with human serum IgE for 18 hours at 37° C. and 5% carbon dioxide. Dilutions of sera from three peanut allergic patients (JB, RW and PEI 163) were optimized by preliminary titrations (final serum dilution in 100 μl MEM were JB 1:100, RW 1:100 and PEI 163 1:80). After sensitization, the adherent cell layer was washed three times with Tyrode's buffer and incubated with 100 μl of serial dilutions of the cross-linking agents (nat Ara h 2, rAra h 2, mut Ara h 2, crude peanut extract, crude soybean extract, or crude pea extract) in Tyrode's buffer containing 50% D$_2$O (Maeyama et al., *J. Biol. Chem.* 261:2583, 1986) for 1 hour at 37° C. For convenience, β-hexosaminidase was measured which has been shown to be released at the same rate as histamine (Schwartz et al., *J. Immunol.* 126:1290, 1981). To determine the enzymatic activity, 30 μl of the supernatant were transferred into a new microtiter plate and incubated with 50 μl of the substrate p-nitrophenyl-N-acetyl-β-D-glucosaminide (1.3 mg/ml in 0.1 M phosphate, 0.05 M citrate, pH 4.5) for 1 hour at 37° C. After addition of 100 μl 0.2 M glycin, pH 10.7, the absorbance was read at 405 nm (reference: 620 nm). As a consistency control for each microtiter plate, cells were sensitized with human myeloma IgE (hu IgE) (Biogenesis, Poole, UK: 1:5000) and stimulated with goat anti-human IgE (Nordic, Tilburg, NL: 1:1000). Spontaneous release (0%) was determined by omitting the cross-linking agents, the total enzyme content (100%) was measured by lysing the cells with 1% Triton X-100. Allergen-specific release was calculated as percent of total mediator content after correction for spontaneous release.

7.3 Results

Figure 10B:
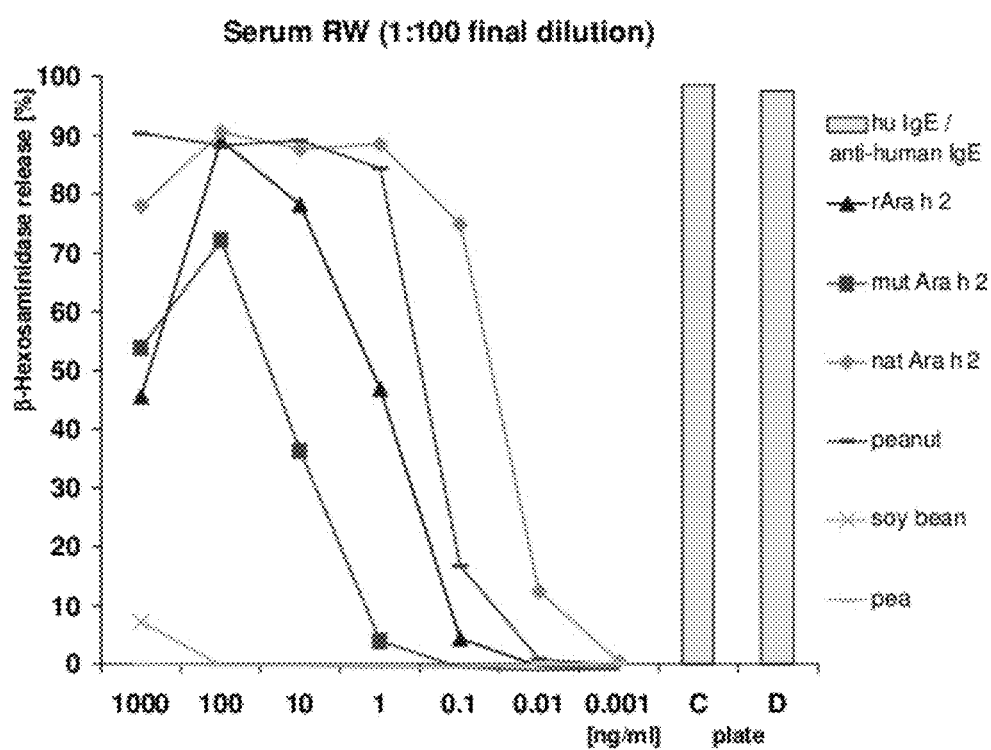
Figure 10C:
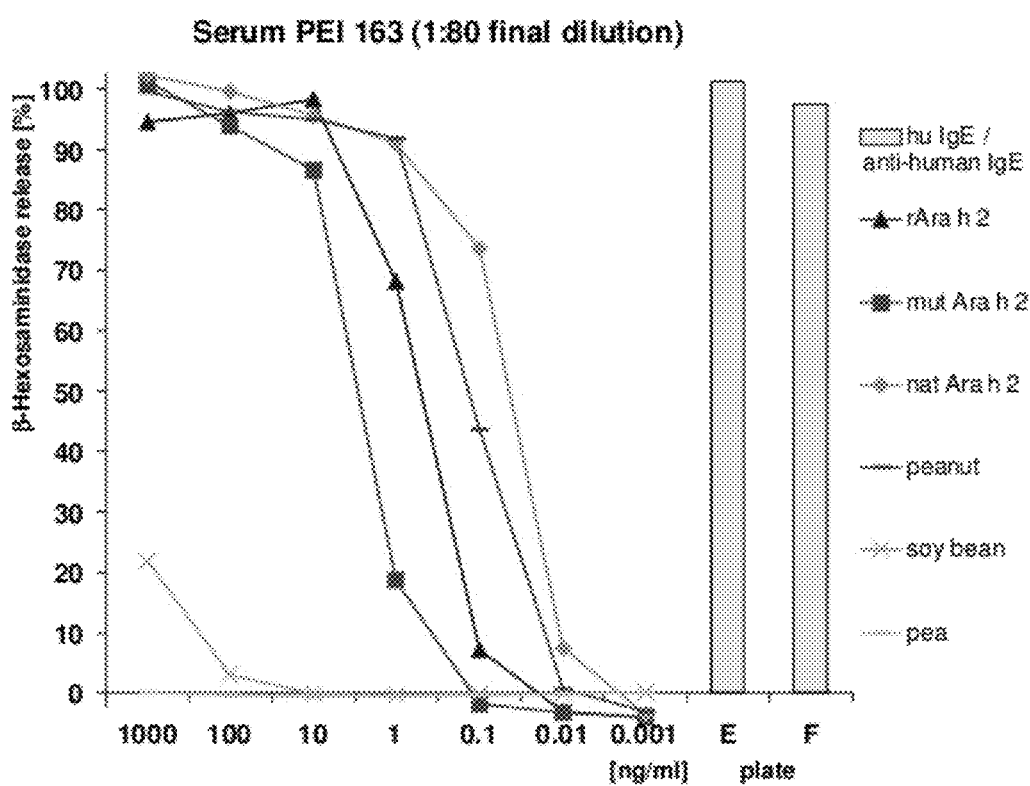

FIGS. 10A-C compare the allergen-specific release levels that were measured when the IgE coated transfectant cells were exposed to a range of concentrations (0.001 to 1000 ng/ml) of the different cross-linking agents. For each patient (JB, RW and PEI 163), the level of release was lowest when the cells were exposed to crude soybean or pea extract and greatest when the cells were exposed to nat Ara h 2. In between, crude peanut extract caused greater release than rAra h 2 which in turn caused greater release than mut Ara h 2.

Example 8

Ara h 3 Mutant Protein with Reduced IgE Binding 8.1 Introduction

In order to modulate IgE reactivity of Ara h 3 a recombinant Ara h 3 protein was constructed with mutations in the immunodominant IgE binding epitopes (see MUT1 in Example 4, Section 4.4 and Table 10). The abilities of the wild-type and mutant recombinant Ara h 3 proteins to react with IgE were then tested in Western blot analysis with sera from peanut-sensitive individuals. As compared to wild-type Ara h 3, the mutant Ara h 3 protein bound less IgE.

8.2 Results

The proteins were probed with serum IgE from three patients previously shown to recognize recombinant Ara h 3. While wild-type Ara h 3 was bound by IgE, the mutated Ara h 3 protein was not recognized by serum IgE from the peanut-sensitive patients.

Example 9

In Vitro and In Vivo Assays with *E. coli* Cells Expressing WT Ara h 1-3

9.1 Methods for Killing *E. coli* Cells

Recombinant wild-type Ara h 1, Ara h 2, and Ara h 3 were produced in *E. coli* BL21 cells as described in Example 4. Several methods of killing the allergen-producing *E. coli* were then tested. As non-limiting examples, *E. coli* cells were killed by heat (at temperatures ranging from 37° C. to 95° C.), by using ethanol (0.1% to 10%), and by using solutions containing iodine (0.1% to 10%). Survival was determined by plating 100 µl of cells onto agar plates, and subsequently counting the resulting colonies. The most reproducible method was heat-killing with incubation at 60° C. for 20 minutes resulting in 100% death.

9.2 Production of Wild-Type Ara h 1-3

The amounts of each allergen that were produced by the *E. coli* cells were measured using an immunoblot assay that made use of the 6×-His tag present on each of the recombinant allergens Ara h 1-3. The amount of allergen produced on a per cell basis varied depending on which clone was tested. For this particular preparation, more Ara h 3 was produced than Ara h 2 and Ara h 1 (Ara h 3>Ara h 2>>Ara h1). Best estimates for the amount of allergen delivered in 100 µl inoculum of *E. coli* cells (O.D. of 2.0 at 600 nm) varied from about 1 µg of Ara h 1 to about 20 µg of Ara h 3.

9.3 Release of Ara h 1-3 from Heat-Killed *E. coli* Cells

In order to determine if the cells remained intact after heat-killing, the amount of allergen released into the media was measured. A dot-blot assay was developed that utilized as controls, purified recombinant allergens (see Example 4, Section 4.6) applied to a filter at known concentrations and serum IgE from peanut-sensitive patients. The assay detected and quantified the amount of allergen present in 100 µl of supernatant after pelleting heat-killed bacteria. The level of allergen released varied and was dependent on the expression vector and protein tested. In general, for this particular preparation, more Ara h 2 was released than Ara h 1 and Ara h 3 (Ara h 2>>Ara h 1>Ara h 3). As described previously, in certain embodiments of the invention, released allergen can be removed from an inventive composition using standard washing methods. For the purpose of these experiments the compositions were not washed.

9.4 Murine Immune Response to Heat-Killed *E. coli* Cells Expressing WT Ara h 1-3

The transformed cells were injected into C3H/HEJ mice to determine if the allergen-expressing *E. coli* elicited an immune response. The following protocol was utilized to assess the immune response. Blood was collected from the tail vein of each mouse used before the first injection. Enough blood was collected to perform an antibody ELISA for each allergen. On day 0 each mouse was injected with 100 µl of the heat-killed *E. coli* samples subcutaneously (sc) in the left hind flank. The mice were given a second boosting injection on day 14 using the same procedure. On day 21, a second blood sample was collected from each mouse. Blood samples at day 0 and day 21 were assayed for IgG1 and IgG2a antibodies to either Ara h 1, Ara h 2, or Ara h 3 by an ELISA assay.

Mice injected with *E. coli* producing Ara h 1 did not give detectable levels of any immunoglobulin to the Ara h 1 allergen. Without limitation to theory, it can be speculated that this may be due to the relatively small amounts of Ara h 1 produced by these cells (see Section 9.2). Mice injected with *E. coli* producing Ara h 2 contained relatively high levels of IgG1 and IgG2a. Again, without limitation to the cause, it can be speculated that this may be due to the amount of Ara h 2 released from these cells (see Section 9.3). Mice injected with *E. coli* producing Ara h 3 contained relatively high levels of IgG2a (indicative of a Th1-type response) and elicited relatively low levels of IgG1 (indicative of a Th2-type response). Overall, the data in this Example should be cautiously interpreted; however, the general trend suggests that more mice exhibited an IgG2a response than IgG1 response when the protein allergen was both expressed to a sufficient level and appropriately encapsulated within the heat-killed *E. coli* cells.

Example 10

In Vivo Safety Assay Using Mice Sensitized to Crude Peanut Extract 10.1 Materials Female C3H/HeJ mice, 5 weeks of age were purchased from the Jackson Laboratory (Bar Harbor, Me.) and maintained on peanut-free chow, under specific pathogen-free conditions. Standard guidelines, Institute of Laboratory Animal Resources Commission of Life Sciences NRC, *National*

Academy Press, 1996, for the care and use of animals were followed.

Crude peanut extract (CPE) was prepared from Southeastern runners as described in Burks et al., *J. Allergy Clin. Immunol.*, 88:172, 1991. Purified native Ara h 1 was prepared from CPE as described in Maleki et al., *J. Immunol.* 164:5844, 2000. Purified native Ara h 2 was prepared from CPE as described in Sen et al., *J. Immunol.* 169:882, 2002. "Wild-type" Ara h 1, Ara h 2 and Ara h 3 allergens were prepared as described in Example 4 above. "Mutant" Ara h 1, Ara h 2 and Ara h 3 allergens were prepared with the mutations of MUT2 Ara h 1 (Table 8), MUT3 Ara h 2 (Table 9) and MUT1 Ara h 3 (Table 10) as described in Example 4 above. Heat-killed *E. Coli* expressing recombinant versions of Ara h 1, Ara h 2 and Ara h 3 were prepared by heating harvested *E. coli* cells to 60° C. for 20 minutes.

10.2 Methods

Figure 11:
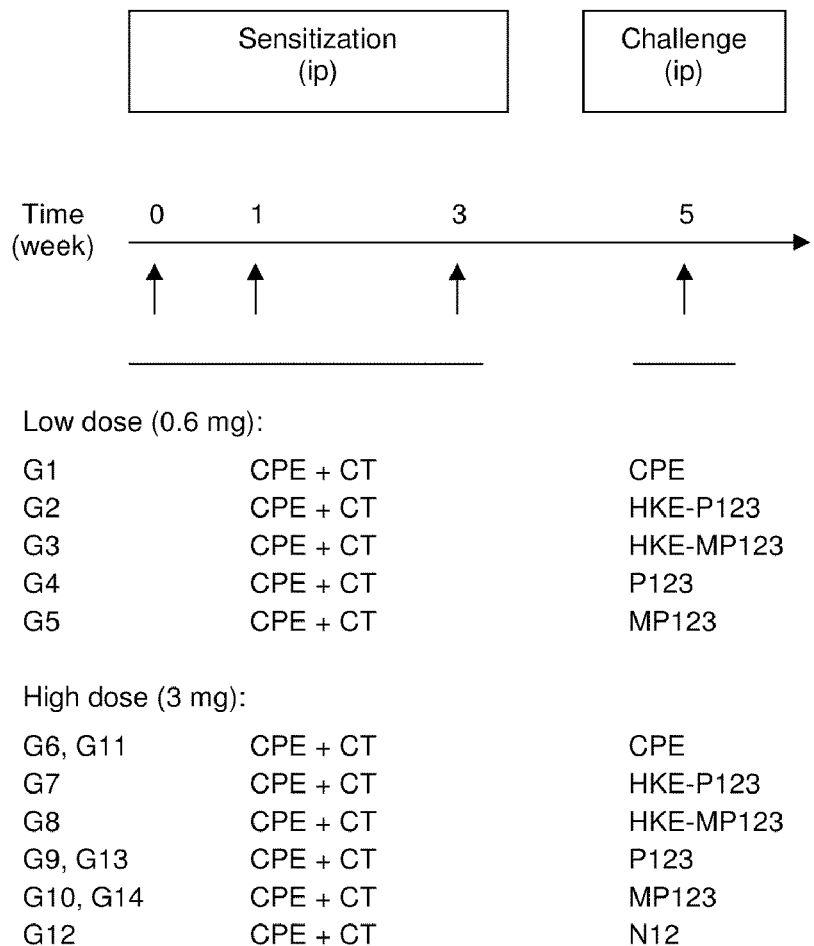
FIG. 11 is an outline of the sensitization and challenge protocols that were used for the fourteen groups of mice (G1-G14) in the experiments of Example 10. Mice were first sensitized intraperitoneally with peanut over a 3 week period. The mice were then challenged intraperitoneally with low or high doses of various compositions 5 weeks after the initial sensitization.
Figure 20:
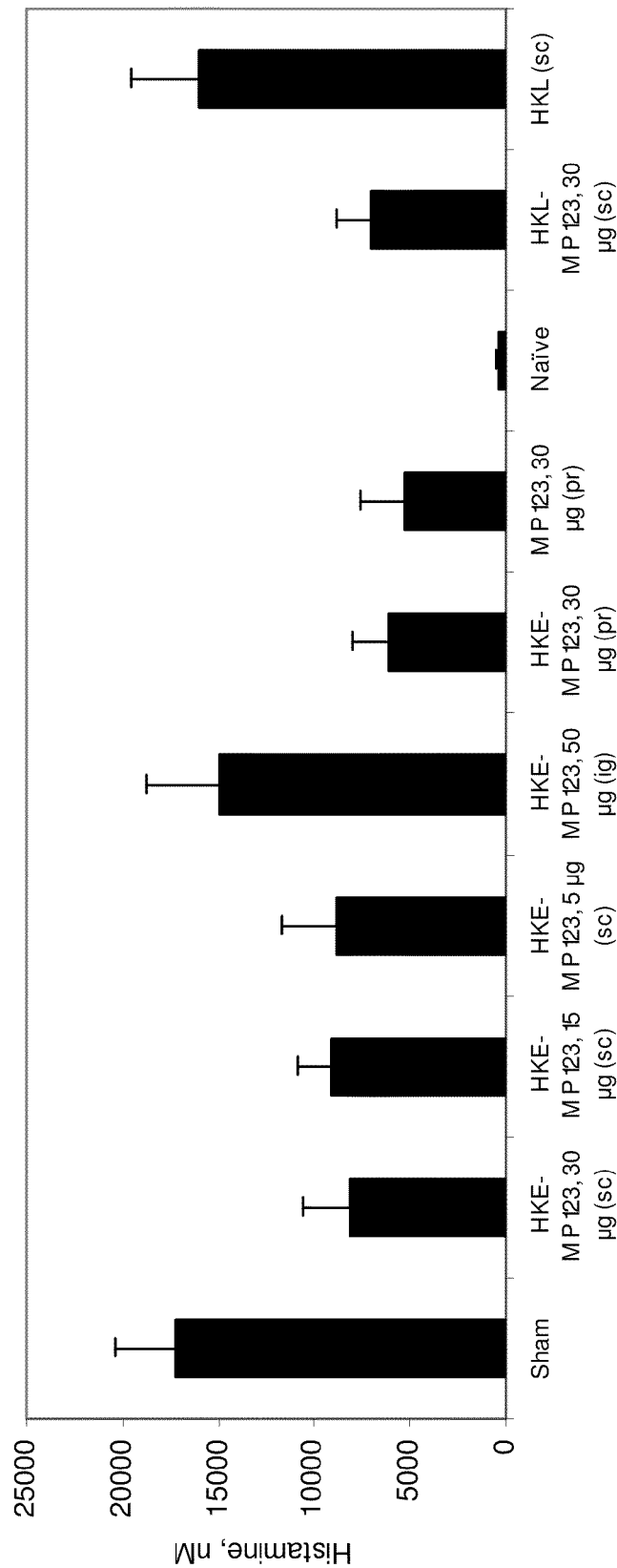
FIG. 20 compares the plasma histamine concentrations (nM) that were determined after challenge for the ten groups of mice (G1-G10) described in FIG. 12.
Figure 21:
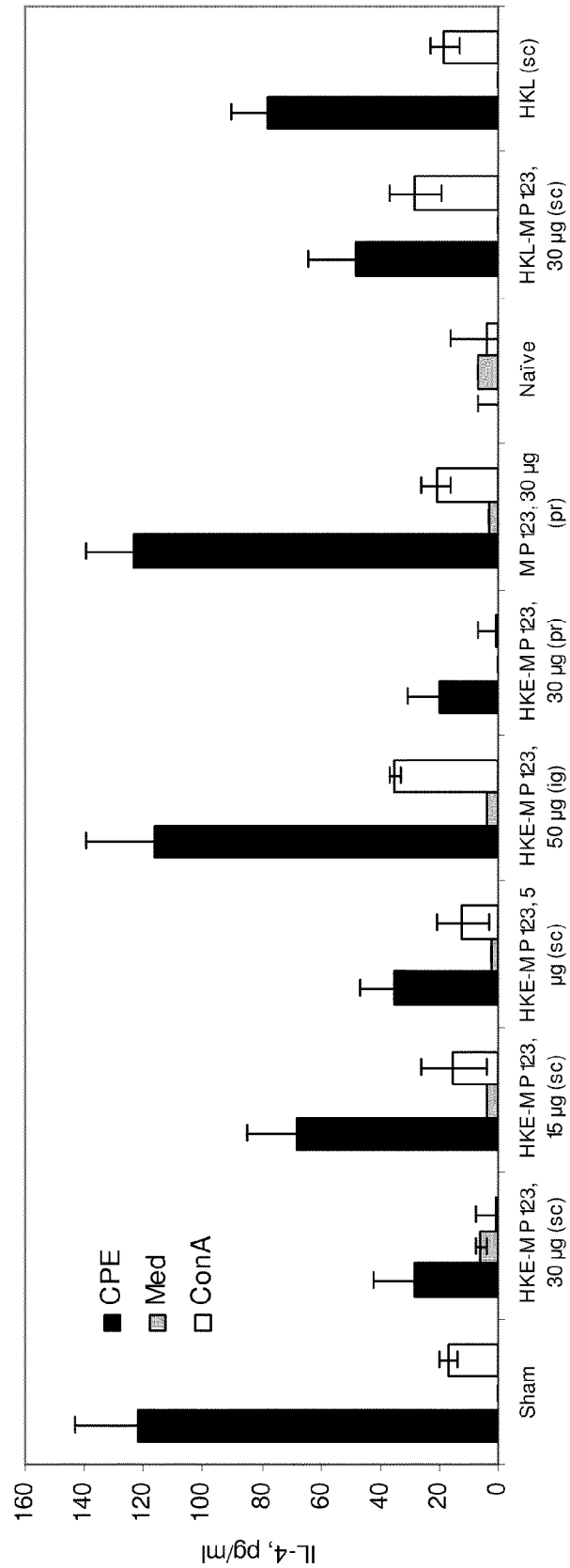
FIG. 21 compares the plasma IL-4 concentrations (pg/ml) that were determined after challenge for the ten groups of mice (G1-G10) described in FIG. 12.
Figure 22:
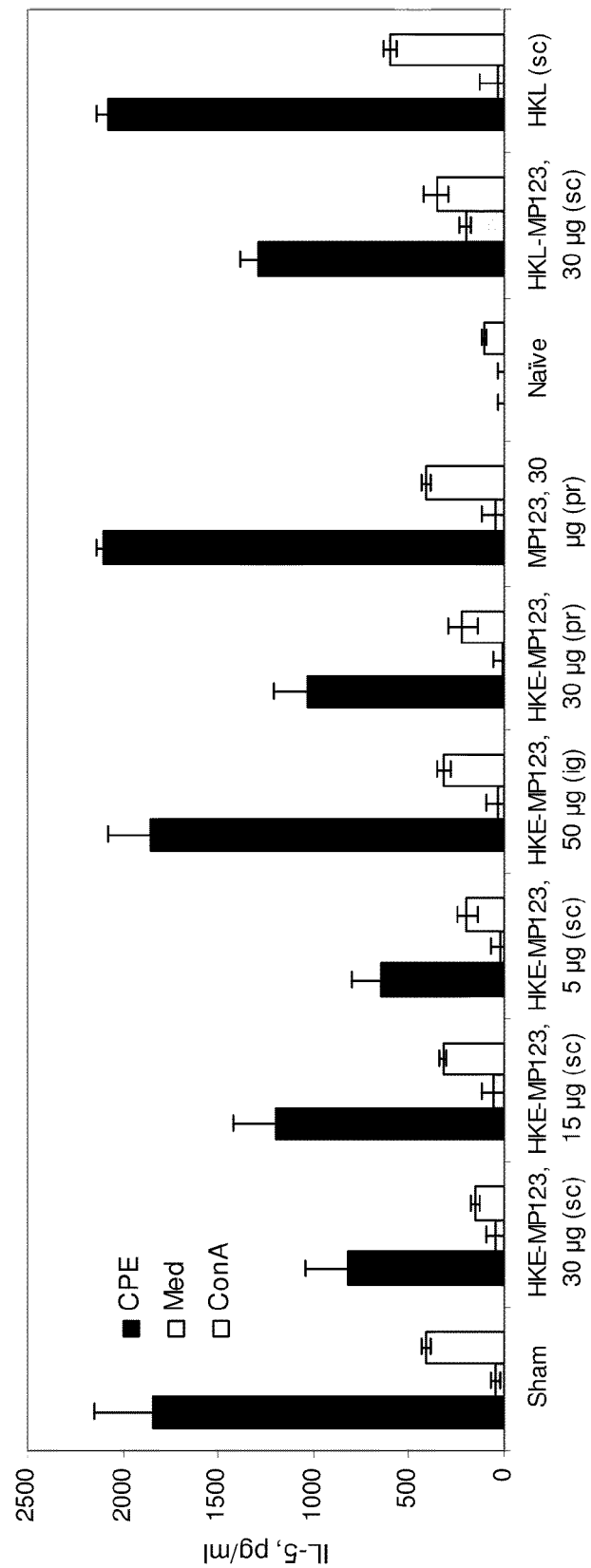
FIG. 22 compares the plasma IL-5 concentrations (pg/ml) that were determined after challenge for the ten groups of mice (G1-G10) described in FIG. 12.
Figure 23:
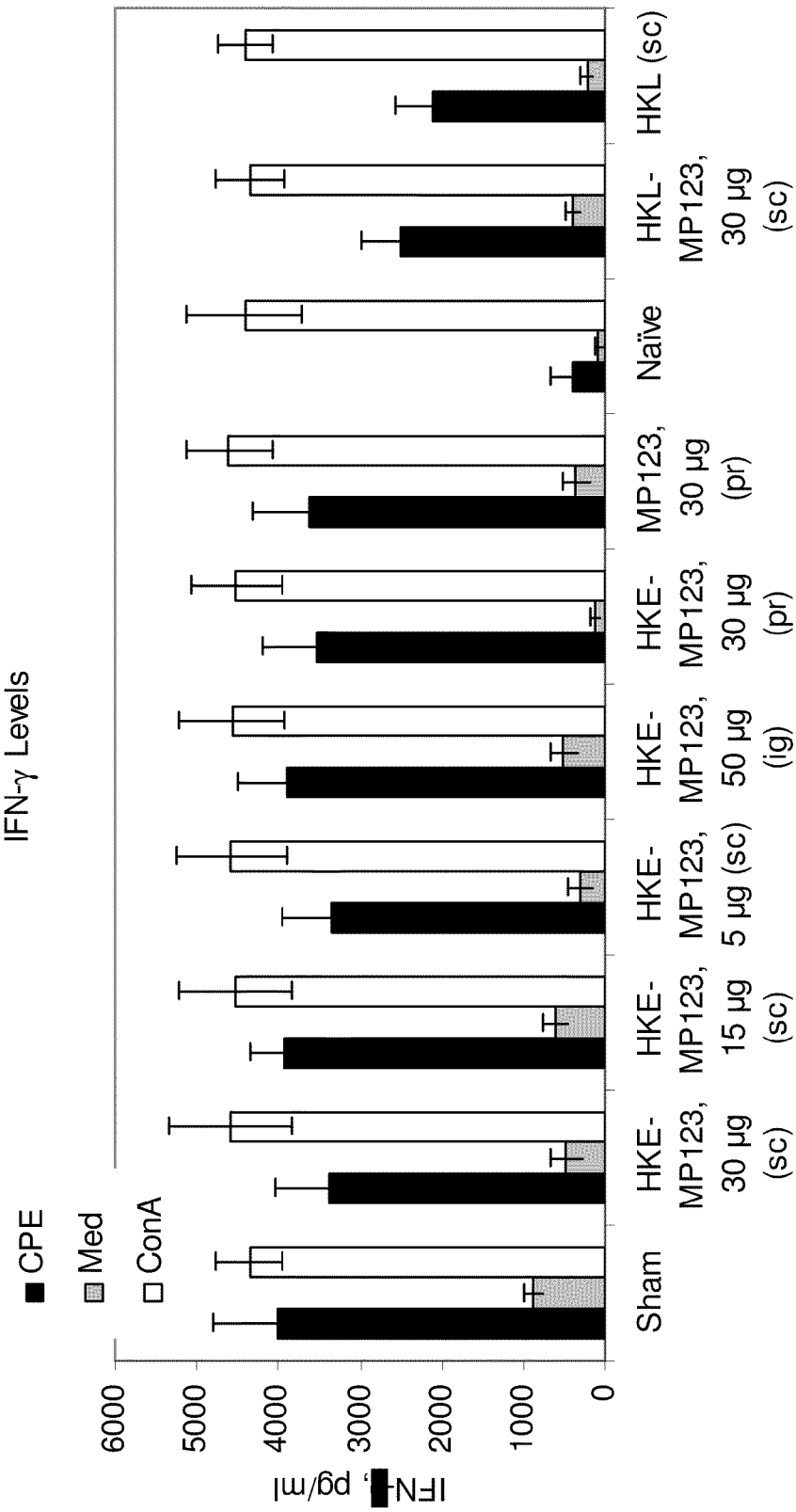
FIG. 23 compares the plasma IFN-γ concentrations (pg/ml) that were determined after challenge for the ten groups of mice (G1-G10) described in FIG. 12.

The sensitization and challenge protocols that were used in this Example are outlined in FIG. 11. All mice were sensitized by intraperitoneal (ip) injection of 500 μg CPE and 2 mg alum in 400 μl phosphate buffered saline (PBS) at weeks 0, 1 and 3.

Tail vein blood was obtained following sensitization (at week 4 or one day prior to challenge at week 5) to detect any potential bias caused by differences in the levels of CPE-specific IgE. Sera were collected and stored at −80° C. Levels of CPE-specific IgE were measured by ELISA as described in Li et al., *J. Allergy Clin. Immunol.* 106:150, 2000.

Five weeks following the initial sensitization, mice were challenged ip with a variety of compositions (see Results and FIG. 11). Anaphylactic symptoms were evaluated 30-40 minutes following challenge utilizing a 0-5 scoring system, modified slightly from previous reports (Li et al., *J. Allergy Clin. Immunol.* 103:206-214; Poulsen et al., *Clin. Allergy;* 17:449-458, 1987; McCaskill et al., *Immunology,* 51:669-677, 1984): 0=no symptoms; 1=scratching and rubbing around the nose and head; 2=puffiness around the eyes and mouth, diarrhea, pilar erecti, reduced activity and/or decreased activity with increased respiratory rate; 3=wheezing, labored respiration, cyanosis around the mouth and the tail; 4=no activity after prodding, or tremor and convulsion; and 5=death.

10.3 Results (G1-G5)

Five groups of five mice (G1-G5) were used in a first sensitization and challenge experiment. The individual and average IgE levels (ng/ml) measured one day prior to challenge at week 5 (i.e., post-sensitization) are compared in Table 14. Although there was some variability between individual mice in each group, the average IgE levels were comparable. The mice in each group were then challenged with an ip injection of one of three different compositions at week 5: G1 mice were challenged with CPE (600 μg); G2 mice were challenged with HKE-P123 (200 μg of each); G3 mice were challenged with HKE-MP123 (200 μg of each); G4 mice were challenged with P123 (200 μg of each); and G5 mice were challenged with MP123 (200 μg of each).

The individual and average symptom scores at week 5 for the five groups of mice are compared in Table 14. While mice challenged with CPE (G1) exhibited wheezing, labored respiration, cyanosis around the mouth and the tail and/or death after plasma collection, mice exposed to recombinant peanut allergens or HKE expressing these peanut allergens (G2-G5) exhibited mild diarrhea or no symptoms. The rectal temperatures of each of the mice were also measured at week 5 and are compared in Table 14.

TABLE 14

In vivo results for G1-G5

| W0, W1, W3 Sensitization | Mouse | W 5[1] IgE (ng/ml) | Challenge | W 5 Score | Temp. (° C.) |
|---|---|---|---|---|---|
| CPE (0.5 mg) G1 | 1 | 2403 | CPE (0.6 mg) | 3 | 36.0 |
|  | 2 | 2555 |  | 3[2] | 36.3 |
|  | 3 | 2510 |  | 3[2] | 35.7 |
|  | 4 | 3133 |  | 3[2] | 36.0 |
|  | 5 | 2363 |  | 3 | 36.1 |
|  | Average | 2593 |  | 3.0 | 36.0 |
| CPE (0.5 mg) G2 | 1 | 2272 | HKE-P123 (0.2 mg each) | 0 | 36.9 |
|  | 2 | 3121 |  | 0 | 35.9 |
|  | 3 | 1936 |  | 0 | 36.7 |
|  | 4 | 1487 |  | 0 | 35.3 |
|  | 5 | 1968 |  | 0 | 36.8 |
|  | Average | 2157 |  | 0.0 | 36.3 |
| CPE (0.5 mg) G3 | 1 | 3157 | HKE-MP123 (0.2 mg each) | 2[3] | 36.0 |
|  | 2 | 3358 |  | 0 | 36.4 |
|  | 3 | 2296 |  | 0 | 36.4 |
|  | 4 | 2679 |  | 2[3] | 36.6 |
|  | 5 | 2515 |  | 0 | 36.3 |
|  | Average | 2801 |  | 0.8 | 36.3 |
| CPE (0.5 mg) G4 | 1 | 2778 | P123 (0.2 mg each) | 0 | 38.0 |
|  | 2 | 2651 |  | 0 | 37.9 |
|  | 3 | 2631 |  | 0 | 37.7 |
|  | 4 | 2451 |  | 0 | 38.4 |
|  | 5 | 2093 |  | 0 | 38.2 |
|  | Average | 2521 |  | 0.0 | 38.0 |
| CPE (0.5 mg) G5 | 1 | 2219 | MP123 (0.2 mg each) | 0 | 37.6 |
|  | 2 | 1893 |  | 0 | 37.3 |
|  | 3 | 1642 |  | 0 | 37.5 |
|  | 4 | 2420 |  | 0 | 37.5 |
|  | 5 | 2498 |  | 0 | 37.5 |
|  | Average | 2187 |  | 0.0 | 37.5 |

[1]IgE values were measured one day prior to challenge at week 5.
[2]Died after plasma collection.
[3]Diarrhea.

10.4 Results (G6-G10)

The sensitization and challenge experiments were repeated at a higher challenge dosage with five new groups (G6-G10) each including two sub-groups A and B of 2-5 mice. Again, the individual and average IgE levels (ng/ml) were measured one day prior to challenge at week 5 for the mice in each of the three groups and are compared in Table 15. Although there was some variability between individual mice in each group, the average IgE levels were again comparable between the five groups.

The mice were challenged with an ip injection of one of three different compositions at week 5: G6 mice were challenged with CPE (3 mg); G7 mice were challenged with HKE-MP123 (1 mg of each); G8 mice were challenged with HKE-MP123 (1 mg of each); G9 mice were challenged with P123 (1 mg of each); and G10 mice were challenged with MP123 (1 mg of each).

The individual and average symptom scores at week 5 for the five groups of mice are compared in Table 15. Again, while mice exposed to CPE (G6) exhibited wheezing, labored respiration, cyanosis around the mouth and the tail and/or death, mice exposed to recombinant peanut allergens or HKE expressing these peanut allergens (G7-G10) exhibited no symptoms. The rectal temperatures of each of the mice were also measured at week 5 and are compared in Table 15.

TABLE 15

In vivo results for G6-G10

| W0, W1, W3 Sensitization | Mouse | W 5[1] IgE (ng/ml) | Challenge | W 5 Score | Temp. (° C.) |
|---|---|---|---|---|---|
| CPE | 1A | 1799 | CPE | 3 | 31.8 |
| (0.5 mg) | 2A | 1702 | (3 mg) | 3 | 32.0 |
|  | 3A | 1956 |  | 5 | 31.3 |
| G6 | 4A | 2092 |  | 5 | 31.6 |
|  | 5A | 1556 |  | 3 | 32.5 |
|  | 1B | 1803 |  | 3 | 32.3 |
|  | 2B | 1902 |  | 5 | 33.5 |
|  | 3B | 1818 |  | 3 | 31.4 |
|  | 4B | 2161 |  | 3 | 33.8 |
|  | Average | 1865 |  | 3.7 | 32.2 |
| CPE | 1A | 1675 | HKE-P123 | 0 | 34.8 |
| (0.5 mg) | 2A | 1991 | (1 mg each) | 0 | 34.5 |
|  | 3A | 1702 |  | 0 | 33.8 |
| G7 | 4A | 1479 |  | 0 | 34.0 |
|  | 1B | 1640 |  | 0 | 34.1 |
|  | 2B | 1819 |  | 0 | 33.8 |
|  | 3B | 1591 |  | 0 | 34.4 |
|  | 4B | 1710 |  | 0 | 34.0 |
|  | Average | 1701 |  | 0.0 | 34.2 |
| CPE | 1A | 2019 | HKE-MP123 | 0 | 35.6 |
| (0.5 mg) | 2A | 1826 | (1 mg each) | 0 | 35.3 |
|  | 3A | 2027 |  | 0 | 35.9 |
| G8 | 4A | 1883 |  | 0 | 36.4 |
|  | 1B | 1990 |  | 0 | 36.2 |
|  | 2B | 1648 |  | 0 | 35.4 |
|  | 3B | 1354 |  | 0 | 35.3 |
|  | 4B | 1536 |  | 0 | 35.9 |
|  | Average | 1786 |  | 0.0 | 35.8 |
| CPE | 1A | 1891 | P123 | 0 | 34.5 |
| (0.5 mg) | 2A | 1726 | (1 mg each) | 0 | 35.5 |
|  | 3A | 2287 |  | 0 | 36.3 |
| G9 | 4A | 1607 |  | 0 | 36.6 |
|  | 1B | 1863 |  | 0 | 35.2 |
|  | 2B | 2254 |  | 0 | 34.9 |
|  | 3B | 1738 |  | 0 | 36.3 |
|  | Average | 1910 |  | 0.0 | 35.6 |
| CPE | 1A | 1363 | MP123 | 0 | 37.4 |
| (0.5 mg) | 2A | 1485 | (1 mg each) | 0 | 36.6 |
|  | 3A | 1669 |  | 0 | 37.0 |
| G10 | 4A | 1844 |  | 0 | 37.0 |
|  | 1B | 1668 |  | 0 | 37.1 |
|  | 2B | 1532 |  | 0 | 35.3 |
|  | Average | 1678 |  | 0.0 | 36.6 |

[1]IgE values were measured one day prior to challenge at week 5.

10.5 Results (G11-G14)

The sensitization and challenge experiments were repeated using a different set of challenge compositions with four more groups (G11-G14) each including 4-6 mice. The mice were challenged with an ip injection of one of three different compositions at week 5: G11 mice were challenged with CPE (3 mg); G12 mice were challenged with NP12 (1 mg of each); G13 mice were challenged with P123 (1 mg of each); and G14 mice were challenged with MP123 (1 mg of each).

The individual and average symptom scores at week 5 for the four groups of mice are compared in Table 16. While the mice exposed to CPE or purified native Ara h 1 and Ara h 2 (G11 and G12) exhibited severe anaphylactic symptoms (i.e., scores of 2-4), the mice that were exposed to wild-type peanut proteins (G13) exhibited mild reactions (i.e., symptom scores of 1-2) and the mice that were exposed to mutant peanut proteins (G14) exhibited no reactions. The rectal temperatures of each of the mice were also measured at week 5 and are compared in Table 16.

TABLE 16

In vivo results for G11-G14

| W0, W1, W3 Sensitization | Mouse | W 5 Challenge | W 5 Score | Temp. (° C.) |
|---|---|---|---|---|
| CPE | 1 | CPE | 2 | 33.4 |
| (0.5 mg) | 2 | (3 mg) | 3 | 32.3 |
|  | 3 |  | 3 | 32.1 |
| G11 | 4 |  | 4 | 31.9 |
|  | Average |  | 3.0 | 32.4 |
| CPE | 1 | NP12 | 4 | 31.5 |
| (0.5 mg) | 2 | (1 mg each) | 2 | 33.3 |
|  | 3 |  | 2 | 34.2 |
| G12 | 4 |  | 2 | 32.8 |
|  | 5 |  | 2 | 34.9 |
|  | Average |  | 2.4 | 33.3 |
| CPE | 1 | P123 | 2 | 34.4 |
| (0.5 mg) | 2 | (1 mg each) | 2 | 35.6 |
|  | 3 |  | 2 | 34.8 |
| G13 | 4 |  | 1 | 34.5 |
|  | 5 |  | 1 | 36.2 |
|  | 6 |  | 1 | 35.5 |
|  | Average |  | 1.5 | 35.2 |
| CPE | 1 | MP123 | 0 | 35.4 |
| (0.5 mg) | 2 | (1 mg each) | 0 | 36.1 |
|  | 3 |  | 0 | 36.2 |
| G14 | 4 |  | 0 | 35.3 |
|  | 5 |  | 0 | 35.6 |
|  | 6 |  | 0 | 36.8 |
|  | Average |  | 0.0 | 35.9 |

Example 11

In Vivo Experiments Testing Different Delivery Routes for Desensitization

11.1 Introduction

The sensitization, desensitization and challenge protocols that were used in this Example are outlined in FIG. 12. Ten groups of mice (G1-G10) were used for these in vivo desensitization experiments. The 5 week old female C3H/HeJ mice (approx. 10 per group) were first sensitized with crude peanut extract and cholera toxin (CT) over a period of 8 weeks (W0-W8). Mice were deprived of food for 2 hours and given 300 µl of 1.5% NaHCO$_3$ 30 minutes before feeding to neutralize stomach acid. Sensitization was then performed by intragastric (ig) administration of 10 mg of crude peanut extract (CPE) together with 20 µg of CT on day 0 (W0), then boosted weekly for 6 weeks (W1-W6) and again at week 8 (W8).

The mice were then treated according to ten different desensitization protocols at weeks 10, 11, and 12 (W10-W12). Finally the mice were challenged intragastrically (ig) with crude peanut extract at week 13 (W13). G1 mice were sham desensitized at weeks 10-12, i.e., treated with a placebo. G2, G3, and G4 mice were desensitized via the subcutaneous (sc) route with HKE-MP123 (30, 15, and 5 µg of each, respectively). G5 mice were desensitized via the intragastric (ig) route with HKE-MP123 (50 µg of each). G6 mice were desensitized via the rectal (pr) route with HKE-MP123 (30 µg of each). G7 mice were desensitized via the rectal (pr) route with MP123 alone (30 µg of each). G8 mice were naïve, i.e., were not sensitized with crude peanut extract and CT during weeks 0-8 and received no desensitization treatment. G9 mice were desensitized via the subcutaneous (sc) route with heat-killed L. monocytogenes (HKL) alone. G10 mice were desensitized via the subcutaneous (sc) route with heat-killed *L. monocytogenes* expressing mutated Ara h 1-3 (HKL-MP123, 30 μg of each).

11.2 Results

The average IgE levels (ng/ml) at weeks 3, 8, 12, and 14 for the ten groups of mice (G1-G10) are shown in FIG. 13. As compared to the sham desensitized mice, the increase in IgE levels during the desensitization period (W10-W12) was dramatically reduced in all the desensitized groups except for the mice that were treated with HKL alone (G9) or via the ig route with HKE-MP123 (G5).

The individual (symbols) and average (solid line) symptom scores (0-5) at week 14 for the ten groups of mice are compared in FIGS. 14 and 15. The improvement in symptom scores parallel the IgE data with dramatic improvements (from an average score of 3.5 to average scores of 0.4 or less) except for the groups of mice that were treated with HKL only (average score of 3.4) or via the ig route with HKE-MP123 (average score of 3.0).

The individual (symbols) and average (solid line) body temperatures (° C.) at week 14 for the ten groups of mice are compared in FIGS. 16 and 17. The trend in average body temperature correlates well with the results in FIGS. 13-15. In all treated groups the average body temperature at week 14 is higher than in the sham sensitized group. However, the increase is smallest for the group of mice that were treated with HKL only or via the ig route with HKE-MP123.

The individual (symbols) and average (solid line) airway responses (peak expiratory flow in ml/min) at week 14 for the ten groups of mice are compared in FIGS. 18 and 19. Peak flow values are dramatically improved in most groups except for the group of mice that were treated with HKL only or via the ig route with HKE-MP123.

FIGS. 20, 21, 22, and 23 compare the plasma histamine (nM), IL-4 (pg/ml), IL-5 (pg/ml), and IFN-γ (pg/ml) concentrations at week 14 for the ten groups of mice (G1-G10).

These experiments suggest that parenteral (e.g., subcutaneous) or rectal delivery of HKE-MP123 produce the best desensitization results. In this context, the inventors have also observed that subcutaneous delivery induces local skin inflammation. In contrast, rectal delivery does not induce local inflammatory reactions (see Example 12, Section 12.3).

Example 12

In Vivo Experiments Testing Different Compositions for Desensitization

This Example refers to various patents, publications, books, articles, and other references that are listed under Section 12.6. The contents of all of these items are hereby incorporated by reference in their entirety.

12.1 Introduction

This Example compares the efficacy of rectally administered HKE-MP123 and MP123 in the treatment of peanut allergy. Peanut allergic C3H/HeJ mice received HKE-MP123 weekly (9 or 90 μg) for 3 weeks or MP123 three times a week (9 or 90 μg) for 4 weeks. Following peanut challenge, anaphylactic symptom scores and plasma histamine levels were determined. Peanut-specific IgE and IgG2a levels were monitored. The effect of treatment on Th1/Th2 cytokine secretion by splenocytes (SPCs) was also determined. HKE-MP123 treatment at both 9 and 90 μg significantly reduced anaphylactic symptom scores, plasma histamine levels and serum peanut-specific IgE levels and increased IgG2a levels as compared to the sham-treated group. Overall, HKE-MP123 treatment was more effective than MP123 treatment. HKE-MP123 treatment significantly reduced IL-4 and IL-5, and increased IFN-γ secretion by SPCs. HKE-MP123 also decreased IL-10 and increased TGF-β. Rectal administration of HKE-MP123 did not cause local mucosal inflammation. This Example confirms that rectally administered HKE-MP123 significantly suppresses peanut allergy.

12.2 Materials

Five-week-old female C3H/HeJ mice were purchased from the Jackson Laboratory (Bar Harbor, Me.) and maintained on peanut-free chow under specific pathogen-free conditions. Standard guidelines for the care and use of animals were followed (see Ref. 15).

Freshly ground whole peanut, and crude peanut extract (CPE) were prepared as described in Ref 16 and employed as antigens. Cholera toxin (CT) was purchased from List Biological Laboratories, Inc. (Campbell, Calif.). Concanavalin A (Con A), and albumin-dinitrophenyl (DNP-albumin) were purchased from Sigma (St. Louis, Mo.). Antibodies for ELISAs (sheep anti-mouse IgE, and biotinylated donkey anti sheep IgG) were purchased from the Binding Site, Inc. (San Diego, Calif.). Anti-DNP IgE and IgG2a were purchased from Accurate Scientific, Inc. (Westbury, N.Y.).

12.3 Methods

Preparation of HKE-MP123 and MP123

*E. coli* BL21 clones expressing mutated Ara h 1 (MUT2, Table 8), Ara h 2 (MUT3, Table 9), and Ara h 3 (MUT1, Table 10), or carrying the pET24(a)+ vector alone, were generated as described previously in Example 4 (see also Refs. 10-11). The bacteria were grown and protein expression was induced following the protocol described in Ref 17. The bacteria were inactivated by incubation in a water bath at 65° C. for 30 minutes, cooled on ice for ~20 minutes and collected by centrifugation at 4,000 g at 4° C. for 30 minutes. The cell pellet was washed with ice-cold phosphate-buffered saline (PBS), centrifuged as above, and resupended in the same buffer. The final HKE-MP123 mixture containing approximately equal quantities of the three modified peanut proteins was prepared according to the specific recombinant protein content of the bacteria. Specific protein expression levels were determined by Western immunoblot analysis using serial dilutions of each individual HKE and known quantities of the purified recombinant protein as standards. In the vector-control HKE suspension (HKE-V), the total number of bacteria, measured as optimal unit (O.U.) at 600 nm, was matched to that in the high dose HKE-MP123. The effectiveness of the heat-inactivation procedure was determined by plating bacterial aliquots taken from the induced culture and the final HKE suspensions on a LB-agar plate containing 30 μg/ml of kanamycin. Less than 0.02% of the HKE bacterial cells were found to be viable. The integrity of the heat-treated bacteria was verified by Western immunoblot analysis of the specific protein content in the bacterial cell pellet and in the culture supernatant from each individual HKE obtained by centrifugation at 4,000 g for 2 minutes at room temperature. More than 99% of the specific recombinant protein was shown to be present in the bacterial cell pellet fraction.

The recombinant mutated Ara h 1, Ara h 2, and Ara h 3 proteins were purified using a HIS•BIND® $Ni^{2+}$-chelating resin (Novagen, Madison, Wis.) according to the protocol described in Example 4 (see also Ref 10). Briefly, 6 to 12 liters of bacteria expressing one of the proteins were grown and induced as above. Bacteria were harvested and sonicated on ice for 20 minutes. The lysate was cleared and loaded on a chromatography column with ~25 ml of the HIS•BIND® resin loaded with $Ni^{2+}$. The column was washed with the binding buffer, the bound protein was renatured using a linear gradient of urea from 6 M to 0 M in the binding buffer. The column was washed with the binding buffer, pH 7.5, and the protein was eluted with a linear gradient of 0 M to 1 M of imidazole in 6 bed volumes of the same buffer. The eluent (~200 ml) was collected and dialyzed against two changes of 20 volumes each of PBS with 1 mM of phenylmethanesulfonyl fluoride (PMSF) at 4° C., for up to 20 hours total. The dialyzed protein was centrifuged at 23,000 g, 4° C. for 20 minutes and concentrated to an appropriate concentration using the AMICON® 8200 Stirred Cell with the YM-10 ultrafiltration membrane (Millipore, Billerica, Mass.). The protein concentration was determined by Micro BCA™ Protein Assay (Pierce, Rockford, Ill.). The purity of the protein was checked by SDS gel-electrophoresis.

Intragastric Antigen-Sensitization, Challenge, and HKE-MP123 Treatment

Figure 24:
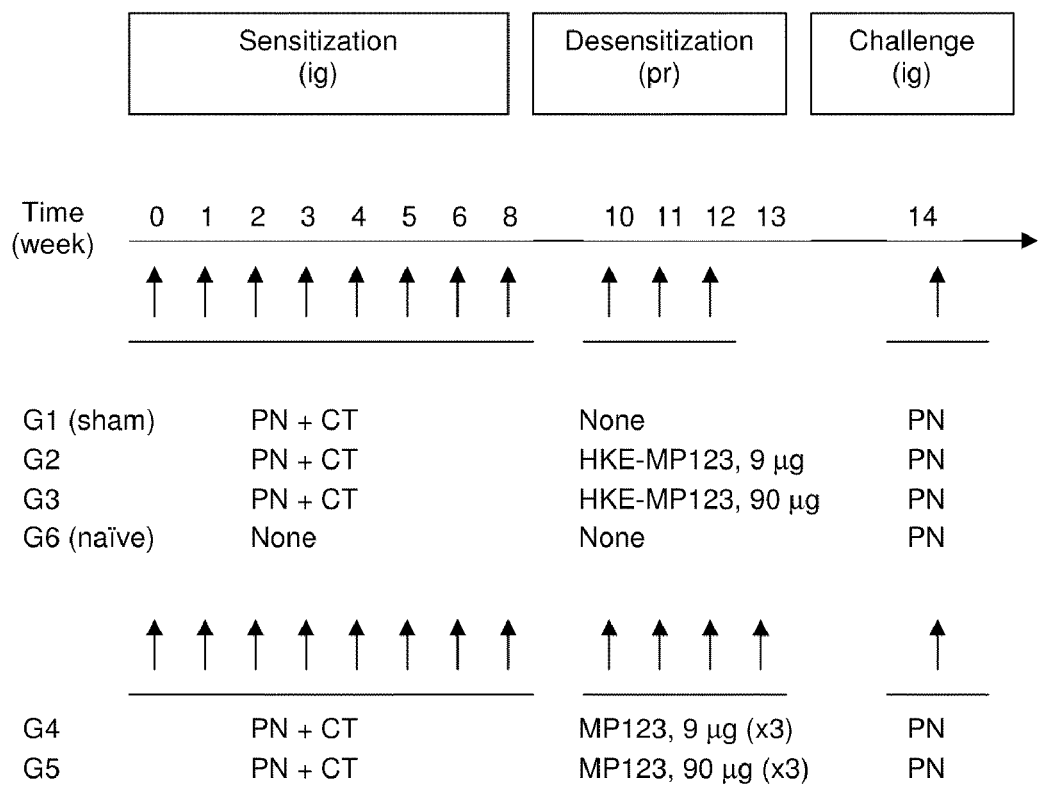
FIG. 24 is an outline of the sensitization, desensitization and challenge protocols that were used for the six groups of mice (G1-G6) in the experiments of Example 12. Mice were sensitized intragastrically with peanut over an 8 week period. Mice were then treated with rectal administrations of different compositions 10-13 weeks after the initial sensitization. All mice were finally challenged intragastrically with peanut 14 weeks after the initial sensitization.

Peanut sensitization and challenge followed the protocol described in Ref 18 and is outlined in FIG. 24. Briefly, mice were deprived of food for 2 hours. Sensitization was then performed by intragastric (ig) administration of 10 mg freshly ground whole peanut together with 20 μg of CT mixed with 300 μl of 1.5% $NaHCO_3$. Mice were then boosted weekly for 6 weeks and again at week 8. Treatment began at week 10. Mice were treated with HKE-MP123 (9 or 90 μg), weekly for 3 weeks (G2 and G3), or with MP123 (9 or 90 μg), three times a week for 4 weeks (G4 and G5). Sham (saline)-treated (G1) and naïve (G8) mice were included as controls. Rectal administration was performed using an 18 gage catheter and 90 μl of each preparation was instilled while the mice were anesthetized with a mixture of ketamine and xylazine (80 mg/kg and 10 mg/kg). The catheter was inserted approximately 1.5 cm. All mice were challenged intragastrically at week 14 with peanut (50 mg/mouse) in 2 divided doses at 30-40 minutes intervals.

Assessment of Hypersensitivity Reactions

Anaphylactic symptoms were evaluated 30-40 minutes after the second challenge dose utilizing the scoring system described in Example 10, Section 10.2 (see also Refs. 14 and 16): 0=no symptoms; 1=scratching and rubbing around the snout and head; 2=puffiness around the eyes and snout, diarrhea, pilar erecti, reduced activity, and/or decreased activity with increased respiratory rate; 3=wheezing, labored respiration, cyanosis around the mouth and the tail; 4=no activity after prodding, or tremor and convulsion; 5=death. Scoring of symptoms was performed in a blinded manner.

Measurement of Plasma Histamine Levels

Plasma histamine levels in blood samples collected 30 minutes after the second ig challenge dose were determined using an enzyme immunoassay kit (ImmunoTECH, Inc., Marseille, France) as described by the manufacturer (see Ref. 19).

Measurement of Serum Peanut Specific IgE and IgG2a

Tail vein blood was obtained during sensitization/boosting, 1 day before treatment and 1 day prior to challenge. Sera were collected and stored at −80° C. Levels of peanut-specific IgE and IgG2a were determined as described in Refs. 14, 16 and 20. Briefly, plates were coated with CPE incubated overnight at 4° C., and then blocked and washed. Samples (1:10 dilutions for IgE and 1:50 for IgG2a) were added to the plates and incubated overnight at 4° C. and plates were then washed. For detecting IgE antibodies, sheep anti-mouse IgE (0.3 μg/ml) was added and incubated for 1 hour and after washing, biotinylated donkey anti-sheep IgG (0.5 μg/ml) was added and incubated at room temperature (RT) for 1 hour. After appropriate washing, avidin-peroxidase was added for an additional 15 minutes at room temperature. The reactions were developed with ABTS (KPL) and read at 405 nm. For IgG2a measurement, biotinylated rat anti-mouse IgG2a monoclonal antibodies (0.25 μg/ml) were used as the detection antibodies. Subsequent steps were the same as those for IgE measurement. Equivalent concentrations of peanut-specific IgE and IgG2a were calculated by comparison with a reference curve generated with anti-DNP IgE and IgG2a mouse monoclonal antibodies, as described in Refs. 16 and 21.

Cell Culture and Cytokine Measurements

SPCs were isolated from pooled spleens removed from each group of mice, which were sacrificed immediately after evaluation of the anaphylactic reactions, and cultured in RPMI 1640 containing 10% fetal bovine serum, 1% penicillin/streptomycin, and 1% glutamine. SPCs were cultured in 24 well plates ($4 \times 10^6$/well/ml) in the presence or absence of CPE (50 μg/ml) or Con A (2 μg/ml). Supernatants were collected after 72 hours of culture and aliquots were stored at −80° C. until analyzed. IL-4, IL-5 and IFN-γ levels were determined by ELISA according to the manufacturer's instructions.

Histology

In a preliminary study, we localized the distribution of rectally administered fluid by injection of 90 μl of 0.5% of Evans blue following the procedure described above, and found that the fluid entered the sigmoid colon. To determine whether rectal administration of HKE-MP123 causes local inflammation, we collected rectum and colon samples from HKE-MP123, and saline treated mice 24 hours following the initial rectal administration as well as following peanut challenge at week 14. Tissues were fixed in 10% neutral buffered formalin and 5-micrometer paraffin sections were stained with hematoxylin and eosin (H and E) and examined by light microscopy.

Statistical Analysis

Data were analyzed using SigmaStat statistical software package (SPSS Inc. Chicago, Ill.). For histamine, IgE, and cytokine levels, the differences between the groups were analyzed by One way ANOVA followed by the Bonferroni's t test for all pairwise comparisons, if the data passed normality testing. For symptom scores, the differences between the groups were analyzed by Kruskal-Wallis One Way Analysis of Variance on Ranks followed by all pairwise comparison procedure (Dunn's), if the data failed to pass the normality test. We computed N, the required sample size per group, for 80% power, using a two tail test at the 0.05 level based on our preliminary study; 5 mice per group are required. p values <0.05 were considered to be of statistical significance.

12.4 Results

Figure 25:
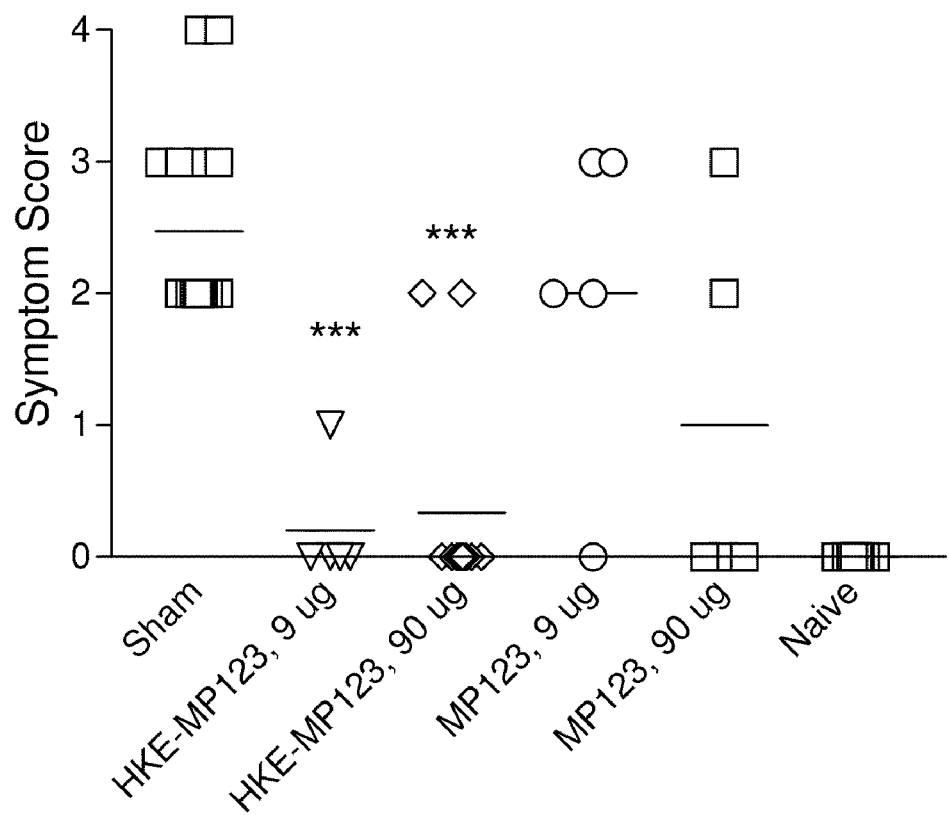
FIG. 25 compares the individual (symbols) and average (solid line) anaphylactic symptom scores that were determined after challenge for the six groups of mice (G1-G6) described in FIG. 24. The number of mice in each group were: G1 (sham)=17; G2 (HKE-MP123, 9 µg)=5; G3 (HKE-MP123, 90 µg)=12; G4 (MP123, 9 µg)=5; G5 (MP123, 90 µg)=5; G6 (naïve)=9. ***, $p<0.001$ vs. G1 (sham).

HKE-MP123 is More Effective than MP123 in Preventing Peanut Hypersensitivity Reactions Since anaphylactic reactions are the hallmark of peanut allergy, we first determined anaphylactic symptom scores 30 minutes following peanut-challenge. The severity of symptom scores in both low and high doses of HKE-MP123-treated groups were significantly reduced as compared with the sham treated group (FIG. 25, p<0.001). On the other hand, the symptom scores in low dose MP123-treated group were essentially the same as the sham-treated group. Although there was some reduction of symptom scores in the high dose MP123-treated group as compared with the sham-treated group, the reduction in this group did not reach statistical significance (p=0.065). These results demonstrate that HKE-MP123 is more effective than MP123 in protecting peanut-allergic mice from peanut-induced anaphylactic reactions. These results were obtained despite administering 9 more doses of MP123 of the same dosage (G4) and even at a dose that was 10 times higher (G5). In addition, treatment with HKE carrying vector alone showed some protective effect, but much less than the HKE-MP123 treatment (data not shown).

HKE-MP123 is More Effective than MP123 in Reducing Histamine Release

Figure 26:
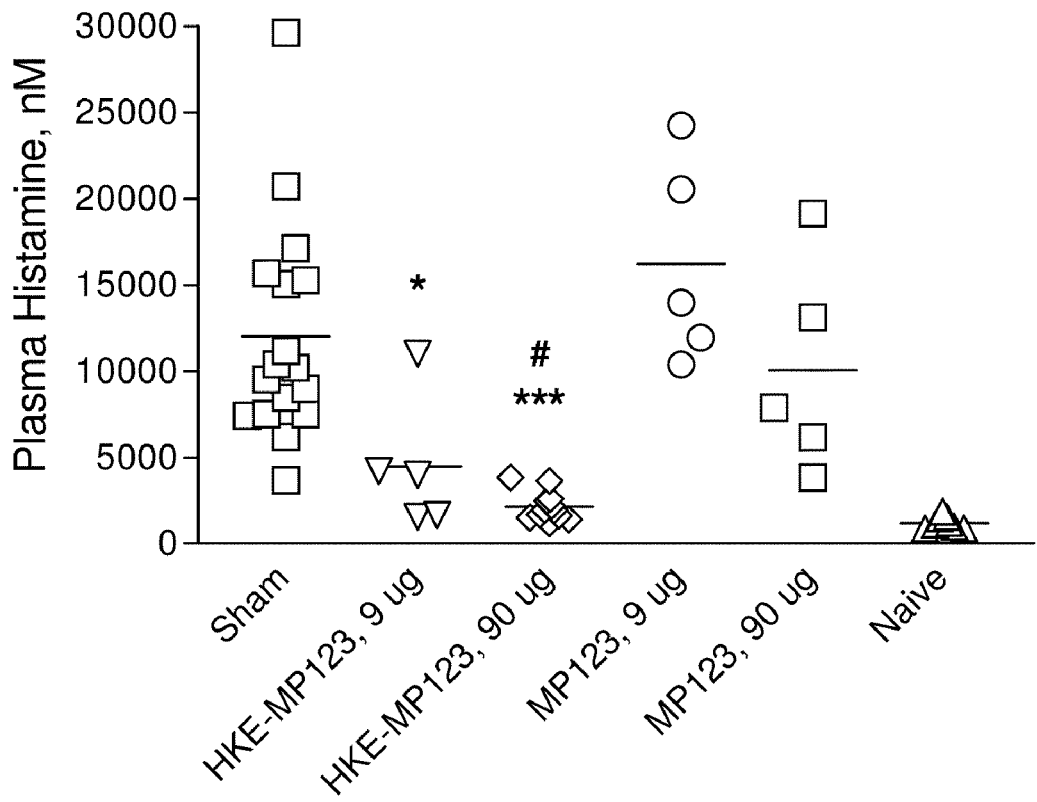
FIG. 26 compares the individual (symbols) and average (solid line) plasma histamine levels that were determined after challenge for the six groups of mice (G1-G6) described in FIG. 24. Blood was collected and plasma was obtained. Histamine levels were determined using an enzyme immunoassay kit. Data are mean±SEM for each group of mice. *, $p<0.05$ and ***, $p<0.001$ vs. G1 (sham). #, $p<0.05$ vs. G2 (HKE-MP123, 9 µg).

Histamine is one of the major mediators associated with anaphylactic reactions. To determine whether the protection against anaphylactic reactions in this model was associated with reduction of histamine release, we measured plasma histamine levels following challenge. We found that histamine levels were markedly reduced in both HKE-MP123 treated groups, being lowest in the high dose treated group (FIG. 26, $p<0.05$ and 0.001 respectively). However, histamine levels in the low and high dose MP123 treated-groups were not significantly different than the sham-treated group. These results support the clinical findings that HKE-MP123 was more effective than MP123 in protecting peanut-sensitized mice.

Figure 27:
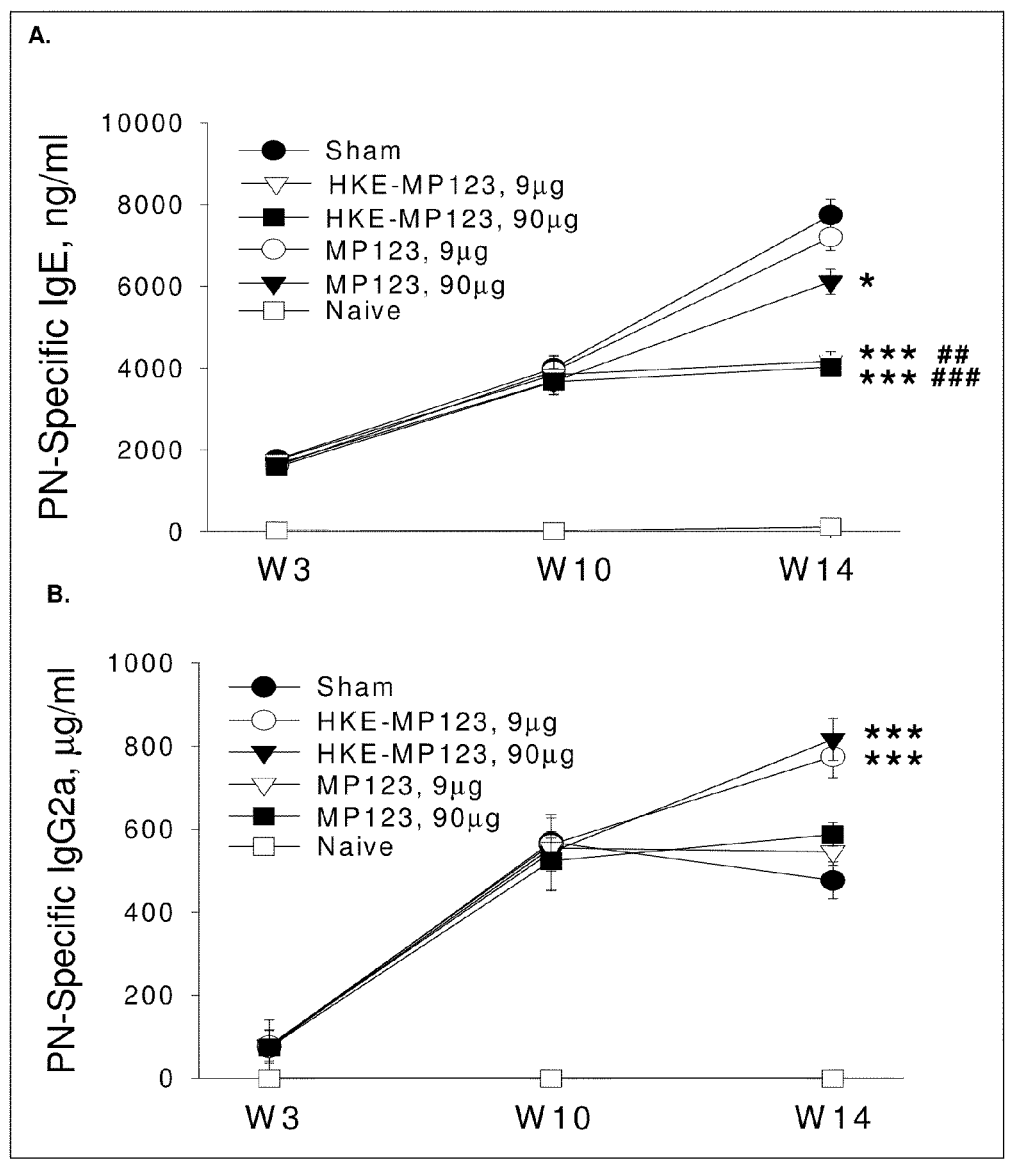
FIG. 27 compares average peanut specific IgE and IgG2a levels at weeks 3, 10, and 14 for the six groups of mice (G1-G6) described in FIG. 24. Sera from all groups of mice were obtained during sensitization (week 3), 1 day before desensitization (week 10) and 1 day before challenge (week 14). IgE levels (A) and IgG2a levels (B) were determined by ELISA. Data are mean±SEM for each group of mice. *, $p<0.05$ and ***, $p<0.001$ vs. G1 (sham). ##, $p<0.01$ and ###, $p<0.001$ vs. MP123.

HKE-MP123 is More Effective than MP123 in Decreasing IgE and Increasing IgG2a Production At week 10 following peanut-sensitization and prior to treatment, peanut-specific IgE levels were markedly elevated in all sensitized groups and were similar in each group. However, IgE levels in both HKE-MP123-treated groups were significantly lower than the sham-treated group at the time of challenge (week 14) (FIG. 27, $p<0.001$). The high dose MP123 treated group, but not the low dose MP123-treated group, also showed significantly lower IgE levels than sham-treated group ($p<0.05$), but significantly higher levels than HKE-MP123 treated groups ($p<0.01$ and 0.001 vs. HKE-MP123 at 9 μg and 90 μg, respectively). Peanut-specific IgG2a levels were significantly increased in both HKE-MP123-treated groups ($p<0.001$) compared to the sham-treated group. However, no significant increase in IgG2a levels was seen in either low or high MP123-treated groups. These results demonstrate that HKE-MP123 treatment is more effective in suppressing IgE and enhancing IgG2 than MP123 protein treatment alone. Although the high dose of MP123 also significantly reduced IgE, the reduction was not accompanied by a protective effect against anaphylactic reactions.

Figure 28:
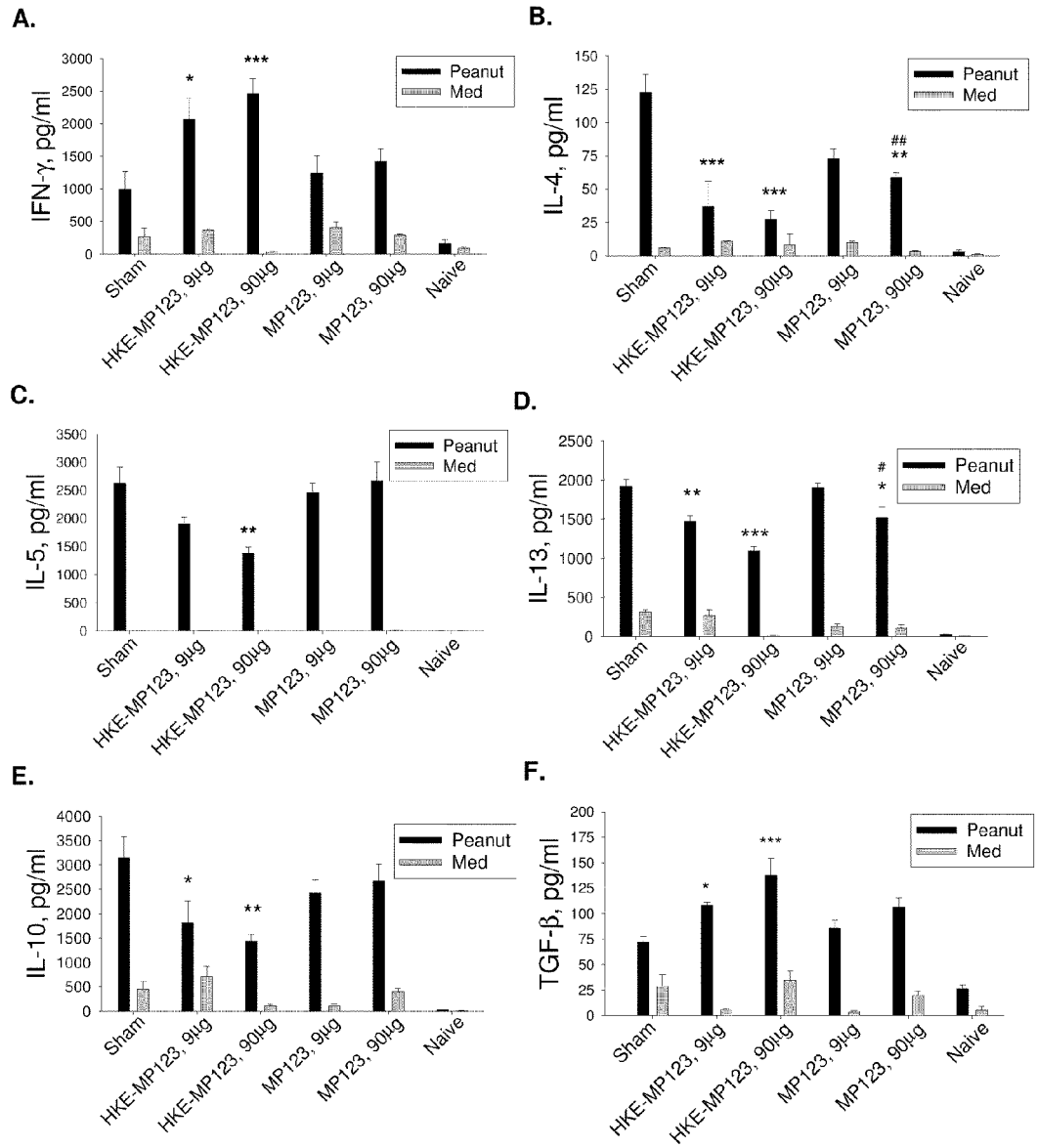
FIG. 28 compares various cytokine levels that were determined from splenocyte (SPC) cultures taken after challenge for the six groups of mice (G1-G6) described in FIG. 24. Cell suspensions were cultured in complete culture medium in the presence (peanut) or absence (med) of CPE. Supernatants were collected 72 hours later, and cytokine levels were determined by ELISA. Results are expressed as mean±SEM of 2 duplicates of cultures (n=4). *, $p<0.05$; , $p<0.01$ and *, $p<0.001$ vs. G1 (sham). #, $p<0.05$ and ##, $p<0.01$ vs. G2 (HKE-MP123, 90 µg).

HKE-MP123 is More Effective than MP123 in Modulating Th1, Th2 and T Regulatory Responses It has been suggested that IFN-γ plays a role in the induction of oral tolerance (see Ref. 22) and that peanut allergy is a Th2-driven immune response (see Ref 23). IFN-γ, IL-4, IL-5 and IL-13 levels were therefore measured in SPC cell culture supernatants from each group of mice. IFN-γ levels were significantly higher in both HKE-MP123-treated groups compared to the sham-treated group (see FIG. 28A. $p<0.05$ and 0.001, respectively). However, there was no significant difference between the MP123-treated groups and the sham-treated group. IL-4, IL-5 and IL-13 levels were significantly reduced in SPC cultures from high dose HKE-MP123-treated groups compared to SPC cultures from sham-treated mice (see FIGS. 28B, C, and D. $p<0.001$, 0.01, and 0.001 respectively), and IL-4 and IL-13 levels were significantly reduced in SPC cultures from low dose HKE-MP123-treated groups compared to SPC cultures from sham-treated mice ($p<0.001$ and 0.01, respectively). On the other hand, IL-4, IL-5 and IL-13 levels were not significantly reduced in the low dose MP123-treated group compared to SPC cultures from sham-treated mice. Although IL-4 and IL-13 levels in the high dose MP123-treated group were also significantly lower than that in SPC cultures from sham-treated mice ($p<0.01$ and 0.05, respectively), they were significantly higher than that in cultures from the high dose HKE-MP123-treated mice ($p<0.01$ and 0.05 respectively).

We also measured TGF-β, a T regulatory cytokine and IL-10, a T suppressor cytokine, which are thought to be important in the development of oral tolerance (see Refs. 24-26). We found that IL-10 was reduced in both HKE-MP123-treated groups as compared with the sham-treated group, being lowest in the HKE-MP123 high dose treated group (see FIG. 28E. $p<0.05$ and 0.01, respectively). In contrast, TGF-β levels were significantly increased in the HKE-MP123-treated groups in a dose dependent manner (see FIG. 28F. $p<0.05$ and 0.001, respectively). MP123 treatment, regardless of the dose, did not produce any effect on either IL-10 or TGF-β production. These results indicate that HKE-MP123 had a broad immunoregulatory effect on Th1, Th2 and T regulatory cytokines and was more effective than MP123 alone.

HKE-MP123 Did not Induce a Local Inflammatory Reaction

Figure 29:
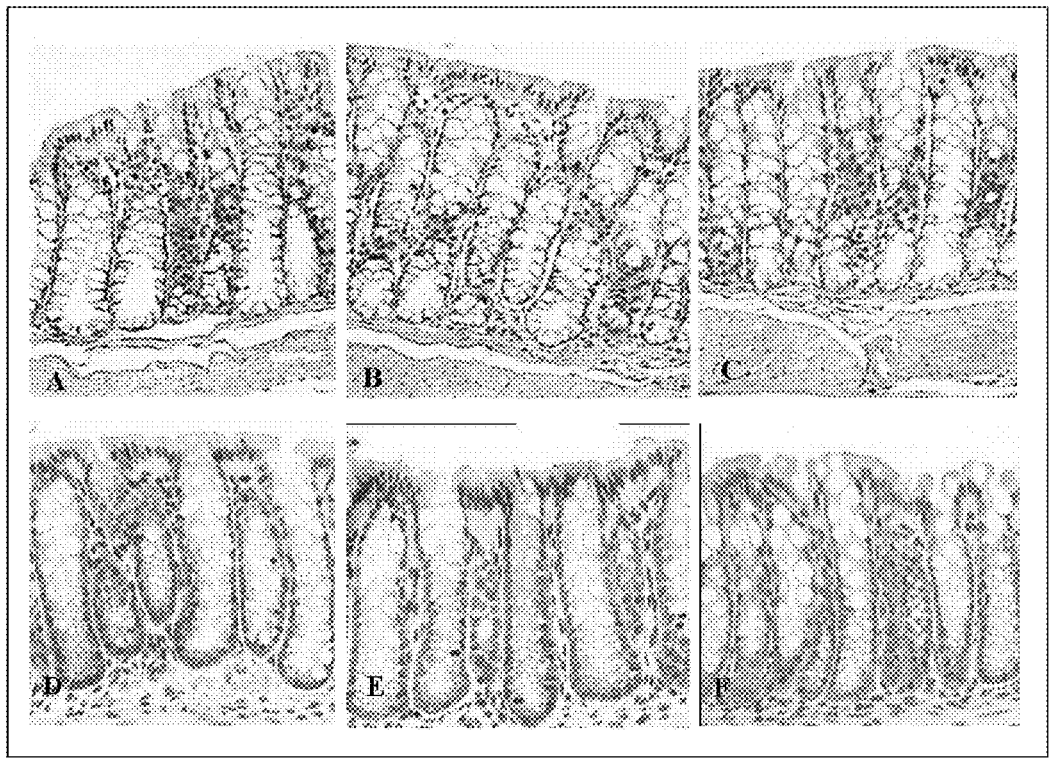
FIG. 29 shows histological images of sigmoid colon samples that were collected from peanut sensitized mice 24 hours after treatment (Panels A-C) or following peanut challenge at week 14 (Panels D-F) and fixed in formalin. Hematoxylin and eosin (H & E) stained sections showed normal histology. Panels A and D are from sham treated mice (G1). Panels B and E are from HKE-MP123, 90 µg treated mice (G2). Panels C and F are from naïve mice (G6).

Sigmoid colons were collected from peanut sensitized mice 24 hours after the final treatment dosage (FIG. 29A-C) and following peanut challenge (FIG. 29D-F). FIG. 29 compares the colons of sham treated mice (Panels A and D), HKE-MP123-treated mice (90 μg, Panels B and E), and naïve mice (Panels C and F). No inflammation was seen in any histologic sections. In addition, histological analyses of sigmoid colons from the MP123-treated group also showed no evidence of inflammation (data not shown).

12.5 Discussion

Peanut-induced anaphylaxis is an IgE mediated type I hypersensitivity, and histamine is one of the major mediators released by mast cells/basophils, which is at least in part responsible for provoking symptoms of anaphylaxis. In the present Example, it has been demonstrated that the rectal administration of HKE containing mutated peanut proteins significantly desensitized peanut allergic mice, as shown by a reduction of peanut-specific IgE levels, post-challenge histamine levels and symptom scores. On the other hand, treatment with MP123 alone, even with nine additional treatments, did not provide significant protection even though there was a moderate reduction in peanut-specific IgE. These results demonstrated that HKE-MP123 is more effective in protecting against anaphylaxis than MP123. The precise mechanisms underlying the enhanced potency of HKE-MP123 in desensitizing peanut allergy are unknown, although it is likely mediated by HKE's adjuvant effect since administering the purified protein alone did not provide significant protection.

In addition to efficacy, HKE-MP123 has several other benefits as a novel immunotherapeutic approach for the treatment of peanut allergy. First, since the engineered recombinant peanut proteins are generated in E. coli, using HKE-MP123 eliminates the need to purify the recombinant peanut proteins from E. coli and therefore is technically easier and less costly. Second, the E. coli organisms are still intact after heat killing and encapsulate the peanut proteins within the organism which prevents them from activating mast cells or basophils, resulting in an additional level of safety. Lastly, since the HKE-MP123 is administered into an environment replete with *E. coli* and other bacteria, there should be little concern about the safety of such vaccine administration. In this context, no evidence of inflammatory reactions was found at the immunization site and no signs of anaphylactic symptoms were observed during the desensitization phase.

It has been suggested that tolerance to food antigens induced via the gut involves IFN-γ (see Refs. 22, 27 and 28). According to the hygiene hypothesis, the increasing incidence of allergy in Westernized societies over the last decades (see Refs. 29-30) may, to some extent, be explained by a reduced microbial load early in infancy (see Refs. 30-32) which results in too little Th1 cell activity, and therefore insufficient IFN-γ to optimally cross-regulate Th2 responses (see Ref 33). A recent study suggests that peanut allergic status is characterized by a Th2 response whereas a Th1-skewed response underlies oral tolerance (see Refs. 23). We recently found that impaired induction of IFN-γ following oral antigen sensitization is associated with the susceptibility of C3H/HeJ mice to both milk allergy and peanut allergy (see Refs. 17 and 34). It is suggested that the goal of allergen-based immunotherapy is reestablishment of immunologic tolerance to allergen by redirecting T-cell immune responses from a Th2-skewed response to a more balanced Th1/Th2 response (see Ref. 35). In this Example, we found both high and low doses of HKE-MP123 induced significant increases in IFN-γ levels and reduced Th2 cytokine levels. This effect was associated with an increase of peanut-specific IgG2a and a reduction of peanut-specific IgE. Therefore, induction of IFN-γ by HKE-MP123 may play an important role in the suppression of Th2 cytokines and the reestablishment of oral tolerance to peanuts in this model.

IL-10, initially characterized as a Th2 cytokine (see Ref 36) which suppressed IFN-γ and IL-12 secretion (see Ref 37) and inflammatory responses in autoimmune diseases (see Ref 38), has been recently suggested to be important in the suppression of allergic inflammation (see Ref. 39). A recent study showed induction of IL-10+ CD25+ T-cells by grass pollen immunotherapy (see Ref 40). However, there are conflicting findings regarding the role of IL-10 in immunotherapy and a protective role of IL-10 in food allergy has not been established. We found that IL-10 levels were significantly increased in peanut allergic mice, which was associated with the induction of Th2 cytokines and reduction of Th1 cytokines (see Ref 41). Previous studies including ours showed that heat-killed *L. monocytogenes* immunotherapy-mediated protection against OVA-induced allergic airway responses and peanut-induced anaphylaxis in mice was associated with reduction of IL-10 (see Refs. 13 and 18). In the present Example, we found that IL-10 levels were reduced in both HKE-MP123-treated groups as compared with the sham-treated group, being lowest in the high dose HKE-MP123-treated group. These results suggest that IL-10 is unlikely to play a beneficial role in the HKE-MP123-mediated protective effect on peanut allergy.

TGF-β is suggested to be important in the development of oral tolerance to food allergens (see Ref. 26). Colostrum TGF-β concentrations were found to be lower in samples from mothers of infants with IgE mediated cow milk allergy than in samples from mothers of infants with non-IgE mediated cow milk allergy (see Ref 42). However, a relationship between allergen immunotherapy-mediated regeneration of oral tolerance to food antigen and TGF-β has not been demonstrated. In this study, we found that TGF-β levels were significantly increased in both HKE-MP123-treated groups, but not the MP123-treated group, and appeared to be dose dependent. These results taken together, suggest that IFN-γ and TGF-β might be important cytokines responsible for a HKE-MP123 mediated therapeutic effect in peanut allergy.

In conclusion, this Example demonstrates that the rectal administration of HKE-MP123 markedly reduces peanut specific-IgE and plasma histamine levels in peanut allergic mice and protects against systemic anaphylaxis. These effects are more effective than administering MP123 alone. The precise mechanisms associated with protection are not fully understood, but the results suggest that the protective effect may be a consequence of down-regulation of Th2 cytokines perhaps due to induction of IFN-γ and/or TGF-β by an HKE adjuvant effect.

12.6 References

1. Sampson, H. A. Food allergy. Part 1: immunopathogenesis and clinical disorders. J. Allergy Clin. Immunol. 1999; 103:717.
2. Yocum, M. W., J. H. Butterfield, J. S. Klein, G. W. Volcheck, D. R. Schroeder, and M. D. Silverstein. Epidemiology of anaphylaxis in Olmsted County: A population-based study. J. Allergy Clin. Immunol. 1999; 104:452.
3. Sampson, H. A., L. Mendelson, and J. P. Rosen. Fatal and near-fatal anaphylactic reactions to food in children and adolescents. N. Engl. J. Med. 1992; 327:380.
4. Bock, S. A., A. Munoz-Furlong, and H. A. Sampson. Fatalities due to anaphylactic reactions to foods. J. Allergy Clin. Immunol. 2001; 107:191.
5. Sicherer, S. H., A. Munoz-Furlong, A. W. Burks, and H. A. Sampson. Prevalence of peanut and tree nut allergy in the US determined by a random digit dial telephone survey. J. Allergy Clin. Immunol. 1999; 103:559.
6. Bock, S. A. The natural history of food sensitivity. J. Allergy Clin. Immunol. 1982; 69:173.
7. Oppenheimer, J. J., H. S. Nelson, S. A. Bock, F. Christensen, and D. Y. Leung. Treatment of peanut allergy with rush immunotherapy. J. Allergy Clin. Immunol. 1992; 90:256.
8. Leung, D. Y., H. A. Sampson, J. W. Yunginger, A. W. J. Burks, L. C. Schneider, C. H. Wortel, F. M. Davis, J. D. Hyun, and W. R. J. Shanahan. Effect of anti-IgE therapy in patients with peanut allergy. N. Engl. J. Med. 2003; 348: 986.
9. Li X. M. and H. A. Sampson. Novel approaches for the treatment of food allergy. Current Opinion in Allergy and Clinical Immunology 2002; 2:273.
10. Burks, A. W., N. King, and G. A. Bannon. Modification of a major peanut allergen leads to loss of IgE binding. Int. Arch. Allergy Immunol. 1999; 118:313.
11. Bannon, G. A., G. Cockrell, C. Connaughton, C. M. West, R. Helm, J. S. Stanley, N. King, P. Rabjohn, H. A. Sampson, and A. W. Burks. Engineering, characterization and in vitro efficacy of the major peanut allergens for use in immunotherapy. Int. Arch. Allergy Immunol. 2001; 124: 70.
12. Yeung, V. P., R. S. Gieni, D. T. Umetsu, and R. H. DeKruyff. Heat-killed *Listeria* monocytogenes as an adjuvant converts established murine Th2-dominated immune responses into Th1-dominated responses. J. Immunol. 1998; 161:4146.
13. Hansen, G., V. P. Yeung, G. Berry, D. T. Umetsu, and R. H. DeKruyff. Vaccination with heat-killed *Listeria* as adjuvant reverses established allergen-induced airway hyper-reactivity and inflammation: role of CD8+ T-cells and IL-18. J. Immunol. 2000; 164:223.
14. Li, X. M., K. Srivastava, J. W. Huleatt, K. Bottomly, A. W. Burks, and H. A. Sampson. Engineered recombinant peanut protein and heat-killed *Listeria* monocytogenes coadministration protects against peanut-induced anaphylaxis in a murine model. J. Immunol. 2003; 170:3289.
15. Institute of Laboratory Animal Resources Commission of Life Sciences, N. R. C. 1996. Guide for the Care and Use of Laboratory Animals. National Academy Press.
16. Li, X. M., D. Serebrisky, S. Y. Lee, C. K. Huang, L. Bardina, B. H. Schofield, J. S. Stanley, A. W. Burks, G. A. Bannon, and H. A. Sampson. A murine model of peanut anaphylaxis: T- and B-cell responses to a major peanut allergen mimic human responses. J. Allergy Clin. Immunol. 2000; 106:150.
17. Burks, A. W., N. King, and G. A. Bannon. Modification of a major peanut allergen leads to loss of IgE binding. Int. Arch. Allergy Immunol. 1999; 118:313.
18. Li, X. M., K. Srivastava, J. W. Huleatt, K. Bottomly, A. W. Burks, and H. A. Sampson. Engineered recombinant peanut protein and heat-killed *Listeria* monocytogenes coadministration protects against peanut-induced anaphylaxis in a murine model. J. Immunol. 2003; 170:3289.
19. Li, X. M., B. H. Schofield, C. K. Huang, G. A. Kleiner, and H. A. Sampson. A Murine Model of IgE Mediated Cow Milk Hypersensitivity. J. Allergy Clin. Immunol. 1999; 103:206.
20. Lee, S. Y., C. K. Huang, T. F. Zhang, B. H. Schofield, A. W. Burks, G. A. Bannon, H. A. Sampson, and X. M. Li. Oral Administration of IL-12 Suppresses Anaphylactic Reactions in a Murine Model of Peanut Hypersensitivity. Clin. Immunol. 2001; 101:220.
21. Lee, S. Y., C. K. Huang, T. F. Zhang, B. H. Schofield, A. W. Burks, G. A. Bannon, H. A. Sampson, and X. M. Li. Oral Administration of IL-12 Suppresses Anaphylactic Reactions in a Murine Model of Peanut Hypersensitivity. Clin. Immunol. 2001; 101:220.
22. Husby, S. Sensitization and tolerance. Curr. Opin. Allergy Clin. Immunol. 2001; 1:237.
23. Turcanu, V., S. J. Maleki, and G. Lack. Characterization of lymphocyte responses to peanuts in normal children, peanut-allergic children, and allergic children who acquired tolerance to peanuts. J. Clin. Invest. 2003; 111:1065.
24. Strobel, S. Oral tolerance, systemic immunoregulation, and autoimmunity. Ann. N Y Acad. Sci. 2002; 958:47.
25. Barnes, P. J. IL-10: a key regulator of allergic disease. Clin. Exp. Allergy 2001; 31:667.
26. Husby, S. Sensitization and tolerance. Curr. Opin. Allergy Clin. Immunol. 2001; 1:237.
27. Weiner, H. L. Oral tolerance: immune mechanisms and treatment of autoimmune diseases. Immunol. Today 1997; 18:335.
28. Strobel, S. and A. M. Mowat. Immune responses to dietary antigens: oral tolerance. Immunol. Today 1998; 19:173.
29. International Study of Asthma and Allergies in Childhood Steering Committee. Worldwide variation in the prevalence of symptoms of asthma, allergic rhinoconjunctivitis and atopic eczema: ISAAC. Lancet 1998; 351:1225.
30. von Mutius, E. The environmental predictors of allergic disease. J. Allergy Clin. Immunol. 2000; 105:9.
31. Rook, G. A. and J. L. Stanford. Give us this day our daily germs. Immunol Today 1998; 19:113.
32. Erb, K. J. Atopic disorders: a default pathway in the absence of infection? Immunol. Today 1999; 20:317.
33. Brandtzaeg, P. Current Understanding of Gastrointestinal Immunoregulation and Its Relation to Food Allergy. Ann. N Y Acad. Sci. 2002; 964:13.
34. Morafo, V., K. Srivastava, C. K. Huang, G. Kleiner, S. Y. Lee, Sampson H A, and Li X. M. 2003. Genetic susceptibility to food allergy is linked to differential $T_H2$-$T_H1$ responses in C3H/HeJ and BALB/c mice. J. Allergy Clin. Immunol. 111:1122.
35. Durham, S. R. and S. J. Till. Immunologic changes associated with allergen immunotherapy. J. Allergy Clin. Immunol. 1998; 102:157.
36. Fiorentino, D. F., M. W. Bond, and T. R. Mosmann. Two types of mouse T helper cell. IV. Th2 clones secrete a factor that inhibits cytokine production by Th1 clones. J. Exp. Med. 1989; 170:2081.
37. Hsu, D. H., K. W. Moore, and H. Spits. Differential effects of IL-4 and IL-10 on IL-2-induced IFN-gamma synthesis and lymphokine-activated killer activity. Int. Immunol. 1992; 4:563.
38. Strobel, S. Oral tolerance, systemic immunoregulation, and autoimmunity. Ann. N Y Acad. Sci. 2002; 958:47.
39. Barnes, P. J. IL-10: a key regulator of allergic disease. Clin. Exp. Allergy 2001; 31:667.
40. Francis, J. N., S. J. Till, and S. R. Durham. Induction of IL-10+CD4+CD25+ T-cells by grass pollen immunotherapy. J. Allergy Clin. Immunol. 2003; 111:1255.
41. Morafo, V., K. Srivastava, C. K. Huang, G. Kleiner, S. Y. Lee, Sampson H A, and Li X. M. Genetic susceptibility to food allergy is linked to differential $T_H2$-$T_H1$ responses in C3H/HeJ and BALB/c mice. J. Allergy Clin. Immunol. 2003; 111:1122.
42. Saarinen, K. M., O. Vaarala, P. Klemetti, and E. Savilahti. Transforming growth factor-beta1 in mothers' colostrum and immune responses to cows' milk proteins in infants with cows' milk allergy. J. Allergy Clin. Immunol. 1999; 104:1093.

Example 13

In Vivo Experiments Demonstrating the Long-Term Benefits of Desensitization

This Example refers to various patents, publications, books, articles, and other references that are listed under Section 13.5. The contents of all of these items are hereby incorporated by reference in their entirety.

13.1 Introduction

The experiments that are described in this Example build on the desensitization results of Example 12 by investigating the long-term immunomodulatory effects of rectally administered HKE-MPE123. After several weeks of sensitization, peanut allergic C3H/HeJ mice received rectal administrations of 0.9 (low dose), 9 (medium dose) or 90 (high dose) μg HKE-MP123, HKE-containing vector (HKE-V) alone, or vehicle alone (sham) weekly for 3 weeks. Mice were challenged 2 weeks later (week 14). A second and third challenge were performed at 4-week intervals (weeks 18 and 22). Following the first challenge, all three HKE-MP123 and HKE-V-treated groups exhibited reduced symptom scores (p<0.01, 0.01, 0.05 and 0.05, respectively) as compared with the sham-treated group. Only the medium and high dose HKE-MP123-treated mice remained protected at week 22. IgE levels were significantly lower in all HKE-MP123 treated groups (p<0.001), being most reduced in the high dose HKE-MP123 treated group at the time of each challenge. IL-4, IL-13, IL-5, and IL-10 production by splenocytes of high dose HKE-MP123-treated mice were significantly decreased (p<0.01, 0.001, 0.001 and 0.001, respectively); and both IFN-γ and TGF-β production were significantly increased (p<0.001 and 0.01, respectively) as compared with sham-treated mice at the time of the last challenge. These results indicate that treatment with rectally administered HKE-MP123 can induce long-term "down-regulation" of peanut hypersensitivity, which may be secondary to decreased antigen-specific Th2 and increased Th1 and T regulatory cytokine production.

13.2 Materials and Methods

All materials and methods that are not described under this Example were obtained, prepared or performed as described in Example 12, Sections 12.2-12.3.

Intragastric Antigen-Sensitization, Challenge, and HKE-MP123 Treatment

Figure 30:
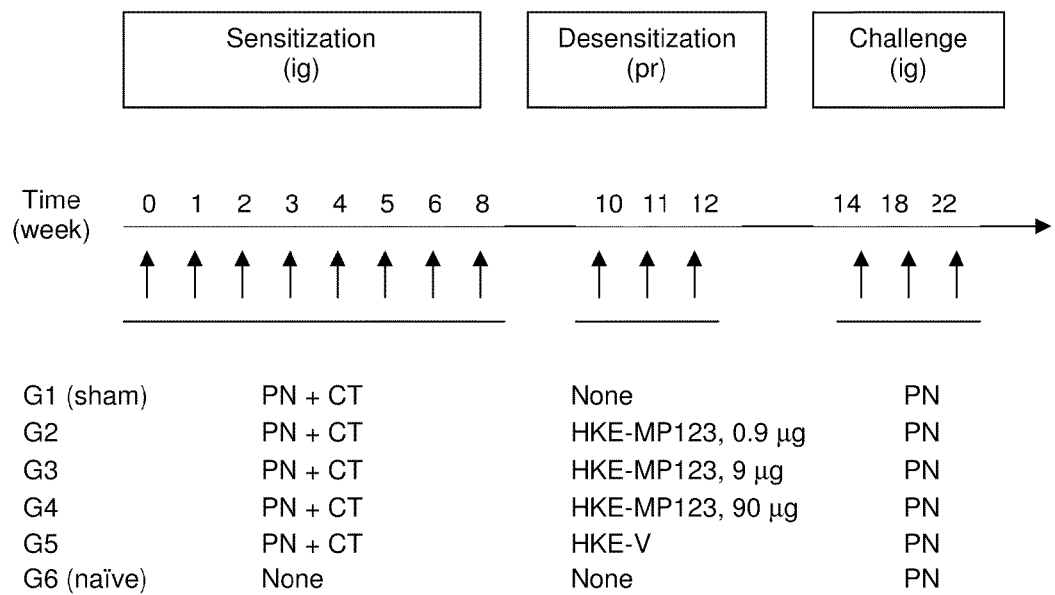
FIG. 30 is an outline of the sensitization and challenge protocols that were used for the six groups of mice (G1-G6) in the experiments of Example 13. Mice were sensitized intragastrically with peanut over an 8 week period. Mice were then treated with rectal administrations of different compositions 10-12 weeks after the initial sensitization. Mice were challenged intragastrically 2, 6 and 10 weeks after the termination of therapy (week 14, 18, and 22 respectively post-desensitization). Following each challenge, 4 mice were sacrificed for collection of blood and tissue samples.

Mice were sensitized with peanut and CT as described in Example 12, Section 12.3 (see also Ref. 11). As depicted in FIG. 30, treatment began at week 10 after the initial peanut sensitization. Six groups (twelve mice per group) were involved. Mice were treated with HKE-MP123 (G2=0.9 µg low dose; G3=9 µg medium dose; G4=90 µg high dose) or HKE-V (G5). Sham (saline)-treated (G1) and naïve (G8) mice were included as controls. Treatments were administered in 90 µl of methylcellulose as vehicle rectally 3 times at weekly intervals. Mice were challenged intragastrically 2, 6 and 10 weeks post-therapy (weeks 14, 18, and 22 post-initial sensitization). Following each challenge, 4 mice were sacrificed to collect samples for immunologic studies.

13.3 Results

Figure 31:
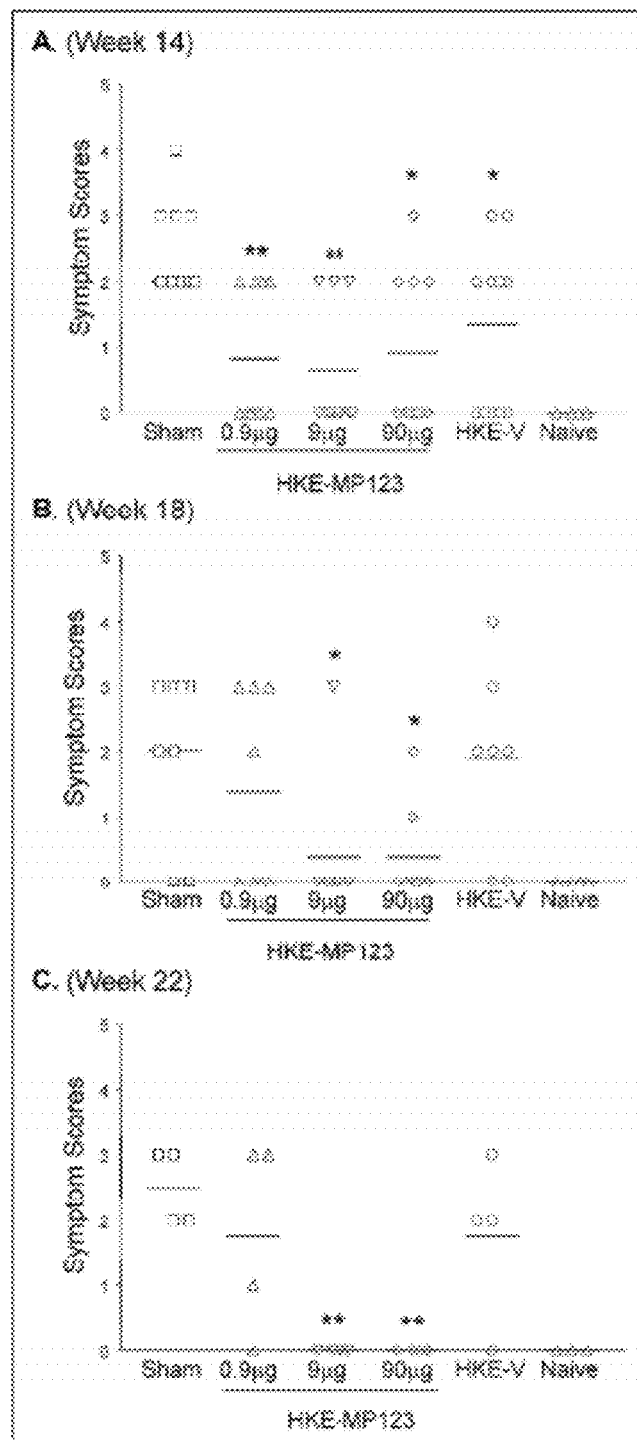
FIG. 31 compares the individual (symbols) and average (solid line) anaphylactic symptom scores that were determined after challenge for the six groups of mice (G1-G6) described in FIG. 30. Mice were challenged at week 14 (Panel A), 18 (Panel B) and 22 (Panel C). Anaphylactic symptom scores were determined 30 min following challenge. Bars indicate the median of 12 mice (Panel A), 8 mice (Panel B) and 4 mice (Panel C) in each group. *, $p<0.05$, and **, $p<0.01$ vs. G1 (sham).

HKE-MP123 Confers Long Lasting Protection Against Peanut-Induced Anaphylaxis Following Oral Peanut Challenge To determine whether HKE-MP123 can provide a long lasting effect on peanut allergy, peanut-sensitized mice were treated with 3 different weekly doses of rectally administered HKE-MP123 in a methylcellulose carrier. Mice were then challenged ig with peanut 2 weeks later (week 14 after the initial sensitization) and again 4 and 8 weeks later (weeks 18 and 22 respectively after the initial sensitization). Anaphylactic symptom scores were evaluated 30 minutes after challenge. Following the first challenge, all three HKE-MP123-treated groups exhibited significantly lower anaphylactic symptom scores compared to the sham-treated group (low, medium and high dose HKE-MP123-treated groups vs. sham: $p<0.01$, 0.01 and 0.01, respectively, FIG. 31A). No dose response difference was observed among the HKE-MP123-treated groups at the time of the first challenge. HKE-V also significantly reduced symptom scores compared to the sham-treated group ($p<0.05$), although the symptom scores tended to be greater in this group compared to the HKE-MP123-treated groups. Following the second challenge (week 18), anaphylactic symptom scores were reduced significantly only in the medium and high dose HKE-MP123-treated groups ($p<0.05$ and $p<0.01$, respectively, FIG. 31B). Similarly, at the third challenge (week 22), only mice receiving the medium and high doses of HKE-MP123 were protected from anaphylactic reactions ($p<0.01$, FIG. 31C). These results demonstrate that higher doses of HKE-MP123 in a methylcellulose carrier resulted in persistent protection lasting at least 10 weeks.

Figure 32:
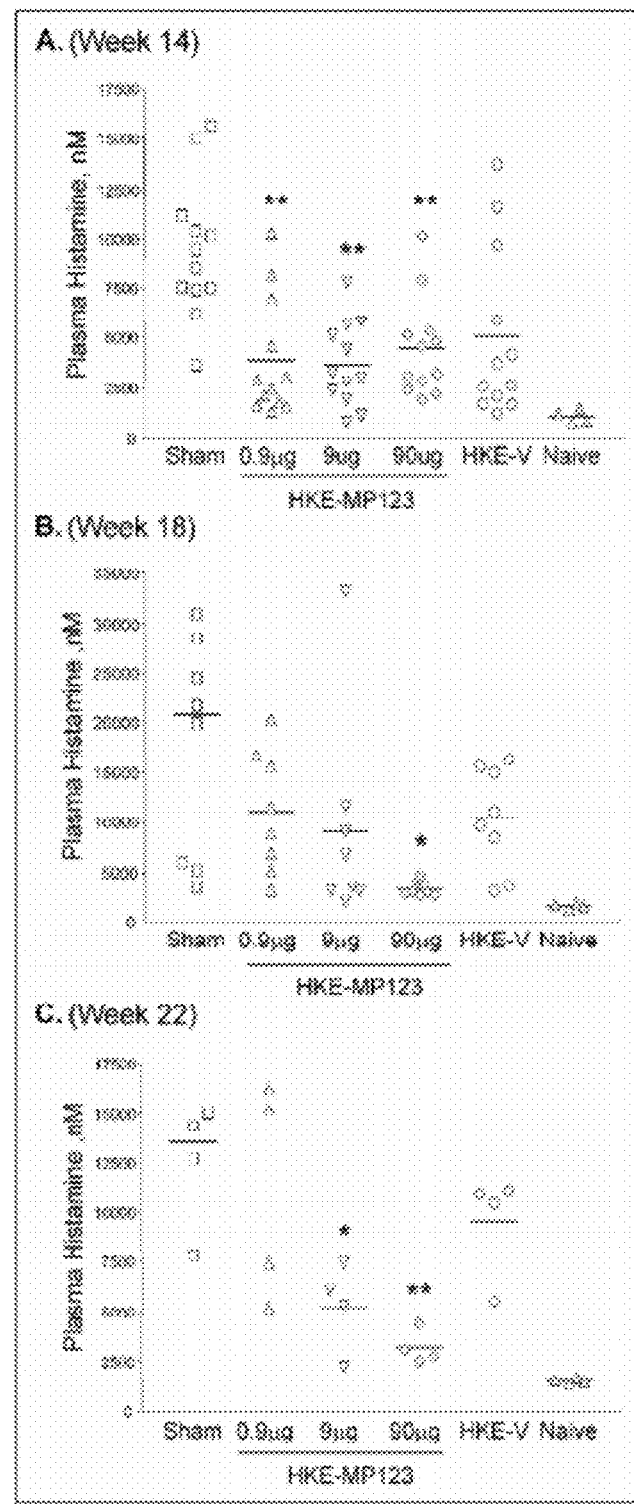
FIG. 32 compares the individual (symbols) and average (solid line) plasma histamine levels that were determined after challenge for the six groups of mice (G1-G6) described in FIG. 30. Blood was collected and plasma was obtained. Histamine levels were measured using an enzyme immunoassay kit. Data are mean±SEM for each group of 12 mice (Panel A), 8 mice (Panel B) and 4 mice (Panel C). *, $p<0.05$, and **, $p<0.01$ vs. G1 (sham).

HKE-MP123 has a Long Lasting Inhibitory Effect on Peanut-Induced Histamine Release Since histamine is associated with the anaphylactic reactions, we also measured plasma histamine levels 30 minutes following each peanut challenge. We found that following the first challenge at week 14, plasma histamine levels were significantly reduced in all three HKE-MP123-treated groups as compared with the sham-treated group ($p<0.01$, FIG. 32A). Reduction of plasma histamine levels in the HKE-V-treated group failed to reach statistical significance. Following the second challenge, only the high dose HKE-MP123-treated group had significantly lower plasma histamine as compared with the sham-treated group ($p<0.01$, FIG. 32B). Following the third challenge, histamine levels were significantly lower in both the medium and high dose HKE-MP123-treated groups as compared with sham-treated group ($p<0.01$, FIG. 32C). Mice treated with low dose of HKE-MP123 and HKE-V did not show a significant reduction in plasma histamine levels as compared with the untreated group following the second and the third challenge (FIG. 32A, B, C). These results parallel the clinical findings in that HKE-MP123 (at medium and high doses) have a long lasting suppressive effect on histamine release, which lasted for at least 10 weeks HKE-MP123 has a Long Lasting Effect on Peanut-Specific IgE and IgG2a Production Peanut-specific IgE levels were monitored during sensitization/boosting, desensitization and following treatment. IgE levels increased markedly over the 8 week sensitization/boosting in each group of mice following peanut sensitization and were similar among the groups prior to treatment at week 10. Following treatment IgE levels were significantly reduced in all HKE-MP123-treated groups at the first, second and the third challenge ($p<0.001$, FIG. 33A) being lowest in the high dose treatment group. IgE levels were also reduced in HKE-V-treated group at the time of the third challenge ($p<0.05$), but were significantly greater than in the high dose HKE-MP123-treated group ($p<0.05$).

Figure 33:
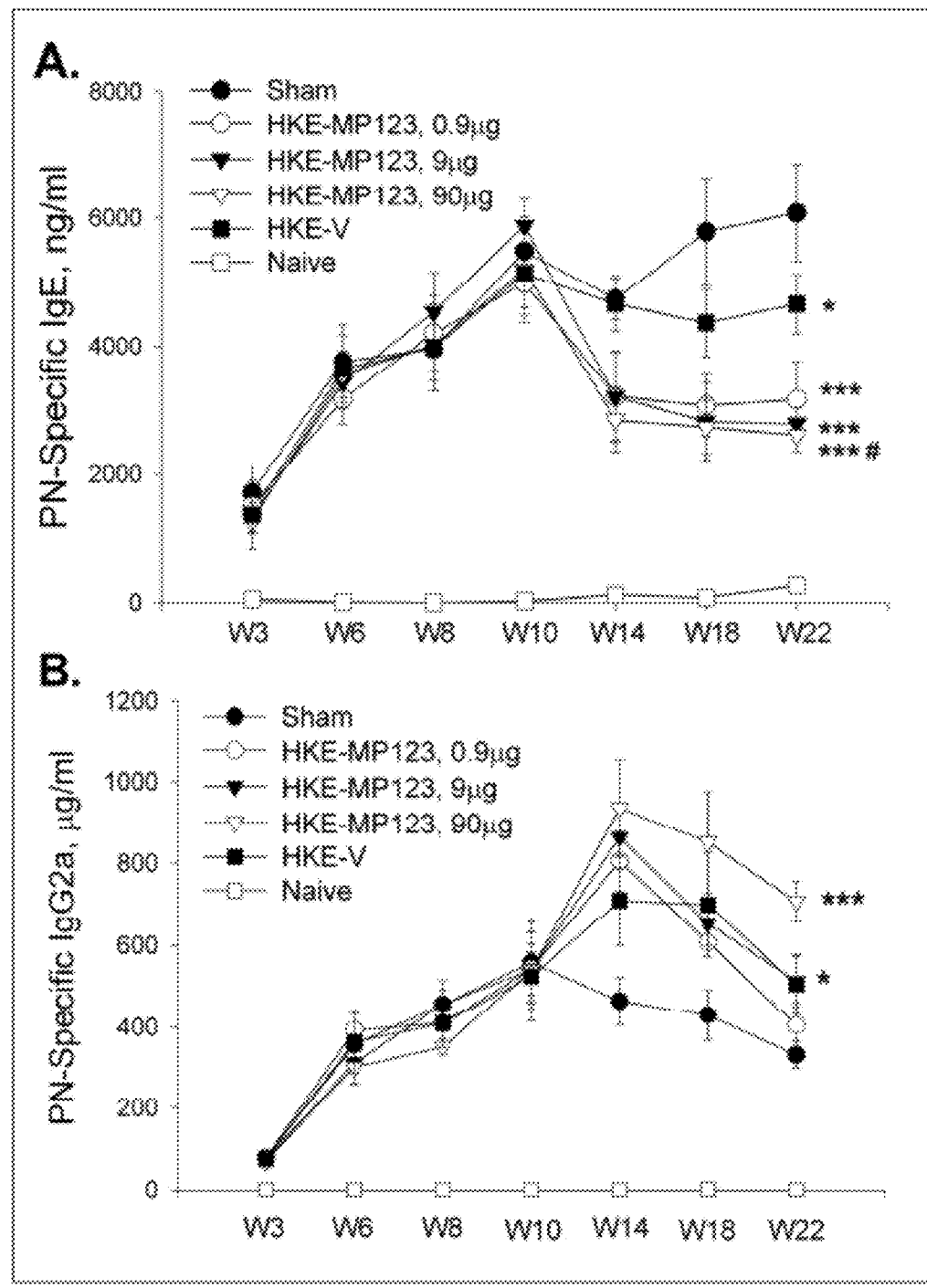
FIG. 33 compares average peanut specific IgE and IgG2a levels at weeks 3, 6, 8, 10, 14, 18 and 22 for the six groups of mice (G1-G6) described in FIG. 30. Sera from all groups of mice were obtained during sensitization (weeks 3, 6 and 8), before treatment (week 10), and one day prior to each challenge (weeks 14, 18 and 22). Peanut-specific IgE (A) and IgG2a (B) levels were determined by ELISA. Data are mean±SEM for each group. *, $p<0.05$ vs. G1 (sham); ***, $p<0.001$ vs. G1 (sham).

IgG2a levels were significantly increased in HKE-MP123 medium and high dose-treated groups at the first ($p<0.01$ and 0.001, respectively), the second ($p<0.05$ and 0.01, respectively) and the third challenges ($p<0.05$ and 0.001, respectively) as compared with the sham-treated group (FIG. 33B). IgG2a levels in the low dose HKE-MP123-treated group were also significantly greater than in the sham-treated group at the time of the first and second challenge, but not at the third challenge. IgG2a levels in the HKE-V-treated group were not significantly different than those of the sham-treated group at the time of the first and the second challenge.

These results indicate that HKE-MP123 suppresses IgE and increases IgG2a production. This effect lasted at least 10 weeks after discontinuing therapy, and the high doses of HKE-MP123 appeared to be the most effective.

HKE-MP123 Modulation of Th1, Th2 and T Regulatory Cytokines

Figure 34:
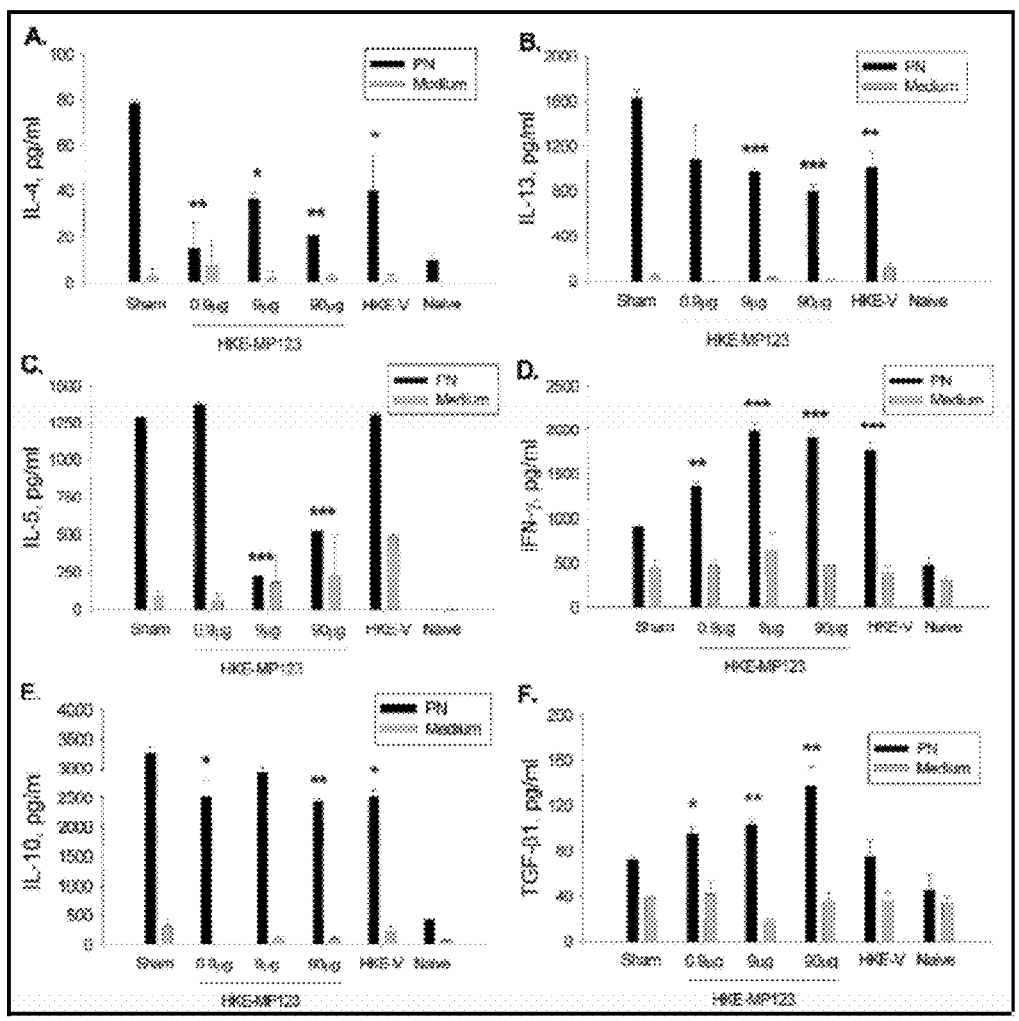
FIG. 34 compares various cytokine levels that were determined from splenocyte (SPC) cultures taken after challenge for the six groups of mice (G1-G6) described in FIG. 30. Cell suspensions were cultured in complete culture medium in the presence of CPE (peanut), or medium (medium) alone or Con A (data not shown). Supernatants were collected 72 hours later, and cytokine levels were determined by ELISA. Results are expressed as mean±SEM of 2 duplicate cultures of 4 mice. *, $p<0.05$; , $p<0.01$ and *, $p<0.001$ vs. G1 (sham).

To determine whether the long-lasting HKE-MP123-mediated protection against peanut allergy was associated with altered SPC cytokine profiles, we analyzed cytokine levels in SPC culture supernatants from each group of mice following the last challenge. IL-4 levels were significantly lower in the low, medium, and high dose HKE-MP123-treated and HKE-V-treated groups compared to the sham-treated group ($p<0.01$, 0.05, 0.01 and 0.05 respectively; FIG. 34A). IL-13 levels also were significantly decreased in the medium and high dose HKE-MP123 groups and the HKE-V group ($p<0.01$, FIG. 34B). However, significant reduction of IL-5 levels was only seen in the medium and high HKE-MP123-treated groups ($p<0.001$, FIG. 34C). IFN-γ levels were increased in all HKE-MP123-treated and HKE-V-treated groups ($p<0.01$, 0.001, 0.001 and 0.001, respectively; FIG. 34D).

As noted in Example 12, IL-10 is a classic Th2 cytokine believed to be involved in the induction of oral tolerance (see Ref 18) and the down-regulation of the allergic response (see Ref 19). TGF-β is also felt to be important in the development of oral tolerance to food allergens (see Ref 20). We found that IL-10 was reduced in all HKE-MP123-treated and HKE-V-treated groups as compared with the sham-treated group, being lowest in the HKE-MP123 high dose treated group (p<0.01, FIG. 34E). In contrast, TGF-β levels were significantly increased only in the HKE-MP123-treated groups in a dose dependent manner (p<0.05, 0.01 and 0.01; FIG. 34F). These results demonstrate that HKE-MP123 has a broad immunoregulatory effect on Th1, Th2 and T regulatory cytokines, which may contribute to its beneficial effect on peanut allergy.

13.4 Discussion

In the present Example, we have demonstrated that three rectal treatments with HKE-MP123 at medium (9 μg) or high doses (90 μg) provides peanut-allergic mice with significant protection from anaphylaxis for at least 10 weeks following the discontinuation of therapy. Low dose (0.9 μg) HKE-MP123, MP123 and HKE-V alone induced temporary protection, i.e., protection against the first challenge, but not subsequent challenges. These results demonstrate that the rectal administration of HKE producing engineered peanut proteins is efficacious for treating peanut allergy.

In addition to suppressing clinical symptoms, we found that HKE-MP123 produced long lasting suppression of histamine release following peanut challenge and a decrease in peanut-specific IgE levels. Peanut-specific IgE levels were also reduced in HKE-V-treated group, but were significantly greater than that seen in the high-dose HKE-MP123-treated group. This may have been due to the effect of CpG motifs in the plasmid vector. IgE levels were not significantly different in mice treated with the different doses of HKE-MP123 suggesting that the reduction in IgE is not solely responsible for the long lasting protection mediated by HKE-MP123. IgG2a levels were significantly increased for at least 10 weeks in the medium- and high-dose HKE-MP123-treated groups, and were associated with the long lasting protection in these two groups. IgG2a, a Th1 driven antibody (see Refs. 23-26) generally considered to be a "blocking antibody" (see Ref 27), was enhanced by HKE-MP123 treatment and may have been at least in part responsible for the long lasting beneficial effect of immunotherapy in this model.

Numerous studies have demonstrated that Th2 cytokines play a central role in the pathogenesis of allergic disorders, including food allergy. IL-4 and IL-13 promote B-cell switching to IgE production and mast cell activation, while IL-5 has been shown to have a potentially autocrine effect on mast cells, in addition to its recognized paracrine effects on eosinophils (see Refs. 28-29). IFN-γ, on the other hand, inhibits Th2 cell activation and mast cell/basophil mediator release upon re-exposure to antigen (see Refs. 30-31). Schade et al. recently demonstrated that T-cell clones generated from infants with cow milk allergy produced high levels of IL-4, IL-5 and IL-13, and low levels of IFN-γ, whereas T-cell clones produced from infants without cow milk allergy had high levels of IFN-γ and low levels of IL-4, IL-5, and IL-13 (see Ref 32). In addition, decreased IFN-γ was correlated with increased IgE levels in peanut allergic patients, and Th2 clones have been generated from patients with peanut allergy (see Refs. 33-34). Allergen-based immunotherapies are believed to reestablish immunologic tolerance to allergen by redirecting T-cell immune responses from a Th2- to Th1-type responses (see Ref 35). In the present study, we found that 10 weeks post-therapy, SPCs from mice treated with the higher doses of HKE-MP123 induced significant reductions of Th2 cytokines and increases in IFN-γ, suggesting a shift from Th2 responses to Th1 responses. The low-dose HKE-MP123-treated group and the HKE-V-treated group both showed induction of IFN-γ, and selective suppression of IL-4, and/or IL-13, but no effect on IL-5 production. These results suggest that higher doses of HKE-MP123 are more effective in regulating Th1 and Th2 responses, which may be associated with the long lasting therapeutic effect on peanut allergy.

While the counter-regulatory effect between Th1 and Th2 responses remains an important paradigm, an appreciation of the regulatory role of TGF-β and IL-10 has developed for both Th1-mediated autoimmune and Th2-mediated allergic responses (see Refs. 18-19, 36 and 38). Colostrum TGF-β concentrations were found to be lower in samples from mothers of infants with IgE mediated cow milk allergy than in samples from mothers of infants with non-IgE mediated cow milk allergy (see Ref 39). A recent study found that IL-10 was essential in parasite infection-mediated protection against peanut allergy in a murine model (see Ref 40). However, any relationship between TGF-β, IL-10 and allergen immunotherapy-mediated regeneration of oral tolerance to food antigen has not been demonstrated. In this Example, we found that TGF-β levels were significantly increased in all HKE-MP123-treated groups, but not the HKE-V-treated group, and appeared to be dose dependent. These results suggest that the induction of TGF-β might also be important for the long lasting therapeutic benefit of HKE-MP123 on peanut allergy. In addition, we found that IL-10 levels were reduced in all three HKE-MP123- and HKE-V-treated groups as compared with the sham-treated group, being lowest in the high dose HKE-MP123-treated group. These results suggest that IL-10 may play a less significant role in the HKE-MP123-mediated protective effect on peanut allergy. We and others recently found that increased IL-10 production appeared to be associated with induction of peanut allergy (see Refs. 40-41). In a study utilizing the co-administration of heat-killed *L. monocytogenes* and OVA in OVA sensitized mice, the suppression of IL-4 and increase in IFN-γ production was associated with a reduction of IL-10 (see Ref 10). The key cytokine(s) and cellular mechanisms responsible for the long-lasting protection against peanut anaphylaxis induced by HKE-MP123 in this study are unknown.

The HKE-V treatment also induced statistically significant protection (although less than HKE-MP123) at the first challenge, which may be due to vector CpGs within the *E. coli* resulting in switching the Th2 response to a Th1 response. However, the HKE-V effect on peanut allergy is unlikely attributable to the vector alone because mock DNA (plasmid DNA alone) had essentially no effect on allergy in a previous study (see Ref. 8).

In conclusion, this Example demonstrates that the rectal administration of high dose HKE-MP123 has a potent and persistent, therapeutic effect on peanut allergy in this model of peanut hypersensitivity. Protection lasted for at least 10 weeks, and was accompanied by persistent reduction of peanut-specific IgE and plasma histamine levels following challenges. The precise mechanisms associated with this long-lasting protection are not fully understood, but the results suggest that the protective effect is likely related to the downregulation of Th2 cytokines, perhaps resulting from up-regulation of IFN-γ and TGF-β.

13.5 References

1. Sampson H A. Food allergy. Part 1: immunopathogenesis and clinical disorders. J. Allergy Clin. Immunol. 1999; 103:717-728.
2. Yocum M W, Butterfield J H, Klein J S, Volcheck G W, Schroeder D R, Silverstein M D. Epidemiology of anaphylaxis in Olmsted County: A population-based study. J. Allergy Clin. Immunol. 1999; 104:452-456.
3. Sampson H A, Mendelson L, Rosen J P. Fatal and near-fatal anaphylactic reactions to food in children and adolescents. N. Engl. J. Med. 1992; 327:380-384.
4. Bock S A, Munoz-Furlong A, Sampson H A. Fatalities due to anaphylactic reactions to foods. J. Allergy Clin. Immunol. 2001; 107:191-193.
5. Sicherer S H, Munoz-Furlong A, Burks A W, Sampson H A. Prevalence of peanut and tree nut allergy in the US determined by a random digit dial telephone survey. J. Allergy Clin. Immunol. 1999; 103:559-562.
6. Bock S A. The natural history of food sensitivity. J Allergy Clin Immunol 1982; 69:173-177.
7. Oppenheimer J J, Nelson H S, Bock S A, Christensen F, Leung D Y. Treatment of peanut allergy with rush immunotherapy. J. Allergy Clin. Immunol. 1992; 90:256-262.
8. Li X, Huang C K, Schofield B H, Burks A W, Bannon G A, Kim K H, Huang S K, Sampson H A. Strain-dependent induction of allergic sensitization caused by peanut allergen DNA immunization in mice. J. Immunol. 1999; 162: 3045-3052.
9. Huang C K, Schofield B H, Burks A W, Bannon G A, Huang S K, Sampson H, Li X M. Strain-dependent protection from allergic reactions by peanut allergen plasmid DNA immunization in mice. J. Allergy Clin. Immunol. 1999; 103:S238 (Abstract)
10. Yeung V P, Gieni R S, Umetsu D T, DeKruyff R H. Heat-killed *Listeria* monocytogenes as an adjuvant converts established murine Th2-dominated immune responses into Th1-dominated responses. J Immunol 1998; 161:4146-4152.
11. Li X M, Srivastava K, Huleatt J W, Bottomly K, Burks A W, Sampson H A. Engineered recombinant peanut protein and heat-killed *Listeria* monocytogenes coadministration protects against peanut-induced anaphylaxis in a murine model. J Immunol 2003; 170:3289-3295.
12. Institute of Laboratory Animal Resources Commission of Life Sciences NRC. Guide for the Care and Use of Laboratory Animals. National Academy Press, 1996:
13. Li X M, Serebrisky D, Lee S Y, Huang C K, Bardina L, Schofield B H, Stanley J S, Burks A W, Bannon G A, Sampson H A. A murine model of peanut anaphylaxis: T- and B-cell responses to a major peanut allergen mimic human responses. J. Allergy Clin. Immunol. 2000; 106: 150-158.
14. Stanley J S, King N, Burks A W, Huang S K, Sampson H, Cockrell G, Helm R M, West C M, Bannon G A. Identification and mutational analysis of the immunodominant IgE binding epitopes of the major peanut allergen Ara h 2. Arch. Biochem. Biophys. 1997; 342:244-253.
15. Burks A W, King N, Bannon G A. Modification of a major peanut allergen leads to loss of IgE binding. Int Arch Allergy Immunol 1999; 118:313-314.
16. Li X M, Schofield B H, Huang C K, Kleiner G A, Sampson H A. A Murine Model of IgE Mediated Cow Milk Hypersensitivity. J. Allergy Clin. Immunol. 1999; 103:206-214.
17. Lee S Y, Huang C K, Zhang T F, Schofield B H, Burks A W, Bannon G A, Sampson H A, Li X M. Oral Administration of IL-12 Suppresses Anaphylactic Reactions in a Murine Model of Peanut Hypersensitivity. Clin Immunol 2001; 101:220-228.
18. Strobel S. Oral tolerance, systemic immunoregulation, and autoimmunity Ann N Y Acad Sci 2002; 958:47-58.
19. Barnes P J. IL-10: a key regulator of allergic disease. Clin Exp Allergy 2001; 31:667-669.
20. Husby S. Sensitization and tolerance. Curr Opin Allergy Clin Immunol 2001; 1:237-241.
21. Leung D Y, Sampson H A, Yunginger J W, Burks A W J, Schneider L C, Wortel C H, Davis F M, Hyun J D, Shanahan W R J. Effect of anti-IgE therapy in patients with peanut allergy. N Engl J Med 2003; 348:986-993.
22. Li X. M., Sampson H A. Novel approaches for the treatment of food allergy. Current Opinion in Allergy and Clinical Immunology 2002; 2:273-278.
23. Snapper C M, Paul W E. Interferon-gamma and B cell stimulatory factor-1 reciprocally regulate Ig isotype production. Science 1987; 236:944-947.
24. Howard M, Paul W E. Regulation of B-cell growth and differentiation by soluble factors. Annu Rev. Immunol. 1983; 1:307-333.
25. Mosmann T R, Coffman R L. TH1 and TH2 cells: different patterns of lymphokine secretion lead to different functional properties. Annu Rev. Immunol. 1989; 7:145-173.
26. Beck L, Spiegelberg H L. The polyclonal and antigen-specific IgE and IgG subclass response of mice injected with ovalbumin in alum or complete Freund's adjuvant. Cell Immunol. 1989; 123:1-8.
27. Kowalski M L, Jutel M. Mechanisms of specific immunotherapy of allergic diseases. Allergy 1998; 53:485-492.
28. Lorentz A, Schwengberg S, Mierke C, Manns M P, Bischoff S C. Human intestinal mast cells produce IL-5 in vitro upon IgE receptor cross-linking and in vivo in the course of intestinal inflammatory disease. Eur J Immunol 1999; 29:1496-1503.
29. Romagnani S. The role of lymphocytes in allergic disease. J. Allergy Clin. Immunol. 2000; 105:399-408.
30. Bissonnette E Y, Befus A D. Inhibition of mast cell-mediated cytotoxicity by IFN-alpha/beta and -gamma. J Immunol 1990; 145:3385-3390.
31. Pierkes M, Bellinghausen I, Hultsch T, Metz G, Knop J, Saloga J. Decreased release of histamine and sulfidoleukotrienes by human peripheral blood leukocytes after wasp venom immunotherapy is partially due to induction of IL-10 and IFN-gamma production of T-cells. J Allergy Clin Immunol 1999; 103:326-332.
32. Schade R P, Ieperen-Van Dijk A G, Van Reijsen F C, Versluis C, Kimpen J L, Knol E F, C. A., Van Hoffen E. Differences in antigen-specific T-cell responses between infants with atopic dermatitis with and without cow's milk allergy: relevance of TH2 cytokines J. Allergy Clin. Immunol. 2000; 106:1155-1162.
33. de Jong E C, Van Zijverden M, Spanhaak S, Koppelman S J, Pellegrom H, Penninks A H. Identification and partial characterization of multiple major allergens in peanut proteins. Clin. Exp. Allergy 1998; 28:743-751.
34. Dorion B J, Burks A W, Harbeck R, Williams L W, Trumble A, Helm R M, Leung D Y. The production of interferon-gamma in response to a major peanut allergy, Ara h II correlates with serum levels of IgE anti-Ara h II. J. Allergy Clin. Immunol. 1994; 93:93-99.
35. Durham S R, Till S J. Immunologic changes associated with allergen immunotherapy. J Allergy Clin Immunol 1998; 102:157-164.
36. Donnet-Hughes A, Duc N, Serrant P, Vidal K, Schiffrin E J. Bioactive molecules in milk and their role in health and disease: the role of transforming growth factor-beta. Immunol Cell Biol 2000; 78:74-79.
37. Zuany-Amorim C, Sawicka E, Manlius C, Le Moine A, Brunet L R, Kemeny D M, Bowen G, Rook G, Walker C. Suppression of airway eosinophilia by killed Mycobacterium vaccae-induced allergen-specific regulatory T-cells. Nat Med 2002; 8:625-629.

38. Kalliomaki M, Ouwehand A, Arvilommi H, Kero P, Isolauri E. Transforming growth factor-beta in breast milk: a potential regulator of atopic disease at an early age. J Allergy Clin Immunol 1999; 104:1251-1257.
39. Saarinen K M, Vaarala O, Klemetti P, Savilahti E. Transforming growth factor-beta1 in mothers' colostrum and immune responses to cows' milk proteins in infants with cows' milk allergy. J Allergy Clin Immunol 1999; 104: 1093-1098.
40. Bashir M E, Andersen P, Fuss I J, Shi H N, Nagler-Anderson C. An enteric helminth infection protects against an allergic response to dietary antigen. J Immunol 2002; 169:3284-3292.
41. Morafo V, Srivastava K, Huang C K, Kleiner G, Lee S Y, Sampson H A, Li X. M. Genetic susceptibility to food allergy is linked to differential th2-th1 responses in C3H/HeJ and BALB/c mice. J. Allergy Clin. Immunol. 2003; 111:1122.

Example 14

Clinical Study of Rectally Delivered HKE-MP123 in Human Subjects 14.1 Introduction Briefly, peanut-allergic subjects will receive 8 weekly rectal administrations of HKE-MP123 of increasing doses, followed by 3 bi-weekly administrations of the highest dose. Without limitation, the starting dose is currently estimated to be about 90 μg of encapsulated modified peanut protein (i.e., consisting of about 30 μg of each of the three modified peanut proteins within heat-killed *E. coli*), and will be doubled each week, if no adverse events occur (e.g., diarrhea, anaphylactic reactions, etc.) to a maximum dose of about 11,520 μg of modified peanut protein (i.e., about 3,840 μg of each of the three modified peanut proteins). Serum peanut-specific IgE levels and prick skin test (PST) titration responses will be measured prior to initiating desensitization and at weeks 4, 8, 12, and 14 of the study to assess the immunologic response to treatment over the course of the study. Blood may also be taken for basophil histamine release assays and optionally for T-cell activation assays. Finally, all subjects who undergo the full desensitization protocol will be challenged by progressive administration of an extract of whole peanut under controlled conditions at the hospital.

The following aspects of the clinical study are described in greater detail below: 1) study population, 2) study design, 3) study duration, 4) statistical plan, 5) rationale for starting dose and dose escalation scheme, 6) rationale for schedule and duration of administration, and 7) rationale for challenge.

14.2 Study Population

Approximately 12 male or female subjects between the ages of 18-55 years of age with peanut allergy will be enrolled in this study. Subjects will have a documented history of systemic responses to peanut exposure (e.g., including any of the following symptoms: urticaria and/or angioedema, lower respiratory symptoms, and hypotension), and a positive prick skin test and/or serum titer of peanut specific IgE greater than or equal to 5 kilounits of allergen (KUA).

Subjects will be excluded from the study if they 1) have suffered an acute illness within one week of the start of the study; 2) have a history of significant neurologic, hepatic, renal, endocrine, cardiovascular, gastrointestinal, pulmonary or metabolic disease; 3) show abnormal hepatic function (SGOT/SGPT and bilirubin >1.25× upper limit of normal); 4) show abnormal renal function (BUN and creatine >1.25× upper limit of normal); show abnormal bone marrow function (WBC, $4 \times 10^3/mm^3$; platelets $<100 \times 10^3/mm^3$; hemoglobin <11 g/dl); 5) have a clinically significant abnormal electrocardiogram; 6) have used systemic steroids within 14 days of screening or during the trial; 7) have used aspirin within 3 days of the screening visit or during dosing visits; 8) have a history of alcohol or drug abuse; 9) are known to have hepatitis or HIV; 10) have participated in another experimental therapy study within 30 days prior to enrollment in this study; 11) have previously enrolled in this study; or 12) are pregnant or lactating.

14.3 Study Design

Figure 35:
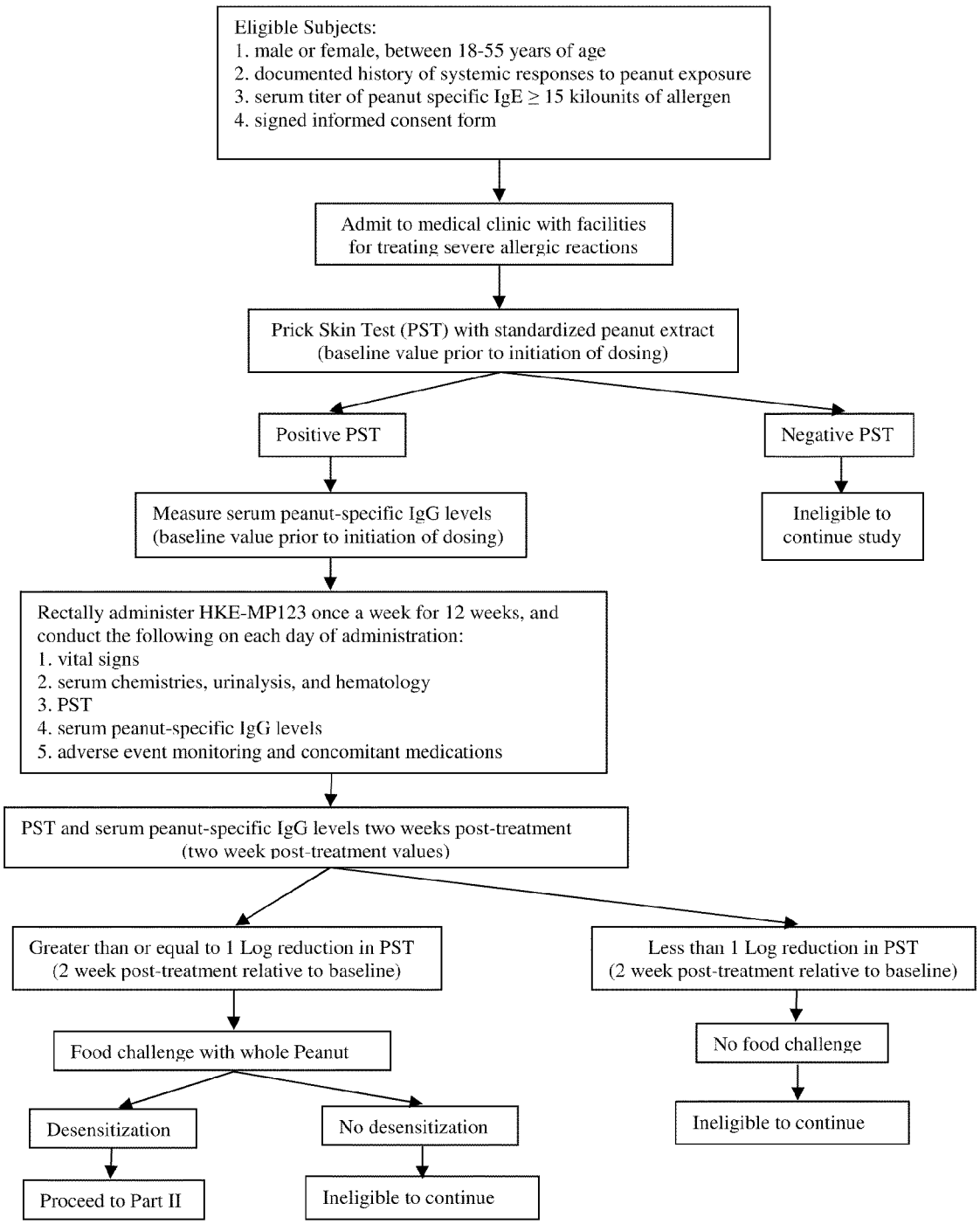
FIG. 35 is a flowchart that outlines the first part of the clinical study of Example 14.
Figure 36:
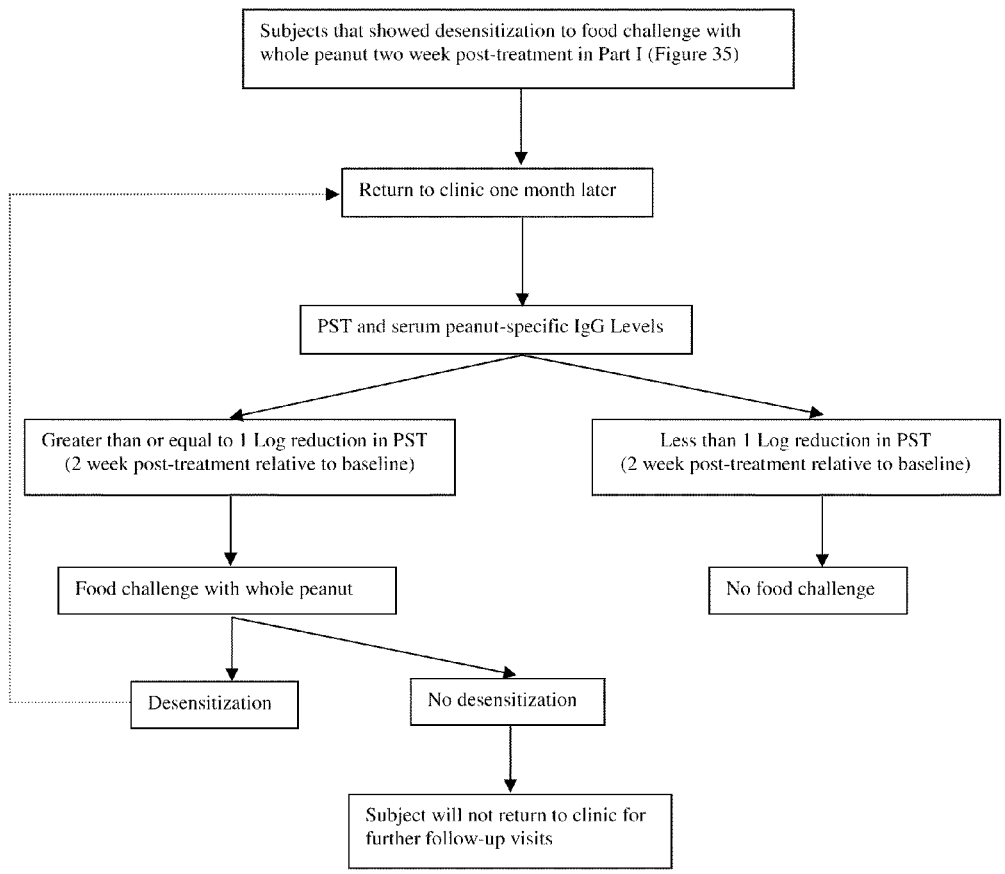
FIG. 36 is a flowchart that outlines the second part of the clinical study of Example 14.

The study will be an open label, single center, safety and efficacy study of multiple rectal administrations of HKE-MP123 in subjects allergic to peanuts. The study will consist of two parts, the first part will assess the preliminary efficacy of HKE-MP123 to demonstrate desensitization two weeks post-treatment, and the second part will assess the duration of the desensitization post-treatment. The flow charts of FIGS. 35 and 36 outline these two parts.

In the first part of the proposed clinical trial for HKE-MP123, eligible subjects who have signed informed consent will be admitted to a medical center with experience in treating severe allergic reactions. A prick skin test (PST) titration will be conducted with standardized peanut extract to obtain a pre-treatment PST score. Subjects with a positive PST score will be eligible to continue in the study, and the PST score will serve as a pre-treatment value against which efficacy will be measured over the course of treatment and post-treatment. Peanut-specific basophil activation and serum peanut-specific IgE levels will also be measured pre-treatment, and will serve as a pre-treatment value against which efficacy will be measured over the course of treatment and post-treatment. T-cell activation assays may also be performed.

Subjects with a positive PST score will be administered one dose of HKE-MP123 rectally once every week for a total of 8 weeks. The current anticipated starting dose will be 90 μg of total modified peanut protein (i.e., 30 μg of each of the three modified peanut proteins), and will be doubled each week, if no adverse events occur, to a maximum dose of 11,520 μg of total modified peanut protein (i.e., 3,840 μg of each of the three modified peanut proteins). Subjects will then receive the maximum HKE-MP123 dose rectally once every two weeks for a total of 6 weeks.

Subjects will remain in the clinic each day of administration for 8 hours. Subjects will have vital signs monitored following each of the administrations and will be queried regarding any adverse events they experience, as well as concomitant medication use. Serum chemistries, including hepatic profiles and renal profiles, urinalyses, and complete blood counts (CBCs) will be monitored for all subjects prior to the initiation of therapy and at weeks 4, 8, 12, and 14. At weeks 4, 8, 12, and 14, prior to rectal administration of HKE-MP123, PST titrations will be conducted and peanut-induced basophil activation and serum peanut-specific IgE levels will be measured. Optionally T-cell activation will also be measured.

At week 28 of the study, after other assays have been conducted, subjects will be challenged with whole peanut. Optionally, in order to determine the long term effects of treatment, PST titration may be conducted and peanut-induced basophil activation and serum peanut-specific IgE levels may be remeasured at later dates (e.g., 3-12 or more weeks after the first challenge). Optionally T-cell activation will also be measured.

14.4 Study Duration

The study duration for each subject, from baseline evaluation to final visit, will be approximately 14 weeks. The screening evaluations will be conducted within 2 weeks prior to the baseline evaluations. As noted, the study may be optionally extended to determine the long term effects of treatment.

14.5 Statistical Plan

Descriptive statistics will be used to evaluate safety and efficacy outcomes of this study. Safety will be assessed based on adverse events, vital signs, serum chemistries, urinalyses, and hematology. Efficacy will be assessed based on 1) prick skin test (PST) titration values during the treatment period and following treatment, compared to values prior to initiation of treatment, 2) dose of peanut extract required to activate patient basophils in vitro, 3) serum peanut-specific IgE levels during the treatment period and following treatment, compared to values prior to initiation of treatment, and 4) food challenge with whole peanut following treatment. Optionally a T-cell activation assay may also be used.

14.6 Starting Dose and Escalation Scheme

The starting dose is based on the dosages that have been shown to be safe and produce desensitization efficacy in mice (see Examples 11-14). The escalation scheme, doubling each week, is based upon standard immunotherapy practice. The highest dose may exceed the normal therapeutic dose, but should provide evidence that the dose can be increased further, as is sometimes necessary in treating bee-sting anaphylaxis patients.

14.7 Rationale for Schedule and Duration of Administration

The once weekly schedule of administration is based upon a well-established immunotherapy paradigm for escalation to "maintenance" doses of immunotherapeutic extracts. The 8 week period for scale-up administration was selected based upon an extrapolation of the murine model data. The biweekly schedule of administration and the 6 week term of the maintenance period were selected in order to ensure that the immune system has a sufficient period of time, with continued but not relentless exposure, to respond to the treatment and become desensitized.

14.8 Rationale for Challenge

All subjects who undergo the full desensitization protocol will be challenged by progressive administration of an extract of whole peanut under controlled conditions at the hospital. This challenge will both provide information about the effectiveness of the proposed therapy, and will allow an investigation of whether measurable immunologic markers can be correlated with likely response to challenge with/exposure to peanut. Unfortunately, to date no immunologic tests have been identified that can reliably predict the likelihood that a particular individual will or will not react to exposure to a given amount of peanut antigen. The present study tracks three specific immunologic markers over time: PST titration to peanut extract, peanut-specific basophil activation, and serum-specific peanut IgE. Optionally antigen-specific T-cell responses may also be assayed.

OTHER EMBODIMENTS

Other embodiments of the invention will be apparent to those skilled in the art from a consideration of the specification or practice of the invention disclosed herein. It is intended that the specification and Examples be considered as exemplary only, with the true scope of the invention being indicated by the following Claims.

APPENDIX 1

| ALLERGEN SOURCE | SYSTEMATIC AND ORIGINAL NAMES | MW (KD) | SEQUENCE DATA[1] | ACCESSION NO. OR REFERENCES |
|---|---|---|---|---|
| colspan=5 | WEED POLLENS | | | |
| colspan=5 | Asterales | | | |
| *Ambrosia artemisiifolia* (short ragweed) | Amb a 1; antigen E | 38 | C | 8, 20 |
| | Amb a 2; antigen K | 38 | C | 8, 21 |
| | Amb a 3; Ra3 | 11 | C | 22 |
| | Amb a 5; Ra5 | 5 | C | 11, 23 |
| | Amb a 6; Ra6 | 10 | C | 24, 25 |
| | Amb a 7; Ra7 | 12 | P | 26 |
| *Ambrosia trifida* (giant ragweed) | Amb t 5; Ra5G | 4.4 | C | 9, 10, 27 |
| *Artemisia vulgaris* (mugwort) | Art v 1 | 27-29 | C | 28 |
| | Art v 2 | 35 | P | 28a |
| | Art v 3; lipid transfer protein | 12 | P | 53 |
| | Art v 4; profilin | 14 | C | 29 |
| *Helianthus annuus* (sunflower) | Hel a 1 | 34 | — | 29A |
| | Hel a 2; profilin | 15.7 | C | Y15210 |
| *Mercurialis annua* | Mer a 1; profilin | 14-15 | C | Y13271 |
| colspan=5 | Carophyllales | | | |
| *Chenopodium album* (lamb's quarters, pigweed, white goosefoot) | Che a 1 | 17 | C | 29B, AY049012 |
| | Che a 2; profilin | 14 | C | AY082337 |
| | Che a 3; polcalcin | 10 | C | AY082338 |
| *Salsola kali* (Russian thistle) | Sal k 1 | 43 | P | 29C |

APPENDIX 1-continued

WEED POLLENS

| ALLERGEN SOURCE | SYSTEMATIC AND ORIGINAL NAMES | MW (KD) | SEQUENCE DATA[1] | ACCESSION NO. OR REFERENCES |
|---|---|---|---|---|
| | Rosales | | | |
| *Humulus japonicus* (Japanese hop) | Hum j 4w | | C | AY335187 |
| *Parietaria judaica* | Par j 1; lipid transfer protein 1 | 15 | C | X77414 |
| | Par j 2; lipid transfer protein 2 | | C | X95865 |
| | Par j 3; profilin | | C | Y15208 |
| *Parietaria officinalis* | Par o 1; lipid transfer protein | 15 | | 29D |

[1] P = Protein sequence, C = cDNA sequence

APPENDIX 2

GRASS POLLENS

| ALLERGEN SOURCE | SYSTEMATIC AND ORIGINAL NAMES | MW (KD) | SEQUENCE DATA | ACCESSION NO. OR REFERENCES |
|---|---|---|---|---|
| | Poales | | | |
| *Cynodon dactylon* (Bermuda grass) | Cyn d 1 | 32 | C | 30, S83343 |
| | Cyn d 7 | | C | 31, X91256 |
| | Cyn d 12; profilin | 14 | C | 31A, Y08390 |
| | Cyn d 15 | 9 | C | AF517686 |
| | Cyn d 22w; enolase | | | Pending |
| | Cyn d 23; Cyn d 14 | 9 | C | AF517685 |
| | Cyn d 24; pathogenesis-related protein | 21 | P | Pending |
| *Dactylis glomerata* (orchard grass) | Dac g 1; AgDg1 | 32 | P | 32 |
| | Dac g 2 | 11 | C | 33, S45354 |
| | Dac g 3 | | C | 33A, U25343 |
| | Dac g 5 | 31 | P | 34 |
| *Festuca pratensis* (meadow fescue) | Fes p 4w | 60 | | |
| *Holcus lanatus* (velvet grass) | Hol l 1 | | C | Z27084 |
| *Lolium perenne* (rye grass) | Lol p 1; group I | 27 | C | 35, 36 |
| | Lol p 2; group II | 11 | C | 37, 37A, X73363 |
| | Lol p 3; group III | 11 | C | 38 |
| | Lol p 5; Lol p IX, Lol p Ib | 31/35 | C | 34, 39 |
| | Lol p 11; trypsin inhibitor | 16 | | 39A |
| *Phalaris aquatica* (canary grass) | Pha a 1 | | C | 40, S80654 |
| *Phleum pratense* (timothy) | Phl p 1 | 27 | C | X78813 |
| | Phl p 2 | | C | 41, X75925 |
| | Phl p 4 | | P | 41A |
| | Phl p 5; Ag25 | 32 | C | 42 |
| | Phl p 6 | | C | 43, Z27082 |
| | Phl p 11; trypsin inhibitor | 20 | C | 43A, AF5211563 |
| | Phl p 12; profilin | | C | 44, X77583 |
| | Phl p 13; polygalacturonase | 55-60 | C | AJ238848 |
| *Poa pratensis* (Kentucky blue grass) | Poa p 1; group I | 33 | P | 46 |
| | Poa p 5 | 31/34 | C | 34, 47 |
| *Sorghum halepense* (Johnson grass) | Sor h 1 | | C | 48 |

APPENDIX 3

| | TREE POLLENS | | | |
|---|---|---|---|---|
| ALLERGEN SOURCE | SYSTEMATIC AND ORIGINAL NAMES | MW (KD) | SEQUENCE DATA | ACCESSION NO. OR REFERENCES |
| | Arecales | | | |
| *Phoenix dactylifera* (date palm) | Pho d 2 | 14.3 | C | Asturias (p.c.) |
| | Fagales | | | |
| *Alnus glutinosa* (alder) | Aln g 1 | 17 | C | S50892 |
| *Betula verrucosa* (birch) | Bet v 1 | 17 | C | X15877 |
| | Bet v 2; profilin | 15 | C | M65179 |
| | Bet v 3 | | C | X79267 |
| | Bet v 4 | 8 | C | X87153, S54819 |
| | Bet v 6; isoflavone reductase | 33.5 | C | AF135127 |
| | Bet v 7; cyclophilin | 18 | P | P81531 |
| *Carpinus betulus* (hornbeam) | Car b 1 | 17 | C | X66932 |
| *Castanea sativa* (chestnut) (also a food) | Cas s 1; Bet v 1 homologue | 22 | P | 52 |
| | Cas s 5; chitinase | 9.7 | P | 53 |
| | Cas s 8; lipid transfer protein | | | |
| *Corylus avellana* (hazel) (also a food) | Cor a 1 | 17 | C | X70999 |
| | Cor a 2; profilin | 14 | C | |
| | Cor a 8; lipid transfer protein | 9 | C | |
| | Cor a 9; 11S globulin-like protein | 40 | C | Beyer (p.c.) |
| | Cor a 10 luminal binding protein | 70 | C | AJ295617 |
| | Cor a 11; 7S vicilin-like protein | 48 | C | AF441864 |
| *Quercus alba* (white oak) | Que a 1 | 17 | P | 54 |
| | Lamiales | | | |
| | Oleaceae | | | |
| *Fraxinus excelsior* (ash) | Fra e 1 | 20 | P | 58A |
| *Ligustrum vulgare* (privet) | Lig v 1 | 20 | P | 58A |
| *Olea europea* (olive) | Ole e 1 | 16 | C | 59, 60 |
| | Ole e 2; profilin | 15-18 | C | 60A |
| | Ole e 3 | 9.2 | | 60B |
| | Ole e 4 | 32 | P | P80741 |
| | Ole e 5; superoxide dismutase | 16 | P | P80740 |
| | Ole e 6 | 10 | C | 60C, U86342 |
| | Ole e 7 | | P | 60D, P81430 |
| | Ole e 8; $Ca^{2+}$-binding protein | 21 | C | 60E, AF078679 |
| | Ole e 9; beta-1,3-glucanase | 46 | C | AF249675 |
| *Syringa vulgaris* (lilac) | Syr v 1 | 20 | P | 58A |
| | Plantaginaceae | | | |
| *Plantago lanceolata* (English plantain) | Pla l 1 | 18 | P | P842242 |
| | Pinales | | | |
| *Cryptomeria japonica* (sugi) | Cry j 1 | 41-45 | C | 55, 56 |
| | Cry j 2 | | C | 57, D29772 |
| *Cupressus arizonica* (cypress) | Cup a 1 | 43 | C | A1243570 |
| *Cupressus sempervirens* (common cypress) | Cup s 1 | 43 | C | AF257491 |
| | Cup s 3w | 34 | C | Pending |
| *Juniperus ashei* (mountain cedar) | Jun a 1 | 43 | P | P81294 |
| | Jun a 2 | | C | 57A, AJ404653 |
| | Jun a 3 | 30 | P | 57B, P81295 |
| *Juniperus oxycedrus* (prickly juniper) | Jun o 4; calmodulin-like | 29 | C | 57C, AF031471 |

APPENDIX 3-continued

TREE POLLENS

| ALLERGEN SOURCE | SYSTEMATIC AND ORIGINAL NAMES | MW (KD) | SEQUENCE DATA | ACCESSION NO. OR REFERENCES |
|---|---|---|---|---|
| *Juniperus sabinoides* (mountain cedar) | Jun s 1 | 50 | P | 58 |
| *Juniperus virginiana* (eastern red cedar) | Jun v 1 | 43 | P | 58B, P81825 |
| Platanaceae | | | | |
| *Platanus acerifolia* (London plane tree) | Pla a 1 | 18 | P | P82817 |
| | Pla a 2 | 43 | P | P82967 |
| | Pla a 3; lipid transfer protein | 10 | P | Iris (p.c.) |

APPENDIX 4

MITE ALLERGENS

| ALLERGEN SOURCE | SYSTEMATIC AND ORIGINAL NAMES | MW (KD) | SEQUENCE DATA | ACCESSION NO. OR REFERENCES |
|---|---|---|---|---|
| *Acarus siro* (mite) | Aca s 13; fatty acid-binding protein | 14* | C | AJ006774 |
| *Blomia tropicalis* (mite) | Blo t 1; cysteine protease | 39 | C | AF277840 |
| | Blo t 3; trypsin | 24* | C | Cheong (p.c.) |
| | Blo t 4; alpha amylase | 56 | C | Cheong (p.c.) |
| | Blo t 5 | | C | U59102 |
| | Blo t 6; chymotrypsin | 25 | C | Cheong (p.c.) |
| | Blo t 10; tropomyosin | 33 | C | 61 |
| | Blo t 11; paramyosin | 110 | C | 61A, AF525465 |
| | Blo t 12; Bt11a | | C | U27479 |
| | Blo t 13; Bt6 fatty acid-binding protein | | C | U58106 |
| | Blo t 11; anti-microbial protein | 7.2 | C | Cheong (p.c.) |
| *Dermatophagoides farinae* (American house dust mite) | Der f 1; cysteine protease | 25 | C | 69 |
| | Der f 2 | 14 | C | 70, 70A |
| | Der f 3; trypsin | 30 | C | 63 |
| | Der f 7 | 24-31 | C | 71, SW: Q26456 |
| | Der f 10; tropomyosin | | C | 72 |
| | Der f 11; paramyosin | 98 | C | 72A |
| | Der f 14; Mag3, apolipophorin | | C | D17686 |
| | Der f 15; 98k chitinase | 98 | C | AF178772 |
| | Der f 16; gelsolin/villin | 53 | C | 71A |
| | Der f 17; $Ca^{2+}$-binding EF protein | 53 | C | 71A |
| | Der f 18w; 60k chitinase | 60 | C | Weber (p.c.) |
| *Dermatophagoides microceras* (mite) | Der m 1; cysteine protease | 25 | P | 68 |
| *Dermatophagoides pteronyssinus* (mite) | Der p 1; antigen P1, cysteine protease | 25 | C | 62 |
| | Der p 2 | 14 | C | 62A-C |
| | Der p 3; trypsin | 28/30 | C | 63 |
| | Der p 4; amylase | 60 | P | 64 |
| | Der p 5 | 14 | C | 65 |
| | Der p 6; chymotrypsin | 25 | P | 66 |
| | Der p 7 | 22/28 | C | 67 |
| | Der p 8; glutathione transferase | | C | 67A |
| | Der p 9; collagenolytic serine protein | | P | 67B |
| | Der p 10; tropomyosin | 36 | C | Y14906 |
| | Der p 14; apolipophorin like protein | | C | Epton (p.c.) |
| *Europglyphus maynei* (mite) | Eur m 2 | | C | AF047613 |
| | Eur m 14; apolipophorin | 177 | C | AF149827 |
| *Glycyphagus domesticus* (storage mite) | Gly d 2 | | C | 72B |

APPENDIX 4-continued

MITE ALLERGENS

| ALLERGEN SOURCE | SYSTEMATIC AND ORIGINAL NAMES | MW (KD) | SEQUENCE DATA | ACCESSION NO. OR REFERENCES |
|---|---|---|---|---|
| *Lepidoglyphus destructor* (storage mite) | Lep d 2 | 15 | C | 73, 74, 74A |
| | Lep d 5 | | C | 75, AJ250278 |
| | Lep d 7 | | C | 75, AJ271058 |
| | Lep d 10; tropomyosin | | C | 75A, AJ250096 |
| | Lep d 13 | | C | 75, AJ250279 |
| *Tyrophagus putrescentiae* (storage mite) | Tyr p 2 | | C | 75B, Y12690 |

APPENDIX 5

ANIMAL ALLERGENS

| ALLERGEN SOURCE | SYSTEMATIC AND ORIGINAL NAMES | MW (KD) | SEQUENCE DATA | ACCESSION NO. OR REFERENCES |
|---|---|---|---|---|
| *Bos domesticus* (domestic cattle) (also a food) | *Bos* d 2; Ag3, lipocalin | 20 | C | 76, L42867 |
| | *Bos* d 3; $Ca^{2+}$-binidng S100 homologue | 11 | C | L39834 |
| | *Bos* d 4; alpha-lactalbumin | 14.2 | C | M18780 |
| | *Bos* d 5; beta-lactoglobulin | 18.3 | C | X14712 |
| | *Bos* d 6; serum albumin | 67 | C | M73993 |
| | *Bos* d 7; immunoglobulin | 160 | | 77 |
| | *Bos* d 8; caseins | 20-30 | | 77 |
| *Canis familiaris* (dog) | Can f 1 | 25 | C | 78, 79 |
| | Can f 2 | 27 | C | 78, 79 |
| | Can f 3; albumin | | C | S72946 |
| | Can f 4 | 18 | P | A59491 |
| *Equus caballus* (domestic horse) | Equ c 1; lipocalin | 25 | C | U70823 |
| | Equ c 2; lipocalin | 18.5 | P | 79A, 79B |
| | Equ c 3; Ag3-albumin | 67 | C | 79C, X74045 |
| | Equ c 4 | 17 | P | 79D |
| | Equ c 5; AgX | 17 | P | Goutran Botros (p.c.) |
| *Felis domesticus* (cat saliva) | Fel d 1; cat-1 | 38 | C | 15 |
| | Fel d 2; albumin | | C | 79E, X84842 |
| | Fel d 3; cystatin | 11 | C | 79F, AF238996 |
| | Fel d 4; lipocalin | 22 | C | AY497902 |
| | Fel d 5w; IgA | 400 | | Adedoyin (p.c.) |
| | Fel d 6w; IgM | 800-1000 | | Adedoyin (p.c.) |
| | Fel d 7w; IgG | 150 | | Adedoyin (p.c.) |
| *Cavia porcellus* (guinea pig) | Cav p 1; lipocalin homologue | 20 | P | 80, SW: P83507 |
| | Cav p 2 | 17 | P | SW: P83508 |
| *Mus musculus* (mouse urine) | *Mus* m 1; MUP | 19 | C | 81, 81A |
| *Rattus norvegius* (rat urine) | Rat n 1 | 17 | C | 82, 83 |

APPENDIX 6

FUNGI ALLERGENS

| ALLERGEN SOURCE | SYSTEMATIC AND ORIGINAL NAMES | MW (KD) | SEQUENCE DATA | ACCESSION NO. OR REFERENCES |
|---|---|---|---|---|
| | Ascomycota Dothidiales | | | |
| *Alternaria alternata* | Alt a 1 | 28 | C | U82633 |
| | Alt a 2 | 25 | C | 83A, U62442 |
| | Alt a 3; heat shock protein | 70 | C | U87807, U87808 |
| | Alt a 4; protein disulfidisomerase | 57 | C | X84217 |
| | Alt a 6; acidic ribosomal protein P2 | 11 | C | X78222, U87806 |

APPENDIX 6-continued

| | FUNGI ALLERGENS | | | |
|---|---|---|---|---|
| ALLERGEN SOURCE | SYSTEMATIC AND ORIGINAL NAMES | MW (KD) | SEQUENCE DATA | ACCESSION NO. OR REFERENCES |
| | Alt a 7; YCP4 protein | 22 | C | X78225 |
| | Alt a 10; aldehyde dehydrogenase | 53 | C | X78227, P42041 |
| | Alt a 11; enolase | 45 | C | U82437 |
| | Alt a 12; acidic ribosomal protein P1 | 11 | C | X84216 |
| *Cladosporium herbarum* | Cla h 1 | 13 | | 83B, 83C |
| | Cla h 2 | 23 | | 83B, 83C |
| | Cla h 3; aldehyde dehydrogenase | 53 | C | X78228 |
| | Cla h 4; acidic ribosomal protein P2 | 11 | C | X78223 |
| | Cla h 5; YCP4 protein | 22 | C | X78224 |
| | Cla h 6; enolase | 46 | C | X78226 |
| | Cla h 12; acidic ribosomal protein P1 | 11 | C | X85180 |
| | Eurotiales | | | |
| *Aspergillus flavus* | Asp fl 13; alkaline serine proteinase | 34 | | 84 |
| *Aspergillus fumigatus* | Asp f 1 | 18 | C | M83781, S39330 |
| | Asp f 2 | 37 | C | U56938 |
| | Asp f 3; peroxisomal protein | 19 | C | U20722 |
| | Asp f 4 | 30 | C | AJ001732 |
| | Asp f 5; metalloprotease | 42 | C | Z30424 |
| | Asp f 6; Mn superoxide dismutase | 26.5 | C | U53561 |
| | Asp f 7 | 12 | C | AJ223315 |
| | Asp f 8; ribosomal protein P2 | 11 | C | AJ224333 |
| | Asp f 9 | 34 | C | AJ223327 |
| | Asp f 10; aspartic protease | 34 | C | X85092 |
| | Asp f 11; peptidyl-prolyl isom | 24 | | 84A |
| | Asp f 12; heat shock protein P90 | 90 | C | 85 |
| | Asp f 13; alkaline serine proteinase | 34 | | 84B |
| | Asp f 15 | 16 | C | AJ002026 |
| | Asp f 16 | 43 | C | g3643813 |
| | Asp f 17 | | C | AJ224865 |
| | Asp f 18; vacuolar serine proteinase | 34 | | 84C |
| | Asp f 22w; enolase | 46 | C | AF284645 |
| | Asp f 23; L3 ribosomal protein | 44 | C | 85A, AF464911 |
| *Aspergillus niger* | Asp n 14; beta-xylosidase | 105 | C | AF108944 |
| | Asp n 18; vacuolar serine proteinase | 34 | C | 84B |
| | Asp n ? | 85 | C | Z84377 |
| *Aspergillus oryzae* | Asp o 13; alkaline serine proteinase | 34 | C | X17561 |
| | Asp o 21; TAKA-amylase A | 53 | C | D00434, M33218 |
| *Penicillium brevicompactum* | Pen b 13; alkaline serine proteinase | 33 | | 86A |
| *Penicillium chrysogenum* | Pen ch 13; alkaline serine proteinase | 34 | | 87 |
| | Pen ch 18; vacuolar serine protease | 32 | | 87 |
| | Pen ch 20; N-acetyl glucosaminidase | 68 | | 87A |
| *Penicillium citrinum* | Pen c 3; peroxisomal membrane protein | 18 | | 86B |
| | Pen c 13; alkaline serine proteinase | 33 | | 86A |
| | Pen c 19; heat shock protein P70 | 70 | C | U64207 |
| | Pen c 22w; enolase | 46 | C | AF254643 |
| | Pen c 24; elongation factor 1 beta | | C | AY363911 |

APPENDIX 6-continued

FUNGI ALLERGENS

| ALLERGEN SOURCE | SYSTEMATIC AND ORIGINAL NAMES | MW (KD) | SEQUENCE DATA | ACCESSION NO. OR REFERENCES |
|---|---|---|---|---|
| *Penicillium oxalicum* | Pen o 18; vacuolar serine proteinase | 34 | | 87B |
| *Hypocreales* | | | | |
| *Fusarium culmorum* | Fus c 1; ribosomal protein P2 | 11* | C | AY077706 |
| | Fus c 2; thioredoxin-like protein | 13* | C | AY077707 |
| *Onygenales* | | | | |
| *Trichophyton rubrum* | Tri r 2 | | C | 88 |
| | Tri r 4; serine protease | | C | 88 |
| *Trichophyton tonsurans* | Tri t 1 | 30 | P | 88A |
| | Tri t 4; serine protease | 83 | C | 88 |
| *Saccharomycetales* | | | | |
| *Candida albicans* | Cand a 1 | 40 | C | 89 |
| | Cand a 3; peroxisomal protein | 29 | C | AY136739 |
| *Candida boidinii* | Cand b 2 | 20 | C | J04984, J04985 |
| *Basidiomycota* | | | | |
| *Hymenomycetes* | | | | |
| *Psilocybe cubensis* | Psi c 1 | | | |
| | Psi c 2; cyclophilin | 16 | | 89A |
| *Coprinus comatus* (shaggy cap) | Cop c 1; leucine zipper protein | 11 | C | AJ132235 |
| | Cop c 2 | | | AJ242791 |
| | Cop c 3 | | | AJ242792 |
| | Cop c 5 | | | AJ242793 |
| | Cop c 7 | | | AJ242794 |
| *Urediniomycetes* | | | | |
| *Rhodotorula mucilaginosa* | Rho m 1; enolase | 47 | C | 89B |
| *Ustilaginomycetes* | | | | |
| *Malassezia furfur* | Mala f 2; MF1 peroxisomal membrane protein | 21 | C | 90, AB011804 |
| | Mala f 3; MF2 peroxisomal membrane protein | 20 | C | 90, AB011805 |
| | Mala f 4; mitochondrial malate dehydrogenase | 35 | C | 90A, AF084828 |
| *Malassezia sympodialis* | Mala s 1 | | C | 91, X96486 |
| | Mala s 5 | 18* | C | AJ011955 |
| | Mala s 6 | 17* | C | AJ011956 |
| | Mala s 7 | | C | 91A, AJ011957 |
| | Mala s 8 | 19* | C | 91A, AJ011958 |
| | Mala s 9 | 37* | C | 91A, AJ011959 |
| | Mala s 10; heat shock protein 79 | 86 | C | AJ428052 |
| | Mala s 11; Mn superoxide dismutase | 23 | C | AJ548421 |
| *Deuteromycotina* | | | | |
| *Tuberculariales* | | | | |
| *Epicoccum purpurascens* | Epi p 1; serine protease | 30 | P | 91B; SW: P83340 |

APPENDIX 7

INSECT ALLERGENS

| ALLERGEN SOURCE | SYSTEMATIC AND ORIGINAL NAMES | MW (KD) | SEQUENCE DATA | ACCESSION NO. OR REFERENCES |
|---|---|---|---|---|
| *Aedes aegyptii* (mosquito) | Aed a 1; Apyrase | 68 | C | L12389 |
| | Aed a 2; | 37 | C | M33157 |
| *Apis mellifera* | Api m 1; phospholipase A2 | 16 | C | 92 |

APPENDIX 7-continued

INSECT ALLERGENS

| ALLERGEN SOURCE | SYSTEMATIC AND ORIGINAL NAMES | MW (KD) | SEQUENCE DATA | ACCESSION NO. OR REFERENCES |
|---|---|---|---|---|
| (honey bee) | Api m 2; hyaluronidase | 44 | C | 93 |
| | Api m 4; melittin | 3 | C | 94 |
| | Api m 6 | 7-8 | P | Kettner (p.c.) |
| | Api m7; CUB serine protease | 39 | C | AY127579 |
| *Bombus pennsylvanicus* (bumble bee) | Bom p 1; phospholipase | 16 | P | 95 |
| | Bom p 4; protease | | P | 95 |
| *Blattella germanica* (German cockroach) | Bla g 1; Bd90k | | C | |
| | Bla g 2; aspartic protease | 36 | C | 96 |
| | Bla g 4; calycin | 21 | C | 97 |
| | Bla g 5; glutathione transf. | 22 | C | 98 |
| | Bla g 6; troponin C | 27 | C | 98 |
| *Periplaneta americana* (American cockroach) | Per a 1; Cr-PII | | C | |
| | Per a 3; Cr-PI | 72-78 | C | 98A |
| | Per a 7; tropomyosin | 37 | C | Y14854 |
| *Chironomus kiiensis* (midge) | Chi k 10; tropomyosin | 32.5* | C | AJ012184 |
| *Chironomus thummi* (midge) | Chi t 1-9; hemoglobin | 16 | C | 99 |
| | Chi t 1.01; component III | 16 | C | P02229 |
| | Chi t 1.02; component IV | 16 | C | P02230 |
| | Chi t 2.0101; component I | 16 | C | P02221 |
| | Chi t 2.0102; component IA | 16 | C | P02221 |
| | Chi t 3; component II-beta | 16 | C | P02222 |
| | Chi t 4; component IIIA | 16 | C | P02231 |
| | Chi t 5; component VI | 16 | C | P02224 |
| | Chi t 6.01; component VIIA | 16 | C | P02226 |
| | Chi t 6.02; component IX | 16 | C | P02223 |
| | Chi t 7; component VIIB | 16 | C | P02225 |
| | Chi t 8; component VIII | 16 | C | P02227 |
| | Chi t 9; component X | 16 | C | P02228 |
| *Ctenocephalides felis felis* (cat flea) | Cte f 1 | | | |
| | Cte f 2; M1b | 27 | C | AF231352 |
| *Thaumetopoea pityocampa* (pine process. moth) | Tha p 1 | 15 | P | 99A, PIR: A59396 |
| *Lepisma saccharina* (silverfish) | Lep s 1; tropomyosin | 36 | C | AJ309202 |
| *Dolichovespula maculata* (white face hornet) | Dol m 1; phospholipase A1 | 35 | C | 100 |
| | Dol m 2; hyaluronidase | 44 | C | 101 |
| | Dol m 5; antigen 5 | 23 | C | 102, 103 |
| *Dolichovespula arenaria* (yellow hornet) | Dol a 5; antigen 5 | 23 | C | 104 |
| *Polistes annularies* (wasp) | Pol a 1; phospholipase A1 | 35 | P | 105 |
| | Pol a 2; hyaluronidase | 44 | P | 105 |
| | Pol a 5; antigen 5 | 23 | C | 104 |
| *Polistes dominulus* (Mediterranean paper wasp) | Pol d 1 | | | Hoffman (p.c.) |
| | Pol d 4; serine protease | 32-34 | C | Hoffman (p.c.) |
| | Pol d 5 | | | P81656 |
| *Polistes exclamans* (wasp) | Pol e 1; phospholipase A1 | 34 | P | 107 |
| | Pol e 5; antigen 5 | 23 | C | 104 |
| *Polistes fuscatus* (wasp) | Pol f 5; antigen 5 | 23 | C | 106 |
| *Polistes metricus* (wasp) | Pol m 5; antigen 5 | 23 | P | 106 |
| *Vespa crabo* (European hornet) | Vesp c 1; phospholipase | 34 | P | 107 |
| | Vesp c 5; antigen 5 | 23 | C | 106 |
| *Vespa mandarina* (giant asian hornet) | Vesp m 1 | | | Hoffman (p.c.) |
| | Vesp m 5 | | | P81657 |
| *Vespula flavopilosa* (yellowjacket) | Ves f 5; antigen 5 | 23 | C | 106 |
| *Vespula germanica* (yellowjacket) | Ves g 5; antigen 5 | 23 | C | 106 |

APPENDIX 7-continued

INSECT ALLERGENS

| ALLERGEN SOURCE | SYSTEMATIC AND ORIGINAL NAMES | MW (KD) | SEQUENCE DATA | ACCESSION NO. OR REFERENCES |
|---|---|---|---|---|
| *Vespula maculifrons* (yellowjacket) | Ves m 1; phospholipase A1 | 33.5 | C | 108 |
| | Ves m 2; hyaluronidase | 44 | P | 109 |
| | Ves m 5; antigen 5 | 23 | C | 104 |
| *Vespula pennsylvanica* (yellowjacket) | Ves p 5; antigen 5 | 23 | C | 106 |
| *Vespula squamosa* (yellowjacket) | Ves s 5; antigen 5 | 23 | C | 106 |
| *Vespula vidua* (wasp) | Ves vi 5 | 23 | C | 106 |
| *Vespula vulgaris* (yellowjacket) | Ves v 1; phopholipase A1 | 35 | C | 105A |
| | Ves v 2; hyaluronidase | 44 | P | 105A |
| | Ves v 5; antigen 5 | 23 | C | 104 |
| *Myrmecia pilosula* (Australian jumper ant) | Myr p 1 | | C | X70256 |
| | Myr p 2 | | C | S81785 |
| *Solenopsis geminata* (tropical fire ant) | Sol g 2 | | | Hoffman (p.c.) |
| | Sol g 4 | | | Hoffman (p.c.) |
| *Solenopsis invicta* (fire ant) | Sol i 2 | 13 | C | 110, 111 |
| | Sol i 3 | 24 | C | 110 |
| | Sol i 4 | 13 | C | 110 |
| *Solenopsis saevissima* (brazilian fire ant) | Sol s 2 | | | Hoffman (p.c.) |
| *Triatoma procracta* (Californian kissing bug) | Tria p 1; procalin | 20 | C | 111A, AF179004 |

APPENDIX 8

FOOD ALLERGENS

| ALLERGEN SOURCE | SYSTEMATIC AND ORIGINAL NAMES | MW (KD) | SEQUENCE DATA | ACCESSION NO. OR REFERENCES |
|---|---|---|---|---|
| *Gadus callarias* (cod) | Gad c 1; allergen M | 12 | C | 112, 113 |
| *Salmo salar* (Atlantic salmon) | Sal s 1; parvalbumin | 12 | C | X97824 X97825 |
| *Bos domesticus* (domestic cattle) (milk) (see also animals) | Bos d 4; alpha-lactalbumin | 14.2 | C | M18780 |
| | Bos d 5; beta-lactoglobulin | 18.3 | C | X14712 |
| | Bos d 6; serum albumin | 67 | C | M73993 |
| | Bos d 7; immunoglobulin | 160 | | 77 |
| | Bos d 8; caseins | 20-30 | | 77 |
| *Gallus domesticus* (chicken) | Gal d 1; ovomucoid | 28 | C | 114, 115 |
| | Gal d 2; ovalbumin | 44 | C | 114, 115 |
| | Gal d 3; Ag22, conalbumin | 78 | C | 114, 115 |
| | Gal d 4; lysozyme | 14 | C | 114, 115 |
| | Gal d 5; serum albumin | 69 | C | X60688 |
| *Metapenaeus ensis* (shrimp) | Met e 1; tropomyosin | | C | U08008 |
| *Penaeus aztecus* (shrimp) | Pen a 1; tropomyosin | 36 | P | 116 |
| *Penaeus indicus* (shrimp) | Pen i 1; tropomyosin | 34 | C | 116A |
| *Penaeus monodon* (black tiger shrimp) | Pen m 1; tropomyosin | 38 | C | |
| | Pen m 2; arginine kinase | 40 | C | 117, AF479772 |
| *Todarodes pacificus* (squid) | Tod p 1; tropomyosin | 38 | P | 117A |
| *Helix aspersa* (brown garden snail) | Hel as 1; tropomyosin | 36 | C | 117B, Y14855 |

APPENDIX 8-continued

FOOD ALLERGENS

| ALLERGEN SOURCE | SYSTEMATIC AND ORIGINAL NAMES | MW (KD) | SEQUENCE DATA | ACCESSION NO. OR REFERENCES |
|---|---|---|---|---|
| *Haliotis Midae* (abalone) | Hal m 1 | 49 | | 117C |
| *Brassica juncea* (oriental mustard) | Bra j 1; 2S albumin | 14 | C | 118 |
| *Brassica napus* (rapeseed) | Bra n 1; 2S albumin | 15 | P | 118A, P80208 |
| *Brassica rapa* (turnip) | Bra r 2; prohevein-like protein | 25 | | P81729 |
| *Hordeum vulgare* (barley) | Hor v 15; BMAI-1 | 15 | C | 119 |
| | Hor v 16; alpha-amylase | | | |
| | Hor v 17; beta-amylase | | | |
| | Hor v 21; gamma-3 hordein | 34 | C | 119A, SW: P80198 |
| *Secale cereale* (rye) | Sec c 20; secalin | | | PIR: S70327 |
| *Triticum aestivum* (wheat) | Tri a 18; agglutinin | | | |
| | Tri a 19; omega-5 gliadin | 65 | P | PIR: A59156 |
| *Zea mays* (maize, corn) | Zea m 14; lipid transfer protein | 9 | P | P19656 |
| *Oryza sativa* (rice) | Ory s 1 | | C | 119B, U31771 |
| *Apium graveolens* (celery) | Api g 1; Bet v 1 homologue | 16* | C | Z48967 |
| | Api g 4; profilin | | | AF129423 |
| | Api g 5 | 55/58 | P | P81943 |
| *Daucus carota* (carrot) | Dau c 1; Bet v 1 homologue | 16 | C | 117D |
| | Dau c 4; profilin | | C | AF456482 |
| *Malus domestica* (apple) | Mal d 1; Bet v 1 homologue | | C | X83672 |
| | Mal d 2; thaumatin homologue | | C | AJ243427 |
| | Mal d 3; lipid transfer protein | 9 | C | Pastorello (p.c.) |
| *Pyrus communis* (pear) | Pyr c 1; Bet v 1 homologue | 18 | C | AF05730 |
| | Pyr c 4; profilin | 14 | C | AF129424 |
| | Pyr c 5; isoflavone transfer protein | 33.5 | C | AF071477 |
| *Persea americana* (avocado) | Pers a 1; endochitinase | 32 | C | Z78202 |
| *Prunus armeniaca* (apricot) | Pru ar 1; Bet v 1 homologue | | C | U93165 |
| | Pru ar 3; lipid transfer protein | 9 | P | |
| *Prunus avium* (sweet cherry) | Pru av 1; Bet v 1 homologue | | C | U66076 |
| | Pru av 2; thaumatin homologue | | C | U32440 |
| | Pru av 3; lipid transfer protein | 10 | C | AF221501 |
| | Pru av 4; profilin | 15 | C | AF129425 |
| *Prunus domestica* (European plum) | Pru d 4; lipid transfer protein | 9 | P | 119C |
| *Prunus persica* (peach) | Pru p 3; lipid transfer protein | 10 | P | P81402 |
| | Pru p 4; profilin | 14 | C | AJ491881 |
| *Asparagus officinalis* (asparagus) | Aspa o 1; lipid transfer protein | 9 | P | 119D |
| *Crocus sativus* (saffron crocus) | Cro s 1 | 21 | | Varasteh (p.c.) |
| *Lactuca sativa* (lettuce) | Lac s 1; lipid transfer protein | 9 | | Vieths (p.c.) |
| *Vitis vinifera* (grape) | Vit v 1; lipid transfer protein | 9 | P | P80274 |
| *Musa x paradisiaca* (banana) | Mus xp 1; profilin | 15 | C | AF377948 |
| *Ananas comosus* (pineapple) | Ana c 1; profilin | 15 | C | AF377949 |
| *Litchi chinensis* (litchi) | Lit c 1; profilin | 15 | C | AY049013 |

APPENDIX 8-continued

| FOOD ALLERGENS | | | | |
|---|---|---|---|---|
| ALLERGEN SOURCE | SYSTEMATIC AND ORIGINAL NAMES | MW (KD) | SEQUENCE DATA | ACCESSION NO. OR REFERENCES |
| *Sinapis alba* (yellow mustard) | Sin a 1; 2S albumin | 14 | C | 120 |
| *Glycine max* (soybean) | Gly m 1; HPS | 7 | P | 120A |
| | Gly m 2; | 8 | P | A57106 |
| | Gly m 3; profilin | 14 | C | AJ223982 |
| | Gly m 4; SAM22 PR-10 protein | 17 | C | 120B, X60043 |
| *Arachis hypogaea* (peanut) | Ara h 1; vicilin | 63.5 | C | L34402 |
| | Ara h 2; conglutin | 17 | C | L77197 |
| | Ara h 3; glycinin | 60 | C | AF093541 |
| | Ara h 4; glycinin | 37 | C | AF086821 |
| | Ara h 5; profilin | 15 | C | AF059616 |
| | Ara h 6; conglutin homologue | 15 | C | AF092846 |
| | Ara h 7; conglutin homologue | 15 | C | AF091737 |
| | Ara h 8; PR-10 protein | 17 | C | AY328088 |
| *Len culinaris* (lentil) | Len c 1; vicilin | 47 | C | AJ551424 |
| | Len c 2; see biotinylated protein | 66 | P | 120C |
| *Pisum savitum* (pea) | Pis s 1; vicilin | 44 | C | AJ626897 |
| | Pis s 2; convicilin | 63 | C | Pending |
| *Actinidia chinensis* (kiwi) | Act c 1; cysteine protease | 30 | P | P00785 |
| | Act c 2; thamautin-like protein | 24 | P | 121, SW: P81370 |
| *Capsicum annuum* (bell pepper) | Cap a 1w; osmotin-like protein | 23 | C | AJ297410 |
| | Cap a 2; profilin | 14 | C | AJ417552 |
| *Lycopersicon esculentum* (tomato) | Lyc e 1; profilin | 14 | C | AJ417553 |
| | Lyc e 2; fructofuranidase | 50 | C | AF465612 |
| *Solanum tuberosum* (potato) | Sola t 1; patatin | 43 | P | P15476 |
| | Sola t 2, cathespin D inhibitor | 21 | P | P16348 |
| | Sola t 3; cysteine protease inhibitor | 21 | P | P20347 |
| | Sola t 4; aspartic protease inhibitor | 16 + 4 | P | P30941 |
| *Bertholletia excelsa* (Brazil nut) | Ber e 1; 2S albumin | 9 | C | P04403, M17146 |
| | Ber e 2; 11S globulin seed storage protein | 29 | C | AY221641 |
| *Juglans nigra* (black walnut) | Jug n 1; 2S albumin | 19* | C | AY102930 |
| | Jug n 2; vicilin-like protein | 56* | C | AY102931 |
| *Juglans regia* (English walnut) | Jug r 1; 2S albumin | | C | U66866 |
| | Jug r 2; vicilin | 44 | C | AF066055 |
| | Jug r 3; lipid transfer protein | 9 | P | Pastorello (p.c.) |
| *Anacardium occidentale* (cashew) | Ana o 1; vicilin-like protein | 50 | C | AF395894 |
| | Ana o 2; legumin-like protein | 55 | C | AF453947 |
| | Ana o 3; 2S albumin | 14 | C | AY081853 |
| *Ricinus communis* (Castor bean) | Ric c 1; 2S albumin | | C | P01089 |
| *Sesamum indicum* (sesame) | Ses i 1; 2S albumin | 9 | C | 121A, AF240005 |
| | Ses i 2; 2S albumin | 7 | C | AF0911841 |
| | Ses i 3; 7S vicilin-like globulin | 45 | C | AF240006 |
| | Ses i 4; oleosin | 17 | C | AAG23840 |
| | Ses i 5; oleosin | 15 | C | AAD42924 |
| *Cucumis melo* (muskmelon) | Cuc m 1; serine protease | 66 | C | D32209 |
| | Cuc m 2; profilin | 14 | C | AY271295 |
| | Cuc m 3; pathogenesis related protein, PR-1 | 16* | P | P83834 |

APPENDIX 9

OTHER ALLERGENS

| ALLERGEN SOURCE | SYSTEMATIC AND ORIGINAL NAMES | MW (KD) | SEQUENCE DATA | ACCESSION NO. OR REFERENCES |
|---|---|---|---|---|
| *Anisakis simplex* (nematode) | Ani s 1 | 24 | P | 121B, A59069 |
| | Ani s 2; paramyosin | 97 | C | AF173004 |
| | Ani s 3; tropomyosin | 41 | C | 121C, Y19221 |
| | Ani s 4 | 9 | P | P83885 |
| *Ascaris suum* (worm) | Asc s 1 | 10 | P | 122 |
| *Dendronephthya nipponica* (soft corral) | Den n 1 | 53 | P | 122A |
| *Hevea brasiliensis* (rubber) | Hev b 1; elongation factor | 58 | P | 123, 124 |
| | Hev b 2; 1,3-glucanase | 34/36 | C | 125 |
| | Hev b 3 | 24 | P | 126, 127 |
| | Hev b 4; component of microhelix protein complex | 100-115 | P | 128 |
| | Hev b 5 | 16 | C | U42640 |
| | Hev b 6.01; hevein precursor | 20 | C | M36986, p02877 |
| | Hev b 6.02; hevein | 5 | C | M36986, p02877 |
| | Hev b 6.03; C-terminal fragment | 14 | C | M36986, p02877 |
| | Hev b 7.01; patatin from B-serum homologue | 42 | C | U80598 |
| | Hev b 7.02, patatin from C-serum homologue | 44 | C | AJ223038 |
| | Hev b 8; profilin | 14 | C | Y15042 |
| | Hev b 9; enolase | 51 | C | AJ132580 |
| | Hev b 10; Mn-superoxide dismutase | 26 | C | AJ249148 |
| | Hev b 11; class 1 chitinase | | C | AJ238579 |
| | Hev b 12; lipid transfer protein | 9.3 | C | AY057860 |
| | Hev b 13; esterase | 42 | P | P83269 |
| *Homo sapiens* (human autoallergens) | Hom s 1 | 73* | C | Y14314 |
| | Hom s 2 | 10.3* | C | X80909 |
| | Hom s 3 | 20.1* | C | X89985 |
| | Hom s 4 | 36* | C | Y17711 |
| | Hom s 5 | 42.6* | C | P02538 |
| *Triplochiton scleroxylon* (obeche) | Trip s 1; class 1 chitinase | 38.5 | P | Kespohl (p.c.) |

APPENDIX 10—REFERENCES

1. Marsh, D. G., and L. R. Freidhoff. 1992. ALBE, an allergen database. IUIS, Baltimore, Md., Edition 1.0.
2. Marsh, D. G., L. Goodfriend, T. P. King, H. Lowenstein, and T. A. E. Platts-Mills. 1986. Allergen nomenclature. Bull WHO 64:767-770.
3. King, T. P., P. S. Norman, and J. T. Cornell. 1964. Isolation and characterization of allergen from ragweed pollen. II. Biochemistry 3:458-468.
4. Lowenstein, H. 1980. Timothy pollen allergens. Allergy 35:188-191.
5. Aukrust, L. 1980. Purification of allergens in *Cladosporium herbarum*. Allergy 35:206-207.
6. Demerec, M., E. A. Adelberg, A. J. Clark, and P. E. Hartman. 1966. A proposal for a uniform nomenclature in bacterial genetics. Genetics 54:61-75.
7. Bodmer, J. G., E. D. Albert, W. F. Bodmer, B. Dupont, H. A. Erlich, B. Mach, S. G. E. Marsh, W. R. Mayr, P. Parham, T. Sasuki, G. M. Th. Schreuder, J. L. Strominger, A. Svejgaard, and P. I. Terasaki. 1991. Nomenclature for factors of the HLA system, 1990. Immunogenetics 33:301-309.
8. Griffith, I. J., J. Pollock, D. G. Klapper, B. L. Rogers, and A. K. Nault. 1991. Sequence polymorphism of Amb a I and Amb a II, the major allergens in *Ambrosia artemisiifolia* (short ragweed). Int. Arch. Allergy Appl. Immunol. 96:296-304.
9. Roebber, M., D. G. Klapper, L. Goodfriend, W. B. Bias, S. H. Hsu, and D. G. Marsh. 1985 Immunochemical and genetic studies of Amb t V (Ra5G), an Ra5 homologue from giant ragweed pollen. J. Immunol. 134:3062-3069.
10. Metzler, W. J., K. Valentine, M. Roebber, M. Friedrichs, D. G. Marsh, and L. Mueller. 1992. Solution structures of ragweed allergen Amb t V. Biochemistry 31:5117-5127.
11. Metzler, W. J., K. Valentine, M. Roebber, D. G. Marsh, and L. Mueller. 1992. Proton resonance assignments and three-dimensional solution structure of the ragweed allergen Amb a V by nuclear magnetic resonance spectroscopy. Biochemistry 31:8697-8705.
12. Goodfriend, L., A. M. Choudhury, J. Del Carpio, and T. P. King. 1979. Cytochromes C: New ragweed pollen allergens. Fed. Proc. 38:1415.
13. Ekramoddoullah, A. K. M., F. T. Kisil, and A. H. Sehon. 1982. Allergenic cross reactivity of cytochrome c from Kentucky bluegrass and perennial ryegrass pollens. Mol. Immunol. 19:1527-1534.

14. Ansari, A. A., E. A. Killoran, and D. G. Marsh. 1987. An investigation of human response to perennial ryegrass (*Lolium perenne*) pollen cytochrome c (Lol p X). J. Allergy Clin. Immunol. 80:229-235.
15. Morgenstern, J. P., I. J. Griffith, A. W. Brauer, B. L. Rogers, J. F. Bond, M. D. Chapman, and M. Kuo. 1991. Amino acid sequence of Fel d I, the major allergen of the domestic cat: protein sequence analysis and cDNA cloning. Proc. Natl. Acad. Sci. USA 88:9690-9694.
16. Griffith, I. J., S. Craig, J. Pollock, X. Yu, J. P. Morgenstern, and B. L. Rogers. 1992. Expression and genomic structure of the genes encoding FdI, the major allergen from the domestic cat. Gene 113:263-268.
17. Weber, A., L. Marz, and F. Altmann. 1986. Characteristics of the asparagine-linked oligosaccharide from honey-bee venom phospholipase A2. Comp. Biochem. Physiol. 83B: 321-324.
18. Weber, A., H. Schroder, K. Thalberg, and L. Marz. 1987. Specific interaction of IgE antibodies with a carbohydrate epitope of honey bee venom phospholipase A2. Allergy 42:464-470.
19. Stanworth, D. R., K. J. Dorrington, T. E. Hugli, K. Reid, and M. W. Turner. 1990. Nomenclature for synthetic peptides representative of immunoglobulin chain sequences. Bulletin WHO 68:109-111.
20. Rafnar, T., I. J. Griffith, M. C. Kuo, J. F. Bond, B. L. Rogers, and D. G. Klapper. 1991. Cloning of Amb a I (Antigen E), the major allergen family of short ragweed pollen. J. Biol. Chem. 266: 1229-1236.
21. Rogers, B. L., J. P. Morgenstern, I. J. Griffith, X. B. Yu, C. M. Counsell, A. W. Brauer, T. P. King, R. D. Garman, and M. C. Kuo. 1991. Complete sequence of the allergen Amb a II: recombinant expression and reactivity with T-cells from ragweed allergic patients. J. Immunol. 147:2547-2552.
22. Klapper, D. G., L. Goodfriend, and J. D. Capra. 1980 Amino acid sequence of ragweed allergen Ra3. Biochemistry 19:5729-5734.
23. Ghosh, B., M. P. Perry, T. Rafnar, and D. G. Marsh. 1993. Cloning and expression of immunologically active recombinant Amb a V allergen of short ragweed (*Ambrosia artemisiifolia*) pollen. J. Immunol. 150:5391-5399.
24. Roebber, M., R. Hussain, D. G. Klapper, and D. G. Marsh. 1983. Isolation and properties of a new short ragweed pollen allergen, Ra6. J. Immunol. 131:706-711.
25. Lubahn, B., and D. G. Klapper. 1993. Cloning and characterization of ragweed allergen Amb a VI (abst). J. Allergy Clin. Immunol. 91:338.
26. Roebber, M., and D. G. Marsh. 1991. Isolation and characterization of allergen Amb a VII from short ragweed pollen. J. Allergy Clin. Immunol. 87:324.
27. Goodfriend L, Choudhury A M, Klapper D G, Coulter K M, Dorval G, DelCarpio J, Osterland C K. Ra5G, a homologue of Ra5 in giant ragweed pollen: isolation, HLA-DR-associated activity and amino acid sequence. Mol Immunol 22: 899-906, 1985.
28. Himly M, Jahn-Schmid B, Dedic A, Kelemen P, Wopfner N, Altmann F, van Ree R, Briza P, Richter K, Ebner C, Ferreira F. Art v 1, the major allergen of mugwort pollen, is a modular glycoprotein with a defensin-like and a hydroxyproline-rich domain. FASEB J 17: 106-108, 2003.
28A. Nilsen, B. M., K. Sletten, M. O'Neill, B. Smestead Paulsen, and H. van Halbeek. 1991. Structural analysis of the glycoprotein allergen Art v II from pollen of mugwort (*Artemesia vulgaris*). J. Biol. Chem. 266:2660-2668.
29. Wopfner N, Willeroidee M, Hebenstreit D, van Ree R, Aalbers M, Briza P, Thalhamer J, Ebner C, Richter K, Ferreira F. Molecular and immunological characterization of profilin from mugwort pollen. Biol Chem 383: 1779-1789, 2002.
29A. Jimenez A, Moreno C, Martinez J, Martinez A, Bartolome B, Guerra F, Palacios R 1994. Sensitization to sunflower pollen: only an occupational allergy? Int Arch Allergy Immunol 105:297-307.
29B. Barderas R, Villalba M, Lombardero M, Rodriguez R. Identification and characterization of Che a 1 allergen from Chenopodium album pollen. Int Arch Allergy Immunol 127: 47-54, 2002.
29C. Carnés J, Fernández-Caldas E, Casanovas M, Lahoz C, Colás C. Immunochemical characterization of Salsola kali pollen extracts. Allergy 56, Supplement 68: 274, 2001.
29D. Giuliani A, Pini C, Bonini S, Mucci N, Ferroni L, Vicari G: Isolation and purification of a major allergen from Parietaria officinalis pollen. Allergy 42: 434-440, 1987.
30. Smith, P. M., Suphioglu, C., Griffith, I. J., Theriault, K., Knox, R. B. and Singh, M. B. 1996. Cloning and expression in yeast *Pichia pastoris* of a biologically active form of Cyn d 1, the major allergen of Bermuda grass pollen. J. Allergy Clin. Immunol. 98:331-343.
31. Suphioglu, C., Ferreira, F. and Knox, R. B. 1997. Molecular cloning and immunological characterisation of Cyn d 7, a novel calcium-binding allergen from Bermuda grass pollen. FEBS Lett. 402:167-172.
31A. Asturias J A, Arilla M C, Gomez-Bayon N, Martinez J, Martinez A, and Palacios R. 1997. Cloning and high level expression of *Cynodon dactylon* (Bermuda grass) pollen profilin (Cyn d 12) in *Escherichia coli*: purification and characterization of the allergen. Clin Exp Allergy 27:1307-1313.
32. Mecheri, S., G. Peltre, and B. David. 1985. Purification and characterization of a major allergen from *Dactylis glomerata* pollen: The Ag Dg 1. Int. Arch. Allergy Appl. Immunol. 78:283-289.
33. Roberts, A. M., L. J. Bevan, P. S. Flora, I. Jepson, and M. R. Walker. 1993. Nucleotide sequence of cDNA encoding the Group II allergen of Cocksfoot/Orchard grass (*Dactylis glomerata*), Dac g II. Allergy 48:615-623.
33A. Guerin-Marchand, C., Senechal, H., Bouin, A. P., Leduc-Brodard, V., Taudou, G., Weyer, A., Peltre, G. and David, B. 1996. Cloning, sequencing and immunological characterization of Dac g 3, a major allergen from *Dactylis glomerata* pollen. Mol. Immunol. 33:797-806.
34. Klysner, S., K. Welinder, H. Lowenstein, and F. Matthiesen. 1992. Group V allergens in grass pollen IV. Similarities in amino acid compositions and amino terminal sequences of the group V allergens from *Lolium perenne, Poa pratensis* and *Dactylis glomerata*. Clin. Exp. Allergy 22: 491-497.
35. Perez, M., G. Y. Ishioka, L. E. Walker, and R. W. Chesnut. 1990. cDNA cloning and immunological characterization of the rye grass allergen Lol p I. J. Biol. Chem. 265:16210-16215.
36. Griffith, I. J., P. M. Smith, J. Pollock, P. Theerakulpisut, A. Avjioglu, S. Davies, T. Hough, M. B. Singh, R. J. Simpson, L. D. Ward, and R. B. Knox. 1991. Cloning and sequencing of Lol p I, the major allergenic protein of rye-grass pollen. FEBS Letters 279:210-215.
37. Ansari, A. A., P. Shenbagamurthi, and D. G. Marsh. 1989. Complete amino acid sequence of a *Lolium perenne* (perennial rye grass) pollen allergen, Lol p II. J. Biol. Chem. 264:11181-11185.
37A. Sidoli, A., Tamborini, E., Giuntini, I., Levi, S., Volonte, G., Paini, C., De Lalla, C., Siccardi, A. G., Baralle, F. E., Galliani, S. and Arosio, P. 1993. Cloning, expression, and immunological characterization of recombinant *Lolium perenne* allergen Lol p II. J. Biol. Chem. 268:21819-21825.

38. Ansari, A. A., P. Shenbagamurthi, and D. G. Marsh. 1989. Complete primary structure of a *Lolium perenne* (perennial rye grass) pollen allergen, Lol p III: Comparison with known Lol p I and II sequences. Biochemistry 28:8665-8670.

39. Singh, M. B., T. Hough, P. Theerakulpisut, A. Avjioglu, S. Davies, P. M. Smith, P. Taylor, R. J. Simpson, L. D. Ward, J. McCluskey, R. Puy, and R. B. Knox. 1991. Isolation of cDNA encoding a newly identified major allergenic protein of rye-grass pollen: Intracellular targeting to the amyloplost. Proc. Natl. Acad. Sci. 88:1384-1388.

39A. van Ree R, Hoffman D R, van Dijk W, Brodard V, Mahieu K, Koeleman C A, Grande M, van Leeuwen W A, Aalberse R C. 1995. Lol p XI, a new major grass pollen allergen, is a member of a family of soybean trypsin inhibitor-related proteins. J Allergy Clin Immunol 95:970-978.

40. Suphioglu, C. and Singh, M. B. 1995. Cloning, sequencing and expression in *Escherichia coli* of Pha a 1 and four isoforms of Pha a 5, the major allergens of canary grass pollen. Clin. Exp. Allergy 25:853-865.

41. Dolecek, C., Vrtala, S., Laffer, S., Steinberger, P., Kraft, D., Scheiner, O. and Valenta, R. 1993. Molecular characterization of Phl p II, a major timothy grass (*Phleum pratense*) pollen allergen. FEBS Lett. 335:299-304.

41A. Fischer S, Grote M, Fahlbusch B, Muller W D, Kraft D, Valenta R. 1996. Characterization of Phl p 4, a major timothy grass (*Phleum pratense*) pollen allergen. J Allergy Clin Immunol 98:189-198.

42. Matthiesen, F., and H. Lowenstein. 1991. Group V allergens in grass pollens. I. Purification and characterization of the group V allergen from *Phleum pratense* pollen, Phl p V. Clin. Exp. Allergy 21:297-307.

43. Petersen, A., Bufe, A., Schramm, G., Schlaak, M. and Becker, W. M. 1995. Characterization of the allergen group VI in timothy grass pollen (Phl p 6). II. cDNA cloning of Phl p 6 and structural comparison to grass group V. Int. Arch. Allergy Immunol. 108:55-59.

43A. Marknell DeWitt A, Niederberger V, Lehtonen P, Spitzauer S, Sperr W R, Valent P, Valenta R, Lidholm J. Molecular and immunological characterization of a novel timothy grass (*Phleum pratense*) pollen allergen, Phl p 11. Clin Exp Allergy 32: 1329-1340, 2002.

44. Valenta, R., Ball, T., Vrtala, S., Duchene, M., Kraft, D. and Scheiner, O. 1994. cDNA cloning and expression of timothy grass (*Phleum pratense*) pollen profilin in *Escherichia coli*: comparison with birch pollen profilin. Biochem. Biophys. Res. Commun. 199:106-118.

46. Esch, R. E., and D. G. Klapper. 1989. Isolation and characterization of a major cross-reactive grass group I allergenic determinant. Mol. Immunol. 26:557-561.

47. Olsen, E., L. Zhang, R. D. Hill, F. T. Kisil, A. H. Sehon, and S. Mohapatra. 1991. Identification and characterization of the Poa p IX group of basic allergens of Kentucky bluegrass pollen. J. Immunol. 147:205-211.

48. Avjioglu, A., M. Singh, and R. B. Knox. 1993. Sequence analysis of Sor h I, the group I allergen of Johnson grass pollen and it comparison to rye-grass Lol p I (abst). J. Allergy Clin. Immunol. 91:340.

52. Kos T, Hoffmann-Sommergruber K, Ferreira F, Hirschwehr R, Ahorn H, Horak F, Jager S, Sperr W, Kraft D, Scheiner O. 1993. Purification, characterization and N-terminal amino acid sequence of a new major allergen from European chestnut pollen—Cas s 1. Biochem Biophys Res Commun 196:1086-92.

53. Diaz-Perales A, Lombardero M, Sánchez-Monge R, García-Sellés F J, Pernas M, Fernández-Rivas M, Barber D, Salcedo G. 2000. Lipid-transfer proteins as potential plant panallergens: cross-reactivity among proteins of Artemisia pollen, Castaneae nut and Rosaceae fruits, with different IgE-binding capacities. Clin Exp Allergy 30:1403-1410.

54. Ipsen, H., and O. C. Hansen. 1991. The NH2-terminal amino acid sequence of the immunochemically partial identical major allergens of alder (*Alnus glutinosa*) Aln g I, birch (*Betula verrucosa*) Bet v I, hornbeam (*Carpinus betulus*) Car b I and oak (*Quercus alba*) Que a I pollens. Mol. Immunol. 28: 1279-1288.

55. Taniai, M., S. Ando, M. Usui, M. Kurimoto, M. Sakaguchi, S. Inouye, and T. Matuhasi. 1988. N-terminal amino acid sequence of a major allergen of Japanese cedar pollen (Cry j I). FEBS Lett. 239:329-332.

56. Griffith, I. J., A. Lussier, R. Garman, R. Koury, H. Yeung, and J. Pollock. 1993. The cDNA cloning of Cry j I, the major allergen of *Cryptomeria japonica* (Japanese cedar) (abst). J. Allergy Clin. Immunol. 91:339.

57. Sakaguchi, M., S. Inouye, M. Taniai, S. Ando, M. Usui, and T. Matuhasi. Identification of the second major allergen of Japanese cedar pollen. Allergy 45: 309-312, 1990.

57A. Yokoyama M, Miyahara M, Shimizu K, Kino K, Tsunoo H. Purification, identification, and cDNA cloning of Jun a 2, the second major allergen of mountain cedar pollen. Biochem Biophys Res Commun 275: 195-202, 2000.

57B. Midoro-Horiuti T, Goldblum R M, Kurosky A, Wood T G, Brooks E G. Variable Expression of Pathogenesis-Related Protein Allergen in Mountain Cedar (*Juniperus ashei*) Pollen. J Immunol 164: 2188-2192, 2000.

57C. Tinghino R., Barletta B., Palumbo S., Afferni C., Iacovacci P., Mari A., Di Felice G., Pini, C. Molecular characterization of a cross-reactive *Juniperus oxycedrus* pollen allergen, Jun o 2: a novel calcium-binding allergen J. Allergy Clin. Immunol. 101: 772-777, 1998.

58. Gross G N, Zimburean J M, Capra J D. Isolation and partial characterization of the allergen in mountain cedar pollen. Scand J Immunol 8: 437-441, 1978.

58[a]. Obispo T M, Melero J A, Carpizo J A, Carreira J, Lombardero M. The main allergen of *Olea europaea* (Ole e I) is also present in other species of the oleaceae family. Clin Exp Allergy 23: 311-316, 1993.

58B. Midoro-Horiuti T, Goldblum R M, Brooks E G. Identification of mutations in the genes for the pollen allergens of eastern red cedar (*Juniperus virginiana*). Clin Exp Allergy 31: 771-778, 2001.

59. Lombardero M., Barbas J. A., Moscoso del Prado J., Carreira J. cDNA sequence analysis of the main olive allergen, Ole e I. Clin. Exp. Allergy 24: 765-770, 1994.

60. Villalba, M., E. Batanero, C. Lopez-Otin, L. M. Sanchez, R. I. Monsalve, M. A. Gonzalez de la Pena, C. Lahoz, and R. Rodriguez Amino acid sequence of Ole e I, the major allergen from olive tree pollen (*Olea europaea*). Eur. J. Biochem. 216: 863-869, 1993.

60A. Asturias J A, Arilla M C, Gomez-Bayon N, Martinez J, Martinez A, Palacios R. Cloning and expression of the panallergen profilin and the major allergen (Ole e 1) from olive tree pollen. J Allergy Clin Immunol 100: 365-372, 1997.

60B. Batanero E, Villalba M, Ledesma A Puente X S, Rodriguez R. Ole e 3, an olive-tree allergen, belongs to a widespread family of pollen proteins. Eur J Biochem 241: 772-778, 1996.

60C. Batanero E, Ledesma A, Villalba M, Rodriguez R. Purification, amino acid sequence and immunological characterization of Ole e 6, a cysteine-enriched allergen from olive tree pollen. FEBS Lett. 410: 293-296, 1997.

60D. Tejera M L, Villalba M, Batanero E, Rodriguez R. Identification, isolation, and characterization of Ole e 7, a new allergen of olive tree pollen. J Allergy Clin Immunol 104: 797-802, 1999.

60E. Ledesma, A., Villalba, M. and Rodriguez, R. Cloning, expression and characterization of a novel four EF-hand Ca(2+)-binding protein from olive pollen with allergenic activity. FEBS Lett. 466: 192-196, 2000.

61. Yi F C, Cheong N, Shek P C, Wang D Y, Chua K Y, Lee B W. Identification of shared and unique immunoglobulin E epitopes of the highly conserved tropomyosins in *Blomia tropicalis* and *Dermatophagoides pteronyssinus*. Clin Exp Allergy 32: 1203-1210, 2002.

61A. Ramos J D, Cheong N, Lee B W, Chua K Y. cDNA cloning and expression of Blo t 11, the *Blomia tropicalis* allergen homologous to paramyosin. Int Arch Allergy Immunol 126: 286-293, 2001.

62. Chua, K. Y., G. A. Stewart, and W. R. Thomas. Sequence analysis of cDNA encoding for a major house dust mite allergen, Der p I. J. Exp. Med. 167: 175-182, 1988.

62A. Chua, K. Y., C. R. Doyle, R. J. Simpson, K. J. Turner, G. A. Stewart, and W. R. Thomas. Isolation of cDNA coding for the major mite allergen Der p II by IgE plaque immunoassay. Int. Arch. Allergy Appl. Immunol. 91: 118-123, 1990.

62B. Smith A M, Benjamin D C, Derewenda U, Smith W A, Thomas W R, Chapman M D. Sequence polymorphisms and antibody binding to the group 2 dust mite allergens. Int Arch Allergy Immunol 124: 61-63, 2001.

62C. Smith A M, Benjamin D C, Hozic N, Derewenda U, Smith W A, Thomas W R, Gafvelin G, van Hage-Hamsten M, Chapman M D. The molecular basis of antigenic cross-reactivity between the group 2 mite allergens. J Allergy Clin Immunol 107: 977-984, 2001.

63. Smith W A, Thomas W R. Comparative analysis of the genes encoding group 3 allergens from *Dermatophagoides pteronyssinus* and *Dermatophagoides farinae*. Int Arch Allergy Immunol 109: 133-140, 1996.

64. Lake, F. R., L. D. Ward, R. J. Simpson, P. J. Thompson, and G. A. Stewart. House dust mite-derived amylase: Allergenicity and physicochemical characterisation. J. Allergy Clin. Immunol. 87: 1035-1042, 1991.

65. Tovey, E. R., M. C. Johnson, A. L. Roche, G. S. Cobon, and B. A. Baldo. Cloning and sequencing of a cDNA expressing a recombinant house dust mite protein that binds human IgE and corresponds to an important low molecular weight allergen. J. Exp. Med. 170: 1457-1462, 1989.

66. Yasueda, H., T. Shida, T. Ando, S. Sugiyama, and H. Yamakawa. 1991. Allergenic and proteolytic properties of fourth allergens from *Dermatophagoides* mites. In: "Dust Mite Allergens and Asthma. Report of the 2nd international workshop" A. Todt, Ed., UCB Institute of Allergy, Brussels, Belgium, pp. 63-64.

67. Shen, H.-D., K.-Y. Chua, K.-L. Lin, K.-H. Hsieh, and W. R. Thomas. Molecular cloning of a house dust mite allergen with common antibody binding specificities with multiple components in mite extracts. Clin. Exp. Allergy 23: 934-940, 1993.

67. O'Neil G M, Donovan G R, Baldo B A. Cloning and charaterisation of a major allergen of the house dust mite *Dermatophagoides pteronyssinus*, homologous with glutathione S-transferase. Biochim Biophys Acta, 1219: 521-528, 1994.

67B. King C, Simpson R J, Moritz R L, Reed G E, Thompson P J, Stewart G A. The isolation and characterization of a novel collagenolytic serine protease allergen (Der p 9) from the dust mite *Dermatophagoides pteronyssinus*. J Allergy Clin Immunol 98: 739-747, 1996.

68. Lind P, Hansen O C, Horn N. The binding of mouse hybridoma and human IgE antibodies to the major fecal allergen, Der p I of *D. pteronyssinus*. J. Immunol. 140: 4256-4262, 1988.

69. Dilworth, R. J., K. Y. Chua, and W. R. Thomas. Sequence analysis of cDNA coding for a mojor house dust allergen Der f I. Clin. Exp. Allergy 21: 25-32, 1991.

70. Nishiyama, C., T. Yunki, T. Takai, Y. Okumura, and H. Okudaira. Determination of three disulfide bonds in a major house dust mite allergen, Der f II. Int. Arch. Allergy Immunol. 101: 159-166, 1993.

70A. Trudinger, M., K. Y. Chua, and W. R. Thomas. cDNA encoding the major dust mite allergen Der f II. Clin. Exp. Allergy 21: 33-38, 1991.

71. Shen H D, Chua K Y, Lin W L, Hsieh K H, Thomas W R. Molecular cloning and immunological characterization of the house dust mite allergen Der f 7. Clin Exp Allergy 25: 1000-1006, 1995.

71A. Tategaki A, Kawamoto S, Aki T, Jyo T, Suzuki O, Shigeta S, Ono K. Newly described house dust mite allergens. ACI International suppl. 1: 74-76, 2000.

72. Aki T, Kodama T, Fujikawa A, Miura K, Shigeta S, Wada T, Jyo T, Murooka Y, Oka S, Ono K Immunochemical characteristion of recombinant and native tropomyosins as a new allergen from the house dust mite *Dermatophagoides farinae*. J Allergy Clin Immunol 96: 74-83, 1995.

72A. Tsai L, Sun Y, Chao P, Ng H, Hung M, Hsieh K, Liaw S, Chua K. Sequence analysis and expression of a cDNA clone encoding a 98-kDa allergen in *Dermatophagoides farinae*. Clin Exp Allergy 29: 1606-1613, 1999.

72B. Gafvelin G, Johansson E, Lundin A, Smith A M, Chapman M D, Benjamin D C, Derewenda U, Van Hage-Hamsten M. Cross-reactivity studies of a new group 2 allergen from the dust mite *Glycyphagus domesticus*, Gly d 2, and group 2 allergens from *Dermatophagoides pteronyssinus, Lepidoglyphus destructor*, and *Tyrophagus putrescentiae* with recombinant allergens. J Allergy Clin Immunol 107: 511-518, 2001.

73. van Hage-Hamsten, M., T. Bergman, E. Johansson, B. Persson, H. Jornvall, B. Harfast, and S. G. O. Johansson. N-terminal amino acid sequence of major allergen of the mite *lepidoglyphus destructor* (abst). J. Allergy Clin. Immunol. 91:353, 1993.

74. Varela J, Ventas P, Carreira J, Barbas J A, Gimenez-Gallego G, Polo F. Primary structure of Lep d I, the main *Lepidoglyphus destructor* allergen. Eur J Biochem 225: 93-98, 1994.

74A. Schmidt M, van der Ploeg I, Olsson S, van Hage Hamsten M. The complete cDNA encoding the *Lepidoglyphus destructor* major allergen Lep d 1. FEBS Lett 370: 11-14, 1995.

75. Eriksson T L J, Rasool O, Huecas S, Whitley P, Crameri R, Appenzeller U, Gafvelin G, van Hage-Hamsten M. Cloning of three new allergens from the dust mite *Lepidoglyphus destructor* using phage surface display technology. Eur. J. Biochem. 268: 287-294, 2001.

75A. Saarne T, Kaiser L, Rasool O, Huecas S, van Hage-Hamsten M, Gafvelin G: Cloning and characterisation of two IgE-binding proteins, homologous to tropomyosin and a-tubulin, from the mite *Lepidoglyphus destructor*. Int Arch Allergy Immunol 130: 258-265, 2003.

75B. Eriksson T L, Johansson E, Whitley P, Schmidt M, Elsayed S, van Hage-Hamsten M. Cloning and characterisation of a group II allergen from the dust mite *Tyrophagus putrescentiae*. Eur. J. Biochem. 251 (1-2), 443-447, 1998.

76. Rautiainen J, Rytkonen M, Pelkonen J, Pentikainen J, Perola O, Virtanen T, Zeiler T, Mantyjarvi R. BDA20, a major bovine dander allergen characterized at the sequence level is Bos d 2. Submitted.

77. Gjesing B, Lowenstein H. Immunochemistry of food antigens. Ann Allergy 53:602, 1984.

78. de Groot, H., K. G. H. Goei, P. van Swieten, and R. C. Aalberse. Affinity purification of a major and a minor allergen from dog extract: Serologic activity of affinity-purified Can f I and Can f I-depleted extract. J. Allergy Clin. Immunol. 87:1056-1065, 1991.

79. Konieczny, A. Personal communication; Immunologic Pharmaceutical Corp.

79A. Bulone, V. Separation of horse dander allergen proteins by two-dimensional electrophoresis. Molecular characterisation and identification of Equ c 2.0101 and Equ c 2.0102 as lipocalin proteins. Eur J Biochem 253: 202-211, 1998.

79B. Swiss-Prot acc. P81216, P81217.

79C. Dandeu J. P., Rabillon J., Divanovic A., Carmi-Leroy A., David B. (1993). Hydrophobic interaction chromatography for isolation and purification of Equ c 1, the horse major allergen. J. Chromatogr. 621:23-31.

79D. Goubran Botros H., Rabillon J., Grégoire C., David B., Dandeu J. P. 1998. Thiophilic absorption chromatography: purification of Equ c 2 and Equ c 3, two horse allergens from horse sweat. J. Chromatogr. B 710:57-65.

79E. Hilger C, Kohnen M, Grigioni F, Lehners C, Hentges F. Allergic cross-reactions between cat and pig serum albumin. Allergy 52:179-187, 1997; and Hilger C, Grigioni F, Hentges F. Sequence of the gene encoding cat (*Felis domesticus*) serum albumin. Gene 169:295-296, 1996.

79F. Ichikawa K, Vailes L D, Pomes A, Chapman M D. Molecular cloning, expression and modeling of cat allergen, cystatin (Fel d 3), a cysteine protease inhibitor. Clin Exp Allergy, In Press 2001.

80. Fahlbusch B, Rudeschko O, Szilagyi U, Schlott B, Henzgen M, Schlenvoigt G, Schubert H. Purification and partial characterization of the major allergen, Cav p 1, from guinea pig *Cavia porcellus*. Allergy 57: 417-422, 2002.

81. McDonald, B., M. C. Kuo, J. L. Ohman, and L. J. Rosenwasser. 1988. A 29 amino acid peptide derived from rat alpha 2 euglobulin triggers murine allergen specific human T-cells (abst). J. Allergy Clin. Immunol. 83:251.

81A. Clarke, A. J., P. M. Cissold, R. A. Shawi, P. Beattie, and J. Bishop. 1984. Structure of mouse urinary protein genes: differential splicing configurations in the 3'-non-coding region. EMBO J 3:1045-1052.

82. Longbottom, J. L. 1983. Chracterization of allergens from the urines of experimental animals. McMillan Press, London, pp. 525-529.

83. Laperche, Y., K. R. Lynch, K. P. Dolans, and P. Feigelsen. 1983. Tissue-specific control of alpha 2u globulin gene expression: constitutive synthesis in submaxillary gland. Cell 32:453-460.

83A. Bush R K, Sanchez H, Geisler D. 1999. Molecular cloning of a major *Alternaria alternata* allergen, rAlt a 2. J Allergy Clin Immunol 104:665-671.

83B. Aukrust L, Borch S M. 1979. Partial purification and characterization of two *Cladosporium herbarum* allergens. Int Arch Allergy Appl Immunol 60:68-79.

83C. Sward-Nordmo M, Paulsen B S, Wold J K. 1988. The glycoprotein allergen Ag-54 (Cla h II) from *Cladosporium herbarum*. Structural studies of the carbohydrate moiety. Int Arch Allergy Appl Immunol 85:288-294.

84. Shen, et al. J. Allergy Clin. Immunol. 103:S157, 1999.

84A. Crameri R. Epidemiology and molecular basis of the involvement of *Aspergillus fumigatus* in allergic diseases. Contrib. Microbiol. Vol. 2, Karger, Basel (in press).

84B. Shen, et al. (manuscript submitted), 1999

84C. Shen H D, Ling W L, Tan M F, Wang S R, Chou H, Han S I H. Vacuolar serine proteinase: A major allergen of *Aspergillus fumigatus*. 10$^{th}$ International Congress of Immunology, Abstract, 1998.

85. Kumar A, Reddy L V, Sochanik A, Kurup V P. 1993. Isolation and characterization of a recombinant heat shock protein of *Aspergillus fumigatus*. J. Allergy Clin. Immunol. 91:1024-1030.

85A. Saxena S, Madan T, Muralidhar K, Sarma P U. 2003. cDNA cloning, expression and characterization of an allergenic L3 ribosomal protein of *Aspergillus fumigatus*. Clin Exp Immunol 134:86-91.

86A. Shen H D, Lin W L, Tsai J J, Liaw S F, Han S H. 1996. Allergenic components in three different species of *Penicillium*: crossreactivity among major allergens. Clin Exp Allergy 26:444-451.

86B. Shen, et al. Abstract; The XVIII Congress of the European Academy of Allergology and Clinical Immunology, Brussels, Belgium, 3-7 Jul. 1999.

87. Shen H D, Lin W L, Tam M F, Wang S R, Tzean S S, Huang M H, Han S H. Characterization of allergens from *Penicillium oxalicum* and *P. notatum* by immunoblotting and N-terminal amino acid sequence analysis. Clin Exp Allergy 29: 642-651, 1999.

87A. Shen H D, Liaw S F, Lin W L, Ro L H, Yang H L, Han S H. Molecular cloning of cDNA coding for the 68 kDa allergen of *Penicillium notatum* using MoAbs. Clin Exp Allergy 25: 350-356, 1995.

87B. Shen H D, Wang C W, Lin W L, Lai H Y, Tam M F, Chou H, Wang S R, Han S H. cDNA cloning and immunologic characterization of Pen o 18, the vacuolar serine protease major allergen of *Penicillium oxalicum*. J Lab Clin Med 137: 115-124, 2001.

88. Woodfolk J A, Wheatley L M, Piyasena R V, Benjamin D C, Platts-Mills T A. 1998. *Trichophyton* antigens associated with IgE antibodies and delayed type hypersensitivity. Sequence homology to two families of serine proteinases. J Biol Chem 273:29489-96.

88A. Deuell, B., L. K. Arruda, M. L. Hayden, M. D. Chapman and T. A. E. Platts-Mills. 1991. *Trichophyton tonsurans* Allergen I. J. Immunol. 147:96-101.

89. Shen, H. D., K. B. Choo, H. H. Lee, J. C. Hsieh, and S. H. Han. 1991. The 40 kd allergen of *Candida albicans* is an alcohol dehydrogenease: molecular cloning and immunological analysis using monoclonal antibodies. Clin. Exp. Allergy 21:675-681.

89A. Homer W E, Reese G, Lehrer S B. 1995. Identification of the allergen Psi c 2 from the basidiomycete *Psilocybe cubensis* as a fungal cyclophilin. Int Arch Allergy Immunol 107:298-300.

89B. Chang C Y, Chou H, Tam M F, Tang R B, Lai H Y, Shen H D. Characterization of Enolase Allergen from *Rhodotorula mucilaginosa*. J Biomed Sci 9: 645-655, 2002.

90. Yasueda H, Hashida-Okado T, Saito A, Uchida K, Kuroda M, Onishi Y, Takahashi K, Yamaguchi H, Takesako K, Akiyama K. Identification and cloning of two novel allergens from the lipophilic yeast, *Malassezia furfur*. Biochem Biophys Res Commun 248: 240-244, 1998. NB:strain TIMM2782 (Teikyo University Institute for Medical Mycology) equal to strain CBS1878 (Central Bureau von Schimmelkulturen).

90A. Onishi Y, Kuroda M, Yasueda H, Saito A, Sono-Koyama E, Tunasawa S, Hashida-Okado T, Yagihara T, Uchida K, Yamaguchi H, Akiyama K, Kato I, Takesako K. Two-dimensional electrophoresis of *Malassezia allergens* for atopic dermatitis and isolation of Mal f 4 homologs with mitochondrial malate dehydrogenase. Eur J Biochem 261: 148-154, 1999. NB: strain TIMM2782 (Teikyo University Institute for Medical Mycology) equal to strain CBS1878 (Central Bureau von Schimmelkulturen).

91. Schmidt M, Zargari A, Holt P, Lindbom L, Hellman U, Whitley P, van der Ploeg I, Harfast B, Scheynius A. The complete cDNA sequence and expression of the first major allergenic protein of *Malassezia furfur*, Mal f 1. Eur J Biochem 246:181-185, 1997. Strain ATCC no. 42132 (American Type Culture Collection).

91A. Rasool O, Zargari A, Almqvist J, Eshaghi H, Whitley P, Scheynius A. Cloning, characterization and expression of complete coding sequences of three IgE binding *Malassezia furfur* allergens, Mal f 7, Mal f 8 and Mal f 9. Eur J Biochem 267: 4355-4361, 2000. Strain ATCC no. 42132 (American Type Culture Collection).

91B. Strain 4625 (Indian Agricultural Research Institute, PUSA; New Delhi, India).

92. Kuchler, K., M. Gmachl, M. J. Sippl, and G. Kreil. 1989. Analysis of the cDNA for phospholipase A2 from honey bee venom glands: The deduced amino acid sequence reveals homology to the corresponding vertebrate enzymes. Eur. J. Biochem. 184:249-254.

93. Gmachl, M., and G. Kreil. 1993. Bee venom hyaluronidase is homologous to a membrane protein of mammalian sperm. Proc. Natl. Acad. Sci. USA 90:3569-3573.

93A. Hoffman D R. 1977. Allergens in bee venom III. Identification of allergen B as an acid phosphatase. J Allergy Clin. Immunol. 59:364-366.

94. Habermann, E. 1972. Bee and wasp venoms. Science 177:314-322.

95. Hoffman D R, Jacobson R S. 1996. Allergens in *Hymenoptera* venom XXVII: Bumblebee venom allergy and allergens. J. Allergy Clin. Immunol. 97:812-821.

95A. Hoffman D R, El-Choufani A E, Smith M M, de Groot H. 2001. Occupational allergy to bumblebee venom: Allergens of *Bombus terrestris*. J Allergy Clin Immunol In press.

95B. Helm R, Cockrell G, Stanley J S, Brenner R J, Burks W, Bannon G A. 1996. Isolation and characterization of a clone encoding a majore allergen (Bla g Bd90K) involved in IgE mediated cockroach hypersensitivity. J Allerg Clin Immunol 98:172-180.

95C. Pomes A, Melen E, Vailes L D, Retief J D, Arruda L K, Chapman M D. 1998. Novel allergen structures with tandem amino acid repeats derived from German and American cockroach. J Biol Chem 273:30801-30807.

96. Arruda L K, Vailes L D, Mann B J, Shannon J, Fox J W, Vedvick T S, Hayden M L, Chapman M D. Molecular cloning of a major cockroach (*Blattella germanica*) allergen, Bla g 2. Sequence homology to the aspartic proteases. J Biol Chem 270:19563-19568, 1995.

97. Arruda L K, Vailes L D, Hayden M L, Benjamin D C, Chapman M D. Cloning of cockroach allergen, Bla g 4, identifies ligand binding proteins (or calycins) as a cause of IgE antibody responses. J Biol Chem 270:31196-31201, 1995.

98. Arruda L K, Vailes L D, Benjamin D C, Chapman M D. Molecular cloning of German Cockroach (*Blattella germanica*) allergens. Int Arch Allergy Immunol 107:295-297, 1995.

98A. Wu C H, Wang N M, Lee M F, Kao C Y Y, Luo S F. 1998. Cloning of the American cockroach Cr-PII allergens: Evidence for the existence of cross-reactive allergens between species. J Allergy Clin Immunol 101:832-840.

98B. Melen E, Pomés A, Vailes L D, Arruda L K, Chapman M D. 1999. Molecular cloning of Per a 1 and definition of the cross-reactive Group 1 cockroach allergens. J Allergy Clin Immunol 103:859-64.

98C. Wu C H, Lee M F, Liao S C, Luo S F. Sequencing analysis of cDNA clones encoding the American cockroach Cr-PI allergens. J Biol Chem 271:17937-17943, 1996.

98D. Wu C H, Lee M F, Wang N M, Luo S F. Sequencing and immunochemical characterization of the American cockroach Per a 3 (Cr-PI) isoallergenic variants. Molecular Immunol 34:1-8, 1997.

98E. Santos A B R, Chapman M D, Aalberse R C, Vailes L D, Ferriani V P L, Oliver C, Rizzo M C, Naspitz C K, Arruda L K. 1999. Cockroach allergens and asthma in Brazil: Identification of tropomyosin as a major allergen with potential cross-reactivity with mite and shrimp allergens. J Allergy Clin Immunol 104:329-337.

98F. Asturias J A, Gómez-Bayón N, Arilla M C, Martinez A, Palacios R, Sánchez-Gascón, Martinez J. 1999. Molecular characterization of American cockroach tropomyosin (*Periplaneta americana* allergen 7), a cross-reactive allergen. J Immunol 162:4342-4348.

99. Mazur, G., X. Baur, and V. Liebers. 1990. Hypersensitivity to hemoglobins of the Diptera family Chironomidae: Structural and functional studies of their immunogenic/allergenic sites. Monog. Allergy 28:121-137.

99A. Moneo I, Vega J M, Caballero M L, Vega J, Alday E. Isolation and characterization of Tha p 1, a major allergen from the pine processionary caterpillar *Thaumetopoea pityocampa*. Allergy 58: 34-37, 2003.

100. Soldatova, L., L. Kochoumian, and T. P. King. 1993. Sequence similarity of a hornet (*D. maculata*) venom allergen phospholipase A1 with mammalian lipases. FEBS Letters 320:145-149.

101. Lu, G., L. Kochoumian and T. P. King. Whiteface hornet venom allergen hyaluronidase: cloning and its sequence similarity with other proteins (abst.). 1994. J. Allergy Clin. Immunol. 93:224.

102. Fang, K. S. F., M. Vitale, P. Fehlner, and T. P. King. 1988. cDNA cloning and primary structure of a white-faced hornet venom allergen, antigen 5. Proc. Natl. Acad. Sci., USA 85:895-899.

103. King, T. P., D. C. Moran, D. F. Wang, L. Kochoumian, and B. T. Chait. 1990. Structural studies of a hornet venom allergen antigen 5, Dol m V and its sequence similarity with other proteins. Prot. Seq. Data Anal. 3:263-266.

104. Lu, G., M. Villalba, M. R. Coscia, D. R. Hoffman, and T. P. King. 1993. Sequence analysis and antigen cross reactivity of a venom allergen antigen 5 from hornets, wasps and yellowjackets. J. Immunol. 150: 2823-2830.

105. King, T. P. and Lu, G. 1997. Unpublished data.

105A. King T P, Lu G, Gonzalez M, Qian N and Soldatova L. 1996. Yellow jacket venom allergens, hyaluronidase and phospholipase: sequence similarity and antigenic cross-reactivity with their hornet and wasp homologs and possible implications for clinical allergy. J. Allergy Clin. Immunol. 98:588-600.

106. Hoffman, D. R. 1993. Allergens in hymenoptera venom XXV: The amino acid sequences of antigen 5 molecules and the structural basis of antigenic cross-reactivity. J. Allergy Clin. Immunol. 92:707-716.
107. Hoffman D R. 1992. Unpublished data.
108. Hoffman D R. The complete amino acid sequence of a yellowjacket venom phospholipase (abst). J. Allergy Clin. Immunol. 91:187, 1993.
109. Jacobson R S, Hoffman D R, Kemeny D M. The cross-reactivity between bee and vespid hyaluronidases has a structural basis (abst). J. Allergy Clin. Immunol. 89:292, 1992.
110. Hoffman D R. Allergens in *Hymenoptera* venom XXIV: The amino acid sequences of imported fire ant venom allergens Sol i II, Sol i III, and Sol i IV. J. Allergy Clin. Immunol 91: 71-78, 1993.
111. Schmidt M, Walker R B, Hoffman D R, McConnell T J. Nucleotide sequence of cDNA encoding the fire ant venom protein Sol i II. FEBS Letters 319: 138-140, 1993.
111A. Paddock C D, McKerrow J H, Hansell E, Foreman K W, Hsieh I, Marshall N. Identification, cloning, and recombinant expression of procalin, a major triatomine allergen. J Immunol 167: 2694-2699, 2001.
112. Elsayed S, Bennich H. The primary structure of Allergen M from cod. Scand J Immunol 3: 683-686, 1974.
113. Elsayed S, Aas K, Sletten K, Johansson S G O. Tryptic cleavage of a homogeneous cod fish allergen and isolation of two active polypeptide fragments. Immunochemistry 9: 647-661, 1972.
114. Hoffman, D. R. 1983 Immunochemical identification of the allergens in egg white. J. Allergy Clin. Immunol. 71: 481-486.
115. Langeland, T. 1983. A clinical and immunological study of allergy to hen's egg white. IV. specific IgE antibodies to individual allergens in hen's egg white related to clinical and immunological parameters in egg-allergic patients. Allergy 38:493-500.
116 Daul C B, Slattery M, Morgan J E, Lehrer S B. 1993. Common crustacea allergens: identification of B cell epitopes with the shrimp specific monoclonal antibodies. In: "Molecular Biology and Immunology of Allergens" (D. Kraft and A. Sehon, eds.). CRC Press, Boca Raton. pp. 291-293.
116A Shanti K N, Martin B M, Nagpal S, Metcalfe D D, Subba Rao P V. Identification of tropomyosin as the major shrimp allergen and characterization of its IgE-binding epitopes. J. Immunol. 151: 5354-5363, 1993.
117. Yu C J, Lin Y F, Chiang B L, Chow L P. Proteomics and Immunological Analysis of a Novel Shrimp Allergen, Pen m 2. J Immunol 170: 445-453, 2003.
117A Miyazawa M, Fukamachi H, Inagaki Y, Reese G, Daul C B, Lehrer S B, Inouye S, Sakaguchi M. Identification of the first major allergen of a squid (*Todarodes pacificus*). J. Allergy Clin. Immunol. 98: 948-953, 1996.
117B. Asturias J A, Eraso E, Arilla M C, Gomez-Bayon N, Inacio F, Martinez A. Cloning, isolation, and IgE-binding properties of *Helix aspersa* (brown garden snail) tropomyosin. Int Arch Allergy Immunol 128: 90-96, 2002.
117C. Lopata A L, Zinn C, Potter P C. Characteristics of hypersensitivity reactions and identification of a unique 49 kd IgE-binding protein (Hal-m-1) in abalone (*Haliotis midae*). J. Allergy Clin. Immunol. 100: 642-648, 1997.
117D. Hoffmann-Sommergruber K, O'Riordain G, Ahorn H, Ebner C, Laimer Da Camara Machado M, Pühringer H, Scheiner O, Breiteneder H. Molecular characterization of Dau c 1, the Bet v 1 homologous protein from carrot and its cross-reactivity with Bet v 1 and Api g 1. Clin. Exp. Allergy 29: 840-847, 1999.
118. Monsalve R I, Gonzalez de la Pena M A, Menendez-Arias L, Lopez-Otin C, Villalba M, Rodriguez R. Characterization of a new mustard allergen, Bra j I E. Detection of an allergenic epitope. Biochem. J. 293: 625-632 1993.
118A. Monsalve R I, Gonzalez de la Pena M A, Lopez-Otin C, Fiandor A, Fernandez C, Villalba M, Rodriguez R. 1997. Detection, isolation and complete amino acid sequence of an aeroallergenic protein from rapeseed flour. Clin Exp Allergy 27:833-841.
119. Mena, M., R. Sanchez-Monge, L. Gomez, G. Salcedo, and P. Carbonero. A major barley allergen associated with baker's asthma disease is a glycosylated monomeric inhibitor of insect alpha-amylase: cDNA cloning and chromosomal location of the gene. Plant Molec. Biol. 20: 451-458, 1992.
119A. Palosuo K, Varjonen E, Kekki O M, Klemola T, Kalkkinen N, Alenius H, Reunala T. Wheat omega-5 gliadin is a major allergen in children with immediate allergy to ingested wheat. J. Allergy Clin. Immunol. 108: 634-638, 2001.
119B. Xu H, Theerakulpisut P, Goulding N, Suphioglu C, Singh M. B. Bhalla P. L. Cloning expression and immunological characterization of Ory s 1, the major allergen of rice pollen. Gene 164: 255-259, 1995.
119C. Pastorello E A, Ortolani C, Farioli L, Pravettoni V, Ispano M, Borga A, Bengtsson A, Incorvaia C, Berti C, Zanussi C. Allergenic cross-reactivity among peach, apricot, plum, and cherry in patients with oral allergy syndrome: an in vivo and in vitro study. J. Allergy Clin. Immunol. 94: 699-707, 1994.
119D. Diaz-Perales A, Tabar A I, Sanchez-Monge R, Garcia B E, Gomez B, Barber D, Salcedo G. Characterization of asparagus allergens: a relevant role of lipid transfer proteins. J Allergy Clin Immun ol 110: 790-796, 2002.
120. Menendez-Arias, L., I. Moneo, J. Dominguez, and R. Rodriguez. 1988. Primary structure of the major allergen of yellow mustard (*Sinapis alba* L.) seed, Sin a I. Eur. J. Biochem. 177:159-166.
120A. Gonzalez R, Varela J, Carreira J, Polo F. Soybean hydrophobic protein and soybean hull allergy. Lancet 346: 48-49, 1995.
120B. Kleine-Tebbe J, Vogel L, Crowell D N, Haustein U F, Vieths S. Severe oral allergy syndrome and anaphylactic reactions caused by a Bet v 1-related PR-10 protein in soybean, SAM22. J Allergy Clin Immun ol 110: 797-804, 2002.
120C. Sanchez-Monge R, Pascual C Y, Diaz-Perales A, Fernandez-Crespo J, Martin-Esteban M, Salcedo G. Isolation and characterization of relevant allergens from boiled lentils. J. Allergy Clin. Immunol. 106: 955-961, 2000.
121. Gavrovic-Jankulovic M, cIrkovic T, Vuckovic O, Atanaskovic-Markovic M, Petersen A, Gojgic G, Burazer L, Jankov R M. Isolation and biochemical characterization of a thaumatin-like kiwi allergen. J Allergy Clin Immun ol 110: 805-810, 2002.
121A. Pastorello E A, Varin E, Farioli L, Pravettoni V, Ortolani C, Trambaioli C, Fortunato D, Giuffrida M G, Rivolta F, Robino A, Calamari A M, Lacava L, Conti A. The major allergen of sesame seeds (*Sesamum indicum*) is a 2S albumin. J. Chromatogr. B Biomed. Sci. Appl. 756: 85-93, 2001.

121B. Moneo I, Caballero M L, Gomez F, Ortega E, Alonso M J. Isolation and characterization of a major allergen from the fish parasite *Anisakis* simplex. J. Allergy Clin. Immunol. 106: 177-182, 2000.

121C. Asturias J A, Eraso E, Martinez A. 2000. Is tropomysoin an allergen in *Anisakis*? Allergy 55:898-890.

122. Christie, J. F., B. Dunbar, I. Davidson, and M. W. Kennedy. 1990. N-terminal amino acid sequence identity between a major allergen of *Ascaris lumbricoides* and *Ascaris suum* and MHC-restricted IgE responses to it. Immunology 69:596-602.

122A. Onizuka R, Kamiya H, Muramoto K, Goto R, Inoue K, Kumamoto K, Nakajima Y, Iida S, Ishigami F. Purification of major allergens from red soft coral (*Dendrophythya nipponica*). Int Arch Allergy Immunol, In press 2001.

123. Czuppon A B, Chen Z, Rennert S, Engelke T, Meyer H E, Heber M, Baur X. The rubber elongation factor of rubber trees (*Hevea brasiliensis*) is the major allergen in latex. J Allergy Clin Immunol 92:690-697, 1993.

124. Attanayaka D P S T G, Kekwick R G O, Franklin F C H. 1991. Molecular cloning and nucleotide sequencing of the rubber elongation factor gene from *hevea brasiliensis*. Plant Mol Biol 16:1079-1081.

125. Chye M L, Cheung K Y. 1995. J 1,3-glucanase is highly expressed in Laticifers of *Hevea brasiliensis*. Plant Mol Biol 26:397-402.

126. Alenius H, Palosuo T, Kelly K, Kurup V, Reunala T, Makinen-Kiljunen S, Turjanmaa K Fink J. 1993. IgE reactivity to 14-kD and 27-kD natural rubber proteins in Latex-allergic children with Spina bifida and other congenital anomalies. Int Arch Allergy Immunol 102:61-66.

127. Yeang H Y, Cheong K F, Sunderasan E, Hamzah S, Chew N P, Hamid S, Hamilton R G, Cardosa M J. 1996. The 14.6 kD (REF, Hev b 1) and 24 kD (Hev b 3) rubber particle proteins are recognized by IgE from Spina Bifida patients with Latex allergy. J Allerg Clin Immunol in press.

128. Sunderasan E, Hamzah S, Hamid S, Ward M A, Yeang H Y, Cardosa M J. 1995. Latex B-serum J-1,3-glucanase (Hev b 2) and a component of the microhelix (Hev b 4) are major Latex allergens. J nat Rubb Res 10:82-99.

---

What is claimed is:

1. A method of treating allergy in a subject susceptible to an allergic response to a protein allergen, the method comprising a step of:

administering to a subject, via the subject's rectum, a composition comprising:

dead *E. coli* that has expressed a protein allergen selected from the group consisting of:

*Ambrosia artemisiifolia* (short ragweed) antigen E (Amb a 1);

*Ambrosia artemisiifolia* (short ragweed) antigen K (Amb a 2);

*Ambrosia artemisiifolia* (short ragweed) Ra3 antigen (Amb a 3);

*Ambrosia artemisiifolia* (short ragweed) Ra5 antigen (Amb a 5);

*Ambrosia artemisiifolia* (short ragweed) Ra6 antigen (Amb a 6);

*Ambrosia artemisiifolia* (short ragweed) Ra7 antigen (Amb a 7);

*Ambrosia trifida* (giant ragweed) Ra5G antigen (Amb t 5);

*Artemisia vulgaris* (mugwort) antigen (Art v 1);

*Artemisia vulgaris* (mugwort) antigen (Art v 2);

*Helianthus annuus* (sunflower) antigen (Hel a 1);

*Helianthus annuus* (sunflower) profilin (Hel a 2);

*Mercurialis annua* (annual mercury) profilin (Mer a 1);

*Cynodon dactylon* (Bermuda grass) antigen (Cyn d 1);

*Cynodon dactylon* (Bermuda grass) antigen (Cyn d 7);

*Cynodon dactylon* (Bermuda grass) profilin (Cyn d 12);

*Dactylis glomerata* (orchard grass) AgDg1 antigen (Dac g 1);

*Dactylis glomerata* (orchard grass) antigen (Dac g 2);
*Dactylis glomerata* (orchard grass) antigen (Dac g 3);
*Dactylis glomerata* (orchard grass) antigen (Dac g 5);
*Holcus lanatus* (velvet grass) antigen (Hol l 1);
*Lolium perenne* (rye grass) group I antigen (Lol p 1);
*Lolium perenne* (rye grass) group II antigen (Lol p 2);
*Lolium perenne* (rye grass) group III antigen (Lol p 3);
*Lolium perenne* (rye grass) group IX antigen (Lol p 5);
*Lolium perenne* (rye grass) antigen (Lol p Ib);
*Lolium perenne* (rye grass) trypsin (Lol p 11);
*Phalaris aquatica* (canary grass) antigen (Pha a 1);
*Phleum pratense* (timothy grass) antigen (Phl p 1);
*Phleum pratense* (timothy grass) antigen (Phl p 2);
*Phleum pratense* (timothy grass) antigen (Phl p 4);
*Phleum pratense* (timothy grass) antigen Ag 25 (Phl p 5);
*Phleum pratense* (timothy grass) antigen (Phl p 6);
*Phleum pratense* (timothy grass) profilin (Phl p 12);
*Phleum pratense* (timothy grass) polygalacturonase (Phl p 13);
*Poa pratensis* (Kentucky blue grass) group I antigen (Poa p 1);
*Poa pratensis* (Kentucky blue grass) antigen (Poa p 5);
*Sorghum halepense* (Johnson grass) antigen (Sor h 1);
*Alnus glutinosa* (alder) antigen (Aln g 1);
*Betula verrucosa* (birch) antigen (Bet v 1);
*Betula verrucosa* (birch) profilin (Bet v 2);
*Betula verrucosa* (birch) antigen (Bet v 3);
*Betula verrucosa* (birch) antigen (Bet v 4);
*Betula verrucosa* (birch) isoflavone reductase homologue (Bet v 5);
*Betula verrucosa* (birch) cyclophilin (Bet v 7);
*Carpinus betulus* (hornbeam) antigen (Car b 1);
*Castanea sativa* (chestnut) Bet v 1 homologue (Cas s 1);
*Castanea sativa* (chestnut) chitinase (Cas s 5);
*Corylus avelana* (hazel) antigen (Cor a 1);
*Quercus alba* (white oak) antigen (Que a 1);
*Cryptomeria japonica* (sugi) antigen (Cry j 1);
*Cryptomeria japonica* (sugi) antigen (Cry j 2);
*Juniperus ashei* (mountain cedar) antigen (Jun a 1);
*Juniperus ashei* (mountain cedar) antigen (Jun a 3);
*Juniperus oxycedrus* (prickly juniper) calmodulin-like antigen (Jun o 2);
*Juniperus sabinoides* (mountain cedar) antigen (Jun s 1);
*Juniperus virginiana* (eastern red cedar) antigen (Jun v 1);
*Fraxinus excelsior* (ash) antigen (Fra e 1);
*Ligustrum vulgare* (privet) antigen (Lig v 1);
*Olea europea* (olive) antigen (Ole e 1);
*Olea europea* (olive) profilin (Ole e 2);
*Olea europea* (olive) antigen (Ole e 3);
*Olea europea* (olive) antigen (Ole e 4);
*Olea europea* (olive) superoxide dismutase (Ole e 5);
*Olea europea* (olive) antigen (Ole e 6);
*Syringa vulgaris* (lilac) antigen (Syr v 1);
*Acarus siro* (mite) fatty acid-binding protein (Aca s 13);
*Blomia tropicalis* (mite) antigen (Blo t 5);
*Blomia tropicalis* (mite) Bt11a antigen (Blo t 12);
*Blomia tropicalis* (mite) Bt6 fatty acid-binding protein (Blo t);
*Dermatophagoides pteronyssinus* (mite) antigen P1 (Der p 1);
*Dermatophagoides pteronyssinus* (mite) antigen (Der p 2);
*Dermatophagoides pteronyssinus* (mite) trypsin (Der p 3);
*Dermatophagoides pteronyssinus* (mite) amylase (Der p 4);
*Dermatophagoides pteronyssinus* (mite) antigen (Der p 5);
*Dermatophagoides pteronyssinus* (mite) chymotrypsin (Der p 6);
*Dermatophagoides pteronyssinus* (mite) antigen (Der p 7);
*Dermatophagoides pteronyssinus* (mite) glutathione transferase (Der p 8);
*Dermatophagoides pteronyssinus* (mite) collagenolytic serine prot (Der p 9);
*Dermatophagoides pteronyssinus* (mite) tropomyosin (Der p 10);
*Dermatophagoides pteronyssinus* (mite) apolipophorin like p (Der p 14);
*Dermatophagoides microceras* (mite) antigen (Der m 1);
*Dermatophagoides farinae* (mite) antigen (Der f 1);
*Dermatophagoides farinae* (mite) antigen (Der f 2);
*Dermatophagoides farinae* (mite) antigen (Der f 3);
*Dermatophagoides farinae* (mite) tropomyosin (Der f 10);
*Dermatophagoides farinae* (mite) paramyosin (Der f 11);
*Dermatophagoides farinae* (mite) Mag 3, apolipophorin (Der f 14);
*Euroglyphus maynei* (mite) apolipophorin (Eur m 14);
*Lepidoglyphus destructor* (storage mite) antigen (Lep d 2.0101);
*Lepidoglyphus destructor* (storage mite) antigen (Lep d 2.0102);
*Bos domesticus* (cow) Ag3, lipocalin (Bos d 2);
*Bos domesticus* (cow) alpha-lactalbumin (Bos d 4);
*Bos domesticus* (cow) beta-lactalbumin (Bos d 5);
*Bos domesticus* (cow) serum albumin (Bos d 6);
*Bos domesticus* (cow) immunoglobulin (Bos d 7);
*Bos domesticus* (cow) casein (Bos d 8);
*Canis familiaris* (dog) antigen (Can f 1);
*Canis familiaris* (dog) antigen (Can f 2);
*Canis familiaris* (dog) albumin (Can f ?);
*Equus caballus* (horse) lipocalin (Equ c 1);
*Equus caballus* (horse) lipocalin (Equ c 2);
*Felis domesticus* (cat) cat-1 antigen (Fel d 1);
*Mus musculus* (mouse) MUP antigen (Mus m 1);
*Rattus norvegius* (rat) antigen (Rat n 1);
*Alternaria alternata* (fungus) antigen (Alt a 1);
*Alternaria alternata* (fungus) antigen (Alt a 2);
*Alternaria alternata* (fungus) heat shock protein (Alt a 3);
*Alternaria alternata* (fungus) ribosomal protein (Alt a 6);
*Alternaria alternata* (fungus) YCP4 protein (Alt a 7);
*Alternaria alternata* (fungus) aldehyde dehydrogenase (Alt a 10);
*Alternaria alternata* (fungus) enloase (Alt a 11);
*Alternaria alternata* (fungus) acid ribosomal protein P1 (Alt a 12);
*Cladosporium herbarum* (fungus) antigen (Cla h 1);
*Cladosporium herbarum* (fungus) antigen (Cla h 2);
*Cladosporium herbarum* (fungus) aldehyde dehydrogenase (Cla h 3);
*Cladosporium herbarum* (fungus) ribosomal protein);
*Cladosporium herbarum* (fungus) YCP4 protein (Cla h 5);
*Cladosporium herbarum* (fungus) enolase (Cla h 6);
*Cladosporium herbarum* (fungus) acid ribosomal protein P1 (Cla h 12);
*Aspergillus flavus* (fungus) alkaline serine proteinase (Asp fl 13);
*Aspergillus Fumigatus* (fungus) antigen (Asp f 1);
*Aspergillus Fumigatus* (fungus) antigen (Asp f 2);
*Aspergillus Fumigatus* (fungus) peroxisomal protein (Asp f 3);
*Aspergillus Fumigatus* (fungus) antigen (Asp f 4);
*Aspergillus Fumigatus* (fungus) metalloprotease (Asp f 5);
*Aspergillus Fumigatus* (fungus) Mn superoxide dismutase (Asp f 6);
*Aspergillus Fumigatus* (fungus) antigen (Asp f 7);

*Aspergillus Fumigatus* (fungus) ribosomal protein P2 (Asp f 8);
*Aspergillus Fumigatus* (fungus) antigen (Asp f 9);
*Aspergillus Fumigatus* (fungus) aspartis protease (Asp f 10);
*Aspergillus Fumigatus* (fungus) peptidyl-prolyl isomerase (Asp f 11);
*Aspergillus Fumigatus* (fungus) heat shock protein P70 (Asp f 12);
*Aspergillus Fumigatus* (fungus) alkaline serine proteinase (Asp f 13);
*Aspergillus Fumigatus* (fungus) antigen (Asp f 15);
*Aspergillus Fumigatus* (fungus) antigen (Asp f 16);
*Aspergillus Fumigatus* (fungus) antigen (Asp f 17);
*Aspergillus Fumigatus* (fungus) vacuolar serine (Asp f 18);
*Aspergillus niger* (fungus) beta-xylosidase (Asp n 14);
*Aspergillus niger* (fungus) antigen (Asp n 18);
*Aspergillus niger* (fungus) vacuolar serine proteinase;
*Aspergillus oryzae* (fungus) TAKA-amylase A (Asp o 2);
*Aspergillus oryzae* (fungus) alkaline serine proteinase (Asp o 13);
*Penicillium brevicompactum* (fungus) alkaline serine proteinase (Pen b 13);
*Penicillium citrinum* (fungus) heat shock protein P70 (Pen c 1);
*Penicillium citrinum* (fungus) peroxisomal membrane protein (Pen c 3);
*Penicillium citrinum* (fungus) alkaline serine proteinase (Pen c 13);
*Penicillium notatum* (fungus) N-acetyl glucosaminidase (Pen n 1);
*Penicillium notatum* (fungus) alkaline serine proteinase (Pen n 13);
*Penicillium notatum* (fungus) vacuolar serine proteinase (Pen n 18);
*Penicillium oxalicum* (fungus) vacuolar serine proteinase (Pen o 18);
*Trichophyton rubrum* (fungus) antigen (Tri r 2);
*Trichophyton rubrum* (fungus) serine protease (Tri r 4);
*Trichophyton tonsurans* (fungus) antigen (Tri t 1);
*Trichophyton tonsurans* (fungus) serine protease (Tri t 4);
*Candida albicans* (fungus) antigen (Cand a 1);
*Candida boidinii* (fungus) antigen (Cand b 2);
*Malassezia furfur* (fungus) antigen (Mal f 1);
*Malassezia furfur* (fungus) MF1 peroxisomal membrane protein (Mal f 2);
*Malassezia furfur* (fungus) MF2 peroxisomal membrane protein (Mal f 3);
*Malassezia furfur* (fungus) antigen (Mal f 4);
*Malassezia furfur* (fungus) antigen (Mal f 5);
*Malassezia furfur* (fungus) cyclophilin homologue (Mal f 6);
*Psilocybe cubensis* (fungus) antigen (Psi c 1);
*Psilocybe cubensis* (fungus) cyclophilin (Psi c 2);
*Coprinus comatus* (shaggy cap) antigen (Cop c 1);
*Coprinus comatus* (shaggy cap) antigen (Cop c 2);
*Coprinus comatus* (shaggy cap) antigen (Cop c 3);
*Coprinus comatus* (shaggy cap) antigen (Cop c 5);
*Coprinus comatus* (shaggy cap) antigen (Cop c 7);
*Aedes aegyptii* (mosquito) apyrase (Aed a 1);
*Aedes aegyptii* (mosquito) antigen (Aed a 2);
*Apis mellifera* (honey bee) phospholipase A2 (Api m 1);
*Apis mellifera* (honey bee) hyaluronidase (Api m 2);
*Apis mellifera* (honey bee) melittin (Api m 4);
*Apis mellifera* (honey bee) antigen (Api m 6);
*Bombus pennsylvanicus* (bumble bee) phospholipase (Bom p 1);
*Bombus pennsylvanicus* (bumble bee) protease (Bom p 4);
*Blattella germanica* (German cockroach) Bd90k (Bla g 1);
*Blattella germanica* (German cockroach) aspartic protease (Bla g 2);
*Blattella germanica* (German cockroach) calycin (Bla g 4);
*Blattella germanica* (German cockroach) glutathione transferase (Bla g 5);
*Blattella germanica* (German cockroach) troponin C (Bla g 6);
*Periplaneta americana* (American cockroach) Cr-PII (Per a 1);
*Periplaneta americana* (American cockroach) Cr-PI (Per a 3);
*Periplaneta americana* (American cockroach) tropomyosin (Per a 7);
*Chironomus thummi thummi* (midge) hemoglobin (Chi t 1-9);
*Chironomus thummi thummi* (midge) component III (Chi t 1.01);
*Chironomus thummi thummi* (midge) component IV (Chi t 1.02);
*Chironomus thummi thummi* (midge) component I (Chi t 2.0101);
*Chironomus thummi thummi* (midge) component IA (Chi t 2.0102);
*Chironomus thummi thummi* (midge) component II-beta (Chi t 3);
*Chironomus thummi thummi* (midge) component IIIA (Chi t 4);
*Chironomus thummi thummi* (midge) component VI (Chi t 5);
*Chironomus thummi thummi* (midge) component VIIA (Chi t 6.01);
*Chironomus thummi thummi* (midge) component IX (Chi t 6.02);
*Chironomus thummi thummi* (midge) component VIIB (Chi t 7);
*Chironomus thummi thummi* (midge) component VIII (Chi t 8);
*Chironomus thummi thummi* (midge) component X (Chi t 9);
*Dolichovespula maculata* (white face hornet) phospholipase (Dol m 1);
*Dolichovespula maculata* (white face hornet) hyaluronidase (Dol m 2);
*Dolichovespula maculata* (white face hornet) antigen 5 (Dol m 5);
*Dolichovespula arenaria* (yellow hornet) antigen 5 (Dol a 5);
*Polistes annularies* (wasp) phospholipase A1 (Pol a 1);
*Polistes annularies* (wasp) hyaluronidase (Pol a 2);
*Polistes annularies* (wasp) antigen 5 (Pol a 5);
*Polistes dominulus* (Mediterranean paper wasp) antigen (Pol d 1);
*Polistes dominulus* (Mediterranean paper wasp) serine protease (Pol d 4);
*Polistes dominulus* (Mediterranean paper wasp) antigen (Pol d 5);
*Polistes exclamans* (wasp) phospholipase A1 (Pol e 1);
*Polistes exclamans* (wasp) antigen 5 (Pol e 5);
*Polistes fuscatus* (wasp) antigen 5 (Pol f 5);
*Polistes metricus* (wasp) antigen 5 (Pol m 5);
*Vespa crabo* (European hornet) phospholipase (Vesp c 1);
*Vespa crabo* (European hornet) antigen 5 (Vesp c 5.0101);
*Vespa crabo* (European hornet) antigen 5 (Vesp c 5.0102);
*Vespa mandarina* (giant Asian hornet) antigen (Vesp m 1.01);

*Vespa mandarina* (giant Asian hornet) antigen (Vesp m 1.02);
*Vespa mandarina* (giant Asian hornet) antigen (Vesp m 5);
*Vespula flavopilosa* (yellowjacket) antigen 5 (Ves f 5);
*Vespula germanica* (yellowjacket) antigen 5 (Ves g 5);
*Vespula maculifrons* (yellowjacket) phospholipase A1 (Ves m 1);
*Vespula maculifrons* (yellowjacket) hyaluronidase (Ves m 2);
*Vespula maculifrons* (yellowjacket) antigen 5 (Ves m 5);
*Vespula pennsylvanica* (yellowjacket) (antigen 5Ves p 5);
*Vespula squamosa* (yellowjacket) antigen 5 (Ves s 5);
*Vespula vidua* (wasp) antigen (Ves vi 5);
*Vespula vulgaris* (yellowjacket) phospholipase A1 (Ves v 1);
*Vespula vulgaris* (yellowjacket) hyaluronidase (Ves v 2);
*Vespula vulgaris* (yellowjacket) antigen 5 (Ves v 5);
*Myrmecia pilosula* (Australian jumper ant) antigen (Myr p 1);
*Myrmecia pilosula* (Australian jumper ant) antigen (Myr p 2);
*Solenopsis geminata* (tropical fire ant) antigen (Sol g 2);
*Solenopsis geminata* (tropical fire ant) antigen (Sol g 4);
*Solenopsis invicta* (fire ant) antigen (Sol i 2);
*Solenopsis invicta* (fire ant) antigen (Sol i 3);
*Solenopsis invicta* (fire ant) antigen (Sol i 4);
*Solenopsis saevissima* (Brazilian fire ant) antigen (Sol s 2);
*Gadus callarias* (cod) allergen M (Gad c 1);
*Salmo salar* (Atlantic salmon) parvalbumin (Sal s 1);
*Gallus domesticus* (chicken) ovomucoid (Gal d 1);
*Gallus domesticus* (chicken) ovalbumin (Gal d 2);
*Gallus domesticus* (chicken) conalbumin; A22 (Gal d 3);
*Gallus domesticus* (chicken) lysozyme (Gal d 4);
*Gallus domesticus* (chicken) serum albumin (Gal d 5);
*Metapenaeus ensis* (shrimp) tropomyosin (Met e 1);
*Penaeus aztecus* (shrimp) tropomyosin (Pen a 1);
*Penaeus indicus* (shrimp) tropomyosin (Pen i 1);
*Todarodes pacificus* (squid) tropomyosin (Tod p 1);
*Haliotis Midae* (abalone) antigen (Hal m 1);
*Apium graveolens* (celery) Bet v 1 homologue (Api g 1);
*Apium graveolens* (celery) profilin (Api g 4);
*Apium graveolens* (celery) antigen (Api g 5);
*Brassica juncea* (oriental mustard) 2S albumin (Bra j 1);
*Brassica rapa* (turnip) prohevein-like protein (Bar r 2);
*Hordeum vulgare* (barley) BMAI-1 (Hor v 1);
*Zea mays* (maize, corn) lipid transfer protein (Zea m 14);
*Corylus avellana* (hazelnut) Bet v 1 homologue (Cor a 1.0401);
*Malus domestica* (apple) Bet v 1 homologue (Mal d 1);
*Malus domestica* (apple) lipid transfer protein (Mal d 3);
*Pyrus communis* (pear) Bet v 1 homologue (Pyr c 1);
*Pyrus communis* (pear) profilin (Pyr c 4);
*Pyrus communis* (pear) isoflavone reductase homologue (Pyr c 5);
*Oryza sativa* (rice) antigen (Ory s 1);
*Persea americana* (avocado) endochitinase (Pers a 1);
*Prunus armeniaca* (apricot) Bet v 1 homologue (Pru ar 1);
*Prunus armeniaca* (apricot) lipid transfer protein (Pru ar 3);
*Prunus avium* (sweet cherry) Bet v 1 homologue (Pru av 1);
*Prunus avium* (sweet cherry) thaumatin homologue (Pru av 2);
*Prunus avium* (sweet cherry) profilin (Pru av 4);
*Prunus persica* (peach) lipid transfer protein (Pru p 3);
*Sinapis alba* (yellow mustard) 2S albumin (Sin a 1);
*Glycine max* (soybean) HPS (Gly m 1.0101);
*Glycine max* (soybean) HPS (Gly m 1.0102);
*Glycine max* (soybean) antigen (Gly m 2);
*Glycine max* (soybean) profilin (Gly m 3);
*Arachis hypogaea* (peanut) vicilin (Ar a h 1);
*Arachis hypogaea* (peanut) (conglutin Ar a h 2);
*Arachis hypogaea* (peanut) glycinin (Ar a h 3);
*Arachis hypogaea* (peanut) glycinin (Ar a h 4);
*Arachis hypogaea* (peanut) (profilin Ar a h 5);
*Arachis hypogaea* (peanut) conglutin homologue (Ar a h 6);
*Arachis hypogaea* (peanut) conglutin homologue (Ar a h 7);
*Actinidia chinensis* (kiwi) cysteine protease (Act c 1);
*Solanum tuberosum* (potato) patatin (Sol t 1);
*Bertholletia excelsa* (Brazil nut) 2S albumin (Ber e 1);
*Juglans regia* (English walnut) 2S albumin (Jug r 1);
*Juglans regia* (English walnut) vicilin (Jug r 2);
*Ricinus communis* (castor bean) 2S albumin (Ric c 1);
*Anisakis simplex* (nematode) antigen (Ani s 1);
*Anisakis simplex* (nematode) paramyosin (Ani s 2);
*Ascaris suum* (worm) antigen (Asc s 1);
*Aedes aegyptii* (mosquito) apyrase (Aed a 1);
*Aedes aegyptii* (mosquito) antigen (Aed a 2);
*Hevea brasiliensis* (rubber) elongation factor (Hev b 1);
*Hevea brasiliensis* (rubber) 1,3-glucanase (Hev b 2);
*Hevea brasiliensis* (rubber) antigen (Hev b 3);
*Hevea brasiliensis* (rubber) component of microhelix protein complex (Hev b 4);
*Hevea brasiliensis* (rubber) antigen (Hev b 5);
*Hevea brasiliensis* (rubber) hevein precursor (Hev b 6.01);
*Hevea brasiliensis* (rubber) hevein (Hev b 6.02);
*Hevea brasiliensis* (rubber) C-terminal fragment antigen (Hev b 6.03);
*Hevea brasiliensis* (rubber) patatin homologue (Hev b 7);
*Hevea brasiliensis* (rubber) profilin (Hev b 8);
*Hevea brasiliensis* (rubber) enolase (Hev b 9);
*Hevea brasiliensis* (rubber) Mn-superoxide dismut (Hev b 10);
*Ctenocephalides felis felis* (cat flea) antigen (Cte f 1);
*Homo sapiens* (human autoallergen) antigen (Hom s 1);
*Homo sapiens* (human autoallergen) antigen (Hom s 2);
*Homo sapiens* (human autoallergen) antigen (Hom s 3);
*Homo sapiens* (human autoallergen) antigen (Hom s 4); and
*Homo sapiens* (human autoallergen) antigen (Hom s 5),
the expressed protein allergen being encapsulated within the dead *E. coli*, so that the expressed protein allergen is not exposed to the subject's IgE antibodies during administration; and
a pharmaceutically acceptable carrier,
so that one or more symptoms of the subject's allergy to the protein allergen is reduced or decreased.

2. A method of treating allergy in a subject susceptible to an allergic response to a protein allergen, the method comprising a step of:
administering to a subject, via the subject's rectum, a composition comprising:
dead *E. coli* that has expressed a protein allergen selected from the group consisting of:
*Ambrosia artemisiifolia* (short ragweed) antigen E (Amb a 1);
*Ambrosia artemisiifolia* (short ragweed) antigen K (Amb a 2);
*Ambrosia artemisiifolia* (short ragweed) Ra3 antigen (Amb a 3);
*Ambrosia artemisiifolia* (short ragweed) Ra5 antigen (Amb a 5);

*Ambrosia artemisiifolia* (short ragweed) Ra6 antigen (Amb a 6);
*Ambrosia artemisiifolia* (short ragweed) Ra7 antigen (Amb a 7);
*Ambrosia trifida* (giant ragweed) Ra5G antigen (Amb t 5);
*Artemisia vulgaris* (mugwort) antigen (Art v 1);
*Artemisia vulgaris* (mugwort) antigen (Art v 2);
*Helianthus annuus* (sunflower) antigen (Hel a 1);
*Helianthus annuus* (sunflower) profilin (Hel a 2);
*Mercurialis annua* (annual mercury) profilin (Mer a 1);
*Cynodon dactylon* (Bermuda grass) antigen (Cyn d 1);
*Cynodon dactylon* (Bermuda grass) antigen (Cyn d 7);
*Cynodon dactylon* (Bermuda grass) profilin (Cyn d 12);
*Dactylis glomerata* (orchard grass) AgDg1 antigen (Dac g 1);
*Dactylis glomerata* (orchard grass) antigen (Dac g 2);
*Dactylis glomerata* (orchard grass) antigen (Dac g 3);
*Dactylis glomerata* (orchard grass) antigen (Dac g 5);
*Holcus lanatus* (velvet grass) antigen (Hol l 1);
*Lolium perenne* (rye grass) group I antigen (Lol p 1);
*Lolium perenne* (rye grass) group II antigen (Lol p 2);
*Lolium perenne* (rye grass) group III antigen (Lol p 3);
*Lolium perenne* (rye grass) group IX antigen (Lol p 5);
*Lolium perenne* (rye grass) antigen (Lol p Ib);
*Lolium perenne* (rye grass) trypsin (Lol p 11);
*Phalaris aquatica* (canary grass) antigen (Pha a 1);
*Phleum pratense* (timothy grass) antigen (Phl p 1);
*Phleum pratense* (timothy grass) antigen (Phl p 2);
*Phleum pratense* (timothy grass) antigen (Phl p 4);
*Phleum pratense* (timothy grass) antigen Ag 25 (Phl p 5);
*Phleum pratense* (timothy grass) antigen (Phl p 6);
*Phleum pratense* (timothy grass) profilin (Phl p 12);
*Phleum pratense* (timothy grass) polygalacturonase (Phl p 13);
*Poa pratensis* (Kentucky blue grass) group I antigen (Poa p 1);
*Poa pratensis* (Kentucky blue grass) antigen (Poa p 5);
*Sorghum halepense* (Johnson grass) antigen (Sor h 1);
*Alnus glutinosa* (alder) antigen (Aln g 1);
*Betula verrucosa* (birch) antigen (Bet v 1);
*Betula verrucosa* (birch) profilin (Bet v 2);
*Betula verrucosa* (birch) antigen (Bet v 3);
*Betula verrucosa* (birch) antigen (Bet v 4);
*Betula verrucosa* (birch) isoflavone reductase homologue (Bet v 5);
*Betula verrucosa* (birch) cyclophilin (Bet v 7);
*Carpinus betulus* (hornbeam) antigen (Car b 1);
*Castanea sativa* (chestnut) Bet v 1 homologue (Cas s 1);
*Castanea sativa* (chestnut) chitinase (Cas s 5);
*Corylus avelana* (hazel) antigen (Cor a 1);
*Quercus alba* (white oak) antigen (Que a 1);
*Cryptomeria japonica* (sugi) antigen (Cry j 1);
*Cryptomeria japonica* (sugi) antigen (Cry j 2);
*Juniperus ashei* (mountain cedar) antigen (Jun a 1);
*Juniperus ashei* (mountain cedar) antigen (Jun a 3);
*Juniperus oxycedrus* (prickly juniper) calmodulin-like antigen (Jun o 2);
*Juniperus sabinoides* (mountain cedar) antigen (Jun s 1);
*Juniperus virginiana* (eastern red cedar) antigen (Jun v 1);
*Fraxinus excelsior* (ash) antigen (Fra e 1);
*Ligustrum vulgare* (privet) antigen (Lig v 1);
*Olea europea* (olive) antigen (Ole e 1);
*Olea europea* (olive) profilin (Ole e 2);
*Olea europea* (olive) antigen (Ole e 3);
*Olea europea* (olive) antigen (Ole e 4);
*Olea europea* (olive) superoxide dismutase (Ole e 5);
*Olea europea* (olive) antigen (Ole e 6);
*Syringa vulgaris* (lilac) antigen (Syr v 1);
*Acarus siro* (mite) fatty acid-binding protein (Aca s 13);
*Blomia tropicalis* (mite) antigen (Blo t 5);
*Blomia tropicalis* (mite) Bt11a antigen (Blo t 12);
*Blomia tropicalis* (mite) Bt6 fatty acid-binding protein (Blo t);
*Dermatophagoides pteronyssinus* (mite) antigen P1 (Der p 1);
*Dermatophagoides pteronyssinus* (mite) antigen (Der p 2);
*Dermatophagoides pteronyssinus* (mite) trypsin (Der p 3);
*Dermatophagoides pteronyssinus* (mite) amylase (Der p 4);
*Dermatophagoides pteronyssinus* (mite) antigen (Der p 5);
*Dermatophagoides pteronyssinus* (mite) chymotrypsin (Der p 6);
*Dermatophagoides pteronyssinus* (mite) antigen (Der p 7);
*Dermatophagoides pteronyssinus* (mite) glutathione transferase (Der p 8);
*Dermatophagoides pteronyssinus* (mite) collagenolytic serine prot. (Der p 9);
*Dermatophagoides pteronyssinus* (mite) tropomyosin (Der p 10);
*Dermatophagoides pteronyssinus* (mite) apolipophorin like p (Der p 14);
*Dermatophagoides microceras* (mite) antigen (Der m 1);
*Dermatophagoides farinae* (mite) antigen (Der f 1);
*Dermatophagoides farinae* (mite) antigen (Der f 2);
*Dermatophagoides farinae* (mite) antigen (Der f 3);
*Dermatophagoides farinae* (mite) tropomyosin (Der f 10);
*Dermatophagoides farinae* (mite) paramyosin (Der f 11);
*Dermatophagoides farinae* (mite) Mag 3, apolipophorin (Der f 14);
*Euroglyphus maynei* (mite) apolipophorin (Eur m 14);
*Lepidoglyphus destructor* (storage mite) antigen (Lep d 2.0101);
*Lepidoglyphus destructor* (storage mite) antigen (Lep d 2.0102);
*Bos domesticus* (cow) Ag3, lipocalin (Bos d 2);
*Bos domesticus* (cow) alpha-lactalbumin (Bos d 4);
*Bos domesticus* (cow) beta-lactalbumin (Bos d 5);
*Bos domesticus* (cow) serum albumin (Bos d 6);
*Bos domesticus* (cow) immunoglobulin (Bos d 7);
*Bos domesticus* (cow) casein (Bos d 8);
*Canis familiaris* (dog) antigen (Can f 1);
*Canis familiaris* (dog) antigen (Can f 2);
*Canis familiaris* (dog) albumin (Can f ?);
*Equus caballus* (horse) lipocalin (Equ c 1);
*Equus caballus* (horse) lipocalin (Equ c 2);
*Felis domesticus* (cat) cat-1 antigen (Fel d 1);
*Mus musculus* (mouse) MUP antigen (Mus m 1);
*Rattus norvegius* (rat) antigen (Rat n 1);
*Alternaria alternata* (fungus) antigen (Alt a 1);
*Alternaria alternata* (fungus) antigen (Alt a 2);
*Alternaria alternata* (fungus) heat shock protein (Alt a 3);
*Alternaria alternata* (fungus) ribosomal protein (Alt a 6);
*Alternaria alternata* (fungus) YCP4 protein (Alt a 7);
*Alternaria alternata* (fungus) aldehyde dehydrogenase (Alt a 10);
*Alternaria alternata* (fungus) enloase (Alt a 11);
*Alternaria alternata* (fungus) acid ribosomal protein P1 (Alt a 12);
*Cladosporium herbarum* (fungus) antigen (Cla h 1);
*Cladosporium herbarum* (fungus) antigen (Cla h 2);
*Cladosporium herbarum* (fungus) aldehyde dehydrogenase (Cla h 3);
*Cladosporium herbarum* (fungus) ribosomal protein);
*Cladosporium herbarum* (fungus) YCP4 protein (Cla h 5);

*Cladosporium herbarum* (fungus) enolase (Cla h 6);
*Cladosporium herbarum* (fungus) acid ribosomal protein P1 (Cla h 12);
*Aspergillus flavus* (fungus) alkaline serine proteinase (Asp fl 13);
*Aspergillus Fumigatus* (fungus) antigen (Asp f 1);
*Aspergillus Fumigatus* (fungus) antigen (Asp f 2);
*Aspergillus Fumigatus* (fungus) peroxisomal protein (Asp f 3);
*Aspergillus Fumigatus* (fungus) antigen (Asp f 4);
*Aspergillus Fumigatus* (fungus) metalloprotease (Asp f 5);
*Aspergillus Fumigatus* (fungus) Mn superoxide dismutase (Asp f 6);
*Aspergillus Fumigatus* (fungus) antigen (Asp f 7);
*Aspergillus Fumigatus* (fungus) ribosomal protein P2 (Asp f 8);
*Aspergillus Fumigatus* (fungus) antigen (Asp f 9);
*Aspergillus Fumigatus* (fungus) aspartis protease (Asp f 10);
*Aspergillus Fumigatus* (fungus) peptidyl-prolyl isomerase (Asp f 11);
*Aspergillus Fumigatus* (fungus) heat shock protein P70 (Asp f 12);
*Aspergillus Fumigatus* (fungus) alkaline serine proteinase (Asp f 13);
*Aspergillus Fumigatus* (fungus) antigen (Asp f 15);
*Aspergillus Fumigatus* (fungus) antigen (Asp f 16);
*Aspergillus Fumigatus* (fungus) antigen (Asp f 17);
*Aspergillus Fumigatus* (fungus) vacuolar serine (Asp f 18);
*Aspergillus niger* (fungus) beta-xylosidase (Asp n 14);
*Aspergillus niger* (fungus) antigen (Asp n 18);
*Aspergillus niger* (fungus) vacuolar serine proteinase;
*Aspergillus oryzae* (fungus) TAKA-amylase A (Asp o 2);
*Aspergillus oryzae* (fungus) alkaline serine proteinase (Asp o 13);
*Penicillium brevicompactum* (fungus) alkaline serine proteinase (Pen b 13);
*Penicillium citrinum* (fungus) heat shock protein P70 (Pen c 1);
*Penicillium citrinum* (fungus) peroxisomal membrane protein (Pen c 3);
*Penicillium citrinum* (fungus) alkaline serine proteinase (Pen c 13);
*Penicillium notatum* (fungus) N-acetyl glucosaminidase (Pen n 1);
*Penicillium notatum* (fungus) alkaline serine proteinase (Pen n 13);
*Penicillium notatum* (fungus) vacuolar serine proteinase (Pen n 18);
*Penicillium oxalicum* (fungus) vacuolar serine proteinase (Pen o 18);
*Trichophyton rubrum* (fungus) antigen (Tri r 2);
*Trichophyton rubrum* (fungus) serine protease (Tri r 4);
*Trichophyton tonsurans* (fungus) antigen (Tri t 1);
*Trichophyton tonsurans* (fungus) serine protease (Tri t 4);
*Candida albicans* (fungus) antigen (Cand a 1);
*Candida boidinii* (fungus) antigen (Cand b 2);
*Malassezia furfur* (fungus) antigen (Mal f 1);
*Malassezia furfur* (fungus) MF1 peroxisomal membrane protein (Mal f 2);
*Malassezia furfur* (fungus) MF2 peroxisomal membrane protein (Mal f 3);
*Malassezia furfur* (fungus) antigen (Mal f 4);
*Malassezia furfur* (fungus) antigen (Mal f 5);
*Malassezia furfur* (fungus) cyclophilin homologue (Mal f 6);
*Psilocybe cubensis* (fungus) antigen (Psi c 1);
*Psilocybe cubensis* (fungus) cyclophilin (Psi c 2);
*Coprinus comatus* (shaggy cap) antigen (Cop c 1);
*Coprinus comatus* (shaggy cap) antigen (Cop c 2);
*Coprinus comatus* (shaggy cap) antigen (Cop c 3);
*Coprinus comatus* (shaggy cap) antigen (Cop c 5);
*Coprinus comatus* (shaggy cap) antigen (Cop c 7);
*Aedes aegyptii* (mosquito) apyrase (Aed a 1);
*Aedes aegyptii* (mosquito) antigen (Aed a 2);
*Apis mellifera* (honey bee) phospholipase A2 (Api m 1);
*Apis mellifera* (honey bee) hyaluronidase (Api m 2);
*Apis mellifera* (honey bee) melittin (Api m 4);
*Apis mellifera* (honey bee) antigen (Api m 6);
*Bombus pennsylvanicus* (bumble bee) phospholipase (Bom p 1);
*Bombus pennsylvanicus* (bumble bee) protease (Bom p 4);
*Blattella germanica* (German cockroach) Bd90k (Bla g 1);
*Blattella germanica* (German cockroach) aspartic protease (Bla g 2);
*Blattella germanica* (German cockroach) calycin (Bla g 4);
*Blattella germanica* (German cockroach) glutathione transferase (Bla g 5);
*Blattella germanica* (German cockroach) troponin C (Bla g 6);
*Periplaneta americana* (American cockroach) Cr-PII (Per a 1);
*Periplaneta americana* (American cockroach) Cr-PI (Per a 3);
*Periplaneta americana* (American cockroach) tropomyosin (Per a 7);
*Chironomus thummi thummi* (midge) hemoglobin (Chi t 1-9);
*Chironomus thummi thummi* (midge) component III (Chi t 1.01);
*Chironomus thummi thummi* (midge) component IV (Chi t 1.02);
*Chironomus thummi thummi* (midge) component I (Chi t 2.0101);
*Chironomus thummi thummi* (midge) component IA (Chi t 2.0102);
*Chironomus thummi thummi* (midge) component II-beta (Chi t 3);
*Chironomus thummi thummi* (midge) component IIIA (Chi t 4);
*Chironomus thummi thummi* (midge) component VI (Chi t 5);
*Chironomus thummi thummi* (midge) component VIIA (Chi t 6.01);
*Chironomus thummi thummi* (midge) component IX (Chi t 6.02);
*Chironomus thummi thummi* (midge) component VIIB (Chi t 7);
*Chironomus thummi thummi* (midge) component VIII (Chi t 8);
*Chironomus thummi thummi* (midge) component X (Chi t 9);
*Dolichovespula maculata* (white face hornet) phospholipase (Dol m 1);
*Dolichovespula maculata* (white face hornet) hyaluronidase (Dol m 2);
*Dolichovespula maculata* (white face hornet) antigen 5 (Dol m 5);
*Dolichovespula arenaria* (yellow hornet) antigen 5 (Dol a 5);
*Polistes annularies* (wasp) phospholipase A1 (Pol a 1);
*Polistes annularies* (wasp) hyaluronidase (Pol a 2);
*Polistes annularies* (wasp) antigen 5 (Pol a 5);

*Polistes dominulus* (Mediterranean paper wasp) antigen (Pol d 1);
*Polistes dominulus* (Mediterranean paper wasp) serine protease (Pol d 4);
*Polistes dominulus* (Mediterranean paper wasp) antigen (Pol d 5);
*Polistes exclamans* (wasp) phospholipase A1 (Pol e 1);
*Polistes exclamans* (wasp) antigen 5 (Pol e 5);
*Polistes fuscatus* (wasp) antigen 5 (Pol f 5);
*Polistes metricus* (wasp) antigen 5 (Pol m 5);
*Vespa crabo* (European hornet) phospholipase (Vesp c 1);
*Vespa crabo* (European hornet) antigen 5 (Vesp c 5.0101);
*Vespa crabo* (European hornet) antigen 5 (Vesp c 5.0102);
*Vespa mandarina* (giant Asian hornet) antigen (Vesp m 1.01);
*Vespa mandarina* (giant Asian hornet) antigen (Vesp m 1.02);
*Vespa mandarina* (giant Asian hornet) antigen (Vesp m 5);
*Vespula flavopilosa* (yellowjacket) antigen 5 (Ves f 5);
*Vespula germanica* (yellowjacket) antigen 5 (Ves g 5);
*Vespula maculifrons* (yellowjacket) phospholipase A1 (Ves m 1);
*Vespula maculifrons* (yellowjacket) hyaluronidase (Ves m 2);
*Vespula maculifrons* (yellowjacket) antigen 5 (Ves m 5);
*Vespula pennsylvanica* (yellowjacket) (antigen 5Ves p 5);
*Vespula squamosa* (yellowjacket) antigen 5 (Ves s 5);
*Vespula vidua* (wasp) antigen (Ves vi 5);
*Vespula vulgaris* (yellowjacket) phospholipase A1 (Ves v 1);
*Vespula vulgaris* (yellowjacket) hyaluronidase (Ves v 2);
*Vespula vulgaris* (yellowjacket) antigen 5 (Ves v 5);
*Myrmecia pilosula* (Australian jumper ant) antigen (Myr p 1);
*Myrmecia pilosula* (Australian jumper ant) antigen (Myr p 2);
*Solenopsis geminata* (tropical fire ant) antigen (Sol g 2);
*Solenopsis geminata* (tropical fire ant) antigen (Sol g 4);
*Solenopsis invicta* (fire ant) antigen (Sol i 2);
*Solenopsis invicta* (fire ant) antigen (Sol i 3);
*Solenopsis invicta* (fire ant) antigen (Sol i 4);
*Solenopsis saevissima* (Brazilian fire ant) antigen (Sol s 2);
*Gadus callarias* (cod) allergen M (Gad c 1);
*Salmo salar* (Atlantic salmon) parvalbumin (Sal s 1);
*Gallus domesticus* (chicken) ovomucoid (Gal d 1);
*Gallus domesticus* (chicken) ovalbumin (Gal d 2);
*Gallus domesticus* (chicken) conalbumin; A22 (Gal d 3);
*Gallus domesticus* (chicken) lysozyme (Gal d 4);
*Gallus domesticus* (chicken) serum albumin (Gal d 5);
*Metapenaeus ensis* (shrimp) tropomyosin (Met e 1);
*Penaeus aztecus* (shrimp) tropomyosin (Pen a 1);
*Penaeus indicus* (shrimp) tropomyosin (Pen i 1);
*Todarodes pacificus* (squid) tropomyosin (Tod p 1);
*Haliotis Midae* (abalone) antigen (Hal m 1);
*Apium graveolens* (celery) Bet v 1 homologue (Api g 1);
*Apium graveolens* (celery) profilin (Api g 4);
*Apium graveolens* (celery) antigen (Api g 5);
*Brassica juncea* (oriental mustard) 2S albumin (Bra j 1);
*Brassica rapa* (turnip) prohevein-like protein (Bar r 2);
*Hordeum vulgare* (barley) BMAI-1 (Hor v 1);
*Zea mays* (maize, corn) lipid transfer protein (Zea m 14);
*Corylus avellana* (hazelnut) Bet v 1 homologue (Cor a 1.0401);
*Malus domestica* (apple) Bet v 1 homologue (Mal d 1);
*Malus domestica* (apple) lipid transfer protein (Mal d 3);
*Pyrus communis* (pear) Bet v 1 homologue (Pyr c 1);
*Pyrus communis* (pear) profilin (Pyr c 4);
*Pyrus communis* (pear) isoflavone reductase homologue (Pyr c 5);
*Oryza sativa* (rice) antigen (Ory s 1);
*Persea americana* (avocado) endochitinase (Pers a 1);
*Prunus armeniaca* (apricot) Bet v 1 homologue (Pru ar 1);
*Prunus armeniaca* (apricot) lipid transfer protein (Pru ar 3);
*Prunus avium* (sweet cherry) Bet v 1 homologue (Pru av 1);
*Prunus avium* (sweet cherry) thaumatin homologue (Pru av 2);
*Prunus avium* (sweet cherry) profilin (Pru av 4);
*Prunus persica* (peach) lipid transfer protein (Pru p 3);
*Sinapis alba* (yellow mustard) 2S albumin (Sin a 1);
*Glycine max* (soybean) HPS (Gly m 1.0101);
*Glycine max* (soybean) HPS (Gly m 1.0102);
*Glycine max* (soybean) antigen (Gly m 2);
*Glycine max* (soybean) profilin (Gly m 3);
*Arachis hypogaea* (peanut) vicilin (Ar a h 1);
*Arachis hypogaea* (peanut) (conglutin Ar a h 2);
*Arachis hypogaea* (peanut) glycinin (Ar a h 3);
*Arachis hypogaea* (peanut) glycinin (Ar a h 4);
*Arachis hypogaea* (peanut) (profilin Ar a h 5);
*Arachis hypogaea* (peanut) conglutin homologue (Ar a h 6);
*Arachis hypogaea* (peanut) conglutin homologue (Ar a h 7);
*Actinidia chinensis* (kiwi) cysteine protease (Act c 1);
*Solanum tuberosum* (potato) patatin (Sol t 1);
*Bertholletia excelsa* (Brazil nut) 2S albumin (Ber e 1);
*Juglans regia* (English walnut) 2S albumin (Jug r 1);
*Juglans regia* (English walnut) vicilin (Jug r 2);
*Ricinus communis* (castor bean) 2S albumin (Ric c 1);
*Anisakis simplex* (nematode) antigen (Ani s 1);
*Anisakis simplex* (nematode) paramyosin (Ani s 2);
*Ascaris suum* (worm) antigen (Asc s 1);
*Aedes aegyptii* (mosquito) apyrase (Aed a 1);
*Aedes aegyptii* (mosquito) antigen (Aed a 2);
*Hevea brasiliensis* (rubber) elongation factor (Hev b 1);
*Hevea brasiliensis* (rubber) 1,3-glucanase (Hev b 2);
*Hevea brasiliensis* (rubber) antigen (Hev b 3);
*Hevea brasiliensis* (rubber) component of microhelix protein complex (Hev b 4);
*Hevea brasiliensis* (rubber) antigen (Hev b 5);
*Hevea brasiliensis* (rubber) hevein precursor (Hev b 6.01);
*Hevea brasiliensis* (rubber) hevein (Hev b 6.02);
*Hevea brasiliensis* (rubber) C-terminal fragment antigen (Hev b 6.03);
*Hevea brasiliensis* (rubber) patatin homologue (Hev b 7);
*Hevea brasiliensis* (rubber) profilin (Hev b 8);
*Hevea brasiliensis* (rubber) enolase (Hev b 9);
*Hevea brasiliensis* (rubber) Mn-superoxide dismut (Hev b 10);
*Ctenocephalides felis felis* (cat flea) antigen (Cte f 1);
*Homo sapiens* (human autoallergen) antigen (Hom s 1);
*Homo sapiens* (human autoallergen) antigen (Hom s 2);
*Homo sapiens* (human autoallergen) antigen (Hom s 3);
*Homo sapiens* (human autoallergen) antigen (Hom s 4); and
*Homo sapiens* (human autoallergen) antigen (Hom s 5),
the expressed protein allergen being encapsulated within the dead *E. coli*; and
a pharmaceutically acceptable carrier,
wherein the administered dead *E. coli* are taken up by antigen presenting cells in the subject, the recombinant version of the allergen protein is released and processed inside the antigen presenting cells, and the processed protein is displayed on the antigen presenting cell surface, so that one or more symptoms of the subject's allergy to the protein allergen is reduced or decreased.

3. A method of treating allergy in a subject susceptible to an allergic response to a protein allergen, the method comprising a step of:
    administering to a subject, via the subject's rectum, a composition comprising:
        dead *E. coli* that has expressed non-secreted version of a protein allergen selected from the group consisting of:
    *Ambrosia artemisiifolia* (short ragweed) antigen E (Amb a 1);
    *Ambrosia artemisiifolia* (short ragweed) antigen K (Amb a 2);
    *Ambrosia artemisiifolia* (short ragweed) Ra3 antigen (Amb a 3);
    *Ambrosia artemisiifolia* (short ragweed) Ra5 antigen (Amb a 5);
    *Ambrosia artemisiifolia* (short ragweed) Ra6 antigen (Amb a 6);
    *Ambrosia artemisiifolia* (short ragweed) Ra7 antigen (Amb a 7);
    *Ambrosia trifida* (giant ragweed) Ra5G antigen (Amb t 5);
    *Artemisia vulgaris* (mugwort) antigen (Art v 1);
    *Artemisia vulgaris* (mugwort) antigen (Art v 2);
    *Helianthus annuus* (sunflower) antigen (Hel a 1);
    *Helianthus annuus* (sunflower) profilin (Hel a 2);
    *Mercurialis annua* (annual mercury) profilin (Mer a 1);
    *Cynodon dactylon* (Bermuda grass) antigen (Cyn d 1);
    *Cynodon dactylon* (Bermuda grass) antigen (Cyn d 7);
    *Cynodon dactylon* (Bermuda grass) profilin (Cyn d 12);
    *Dactylis glomerata* (orchard grass) AgDg1 antigen (Dac g 1);
    *Dactylis glomerata* (orchard grass) antigen (Dac g 2);
    *Dactylis glomerata* (orchard grass) antigen (Dac g 3);
    *Dactylis glomerata* (orchard grass) antigen (Dac g 5);
    *Holcus lanatus* (velvet grass) antigen (Hol l 1);
    *Lolium perenne* (rye grass) group I antigen (Lol p 1);
    *Lolium perenne* (rye grass) group II antigen (Lol p 2);
    *Lolium perenne* (rye grass) group III antigen (Lol p 3);
    *Lolium perenne* (rye grass) group IX antigen (Lol p 5);
    *Lolium perenne* (rye grass) antigen (Lol p Ib);
    *Lolium perenne* (rye grass) trypsin (Lol p 11);
    *Phalaris aquatica* (canary grass) antigen (Pha a 1);
    *Phleum pratense* (timothy grass) antigen (Phl p 1);
    *Phleum pratense* (timothy grass) antigen (Phl p 2);
    *Phleum pratense* (timothy grass) antigen (Phl p 4);
    *Phleum pratense* (timothy grass) antigen Ag 25 (Phl p 5);
    *Phleum pratense* (timothy grass) antigen (Phl p 6);
    *Phleum pratense* (timothy grass) profilin (Phl p 12);
    *Phleum pratense* (timothy grass) polygalacturonase (Phl p 13);
    *Poa pratensis* (Kentucky blue grass) group I antigen (Poa p 1);
    *Poa pratensis* (Kentucky blue grass) antigen (Poa p 5);
    *Sorghum halepense* (Johnson grass) antigen (Sor h 1);
    *Alnus glutinosa* (alder) antigen (Aln g 1);
    *Betula verrucosa* (birch) antigen (Bet v 1);
    *Betula verrucosa* (birch) profilin (Bet v 2);
    *Betula verrucosa* (birch) antigen (Bet v 3);
    *Betula verrucosa* (birch) antigen (Bet v 4);
    *Betula verrucosa* (birch) isoflavone reductase homologue (Bet v 5);
    *Betula verrucosa* (birch) cyclophilin (Bet v 7);
    *Carpinus betulus* (hornbeam) antigen (Car b 1);
    *Castanea sativa* (chestnut) Bet v 1 homologue (Cas s 1);
    *Castanea sativa* (chestnut) chitinase (Cas s 5);
    *Corylus avelana* (hazel) antigen (Cor a 1);
    *Quercus alba* (white oak) antigen (Que a 1);
    *Cryptomeria japonica* (sugi) antigen (Cry j 1);
    *Cryptomeria japonica* (sugi) antigen (Cry j 2);
    *Juniperus ashei* (mountain cedar) antigen (Jun a 1);
    *Juniperus ashei* (mountain cedar) antigen (Jun a 3);
    *Juniperus oxycedrus* (prickly juniper) calmodulin-like antigen (Jun o 2);
    *Juniperus sabinoides* (mountain cedar) antigen (Jun s 1);
    *Juniperus virginiana* (eastern red cedar) antigen (Jun v 1);
    *Fraxinus excelsior* (ash) antigen (Fra e 1);
    *Ligustrum vulgare* (privet) antigen (Lig v 1);
    *Olea europea* (olive) antigen (Ole e 1);
    *Olea europea* (olive) profilin (Ole e 2);
    *Olea europea* (olive) antigen (Ole e 3);
    *Olea europea* (olive) antigen (Ole e 4);
    *Olea europea* (olive) superoxide dismutase (Ole e 5);
    *Olea europea* (olive) antigen (Ole e 6);
    *Syringa vulgaris* (lilac) antigen (Syr v 1);
    *Acarus siro* (mite) fatty acid-binding protein (Aca s 13);
    *Blomia tropicalis* (mite) antigen (Blo t 5);
    *Blomia tropicalis* (mite) Bt11a antigen (Blo t 12);
    *Blomia tropicalis* (mite) Bt6 fatty acid-binding protein (Blo t);
    *Dermatophagoides pteronyssinus* (mite) antigen P1 (Der p 1);
    *Dermatophagoides pteronyssinus* (mite) antigen (Der p 2);
    *Dermatophagoides pteronyssinus* (mite) trypsin (Der p 3);
    *Dermatophagoides pteronyssinus* (mite) amylase (Der p 4);
    *Dermatophagoides pteronyssinus* (mite) antigen (Der p 5);
    *Dermatophagoides pteronyssinus* (mite) chymotrypsin (Der p 6);
    *Dermatophagoides pteronyssinus* (mite) antigen (Der p 7);
    *Dermatophagoides pteronyssinus* (mite) glutathione transferase (Der p 8);
    *Dermatophagoides pteronyssinus* (mite) collagenolytic serine prot. (Der p 9);
    *Dermatophagoides pteronyssinus* (mite) tropomyosin (Der p 10);
    *Dermatophagoides pteronyssinus* (mite) apolipophorin like p (Der p 14);
    *Dermatophagoides microceras* (mite) antigen (Der m 1);
    *Dermatophagoides farinae* (mite) antigen (Der f 1);
    *Dermatophagoides farinae* (mite) antigen (Der f 2);
    *Dermatophagoides farinae* (mite) antigen (Der f 3);
    *Dermatophagoides farinae* (mite) tropomyosin (Der f 10);
    *Dermatophagoides farinae* (mite) paramyosin (Der f 11);
    *Dermatophagoides farinae* (mite) Mag 3, apolipophorin (Der f 14);
    *Euroglyphus maynei* (mite) apolipophorin (Eur m 14);
    *Lepidoglyphus destructor* (storage mite) antigen (Lep d 2.0101);
    *Lepidoglyphus destructor* (storage mite) antigen (Lep d 2.0102);
    *Bos domesticus* (cow) Ag3, lipocalin (Bos d 2);
    *Bos domesticus* (cow) alpha-lactalbumin (Bos d 4);
    *Bos domesticus* (cow) beta-lactalbumin (Bos d 5);
    *Bos domesticus* (cow) serum albumin (Bos d 6);
    *Bos domesticus* (cow) immunoglobulin (Bos d 7);
    *Bos domesticus* (cow) casein (Bos d 8);
    *Canis familiaris* (dog) antigen (Can f 1);
    *Canis familiaris* (dog) antigen (Can f 2);
    *Canis familiaris* (dog) albumin (Can f ?);
    *Equus caballus* (horse) lipocalin (Equ c 1);
    *Equus caballus* (horse) lipocalin (Equ c 2);
    *Felis domesticus* (cat) cat-1 antigen (Fel d 1);
    *Mus musculus* (mouse) MUP antigen (Mus m 1);

*Rattus norvegius* (rat) antigen (Rat n 1);
*Alternaria alternata* (fungus) antigen (Alt a 1);
*Alternaria alternata* (fungus) antigen (Alt a 2);
*Alternaria alternata* (fungus) heat shock protein (Alt a 3);
*Alternaria alternata* (fungus) ribosomal protein (Alt a 6);
*Alternaria alternata* (fungus) YCP4 protein (Alt a 7);
*Alternaria alternata* (fungus) aldehyde dehydrogenase (Alt a 10);
*Alternaria alternata* (fungus) enloase (Alt a 11);
*Alternaria alternata* (fungus) acid ribosomal protein P1 (Alt a 12);
*Cladosporium herbarum* (fungus) antigen (Cla h 1);
*Cladosporium herbarum* (fungus) antigen (Cla h 2);
*Cladosporium herbarum* (fungus) aldehyde dehydrogenase (Cla h 3);
*Cladosporium herbarum* (fungus) ribosomal protein);
*Cladosporium herbarum* (fungus) YCP4 protein (Cla h 5);
*Cladosporium herbarum* (fungus) enolase (Cla h 6);
*Cladosporium herbarum* (fungus) acid ribosomal protein P1 (Cla h 12);
*Aspergillus flavus* (fungus) alkaline serine proteinase (Asp fl 13);
*Aspergillus Fumigatus* (fungus) antigen (Asp f 1);
*Aspergillus Fumigatus* (fungus) antigen (Asp f 2);
*Aspergillus Fumigatus* (fungus) peroxisomal protein (Asp f 3);
*Aspergillus Fumigatus* (fungus) antigen (Asp f 4);
*Aspergillus Fumigatus* (fungus) metalloprotease (Asp f 5);
*Aspergillus Fumigatus* (fungus) Mn superoxide dismutase (Asp f 6);
*Aspergillus Fumigatus* (fungus) antigen (Asp f 7);
*Aspergillus Fumigatus* (fungus) ribosomal protein P2 (Asp f 8);
*Aspergillus Fumigatus* (fungus) antigen (Asp f 9);
*Aspergillus Fumigatus* (fungus) aspartis protease (Asp f 10);
*Aspergillus Fumigatus* (fungus) peptidyl-prolyl isomerase (Asp f 11);
*Aspergillus Fumigatus* (fungus) heat shock protein P70 (Asp f 12);
*Aspergillus Fumigatus* (fungus) alkaline serine proteinase (Asp f 13);
*Aspergillus Fumigatus* (fungus) antigen (Asp f 15);
*Aspergillus Fumigatus* (fungus) antigen (Asp f 16);
*Aspergillus Fumigatus* (fungus) antigen (Asp f 17);
*Aspergillus Fumigatus* (fungus) vacuolar serine (Asp f 18);
*Aspergillus niger* (fungus) beta-xylosidase (Asp n 14);
*Aspergillus niger* (fungus) antigen (Asp n 18);
*Aspergillus niger* (fungus) vacuolar serine proteinase;
*Aspergillus oryzae* (fungus) TAKA-amylase A (Asp o 2);
*Aspergillus oryzae* (fungus) alkaline serine proteinase (Asp o 13);
*Penicillium brevicompactum* (fungus) alkaline serine proteinase (Pen b 13);
*Penicillium citrinum* (fungus) heat shock protein P70 (Pen c 1);
*Penicillium citrinum* (fungus) peroxisomal membrane protein (Pen c 3);
*Penicillium citrinum* (fungus) alkaline serine proteinase (Pen c 13);
*Penicillium notatum* (fungus) N-acetyl glucosaminidase (Pen n 1);
*Penicillium notatum* (fungus) alkaline serine proteinase (Pen n 13);
*Penicillium notatum* (fungus) vacuolar serine proteinase (Pen n 18);
*Penicillium oxalicum* (fungus) vacuolar serine proteinase (Pen o 18);
*Trichophyton rubrum* (fungus) antigen (Tri r 2);
*Trichophyton rubrum* (fungus) serine protease (Tri r 4);
*Trichophyton tonsurans* (fungus) antigen (Tri t 1);
*Trichophyton tonsurans* (fungus) serine protease (Tri t 4);
*Candida albicans* (fungus) antigen (Cand a 1);
*Candida boidinii* (fungus) antigen (Cand b 2);
*Malassezia furfur* (fungus) antigen (Mal f 1);
*Malassezia furfur* (fungus) MF1 peroxisomal membrane protein (Mal f 2);
*Malassezia furfur* (fungus) MF2 peroxisomal membrane protein (Mal f 3);
*Malassezia furfur* (fungus) antigen (Mal f 4);
*Malassezia furfur* (fungus) antigen (Mal f 5);
*Malassezia furfur* (fungus) cyclophilin homologue (Mal f 6);
*Psilocybe cubensis* (fungus) antigen (Psi c 1);
*Psilocybe cubensis* (fungus) cyclophilin (Psi c 2);
*Coprinus comatus* (shaggy cap) antigen (Cop c 1);
*Coprinus comatus* (shaggy cap) antigen (Cop c 2);
*Coprinus comatus* (shaggy cap) antigen (Cop c 3);
*Coprinus comatus* (shaggy cap) antigen (Cop c 5);
*Coprinus comatus* (shaggy cap) antigen (Cop c 7);
*Aedes aegyptii* (mosquito) apyrase (Aed a 1);
*Aedes aegyptii* (mosquito) antigen (Aed a 2);
*Apis mellifera* (honey bee) phospholipase A2 (Api m 1);
*Apis mellifera* (honey bee) hyaluronidase (Api m 2);
*Apis mellifera* (honey bee) melittin (Api m 4);
*Apis mellifera* (honey bee) antigen (Api m 6);
*Bombus pennsylvanicus* (bumble bee) phospholipase (Bom p 1);
*Bombus pennsylvanicus* (bumble bee) protease (Bom p 4);
*Blattella germanica* (German cockroach) Bd90k (Bla g 1);
*Blattella germanica* (German cockroach) aspartic protease (Bla g 2);
*Blattella germanica* (German cockroach) calycin (Bla g 4);
*Blattella germanica* (German cockroach) glutathione transferase (Bla g 5);
*Blattella germanica* (German cockroach) troponin C (Bla g 6);
*Periplaneta americana* (American cockroach) Cr-PII (Per a 1);
*Periplaneta americana* (American cockroach) Cr-PI (Per a 3);
*Periplaneta americana* (American cockroach) tropomyosin (Per a 7);
*Chironomus thummi thummi* (midge) hemoglobin (Chi t 1-9);
*Chironomus thummi thummi* (midge) component III (Chi t 1.01);
*Chironomus thummi thummi* (midge) component IV (Chi t 1.02);
*Chironomus thummi thummi* (midge) component I (Chi t 2.0101);
*Chironomus thummi thummi* (midge) component IA (Chi t 2.0102);
*Chironomus thummi thummi* (midge) component II-beta (Chi t 3);
*Chironomus thummi thummi* (midge) component IIIA (Chi t 4);
*Chironomus thummi thummi* (midge) component VI (Chi t 5);
*Chironomus thummi thummi* (midge) component VIIA (Chi t 6.01);
*Chironomus thummi thummi* (midge) component IX (Chi t 6.02);

*Chironomus thummi thummi* (midge) component VIIB (Chi t 7);
*Chironomus thummi thummi* (midge) component VIII (Chi t 8);
*Chironomus thummi thummi* (midge) component X (Chi t 9);
*Dolichovespula maculata* (white face hornet) phospholipase (Dol m 1);
*Dolichovespula maculata* (white face hornet) hyaluronidase (Dol m 2);
*Dolichovespula maculata* (white face hornet) antigen 5 (Dol m 5);
*Dolichovespula arenaria* (yellow hornet) antigen 5 (Dol a 5);
*Polistes annularies* (wasp) phospholipase A1 (Pol a 1);
*Polistes annularies* (wasp) hyaluronidase (Pol a 2);
*Polistes annularies* (wasp) antigen 5 (Pol a 5);
*Polistes dominulus* (Mediterranean paper wasp) antigen (Pol d 1);
*Polistes dominulus* (Mediterranean paper wasp) serine protease (Pol d 4);
*Polistes dominulus* (Mediterranean paper wasp) antigen (Pol d 5);
*Polistes exclamans* (wasp) phospholipase A1 (Pol e 1);
*Polistes exclamans* (wasp) antigen 5 (Pol e 5);
*Polistes fuscatus* (wasp) antigen 5 (Pol f 5);
*Polistes metricus* (wasp) antigen 5 (Pol m 5);
*Vespa crabo* (European hornet) phospholipase (Vesp c 1);
*Vespa crabo* (European hornet) antigen 5 (Vesp c 5.0101);
*Vespa crabo* (European hornet) antigen 5 (Vesp c 5.0102);
*Vespa mandarina* (giant Asian hornet) antigen (Vesp m 1.01);
*Vespa mandarina* (giant Asian hornet) antigen (Vesp m 1.02);
*Vespa mandarina* (giant Asian hornet) antigen (Vesp m 5);
*Vespula flavopilosa* (yellowjacket) antigen 5 (Ves f 5);
*Vespula germanica* (yellowjacket) antigen 5 (Ves g 5);
*Vespula maculifrons* (yellowjacket) phospholipase A1 (Ves m 1);
*Vespula maculifrons* (yellowjacket) hyaluronidase (Ves m 2);
*Vespula maculifrons* (yellowjacket) antigen 5 (Ves m 5);
*Vespula pennsylvanica* (yellowjacket) (antigen 5Ves p 5);
*Vespula squamosa* (yellowjacket) antigen 5 (Ves s 5);
*Vespula vidua* (wasp) antigen (Ves vi 5);
*Vespula vulgaris* (yellowjacket) phospholipase A1 (Ves v 1);
*Vespula vulgaris* (yellowjacket) hyaluronidase (Ves v 2);
*Vespula vulgaris* (yellowjacket) antigen 5 (Ves v 5);
*Myrmecia pilosula* (Australian jumper ant) antigen (Myr p 1);
*Myrmecia pilosula* (Australian jumper ant) antigen (Myr p 2);
*Solenopsis geminata* (tropical fire ant) antigen (Sol g 2);
*Solenopsis geminata* (tropical fire ant) antigen (Sol g 4);
*Solenopsis invicta* (fire ant) antigen (Sol i 2);
*Solenopsis invicta* (fire ant) antigen (Sol i 3);
*Solenopsis invicta* (fire ant) antigen (Sol i 4);
*Solenopsis saevissima* (Brazilian fire ant) antigen (Sol s 2);
*Gadus callarias* (cod) allergen M (Gad c 1);
*Salmo salar* (Atlantic salmon) parvalbumin (Sal s 1);
*Gallus domesticus* (chicken) ovomucoid (Gal d 1);
*Gallus domesticus* (chicken) ovalbumin (Gal d 2);
*Gallus domesticus* (chicken) conalbumin; A22 (Gal d 3);
*Gallus domesticus* (chicken) lysozyme (Gal d 4);
*Gallus domesticus* (chicken) serum albumin (Gal d 5);
*Metapenaeus ensis* (shrimp) tropomyosin (Met e 1);
*Penaeus aztecus* (shrimp) tropomyosin (Pen a 1);
*Penaeus indicus* (shrimp) tropomyosin (Pen i 1);
*Todarodes pacificus* (squid) tropomyosin (Tod p 1);
*Haliotis Midae* (abalone) antigen (Hal m 1);
*Apium graveolens* (celery) Bet v 1 homologue (Api g 1);
*Apium graveolens* (celery) profilin (Api g 4);
*Apium graveolens* (celery) antigen (Api g 5);
*Brassica juncea* (oriental mustard) 2S albumin (Bra j 1);
*Brassica rapa* (turnip) prohevein-like protein (Bar r 2);
*Hordeum vulgare* (barley) BMAI-1 (Hor v 1);
*Zea mays* (maize, corn) lipid transfer protein (Zea m 14);
*Corylus avellana* (hazelnut) Bet v 1 homologue (Cor a 1.0401);
*Malus domestica* (apple) Bet v 1 homologue (Mal d 1);
*Malus domestica* (apple) lipid transfer protein (Mal d 3);
*Pyrus communis* (pear) Bet v 1 homologue (Pyr c 1);
*Pyrus communis* (pear) profilin (Pyr c 4);
*Pyrus communis* (pear) isoflavone reductase homologue (Pyr c 5);
*Oryza sativa* (rice) antigen (Ory s 1);
*Persea americana* (avocado) endochitinase (Pers a 1);
*Prunus armeniaca* (apricot) Bet v 1 homologue (Pru ar 1);
*Prunus armeniaca* (apricot) lipid transfer protein (Pru ar 3);
*Prunus avium* (sweet cherry) Bet v 1 homologue (Pru av 1);
*Prunus avium* (sweet cherry) thaumatin homologue (Pru av 2);
*Prunus avium* (sweet cherry) profilin (Pru av 4);
*Prunus persica* (peach) lipid transfer protein (Pru p 3);
*Sinapis alba* (yellow mustard) 2S albumin (Sin a 1);
*Glycine max* (soybean) HPS (Gly m 1.0101);
*Glycine max* (soybean) HPS (Gly m 1.0102);
*Glycine max* (soybean) antigen (Gly m 2);
*Glycine max* (soybean) profilin (Gly m 3);
*Arachis hypogaea* (peanut) vicilin (Ar a h 1);
*Arachis hypogaea* (peanut) (conglutin Ar a h 2);
*Arachis hypogaea* (peanut) glycinin (Ar a h 3);
*Arachis hypogaea* (peanut) glycinin (Ar a h 4);
*Arachis hypogaea* (peanut) (profilin Ar a h 5);
*Arachis hypogaea* (peanut) conglutin homologue (Ar a h 6);
*Arachis hypogaea* (peanut) conglutin homologue (Ar a h 7);
*Actinidia chinensis* (kiwi) cysteine protease (Act c 1);
*Solanum tuberosum* (potato) patatin (Sol t 1);
*Bertholletia excelsa* (Brazil nut) 2S albumin (Ber e 1);
*Juglans regia* (English walnut) 2S albumin (Jug r 1);
*Juglans regia* (English walnut) vicilin (Jug r 2);
*Ricinus communis* (castor bean) 2S albumin (Ric c 1);
*Anisakis simplex* (nematode) antigen (Ani s 1);
*Anisakis simplex* (nematode) paramyosin (Ani s 2);
*Ascaris suum* (worm) antigen (Asc s 1);
*Aedes aegyptii* (mosquito) apyrase (Aed a 1);
*Aedes aegyptii* (mosquito) antigen (Aed a 2);
*Hevea brasiliensis* (rubber) elongation factor (Hev b 1);
*Hevea brasiliensis* (rubber) 1,3-glucanase (Hev b 2);
*Hevea brasiliensis* (rubber) antigen (Hev b 3);
*Hevea brasiliensis* (rubber) component of microhelix protein complex (Hev b 4);
*Hevea brasiliensis* (rubber) antigen (Hev b 5);
*Hevea brasiliensis* (rubber) hevein precursor (Hev b 6.01);
*Hevea brasiliensis* (rubber) hevein (Hev b 6.02);
*Hevea brasiliensis* (rubber) C-terminal fragment antigen (Hev b 6.03);
*Hevea brasiliensis* (rubber) patatin homologue (Hev b 7);
*Hevea brasiliensis* (rubber) profilin (Hev b 8);
*Hevea brasiliensis* (rubber) enolase (Hev b 9);

Hevea brasiliensis (rubber) Mn-superoxide dismut (Hev b 10);
Ctenocephalides felis felis (cat flea) antigen (Cte f 1);
Homo sapiens (human autoallergen) antigen (Hom s 1);
Homo sapiens (human autoallergen) antigen (Hom s 2);
Homo sapiens (human autoallergen) antigen (Hom s 3);
Homo sapiens (human autoallergen) antigen (Hom s 4); and
Homo sapiens (human autoallergen) antigen (Hom s 5),
the expressed protein allergen being encapsulated within the dead E. coli; and
a pharmaceutically acceptable carrier,
so that one or more symptoms of the subject's allergy to the protein allergen is reduced or decreased.

4. A method of treating peanut allergy in a subject susceptible to an allergic response to a protein allergen, the method comprising a step of:
   administering to a subject, via the subject's rectum, a composition comprising:
      dead E. coli that has expressed a protein allergen selected from the group consisting of peanut allergens Ara h 1, Ara h 2, and Ara h 3, the expressed protein allergen being encapsulated within the dead E. coli; and
      a pharmaceutically acceptable carrier,
   wherein the administered dead E. coli are taken up by antigen presenting cells in the subject, the recombinant version of the peanut allergen is released and processed inside the antigen presenting cells, and the processed allergen is displayed on the antigen presenting cell surface,
   so that one or more symptoms of the subject's allergy to the protein allergen is reduced or decreased.

5. A method of treating peanut allergy in a subject susceptible to an allergic response to a protein allergen, the method comprising a step of:
   administering to a subject, via the subject's rectum, a composition comprising:
      dead E. coli that has expressed a non-secreted version of a protein allergen selected from the group consisting of peanut allergens Ara h 1, Ara h 2, and Ara h 3, the expressed protein allergen being encapsulated within the dead E. coli; and
      a pharmaceutically acceptable carrier,
   so that one or more symptoms of the subject's allergy to the protein allergen is reduced or decreased.

6. The method of any one of claims 1, 2 and 3, wherein the subject is a mammal.

7. The method of any one of claims 1, 2 and 3, wherein the subject is a human.

8. The method of any one of claims 1, 2 and 3, wherein in the step of administering, the composition is delivered in the form of a suppository.

9. The method of any one of claims 1, 2 and 3, wherein in the step of administering, the composition is delivered in the form of an enema.

10. The method of any one of claims 1, 2 and 3, wherein in the step of administering, the composition is delivered using a rectal catheter.

11. The method of any one of claims 1, 2 and 3, further comprising a step of identifying a subject susceptible to an allergic response to a protein allergen, wherein the subject is identified as an individual with an elevated level of IgE antibodies that bind with the protein allergen, and wherein the step of administering comprises administering to the identified subject.

12. The method of any one of claims 1, 2 and 3, further comprising a step of identifying a subject susceptible to an allergic response to a protein allergen, wherein the subject is identified as an individual with a positive skin prick test to the protein allergen, and wherein the step of administering comprises administering to the identified subject.

13. The method of any one of claims 1, 2 and 3, further comprising a step of identifying a subject susceptible to an allergic response to a protein allergen, wherein the subject is identified as an individual having a characteristic selected from the group consisting of a prior display of allergic symptoms when exposed to the protein allergen and a familial relationship with an individual who previously displayed allergic symptoms when exposed to the protein allergen, and wherein the step of administering comprises administering to the identified subject.

14. A method of treating peanut allergy in a subject susceptible to an allergic response to a protein allergen selected from the group consisting of peanut allergens Ara h 1, Ara h 2, and Ara h 3, the method comprising:
   administering to a subject, via the subject's rectum, a composition comprising:
      dead E. coli cells having expressed a peanut allergen selected from the group consisting of Ara h1 of SEQ ID NO: 2, Ara h2 of SEQ ID NO: 4 and Ara h3 of SEQ ID NO: 6 so that the expressed allergen is encapsulated within the dead E. coli cells and is not exposed to the subject's IgE antibodies during administration; and
      a pharmaceutically acceptable carrier,
   so that one or more symptoms of the subject's allergy to the protein allergen is reduced or decreased.

15. The method of any one of claims 4, 5 and 14, wherein the protein allergen is a modified peanut allergen protein whose amino acid sequence differs from that of an intact wild-type peanut allergen protein in that at least one IgE epitope has a substitution in the modified peanut allergen protein such that the modified peanut allergen protein has a reduced ability to bind to or cross-link IgE as compared with the unmodified peanut allergen protein, the at least one IgE epitope being one that is recognized when the unmodified peanut allergen protein is contacted with serum IgE from an individual that is allergic to the unmodified peanut allergen protein, wherein:
   when the wild-type peanut protein has the amino acid sequence of SEQ ID NO: 2, the substitution is in an IgE epitope selected from the group consisting of:
      an epitope found between amino acids 25 and 34 of SEQ ID NO: 2;
      an epitope found between amino acids 48 and 57 of SEQ ID NO: 2;
      an epitope found between amino acids 65 and 74 of SEQ ID NO: 2;
      an epitope found between amino acids 89 and 98 of SEQ ID NO: 2;
      an epitope found between amino acids 97 and 106 of SEQ ID NO: 2;
      an epitope found between amino acids 107 and 116 of SEQ ID NO: 2;
      an epitope found between amino acids 123 and 132 of SEQ ID NO: 2;
      an epitope found between amino acids 134 and 143 of SEQ ID NO: 2;
      an epitope found between amino acids 294 and 303 of SEQ ID NO: 2;
      an epitope found between amino acids 311 and 320 of SEQ ID NO: 2;
      an epitope found between amino acids 325 and 334 of SEQ ID NO: 2;

an epitope found between amino acids 344 and 353 of SEQ ID NO: 2;
an epitope found between amino acids 393 and 402 of SEQ ID NO: 2;
an epitope found between amino acids 409 and 418 of SEQ ID NO: 2;
an epitope found between amino acids 461 and 470 of SEQ ID NO: 2;
an epitope found between amino acids 498 and 507 of SEQ ID NO: 2;
an epitope found between amino acids 525 and 534 of SEQ ID NO: 2;
an epitope found between amino acids 539 and 548 of SEQ ID NO: 2;
an epitope found between amino acids 551 and 560 of SEQ ID NO: 2;
an epitope found between amino acids 559 and 568 of SEQ ID NO: 2;
an epitope found between amino acids 578 and 587 of SEQ ID NO: 2;
an epitope found between amino acids 597 and 606 of SEQ ID NO: 2;
and a combination thereof; and
when the wild-type peanut protein has the amino acid sequence of SEQ ID NO: 4, the substitution is in an IgE epitope selected from the group consisting of:
an epitope found between amino acids 15 and 24 of SEQ ID NO: 4;
an epitope found between amino acids 21 and 30 of SEQ ID NO: 4;
an epitope found between amino acids 27 and 36 of SEQ ID NO: 4;
an epitope found between amino acids 39 and 48 of SEQ ID NO: 4;
an epitope found between amino acids 49 and 58 of SEQ ID NO: 4;
an epitope found between amino acids 57 and 66 of SEQ ID NO: 4;
an epitope found between amino acids 65 and 74 of SEQ ID NO: 4;
an epitope found between amino acids 115 and 124 of SEQ ID NO: 4;
an epitope found between amino acids 127 and 136 of SEQ ID NO: 4;
an epitope found between amino acids 143 and 152 of SEQ ID NO: 4;
and a combination thereof; and
when the wild-type peanut protein has the amino acid sequence of SEQ ID NO: 6, the substitution is in an IgE epitope selected from the group consisting of:
an epitope found between amino acids 33 and 47 of SEQ ID NO: 6;
an epitope found between amino acids 240 and 254 of SEQ ID NO: 6;
an epitope found between amino acids 279 and 293 of SEQ ID NO: 6;
an epitope found between amino acids 303 and 317 of SEQ ID NO: 6;
and a combination thereof.

16. The method of any one of claims 4, 5 and 14, wherein the subject is a mammal.

17. The method of any one of claims 4, 5 and 14, wherein the subject is a human.

18. The method of any one of claims 4, 5 and 14, wherein in the step of administering, the composition is delivered in the form of a suppository.

19. The method of any one of claims 4, 5 and 14, wherein in the step of administering, the composition is delivered in the form of an enema.

20. The method of any one of claims 4, 5 and 14, wherein in the step of administering, the composition is delivered using a rectal catheter.

21. The method of any one of claims 4, 5 and 14, further comprising a step of identifying a subject susceptible to an allergic response to a protein allergen, wherein the subject is identified as an individual with an elevated level of IgE antibodies that bind with the protein allergen, and wherein the step of administering comprises administering to the identified subject.

22. The method of any one of claims 4, 5 and 14, further comprising a step of identifying a subject susceptible to an allergic response to a protein allergen, wherein the subject is identified as an individual with a positive skin prick test to the protein allergen, and wherein the step of administering comprises administering to the identified subject.

23. The method of any one of claims 4, 5 and 14, further comprising a step of identifying a subject susceptible to an allergic response to a protein allergen, wherein the subject is identified as an individual having a characteristic selected from the group consisting of a prior display of allergic symptoms when exposed to the protein allergen and a familial relationship with an individual who previously displayed allergic symptoms when exposed to the protein allergen, and wherein the step of administering comprises administering to the identified subject.

24. The method of any one of claims 4, 5 and 14, wherein the protein allergen has an amino acid sequence that shows 100% identity with that of a wild-type allergen as it occurs in nature.

* * * * *

UNITED STATES PATENT AND TRADEMARK OFFICE
CERTIFICATE OF CORRECTION

Page 1 of 2

PATENT NO. : 8,246,945 B2
APPLICATION NO. : 12/572599
DATED : August 21, 2012
INVENTOR(S) : Michael J. Caplan et al.

It is certified that error appears in the above-identified patent and that said Letters Patent is hereby corrected as shown below:

On the Front page, within Field Code (63) Related U.S. Application Data please delete:

"Continuation of application No. 10/899,551, filed on Jul. 26, 2004, now abandoned, which is a continuation-in-part of application No. 09/731,375, filed on Dec. 6, 2000, now Pat. No. 8,153,414, application No. 12/572,599, which is a continuation-in-part of application No. 10/100,303, filed on Mar. 18, 2002, now abandoned."

and insert:

--Continuation of application No. 10/899,551, filed on Jul. 26, 2004, now abandoned, which is a continuation-in-part of application No. 10/100,303, filed on Mar. 18, 2002, now abandoned, which is a continuation-in-part of application No. 09/731,375, filed on Dec. 6, 2000, now Pat. No. 8,153,414.--

On the Front page, within Field Code (74) Attorney, Agent, or Firm please delete:

"Choata, Hall & Stewart LLP, Brenda Herschbach Jarrell; Brian E. Reese"

and insert:

--Choate, Hall & Stewart LLP, Brenda Herschbach Jarrell; Brian E. Reese--

In column 1, line 22, please delete:

"In accordance with 37 C.F.R §1.52(e)(5), a Sequence Listing in the form of a text file (entitled "Sequence_Listing.txt," created on Dec. 2, 2009, and 36 kilobytes) is incorporated herein by reference in its entirety."

and replace with the following new heading and new paragraph:

Signed and Sealed this
Thirteenth Day of November, 2012

David J. Kappos
*Director of the United States Patent and Trademark Office*

Sequence Listing

In accordance with 37 C.F.R §1.52(e)(5), a Sequence Listing in the form of a text file (entitled "Sequence_Listing.txt" created on March 8, 2010, and 38 kilobytes) is incorporated herein by reference in its entirety.